US012617757B2

(12) United States Patent
Disney et al.

(10) Patent No.: US 12,617,757 B2
(45) Date of Patent: May 5, 2026

(54) COMPOUNDS AND MODULES FOR INHIBITION OF PRE-miR-21 AND THEIR USE IN TREATMENT OF CERTAIN CANCERS

(71) Applicant: University of Florida Research Foundation, Incorporated, Gainesville, FL (US)

(72) Inventors: Matthew David Disney, Jupiter, FL (US); Jessica L. Childs-Disney, Jupiter, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 1015 days.

(21) Appl. No.: 17/755,105

(22) PCT Filed: Oct. 29, 2020

(86) PCT No.: PCT/US2020/057914
§ 371 (c)(1),
(2) Date: Apr. 21, 2022

(87) PCT Pub. No.: WO2021/087084
PCT Pub. Date: May 6, 2021

(65) Prior Publication Data

US 2023/0002329 A1 Jan. 5, 2023

Related U.S. Application Data

(60) Provisional application No. 62/927,247, filed on Oct. 29, 2019.

(51) Int. Cl.

| | |
|---|---|
| ***C07D 235/18*** | (2006.01) |
| ***A61P 35/00*** | (2006.01) |
| ***C07D 333/36*** | (2006.01) |
| ***C07D 403/14*** | (2006.01) |
| ***C07D 409/14*** | (2006.01) |
| ***C07K 7/06*** | (2006.01) |

(52) U.S. Cl.
CPC ............ *C07D 235/18* (2013.01); *A61P 35/00* (2018.01); *C07D 333/36* (2013.01); *C07D 403/14* (2013.01); *C07D 409/14* (2013.01); *C07K 7/06* (2013.01)

(58) Field of Classification Search
CPC .. C07D 235/18; C07D 333/36; C07D 403/14; C07D 409/14; C07D 333/38; A61P 35/00; A61P 31/00; C07K 7/06
See application file for complete search history.

(56) References Cited

U.S. PATENT DOCUMENTS

| | | | |
|---|---|---|---|
| 8,071,562 | B2 | 12/2011 | Bader et al. |
| 9,586,944 | B2 | 3/2017 | Disney et al. |
| 9,933,419 | B2 | 4/2018 | Disney et al. |
| 10,157,261 | B2 | 12/2018 | Disney et al. |
| 11,636,918 | B2 | 4/2023 | Disney et al. |
| 2008/0188377 | A1 | 8/2008 | Disney et al. |
| 2008/0227213 | A1 | 9/2008 | Disney |
| 2010/0190826 | A1 | 7/2010 | Kakefuda et al. |
| 2012/0277178 | A1 | 11/2012 | Jin et al. |
| 2014/0212945 | A1 | 7/2014 | Disney |
| 2016/0188791 | A1 | 6/2016 | Disney |
| 2016/0194696 | A1 | 7/2016 | Guan et al. |
| 2017/0029370 | A1 | 2/2017 | Narayanan et al. |
| 2017/0362650 | A1 | 12/2017 | Zeitlinger et al. |
| 2018/0066262 | A1 | 3/2018 | Domenyuk et al. |
| 2018/0267028 | A1 | 9/2018 | Disney et al. |
| 2019/0156912 | A1 | 5/2019 | Disney et al. |
| 2019/0270723 | A1 | 9/2019 | Kumaravel et al. |
| 2020/0115372 | A1 | 4/2020 | Petter et al. |
| 2020/0324287 | A1 | 10/2020 | Vijayan et al. |
| 2020/0385709 | A1 | 12/2020 | Wagner |
| 2021/0008208 | A1 | 1/2021 | Poma et al. |
| 2021/0379188 | A1 | 12/2021 | Disney |
| 2022/0073910 | A1 | 3/2022 | Disney |
| 2022/0119868 | A1 | 4/2022 | Disney |
| 2022/0251545 | A1 | 8/2022 | Disney |
| 2022/0267839 | A1 | 8/2022 | Disney |
| 2023/0041228 | A1 | 2/2023 | Disney |
| 2023/0149554 | A1 | 5/2023 | Disney |

(Continued)

FOREIGN PATENT DOCUMENTS

| | | | |
|---|---|---|---|
| CN | 110494443 A | | 11/2019 |
| WO | WO 2005/068433 | A1 | 7/2005 |
| WO | WO 2006/133022 | A2 | 12/2006 |

(Continued)

OTHER PUBLICATIONS

"Defining RNA—Small Molecule Affinity Landscapes Enables Design of a Small Molecule Inhibitor of an Oncogenic Noncoding RNA" SP Velagapudi, Y Luo, T Tran, HS Haniff, Y Nakai, M Fallahi, GJ Martinez, JL Childs-Disney, and MD Disney ACS Cent. Sci. 2017, 3, 205-216 (Year: 2017).*

"Defining RNA—Small Molecule Affinity Landscapes Enables Design of a Small Molecule Inhibitor of an Oncogenic Noncoding RNA" Sp Velagapudi, Y Luo, T Tran, HS Haniff, Y Nakai, M Fallahi, GJ Martinez, JL Childs-Disney, and MD Disney ACS Cent. Sci. 2017, 3, 205-216, Supplementary Information (Year: 2017).*

Albany Molecular Research, Inc. CAS Registry Number: RN 1045308-20-0 [Database Registry Chemical Abstracts Service, Columbus, Ohio, Accession No. RN 1045308-20-0, Entered STN: Aug. 13, 2008] (Year: 2008).*

(Continued)

*Primary Examiner* — Kara R. Mcmillian
*Assistant Examiner* — Sophia P Hirakis
(74) *Attorney, Agent, or Firm* — Wolf, Greenfield & Sacks, P.C.

(57) ABSTRACT

Small molecule compounds and corresponding dimers having inhibitory activity against pre-miR-21 RNA and related methods for treatment of neoplastic disease such as cancer and especially cancers expressing miR-21 are disclosed.

6 Claims, 103 Drawing Sheets

Specification includes a Sequence Listing.

(56) References Cited

U.S. PATENT DOCUMENTS

| | | | |
|---|---|---|---|
| 2024/0293398 | A1 | 9/2024 | Disney et al. |
| 2025/0051762 | A1 | 2/2025 | Disney et al. |

FOREIGN PATENT DOCUMENTS

| | | | | |
|---|---|---|---|---|
| WO | WO-2007127212 | A2 * | 11/2007 | .............. A61P 31/22 |
| WO | WO 2008/066873 | A2 | 6/2008 | |
| WO | WO 2008/103489 | A2 | 8/2008 | |
| WO | WO-2009036000 | A2 | 3/2009 | |
| WO | WO 2011/150494 | A1 | 12/2011 | |
| WO | WO 2013/019469 | A1 | 2/2013 | |
| WO | WO-2015009678 | A2 | 1/2015 | |
| WO | WO 2015/021415 | A1 | 2/2015 | |
| WO | WO 2016/085659 | A1 | 6/2016 | |
| WO | WO 2016/191604 | A1 | 12/2016 | |
| WO | WO 2017/196264 | A1 | 11/2017 | |
| WO | WO 2018/006074 | A2 | 1/2018 | |
| WO | WO 2018/098297 | A1 | 5/2018 | |
| WO | WO-2018151810 | A1 | 8/2018 | |
| WO | WO 2019/109046 | A1 | 6/2019 | |
| WO | WO 2019/209975 | A1 | 10/2019 | |
| WO | WO 2019/231821 | A1 | 12/2019 | |
| WO | WO 2020/076511 | A1 | 4/2020 | |
| WO | WO-2021087084 | A1 | 5/2021 | |

OTHER PUBLICATIONS

Defining RNA—Small Molecule Affinity Landscapes Enables Design of a Small Molecule Inhibitor of an Oncogenic Noncoding RNA Velagapudi et al. ACS Central Science, 3(3), p. 205-216 (Year: 2017).*

Synthesis of Linear Polyether Polyol Derivatives As New Materials for Bioconjugation Li and Chau Bioconjugate Chem, 2009 20, p. 780-789 (Year: 2009).*

Posttranscriptional Regulation of miRNAs Harboring Conserved Terminal Loops G Michlewski, et al. Mol Cell 32(3) p. 383-393 (Year: 2008).*

Agarwal et al., Predicting effective microRNA target sites in mammalian mRNAs. Elife. Aug. 12, 2015;4:e05005. doi: 10.7554/eLife.05005.

Benhamou et al., DNA-encoded library versus RNA-encoded library selection enables design of an oncogenic noncoding RNA inhibitor. Proc Natl Acad Sci U S A. Feb. 8, 2022;119(6):e2114971119. doi: 10.1073/pnas.2114971119. Supporting Information included. 80 pages total.

Childs-Disney et al., A Small Molecule Microarray Program Platform to Select RNA Internal Loop-Ligand Interactions. ACS Chem Biol. Nov. 20, 2007;2(11):745-54. doi: 10.1021/cb700174r. Epub Nov. 2, 2007.

Childs-Disney et al., Induction and reversal of myotonic dystrophy type 1 pre-mRNA splicing defects by small molecules. Nat Commun. 2013;4:2044. doi: 10.1038/ncomms3044. Author manuscript, 28 pages.

Childs-Disney et al., Using modularly assembled ligands to bind RNA internal loops separated by different distances. Chembiochem. Sep. 19, 2011;12(14):2143-6. doi: 10.1002/cbic.201100298. Epub Aug. 9, 2011. Author manuscript, 9 pages.

Costales et al., Small Molecule Inhibition of microRNA-210 Reprograms an Oncogenic Hypoxic Circuit. J Am Chem Soc. Mar. 8, 2017;139(9):3446-3455. doi: 10.1021/jacs.6b11273. Epub Feb. 27, 2017. Author manuscript, 24 pages.

Costales et al., Small Molecule Targeted Recruitment of a Nuclease to RNA. J Am Chem Soc. Jun. 6, 2018;140(22):6741-6744. doi: 10.1021/jacs.8b01233. Epub May 24, 2018. Author manuscript, 8 pages.

Costales et al., Small-molecule targeted recruitment of a nuclease to cleave an oncogenic RNA in a mouse model of metastatic cancer. Proc Natl Acad Sci U S A. Feb. 4, 2020;117(5):2406-2411. doi: 10.1073/pnas.1914286117. Epub Jan. 21, 2020. Correction to Supporting Information for Small-molecule targeted recruitment of a nuclease to cleave an oncogenic RNA in a mouse model of metastatic cancer. Proc Natl Acad Sci U S A. May 3, 2022;119(18):e2204149119. doi: 10.1073/pnas.2204149119. Epub Apr. 26, 2022. Supporting information included. 149 pages total.

Costales et al., Targeted Degradation of a Hypoxia-Associated Non-coding RNA Enhances the Selectivity of a Small Molecule Interacting with RNA. Cell Chem Biol. Aug. 15, 2019;26(8):1180-1186.e5. doi: 10.1016/j.chembiol.2019.04.008. Epub May 23, 2019.

Disney et al., Inforna 2.0: A Platform for the Sequence-Based Design of Small Molecules Targeting Structured RNAs. ACS Chem Biol. Jun. 17, 2016;11(6):1720-8. doi: 10.1021/acschembio.6b00001. Epub Apr. 20, 2016. Author manuscript, 19 pages.

Disney et al., Two-Dimensional Combinational Screening Identifies Specific Aminoglycoside—RNA Internal Loop Partners. J Am Chem Soc. Aug. 20, 2008;130(33):11185-94. doi: 10.1021/ja803234t. Epub Jul. 25, 2008.

Disney, Targeting RNA with Small Molecules To Capture Opportunities at the Intersection of Chemistry, Biology, and Medicine. J Am Chem Soc. May 1, 2019;141(17):6776-6790. doi: 10.1021/jacs.8b13419. Epub Apr. 19, 2019. Author manuscript, 29 pages.

Frankel et al., Programmed cell death 4 (PDCD4) is an important functional target of the microRNA miR-21 in breast cancer cells. J Biol Chem. Jan. 11, 2008;283(2):1026-33. doi: 10.1074/jbc.M707224200. Epub Nov. 8, 2007.

Griffiths-Jones et al., miRBase: tools for microRNA genomics. Nucleic Acids Res. Jan. 2008;36(Database issue):D154-8. doi: 10.1093/nar/gkm952. Epub Nov. 8, 2007.

Guan et al., Recent Advances in Developing Small Molecules Targeting RNA. ACS Chem Biol. Jan. 20, 2012;7(1):73-86. doi: 10.1021/cb200447r. Epub Jan. 12, 2012.

Iliopoulos et al., STAT3 activation of miR-21 and miR-181b-1 via PTEN and CYLD are part of the epigenetic switch linking inflammation to cancer. Mol Cell. Aug. 27, 2010;39(4):493-506. doi: 10.1016/j.molcel.2010.07.023.

Krichevsky et al., miR-21: a small multi-faceted RNA. J Cell Mol Med. Jan. 2009;13(1):39-53. doi: 10.1111/j.1582-4934.2008.00556.x.

Kunig et al., DNA-encoded libraries—an efficient small molecule discovery technology for the biomedical sciences. Biol Chem. Jun. 27, 2018;399(7):691-710. doi: 10.1515/hsz-2018-0119.

Lang et al., DOCK 6: combining techniques to model RNA-small molecule complexes. RNA. Jun. 2009;15(6):1219-30. doi: 10.1261/rna.1563609. Epub Apr. 15, 2009.

Li Y. et al., Precise Small Molecule Degradation of a Noncoding RNA Identifies Cellular Binding Sites and Modulates an Oncogenic Phenotype. ACS Chem Biol. Nov. 16, 2018;13(11):3065-3071. doi: 10.1021/acschembio.8b00827. Epub Oct. 30, 2018. Author Manuscript 15 pages.

Liu et al., Analysis of secondary structural elements in human microRNA hairpin precursors. BMC Bioinformatics. Mar. 1, 2016;17:112. doi: 10.1186/s12859-016-0960-6.

Liu et al., Targeted Degradation of the Oncogenic MicroRNA 17-92 Cluster by Structure-Targeting Ligands. J Am Chem Soc. Apr. 15, 2020;142(15):6970-6982. doi: 10.1021/jacs.9b13159. Epub Apr. 1, 2020. Author Manuscript 26 pages. Supporting information included. 78 pages total.

Mathews et al., Incorporating chemical modification constraints into a dynamic programming algorithm for prediction of RNA secondary structure. Proc Natl Acad Sci U S A. May 11, 2004;101(19):7287-92. doi: 10.1073/pnas.0401799101. Epub May 3, 2004.

Milligan et al., Synthesis of small RNAs using T7 RNA polymerase. Methods Enzymol. 1989;180:51-62. doi: 10.1016/0076-6879(89)80091-6.

Mogilyansky et al., The miR-17/92 cluster: a comprehensive update on its genomics, genetics, functions and increasingly important and numerous roles in health and disease. Cell Death Differ. Dec. 2013;20(12):1603-14. doi: 10.1038/cdd.2013.125.

Paul et al., Two-dimensional combinatorial screening and the RNA Privileged Space Predictor program efficiently identify aminoglycoside-RNA hairpin loop interactions. Nucleic Acids Res. Sep. 2009;37(17):5894-907. doi: 10.1093/nar/gkp594. Epub Sep. 2, 2009.

(56) References Cited

OTHER PUBLICATIONS

Rädle et al., Metabolic labeling of newly transcribed RNA for high resolution gene expression profiling of RNA synthesis, processing and decay in cell culture. J Vis Exp. Aug. 8, 2013;(78):50195. doi: 10.3791/50195. 11 pages.
Seike et al., MiR-21 is an EGFR-regulated anti-apoptotic factor in lung cancer in never-smokers. Proc Natl Acad Sci U S A. Jul. 21, 2009;106(29):12085-90. doi: 10.1073/pnas.0905234106. Epub Jul. 13, 2009.
Setny et al., Search for novel aminoglycosides by combining fragment-based virtual screening and 3D-QSAR scoring. J Chem Inf Model. Feb. 2009;49(2):390-400. doi: 10.1021/ci800361a. Author manuscript, 27 pages.
Sicard et al., Targeting miR-21 for the therapy of pancreatic cancer. Mol Ther. May 2013;21(5):986-94. doi: 10.1038/mt.2013.35. Epub Mar. 12, 2013.
Thakur et al., Small-molecule activators of RNase L with broad-spectrum antiviral activity. Proc Natl Acad Sci U S A. Jun. 5, 2007;104(23):9585-90. doi: 10.1073/pnas.0700590104. Epub May 29, 2007.
Thomas et al., Targeting RNA with small molecules. Chem Rev. Apr. 2008;108(4):1171-224. doi: 10.1021/cr0681546. Epub Mar. 25, 2008.
Van Meter et al., A review of currently identified small molecule modulators of microRNA function. Eur J Med Chem. Feb. 15, 2020;188:112008. doi: 10.1016/j.ejmech.2019.112008. Epub Dec. 23, 2019.
Velagapudi et al., Defining the RNA Internal Loops Preferred by Benzimidazole Derivatives via 2D Combinational Screening and Computational Analysis. J Am Chem Soc. Jul. 6, 2011;133(26):10111-8. doi: 10.1021/ja200212b. Epub Jun. 9, 2011. Author manuscript, 17 pages.
Velagapudi et al., Design of a small molecule against an oncogenic noncoding RNA. Proc Natl Acad Sci U S A. May 24, 2016;113(21):5898-903. doi: 10.1073/pnas.1523975113. Epub May 11, 2016.
Velagapudi et al., Sequence-based design of bioactive small molecules that target precursor microRNAs. Nat Chem Biol. Apr. 2014;10(4):291-7. doi: 10.1038/nchembio.1452. Epub Feb. 9, 2014. Author manuscript, 23 pages.
Velagapudi et al., Structure-activity relationships through sequencing (StARTS) defines optimal and suboptimal RNA motif targets for small molecules. Angew Chem Int Ed Engl. May 17, 2010;49(22):3816-8. doi: 10.1002/anie.200907257.
Yang et al., Design of a bioactive small molecule that targets r(AUUCU) repeats in spinocerebellar ataxia 10. Nat Commun. Jun. 1, 2016;7:11647. doi: 10.1038/ncomms11647.
Yang et al., Inhibition of Non-ATG Translational Events in Cells via Covalent Small Molecules Targeting RNA. J Am Chem Soc. Apr. 29, 2015;137(16):5336-45. doi: 10.1021/ja507448y. Epub Apr. 15, 2015. Author manuscript, 22 pages.
Yang et al., Mouse models for tumor metastasis. Methods Mol Biol. 2012;928:221-8. doi: 10.1007/978-1-62703-008-3_17. Author manuscript, 6 pages.
Zhang et al., miR-17-92 cluster and autophagy in cancer. Chinese Bulletin of Life Sciences. Nov. 2017;29(11):1149-55.
"International Application Serial No. PCT US2020 057914, International Preliminary Report on Patentability mailed May 12, 2022", 11 pgs.
"European Application Serial No. 20811845.5, Response to Communication Pursuant to Rules 161 and 162 EPC filed Dec. 20, 2022", 14 pgs.
"International Application Serial No. PCT/US2020/057914, International Search Report mailed Apr. 14, 2021", 8 pgs.
"International Application Serial No. PCT/US2020/057914, Invitation to Pay Additional Fees and Partial Search Report mailed Feb. 19, 2021", 13 pgs.
"International Application Serial No. PCT/US2020/057914, Written Opinion mailed Apr. 14, 2021", 9 pgs.
Costales, Matthew G, et al., "A Designed Small Molecule Inhibitor of a Non-Coding RNA Sensitizes HER2 Negative Cancers to Herceptin", Journal Of The American Chemical Society, vol. 141, No. 7, (Feb. 6, 2019), 2960-2974.
Costales, Matthew G, et al., "Small-molecule targeted recruitment of a nuclease to cleave an oncogenic RNA in a mouse model of metastatic cancer", Proceedings Of The National Academy Of Sciences, vol. 117, No. 5, (Jan. 21, 2020), 2406-2411.
Matthew, Disney D, et al., "Identifying and validating small molecules interacting with RNA (SMIRNAs)", Isotope Labeling of Biomolecules—Applications, (May 15, 2019), 45-66.
Norgren, A S, et al., "On-Resin click-glycoconjugation of peptoids", Synthesis, Georg Thieme Verlag, Stuttgart, DE, No. 3, (Jan. 9, 2009), 488-494.
Abraham et al., RNA cleavage and inhibition of protein synthesis by bleomycin. Chem Biol. Jan. 2003;10(1):45-52. doi: 10.1016/s1074-5521(02)00306-x.
Angelbello et al., Bleomycin Can Cleave an Oncogenic Noncoding RNA. Chembiochem. Jan. 4, 2018;19(1):43-47. doi: 10.1002/cbic.201700581. Epub Nov. 22, 2017. Author manuscript, 10 pages.
Berger et al., Activity-based protein profiling: applications to biomarker discovery, in vivo imaging and drug discovery. Am J Pharmacogenomics. 2004;4(6):371-81. doi: 10.2165/00129785-200404060-00004.
Berry et al., DNA damage and growth inhibition in cultured human cells by bleomycin congeners. Biochemistry. Jun. 18, 1985;24(13):3207-14. doi: 10.1021/bi00334a020.
Bevilacqua et al., Genome-Wide Analysis of RNA Secondary Structure. Annu Rev Genet. Nov. 23, 2016;50:235-266. doi: 10.1146/annurev-genet-120215-035034. Epub Sep. 14, 2016.
Boger et al., Definition of the Effect and Role of the Bleomycin A2 Valerate Substituents: Preorganization of a Rigid, Compact Conformation Implicated in Sequence-Selective DNA Cleavage. J. Am. Chem. Soc. 1998; 120(36):9149-58.
Boger et al., Synthesis of key analogs of bleomycin A2 that permit a systematic evaluation of the linker region: identification of an exceptionally prominent role for the L-threonine substituent. Bioorg Med Chem. Sep. 1995;3(9):1281-95. doi: 10.1016/0968-0896(95)00113-u.
Boger et al., Total Synthesis of Bleomycin A2 and Related Agents. 1. Synthesis and DNA Binding Properties of the Extended C-Terminus: Tripeptide S, Tetrapeptide S, Pentapeptide S, and Related Agents. J. Am. Chem. Soc. Jun. 1994;116(13):5607-18.
Burger, Cleavage of Nucleic Acids by Bleomycin. Chem Rev. May 7, 1998;98(3):1153-1169. doi: 10.1021/cr960438a.
Carter et al., Site-specific cleavage of RNA by Fe(II).bleomycin. Proc Natl Acad Sci U S A. Dec. 1990;87(23):9373-7. doi: 10.1073/pnas.87.23.9373.
Childs-Disney et al., A Massively Parallel Selection of Small Molecule-RNA Motif Binding Partners Informs Design of an Antiviral from Sequence. Chem. Oct. 11, 2018;4(10):2384-2404. doi: 10.1016/j.chempr.2018.08.003. Epub Sep. 13, 2018.
Childs-Disney et al., Approaches to Validate and Manipulate RNA Targets with Small Molecules in Cells. Annu Rev Pharmacol Toxicol. 2016;56:123-40. doi: 10.1146/annurev-pharmtox-010715-103910. Epub Oct. 22, 2015.
Childs-Disney et al., Rationally designed small molecules targeting the RNA that causes myotonic dystrophy type 1 are potently bioactive. ACS Chem Biol. May 18, 2012;7(5):856-62. doi: 10.1021/cb200408a. Epub Mar. 5, 2012. Author manuscript, 16 pages.
Cravatt et al., Activity-based protein profiling: from enzyme chemistry to proteomic chemistry. Annu Rev Biochem. 2008;77:383-414. doi: 10.1146/annurev.biochem.75.101304.124125.
Disney et al., Drugging the RNA World. Cold Spring Harb Perspect Biol. Nov. 1, 2018;10(11):a034769. doi: 10.1101/cshperspect.a034769.
Disney et al., Rational Design of Small Molecules Targeting Oncogenic Noncoding RNAs from Sequence. Acc Chem Res. Dec. 20, 2016;49(12):2698-2704. doi: 10.1021/acs.accounts.6b00326. Epub Nov. 22, 2016. Author manuscript, 16 pages.
ENCODE Project Consortium. An integrated encyclopedia of DNA elements in the human genome. Nature. Sep. 6, 2012;489(7414):57-74. doi: 10.1038/nature11247. Author manuscript, 48 pages.

(56) References Cited

OTHER PUBLICATIONS

Graczyk, Gini coefficient: a new way to express selectivity of kinase inhibitors against a family of kinases. J Med Chem. Nov. 15, 2007;50(23):5773-9. doi: 10.1021/jm070562u. Epub Oct. 19, 2007.
Guan et al., Covalent small-molecule-RNA complex formation enables cellular profiling of small-molecule-RNA interactions. Angew Chem Int Ed Engl. Sep. 16, 2013;52(38):10010-3. doi: 10.1002/anie.201301639. Epub Aug. 1, 2013. Author manuscript, 9 pages.
Guan et al., Small-molecule-mediated cleavage of RNA in living cells. Angew Chem Int Ed Engl. Jan. 28, 2013;52(5):1462-5. doi: 10.1002/anie.201206888. Epub Dec. 20, 2012. Author manuscript, 11 pages.
Guttilla et al., Coordinate regulation of FOXO1 by miR-27a, miR-96, and miR-182 in breast cancer cells. J Biol Chem. Aug. 28, 2009;284(35):23204-16. doi: 10.1074/jbc.M109.031427. Epub Jul. 1, 2009.
Hecht, The Chemistry of Activated Bleomycin. Acc. Chem. Res. Dec. 1986;19:383-91.
Hermann, Small molecules targeting viral RNA. Wiley Interdiscip Rev RNA. Nov. 2016;7(6):726-743. doi: 10.1002/wrna.1373. Epub Jun. 16, 2016.
Howe et al., Selective small-molecule inhibition of an RNA structural element. Nature. Oct. 29, 2015;526(7575):672-7. doi: 10.1038/nature15542. Epub Sep. 30, 2015.
Huang et al., MiR-210—micromanager of the hypoxia pathway. Trends Mol Med. May 2010;16(5):230-7. doi: 10.1016/j.molmed.2010.03.004. Epub Apr. 29, 2010. Author manuscript, 16 pages.
Im et al., Identification of aminosulfonylarylisoxazole as microRNA-31 regulators. PLoS One. Aug. 4, 2017;12(8):e0182331. doi: 10.1371/journal.pone.0182331.
Kane et al., Polynucleotide recognition and degradation by bleomycin. Prog Nucleic Acid Res Mol Biol. 1994;49:313-52. doi: 10.1016/s0079-6603(08)60054-9.
Kwok et al., Determination of in vivo RNA structure in low-abundance transcripts. Nat Commun. 2013;4:2971. doi: 10.1038/ncomms3971.
Lee et al., Controlling the specificity of modularly assembled small molecules for RNA via ligand module spacing: targeting the RNAs that cause myotonic muscular dystrophy. J Am Chem Soc. Dec. 2, 2009;131(47):17464-72. doi: 10.1021/ja906877y.
Lu et al., Decoding the RNA structurome. Curr Opin Struct Biol. Feb. 2016;36:142-8. doi: 10.1016/j.sbi.2016.01.007. Epub Feb. 26, 2016. Author manuscript, 11 pages.
Ma et al., Biochemical Evaluation of a 108-Member Deglycobleomycin Library: Viability of a Selection Strategy for Identifying Bleomycin Analogues with Altered Properties. J. Am. Chem. Soc. Sep. 2007;129(41):12439-52.
Mukherjee et al., PEARL-seq: A Photoaffinity Platform for the Analysis of Small Molecule-RNA Interactions. ACS Chem Biol. Sep. 18, 2020;15(9):2374-2381. doi: 10.1021/acschembio.0c00357. Epub Aug. 17, 2020.
Nakamoto et al., Diazirine-containing tag-free RNA probes for efficient RISC-loading and photoaffinity labeling of microRNA targets. Bioorg Med Chem Lett. Sep. 15, 2018;28(17):2906-2909. doi: 10.1016/j.bmcl.2018.07.020. Epub Jul. 11, 2018.
Nakamoto et al., Labeling of target mRNAs using a photo-reactive microRNA probe. Chem Commun (Camb). May 10, 2016;52(40):6720-2. doi: 10.1039/c6cc01360k.
Naryshkin et al., SMN2 splicing modifiers improve motor function and longevity in mice with spinal muscular atrophy. Science. Aug. 8, 2014;345(6197):688-93. doi: 10.1126/science.1250127.
Nguyen et al., Rationally designed small molecules that target both the DNA and RNA causing myotonic dystrophy type 1. J Am Chem Soc. Nov. 11, 2015;137(44):14180-9. doi: 10.1021/jacs.5b09266. Epub Nov. 3, 2015.
Osborn et al., Platinum-RNA modifications following drug treatment in *S. cerevisiae* identified by click chemistry and enzymatic mapping. ACS Chem Biol. Oct. 17, 2014;9(10):2404-11. doi: 10.1021/cb500395z. Epub Aug. 15, 2014.
Otsuka et al., Man-designed bleomycin with altered sequence specificity in DNA cleavage. J. Am. Chem. Soc. Jan. 1990;112(2):838-45.
Owa et al., Man-designed bleomycins: Significance of the binding sites as enzyme models and of the stereochemistry of the linker moiety. Tetrahedron. 1992;48(7):1193-208.
Palacino et al., SMN2 splice modulators enhance U1-pre-mRNA association and rescue SMA mice. Nat Chem Biol. Jul. 2015;11(7):511-7. doi: 10.1038/nchembio.1837. Epub Jun. 1, 2015. Erratum in: Nat Chem Biol. Sep. 2015;11(9):741. doi: 10.1038/nchembio0915-741a. Erratum in: Nat Chem Biol. Apr. 2016;12(4):304. doi: 10.1038/nchembio0416-304c.
Parker et al., Ligand and Target Discovery by Fragment-Based Screening in Human Cells. Cell. Jan. 26, 2017;168(3):527-541.e29. doi: 10.1016/j.cell.2016.12.029. Epub Jan. 19, 2017.
Ratmeyer et al., An ethidium analog that binds with high specificity to a base-bulged duplex from the TAR RNA region of the HIV-1 genome. Journal of Medicinal Chemistry. Mar. 1992;35(5):966-8.
Rupaimoole et al., MicroRNA therapeutics: towards a new era for the management of cancer and other diseases. Nat Rev Drug Discov. Mar. 2017;16(3):203-222. doi: 10.1038/nrd.2016.246. Epub Feb. 17, 2017.
Rupaimoole et al., miRNA Deregulation in Cancer Cells and the Tumor Microenvironment. Cancer Discov. Mar. 2016;6(3):235-46. doi: 10.1158/2159-8290.CD-15-0893. Epub Feb. 10, 2016. Author manuscript, 20 pages.
Rzuczek et al., Precise small-molecule recognition of a toxic CUG RNA repeat expansion. Nat Chem Biol. Feb. 2017;13(2):188-193. doi: 10.1038/nchembio.2251. Epub Dec. 12, 2016.
Sexton et al., Interpreting Reverse Transcriptase Termination and Mutation Events for Greater Insight into the Chemical Probing of RNA. Biochemistry. Sep. 5, 2017;56(35):4713-4721. doi: 10.1021/acs.biochem.7b00323. Epub Aug. 18, 2017. Author manuscript, 17 pages.
Shi et al., Overexpression of microRNA-96-5p inhibits autophagy and apoptosis and enhances the proliferation, migration and invasiveness of human breast cancer cells. Oncol Lett. Jun. 2017;13(6):4402-4412. doi: 10.3892/ol.2017.6025. Epub Apr. 11, 2017.
Stelzer et al., Discovery of selective bioactive small molecules by targeting an RNA dynamic ensemble. Nat Chem Biol. Jun. 26, 2011;7(8):553-9. doi: 10.1038/nchembio.596. Author manuscript, 15 pages.
Stubbe et al., Mechanisms of bleomycin-induced DNA degradation. Chem. Rev. Oct. 1987;87(5):1107-36.
Suresh et al., A general fragment-based approach to identify and optimize bioactive ligands targeting RNA. Proc Natl Acad Sci U S A. Dec. 29, 2020;117(52):33197-33203. doi: 10.1073/pnas.2012217117. Epub Dec. 14, 2020.
Tenson et al., Antibiotics and the ribosome. Mol Microbiol. Mar. 2006;59(6):1664-77. doi: 10.1111/j.1365-2958.2006.05063.x.
Thomas et al., Solid-Phase Synthesis of Bleomycin A5 and Three Monosaccharide Analogues: Exploring the Role of the Carbohydrate Moiety in RNA Cleavage. J. Am. Chem. Soc. Oct. 2002;124(44):12926-7.
Ule et al., CLIP identifies Nova-regulated RNA networks in the brain. Science. Nov. 14, 2003;302(5648):1212-5. doi: 10.1126/science.1090095.
Velagapudi et al., A cross-linking approach to map small molecule-RNA binding sites in cells. Bioorg Med Chem Lett. Jun. 15, 2019;29(12):1532-1536. doi: 10.1016/j.bmcl.2019.04.001. Epub Apr. 2, 2019. Author manuscript, 9 pages.
Wang et al., Mechanistic studies of a small-molecule modulator of SMN2 splicing. Proc Natl Acad Sci U S A. May 15, 2018;115(20):E4604-E4612. doi: 10.1073/pnas.1800260115. Epub Apr. 30, 2018.
Xu et al., Synthesis, biological evaluation and DNA binding properties of novel bleomycin analogues. Bioorg Med Chem Lett. Aug. 4, 2003;13(15):2595-9. doi: 10.1016/s0960-894x(03)00435-9.
Yan et al., Design, synthesis and activity of light deactivatable microRNA inhibitor. Bioorg Chem. Oct. 2018;80:492-497. doi: 10.1016/j.bioorg.2018.07.003. Epub Jul. 2, 2018. Author manuscript, 14 pages.

(56) References Cited

OTHER PUBLICATIONS

Yan et al., Regulating miRNA-21 Biogenesis By Bifunctional Small Molecules. J Am Chem Soc. Apr. 12, 2017;139(14):4987-4990. doi: 10.1021/jacs.7b00610. Epub Mar. 29, 2017. Author manuscript, 11 pages.

* cited by examiner 1
miR-21 Binder

2
Assembled miR-21 Dimer

3

X-ray Structure of 3

Active RNase L Recruiter

4

Inactive RNase L Recruiter

5
Active miR-21
RIBOTAC

6
Negative Control
RIBOTAC

7
Inactive miR-21
RIBOTAC

2

10

5

21

8

9

10

Parent C1

Parent C2

*C1 series*

| | $R^1$ | $R^2$ | $R^3$ | $R^4$ | $R^5$ | $F_{norm}$ % |
|---|---|---|---|---|---|---|
| C1 | Et | H | OH | H | H | 24 |
| C1-2 | Me | F | OH | H | H | 5 |
| C1-3 (**3**) | Et | H | OH | OMe | H | 48 |
| C1-4 (**4**) | Et | H | OMe | OH | H | -10 |
| C1-5 | Et | H | OMe | OH | OMe | -10 |
| C1-6 | Et | H | H | $NMe_2$ | H | 15 |

| | $R^1$ | $R^2$ | $R^3$ | $F_{norm}$ % |
|---|---|---|---|---|
| C2-1 |  | | Cl | -50 |
| C2-2 | Me | Me | Cl | -46 |
| C2-3 | Me | Me |  | 13 |

*C2 series*

$R^1$, $R^2$ = Me, Me (I)
$-(CH_2)_4-$ (II)

| | $F_{norm}$ % | | $F_{norm}$ % |
|---|---|---|---|
| C2-4 (**IIa**) | -39 | C2-12 (**IIi**) | -41 |
| C2-5 (**IIb**) | -7 | C2-13 (**IIj**) | -22 |
| C2-6 (**IIc**) | -32 | C2-14 (**IIk**) | -20 |
| C2-7 (**IId**) | -17 | C2-15 (**IIl**) | -8 |
| C2-8 (**Ie**) | -85 | C2-16 (**IIm**) | -3 |
| C2-9 (**IIf**) | -15 | C2-17 (**IIn**) | -22 |
| C2-10 (**IIg**) | -29 | C2-18 (**IIo**) | -35 |
| C2-11 (**IIh**) | -20 | C2-19 (**IIp**) | -6 |
| | | C2 (**IIq**) | -37 |

$R^3$ =

25

26

Vehicle

5 (10 mg/kg)

SEQUENCE LISTING

```
<160> NUMBER OF SEQ ID NOS: 33

<210> SEQ ID NO 1
<211> LENGTH: 25
<212> TYPE: RNA
<213> ORGANISM: Artificial Sequence
<220> FEATURE:
<223> OTHER INFORMATION: A synthetic oligonucleotide sequence

<400> SEQUENCE: 1

guugacuguu gaaucucaug gcaac                                       25


<210> SEQ ID NO 2
<211> LENGTH: 27
<212> TYPE: RNA
<213> ORGANISM: Artificial Sequence
<220> FEATURE:
<223> OTHER INFORMATION: A synthetic oligonucleotide sequence
```

-continued

<400> SEQUENCE: 2
guugacuguu gaaucucaau ggucaac 27

<210> SEQ ID NO 3
<211> LENGTH: 36
<212> TYPE: RNA
<213> ORGANISM: Artificial Sequence
<220> FEATURE:
<223> OTHER INFORMATION: A synthetic oligonucleotide sequence

<400> SEQUENCE: 3
uuaucaaauu cuuauuugcc ccauuuuuuu gguuua 36

<210> SEQ ID NO 4
<211> LENGTH: 58
<212> TYPE: RNA
<213> ORGANISM: Artificial Sequence
<220> FEATURE:
<223> OTHER INFORMATION: A synthetic oligonucleotide sequence

<400> SEQUENCE: 4
uagcuuauca gacugauguu gacuguugaa ucucauggca acaccagucg augggcug 58

<210> SEQ ID NO 5
<211> LENGTH: 70
<212> TYPE: DNA
<213> ORGANISM: Artificial Sequence
<220> FEATURE:
<223> OTHER INFORMATION: A synthetic oligonucleotide sequence

<400> SEQUENCE: 5
gtcgggtagc ttatcagact gatgttgact gttgaatctc atggcaacac cagtcgatgg 60
gctgtctgac 70

<210> SEQ ID NO 6
<211> LENGTH: 33
<212> TYPE: DNA
<213> ORGANISM: Artificial Sequence
<220> FEATURE:
<223> OTHER INFORMATION: A synthetic oligonucleotide sequence

<400> SEQUENCE: 6
taatacgact cactataggt cgggtagctt atc 33

<210> SEQ ID NO 7
<211> LENGTH: 18
<212> TYPE: DNA
<213> ORGANISM: Artificial Sequence
<220> FEATURE:
<223> OTHER INFORMATION: A synthetic oligonucleotide sequence

<400> SEQUENCE: 7
gtcagacagc ccatcgac 18

<210> SEQ ID NO 8
<211> LENGTH: 58
<212> TYPE: DNA
<213> ORGANISM: Artificial Sequence
<220> FEATURE:
<223> OTHER INFORMATION: A synthetic oligonucleotide sequence

<400> SEQUENCE: 8
tagcttatca gactgatgtt gactgttgaa tctcatggca acaccagtcg atgggctg 58

<210> SEQ ID NO 9
<211> LENGTH: 60
<212> TYPE: DNA
<213> ORGANISM: Artificial Sequence
<220> FEATURE:
<223> OTHER INFORMATION: A synthetic oligonucleotide sequence

<400> SEQUENCE: 9
tagcttatca gactgatgtt gactgttgaa tctcaatggt caacaccagt cgatgggctg 60

<210> SEQ ID NO 10
<211> LENGTH: 33
<212> TYPE: DNA
<213> ORGANISM: Artificial Sequence
<220> FEATURE:
<223> OTHER INFORMATION: A synthetic oligonucleotide sequence

<400> SEQUENCE: 10
taatacgact cactatagta gcttatcaga ctg 33

<210> SEQ ID NO 11
<211> LENGTH: 15
<212> TYPE: DNA
<213> ORGANISM: Artificial Sequence
<220> FEATURE:
<223> OTHER INFORMATION: A synthetic oligonucleotide sequence

<400> SEQUENCE: 11
cagcccatcg actgg 15

<210> SEQ ID NO 12
<211> LENGTH: 46
<212> TYPE: DNA
<213> ORGANISM: Artificial Sequence
<220> FEATURE:
<223> OTHER INFORMATION: A synthetic oligonucleotide sequence

<400> SEQUENCE: 12
cagacgtgtg ctcttccgat ctgagaacat tggatatgga tggtca 46

<210> SEQ ID NO 13
<211> LENGTH: 25
<212> TYPE: DNA
<213> ORGANISM: Artificial Sequence
<220> FEATURE:
<223> OTHER INFORMATION: A synthetic oligonucleotide sequence
<220> FEATURE:
<221> NAME/KEY: misc_difference
<222> LOCATION: (1)..(3)
<223> OTHER INFORMATION: n = A,T,C or G
<220> FEATURE:
<221> NAME/KEY: misc_feature
<222> LOCATION: (1)..(3)
<223> OTHER INFORMATION: n is a, c, g, or t

<400> SEQUENCE: 13
nnnagatcgg aagagcgtcg tgtag 25

<210> SEQ ID NO 14
<211> LENGTH: 21
<212> TYPE: DNA
<213> ORGANISM: Artificial Sequence
<220> FEATURE:
<223> OTHER INFORMATION: A synthetic oligonucleotide sequence

<400> SEQUENCE: 14
cagacgtgtg ctcttccgat c 21

<210> SEQ ID NO 15
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 15
ctacacgacg ctcttccgat ct 22

<210> SEQ ID NO 16
<211> LENGTH: 9
<212> TYPE: DNA
<213> ORGANISM: Artificial Sequence
<220> FEATURE:
<223> OTHER INFORMATION: A synthetic oligonucleotide sequence

<400> SEQUENCE: 16 cgcgacgcg 9

<210> SEQ ID NO 17
<211> LENGTH: 8
<212> TYPE: DNA
<213> ORGANISM: Artificial Sequence
<220> FEATURE:
<223> OTHER INFORMATION: A synthetic oligonucleotide sequence

<400> SEQUENCE: 17 cgcgcgcg 8

<210> SEQ ID NO 18
<211> LENGTH: 17
<212> TYPE: RNA
<213> ORGANISM: Artificial Sequence
<220> FEATURE:
<223> OTHER INFORMATION: A synthetic oligonucleotide sequence

<400> SEQUENCE: 18
gcguugcgcg cgcacgc 17

<210> SEQ ID NO 19
<211> LENGTH: 71
<212> TYPE: RNA
<213> ORGANISM: Artificial Sequence
<220> FEATURE:
<223> OTHER INFORMATION: A synthetic oligonucleotide sequence

<400> SEQUENCE: 19
ugucggguag cuuaucagac ugauguugac uguugaaucu cauggcaaca ccagucgaug 60
gcugucugac a 71

<210> SEQ ID NO 20

<400> SEQUENCE: 20

000

<210> SEQ ID NO 21
<211> LENGTH: 60
<212> TYPE: RNA
<213> ORGANISM: Artificial Sequence
<220> FEATURE:
<223> OTHER INFORMATION: A synthetic oligonucleotide sequence

<400> SEQUENCE: 21
uagcuuauca gacugauguu gacuguugaa ucucaauggu caacaccagu cgaugggcug 60

<210> SEQ ID NO 22
<211> LENGTH: 58
<212> TYPE: RNA
<213> ORGANISM: Artificial Sequence
<220> FEATURE:
<223> OTHER INFORMATION: A synthetic oligonucleotide sequence

<400> SEQUENCE: 22
uagcuuauca gacugauguu gacuguugaa ucucauggca acaccagucg augggcug 58

<210> SEQ ID NO 23
<211> LENGTH: 58
<212> TYPE: RNA
<213> ORGANISM: Artificial Sequence
<220> FEATURE:
<223> OTHER INFORMATION: A synthetic oligonucleotide sequence

<400> SEQUENCE: 23
uagcuuauca gacugauguu gacuguugaa ucucauggca acaccagucg augggcug 58

<210> SEQ ID NO 24
<211> LENGTH: 75
<212> TYPE: RNA
<213> ORGANISM: Artificial Sequence
<220> FEATURE:
<223> OTHER INFORMATION: A synthetic oligonucleotide sequence

<400> SEQUENCE: 24
gggugucggg uagcuuauca gacugauguu gacuguugaa ucucauggca acaccagucg 60
augggcuguc ugaca 75

<210> SEQ ID NO 25
<211> LENGTH: 59
<212> TYPE: RNA
<213> ORGANISM: Artificial Sequence
<220> FEATURE:
<223> OTHER INFORMATION: A synthetic oligonucleotide sequence

<400> SEQUENCE: 25
uagcuuauca gacugauguu gacuguugaa ucucauggca acaccagucg augggcugu 59

<210> SEQ ID NO 26
<211> LENGTH: 23
<212> TYPE: RNA
<213> ORGANISM: Artificial Sequence
<220> FEATURE:
<223> OTHER INFORMATION: A synthetic oligonucleotide sequence

<400> SEQUENCE: 26
uaguacucug guuguuaagc uag 23

<210> SEQ ID NO 27
<211> LENGTH: 48
<212> TYPE: DNA
<213> ORGANISM: Artificial Sequence
<220> FEATURE:
<223> OTHER INFORMATION: A synthetic oligonucleotide sequence

<400> SEQUENCE: 27
cacgacgctc ttccgatctg ataacaccag tcgatgggct gtctgaca 48

<210> SEQ ID NO 28
<211> LENGTH: 35

<212> TYPE: RNA
<213> ORGANISM: Artificial Sequence
<220> FEATURE:
<223> OTHER INFORMATION: A synthetic oligonucleotide sequence

<400> SEQUENCE: 28
uuaucaaauu cuuauuugcc ccauuuuuuu gguuu 35

<210> SEQ ID NO 29
<211> LENGTH: 58
<212> TYPE: RNA
<213> ORGANISM: Artificial Sequence
<220> FEATURE:
<223> OTHER INFORMATION: A synthetic oligonucleotide sequence

<400> SEQUENCE: 29
uagcuuauca gacugauguu gacuguugaa ucucauggca acaccagucg augggcug 58

<210> SEQ ID NO 30
<211> LENGTH: 57
<212> TYPE: RNA
<213> ORGANISM: Artificial Sequence
<220> FEATURE:
<223> OTHER INFORMATION: A synthetic oligonucleotide sequence

<400> SEQUENCE: 30
uagcuuauca gacugauguu gacuguugaa ucucauggca acaccagucg augggcu 57

<210> SEQ ID NO 31
<211> LENGTH: 70
<212> TYPE: RNA
<213> ORGANISM: Artificial Sequence
<220> FEATURE:
<223> OTHER INFORMATION: A synthetic oligonucleotide sequence

<400> SEQUENCE: 31
gucggguagc uuaucagacu gauguugacu guugaaucuc auggcaacac cagucgaugg 60
gcugucugac 70

<210> SEQ ID NO 32

<400> SEQUENCE: 32

000

<210> SEQ ID NO 33
<211> LENGTH: 22
<212> TYPE: RNA
<213> ORGANISM: Artificial Sequence
<220> FEATURE:
<223> OTHER INFORMATION: A synthetic oligonucleotide sequence

<400> SEQUENCE: 33
uagcuuauca gacugauguu ga 22

COMPOUNDS AND MODULES FOR INHIBITION OF PRE-miR-21 AND THEIR USE IN TREATMENT OF CERTAIN CANCERS

CROSS-REFERENCE TO RELATED APPLICATION

This application is a U.S. national stage filing under 35 U.S.C. § 371 from International Application No. PCT/US2020/057914, filed on 29 Oct. 2020, and published as WO2021/087084 on 6 May 2021, which claims the priority of U.S. provisional application Ser. No. 62/927,247, filed Oct. 29, 2019, the benefit of priority of each of which is claimed herein, and which applications and publication are hereby incorporated by reference in their entirety.

STATEMENT OF GOVERNMENT SUPPORT

This invention was made with Government support under R01GM097455-09 awarded by the National Institutes of Health. The Government has certain rights in this invention.

REFERENCE TO AN ELECTRONIC SEQUENCE LISTING

The contents of the electronic sequence listing (U120270138US01-SEQ-CLL.txt; Size: 7,417 bytes; and Date of Creation: Sep. 23, 2025) are herein incorporated by reference in its entirety.

BACKGROUND

RNA is involved with a myriad of cellular roles beyond merely encoding and assembling proteins. The Encyclopedia of DNA Elements project and subsequent analyses showed that only 1-2% of our genome encodes for protein yet about 80% of it is transcribed into RNA (ENCODE, 2012). Although the majority of transcribed RNAs are non-coding, many non-coding RNAs are functionally involved in modulating cell activities and disease states. Such functional, non-coding RNAs represent a potential therapeutic target.

Indeed, RNA structures have been shown to be key players in important biological processes and in diseased states. Because RNA biology is often mediated by the structures that it forms, approaches to target structured RNAs could be advantageous. Currently, the approach to target RNA has been the use of oligonucleotide compounds that preferentially target unstructured regions[1] Thus, the development of therapeutics that target RNA has mostly centered on using oligonucleotides.

Small molecules interacting with a RNA's three-dimensional structure could allow one to preferentially target RNA structure. However, interactions between RNA and small molecule compounds are poorly understood which has led to the perception that RNA is "undruggable". (Guan & Disney, 2012; Thomas & Hergenrother, 2008). Nevertheless, small molecules have shown an ability to target RNA. For example, small molecules have been investigated for targeting the three-dimensional structure of ribosome, riboswitches, certain viral RNA and nucleotide repeat expansions. (Blount and Breaker, 2006; U.S. Pat. No. 9,586,944 B2; U.S. Patent Application Publication No. 2016/0188791 A1).

One class of structured RNAs that play roles in disease biology are non-coding microRNAs (miRs). They are produced from highly structured precursors that are processed in the nucleus (pri-miRs) and cytoplasm (pre-miRs) by the nucleases Drosha and Dicer, respectively see FIGS. 1A-1B. Many miRs play significant roles in human disease biology, see D. P. Bartel, MicroRNAs: genomics, biogenesis, mechanism, and function. *Cell* 116, 281-297 (2004). For example, miR-21's expression negatively correlates with survival in triple negative breast cancer patients and is expressed in solid tumors, see A. M. Krichevsky, G. Gabriely, miR-21: a small multi-faceted RNA. *J. Cell. Mol. Med.* 13, 39-53 (2009).

Therefore, an object of the present invention is the development of small molecules that achieve modification, amelioration and/or negation of miR-21 activity. Another object of the present invention is the development of small molecules that selectively inhibit pre-miR-21 so as to silence, modify and/or ameliorate the expression of miR-21. Yet another object is to target pre-miR-21 for enzymatic cleavage. A further object is to develop an inhibitory and degradation small molecule module that displays high binding and selectivity targeting of pre-miR-21.

SUMMARY OF THE INVENTION

These and other objects are achieved by embodiments of the present invention that are directed to a small molecule compound comprising Formula 1 and the pharmaceutically acceptable salts thereof.

Formula 1

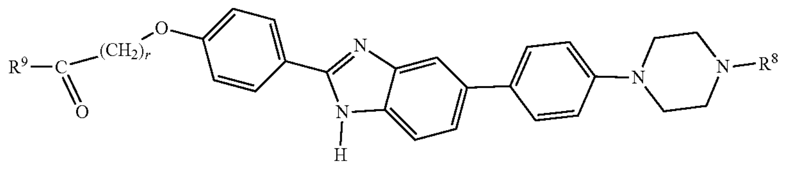

For Formula 1, $R^8$ is hydrogen or methyl, $R^9$ is hydroxyl, $H_2N—(CH_2)_q—NH—$ or $N_3—(CH_2)_q—NH—$, designator q is an integer of 2 to 6 and designator r is an integer of 2 to 6. Preferably, $R^8$ is methyl. Embodiments of Formula 1 including those when $R^9$ is hydroxyl or α, ω-diaminoalkylenyl, or $N_3—(CH_2)_q—NH—$ display inhibitory activity against expression of the structured RNA pre-miR-21.

The embodiments of Formula 1 and especially those comprising $R^9$ as the azidoalkylamino group, $N_3—(CH_2)_q—NH—$ display inhibition of the expression of RNA pre-miR-21 so that production of miR-21 is ameliorated, curtailed, minimized and/or silenced. The interaction of embodiments of Formula 1 with pre-miR-21 enable treatment of diseases associated with expression of miR-21, such as neoplastic disease, cancer and especially lung and breast cancer. The inhibition of the expression of miR-21 and associated nuclease degradation leads to programmed cell death such as by PCED4 and PTEN. In addition, inhibition of the expression of miR-21 inhibits metastatic properties of neoplastic cells.

Additional embodiments of the present invention are directed to a ligated dimer of Formula 1. When embodiments of Formula 1 have $R^9$ as the azidoalkylamino group, Formula 1 may be dimerized through its linkage with an oligo-amide of multiple modified glycine moieties to provide embodiments of the invention directed to the ligated dimer. These embodiments of the ligated dimer are directed to and comprise a compound of Formula 2 and the pharmaceutically acceptable salts thereof.

ing but not limited to an embodiment of Formula C1, or may be a nuclease cleavage molecule including but not limited to a bleomycin derivative. The group EG may be an ethylene glycol or propylene glycol moiety. The group Y is oxygen or —NH—. The integer designators are: designator m is an integer of 1 to 6, designator n is an integer of 1 to 4, designator o is zero or one, designator p is an integer of 1 to 6 and designator t is an integer of 1 to 4.

Additional embodiments of the present invention are directed to a nuclease enzyme recruitment molecule comprising Formula C1 (a styrenyl thiophenyl compound) and the pharmaceutically acceptable salts thereof.

Formula 2

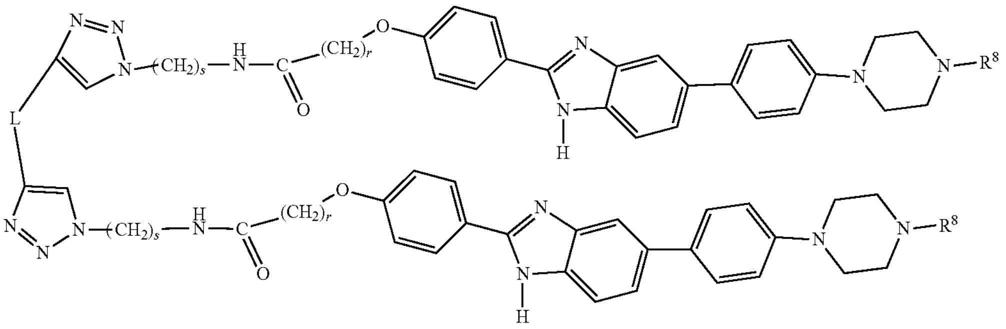

For embodiments of Formula 2, L may be a ligand oligomeric amide of 3 to 8 glycine residues wherein one terminus of the oligomeric amide ends with the amine of glycine (terminal amine) and the other terminus of the oligomeric amide ends with the carboxyl of glycine (terminal carboxyl). The nitrogens of the terminal glycine residues are bound through mono, di, tri or tetra methylene groups to the triazolyl groups. The nitrogens of the non-terminal glycine residues are substituted by alkyl of 1 to 3 carbons. The amine terminal of the ligand oligomeric amide may be substituted with an alkyl group of 1 to 3 carbons or may be acylated with an acyl group of 2 to 4 carbons. The carboxyl terminal of the ligand oligomeric amide may be substituted with a variety of groups including hydrogen, polyol, polyol extension to another biologically active group or may be esterified with an alkanol of 1 to 3 carbons or diol of 2 to 6 carbons or amidated with an alkyl mono amine of 1 to 3 carbons or an alkyl diamine of 2 to 6 carbons. The group $R^8$ is the same as given for Formula 1. For Formula 2, the designator r is an integer of 2 to 6 and designator s is an integer of 2 to 6. Preferably, embodiments of the ligated dimer of Formula 2 have each designator r as 3, each designator s as 3, and the ligand L is bonded to each triazole group by a monomethylene group.

According to the invention, the preferred embodiments of the ligated dimer of Formula 2 include embodiments of ligand L comprising Formula L-1.

$$Nr\text{-}((EG)_m\text{-}(CH_2)_n)_o\text{—}Y\text{—}CO\text{—}CH_2\text{—}N(My)\text{-}[CO\text{—}CH_2\text{—}N(R^{10})\text{—}]_p\text{—}CO\text{—}CH_2N(My)\text{-}R^{11} \quad \text{Formula L-1}$$

For embodiments of Formula L-1, My is an oligomethylenyl group of the formula $$(\text{—}CH_2\text{—})_t$$

which connects the nitrogens of the N(My) groups with the triazole groups of Formula 2. The group $R^{10}$ is alkyl of 1 to 4 carbons. The group $R^{11}$ is hydrogen or acetyl. The group Nr may be hydrogen, a nuclease recruitment moiety includ- Formula C1

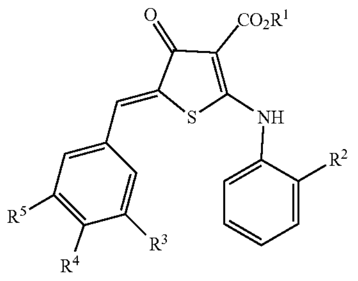

Embodiments of Formula C1 have $R^1$ as alkyl of 1 to 3 carbons, $R^2$ as hydrogen or fluoro, $R^3$ as hydroxyl or methoxy, $R^4$ as methoxy and $R^5$ as hydrogen or methoxy. Nuclease enzyme recruitment activity of Formula C1 is preferably achieved when $R^3$ is hydroxyl $R^5$ is hydrogen, $R^4$ is methoxy, $R^2$ is hydrogen and $R^1$ is ethyl.

Another embodiment of the present invention is directed to a compound comprising Formula 5 and the pharmaceutically acceptable salts thereof. Formula 5 is a preferred embodiment of Formula 2 with a preferred version of the ligand of Formula L-1 and Nr as the preferred embodiment of Formula C1. For embodiments of Formula 5, designator m is an integer of 2 to 6 and $R^8$ is hydrogen or methyl. Preferably for these embodiments, designator m is 4.

Formula 5

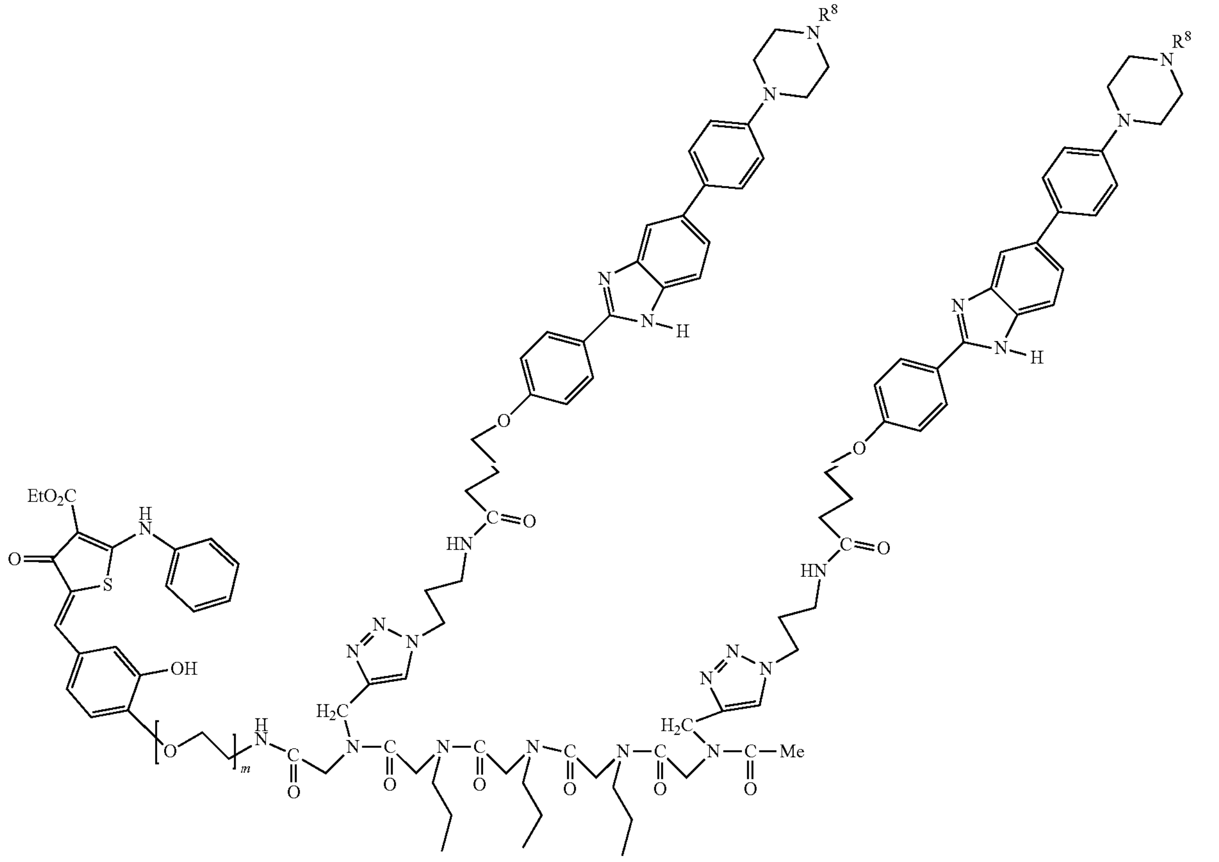

Additional embodiments of the invention are directed to the use of embodiments of Formulas 1, 2, 5, C1, their pharmaceutically acceptable salts and the application of Formula L-1 to Formula 2. These embodiments comprise pharmaceutical compositions of any one or more of Formulas 1, 2, 5, C1 and their pharmaceutically acceptable salts in combination with a pharmaceutically acceptable carrier. The pharmaceutical compositions comprise effective amounts of any one or more of Formulas 1, 2, 5, C1, and their pharmaceutically acceptable salts which are useful for treatment of neoplastic disease, especially malignant neoplastic disease, associated with expression of pre-miR-21, especially oncogenic expression of pre-miR-21.

Embodiments of the method for treatment of neoplastic disease, especially malignant neoplastic disease including but not limited to localized cancers and metastasized cancers are directed to pharmaceutical compositions comprising a pharmaceutically acceptable carrier and a compound of Formula 1, 2, 5 and/or the application of Formula L-1 to Formula 2 and the pharmaceutically acceptable salts thereof. Embodiments of the methods preferably are directed to patients with cancers that express miR-21 especially in oncogenic capacity such as but not limited to breast cancer, lung cancer, pancreatic cancer, melanoma or cancer cells mediated by miR-21. Preferably, the cancer is breast or lung cancer.

Embodiments of the method for treatment of malignant neoplastic disease further include conjoint administration of the pharmaceutical composition of one or more of Formulas 1, 2, 5, C1 and known anti-cancer agents. The known anti-cancer agents may be selected from the list described below and may be administered prior to, simultaneous with, sequentially with or following administration of the pharmaceutical composition embodiments of the invention.

Additional embodiments of the invention include methods for screening and identifying small molecule compounds that exhibit binding with RNA motifs and the use of the results of such methods to map common chemical features of the compounds and develop new small molecule compounds having such common chemical features that bind strongly with a set or a particular RNA motif or individual RNA sequence. These embodiments include a method for RNA target validation and profiling comprising applying an RNA motif library of RNA molecules to a microarray of a gel containing a library of organic small molecule compounds to provide microarray sites with bound RNA molecules. The small molecule compounds are individually and separately located on the gel so that the separate locations provide the identities of individual small molecule compounds. Following the combination of the RNA library with the microarray, the sites where RNA molecules bound to the microarray are mapped. Those sites also provide the identities of the individual small molecule compounds binding the RNA molecules because of the discrete unique locations of the compounds on the microarray. The map of bound RNA molecules is correlated with the identities of the small molecule compounds at the binding sites to provide a map of bound small molecule compounds. The compound map is used to identify chemical structure features of the mapped small molecule compounds that are common to at least some, preferably at least twenty percent, more preferably at least thirty percent and most preferably at least forty percent of the mapped small molecule compounds. Especially most preferably chemical features that are common to at least fifty percent or at least sixty percent of the small molecule compounds are mapped. The library of organic small molecule compounds can be a known library, or can be a library of synthesized organic small molecule compounds which incorporate chemical structure features identified by prior use of this method applied to a known library of organic small molecule compounds.

Further embodiments include methods of cellular destruction by targeting an oncogenic non-coding RNA precursor. The method comprises contacting a cell expressing the non-coding RNA precursor with a pharmaceutical composition incorporating the compounds of Formulas 1, 2 and/or 5 with a pharmaceutically acceptable carrier. Preferably the non-coding RNA precursor is an oncogenic non-coding RNA precursor. In such methods, the pharmaceutical composition comprises the compounds of Formula 2 and the carboxyl terminus of L is an alkyl ester or alkyl amide. Also, preferably, pharmaceutical composition comprises the compounds of Formula 2 and the carboxyl terminus L has a Nu substitution. Preferably for the Nu substitution, Nu may be Formula C1.

Pursuant to the foregoing methods involving non-coding RNA precursors, the oncogenic non-coding RNA precursor more preferably comprises oncogenic pre-microRNA-21 (pre-miR-21).

In additional embodiments of the invention relating to non-coding RNA precursors such as oncogenic pre-miR-21, the foregoing methods also involve enhancing expression of PTEN protein in breast cancer, lung cancer, pancreatic cancer, melanoma or cancer cells mediated by miR-21, by contacting such cells with one or more pharmaceutical compositions as described above for the compounds of Formulas 1, 2 and/or 5.

In additional embodiments of the invention, the foregoing methods involve enhancing expression of PDCD4 protein in breast cancer cells lung cancer, pancreatic cancer, melanoma or cancer cells mediated by miR-21, by contacting such cells with one or more pharmaceutical compositions as described above and set out in detail in the following sections. Preferably, the cancer cells are present in a human patient. In these methods the pharmaceutical composition preferably includes the compound of Formula 2, Formula 2 which includes Nu and Nu is Formula C1 covalently bonded to L or wherein the compound is Formula 5.

A preferred target of any of the foregoing embodiments of methods involves inhibiting invasion in triple negative breast cancer cells by contacting the cells with one or more of the foregoing pharmaceutical compositions, especially where the pharmaceutical composition comprises the compound of Formula 2 wherein L of Formula 2 is substituted by Nu and Nu is Formula C1 covalently bonded to L. This embodiment of the methods of the invention focuses on breast cancer cells present in a human patient. This embodiment of the method especially involves the breast cancer expressing oncogenic precursor microRNA-21 (pre-miR-21). Especially, the compound of the pharmaceutical composition for treatment of this kind of targeted breast cancer is the compound of Formula 2 wherein L of Formula L is substituted by Nu and Nu is Formula CL.

Additional embodiments of the method for screening, identification and inhibiting or blocking of aberrant RNA involves an RNA library comprising one or more transcriptomes. The transcriptomes may be viral, mammalian, bacterial or one or more of synthetic, semi-synthetic, or natural RNA or genome of an RNA virus.

Embodiments of these methods may be carried out in vitro, may be carried out in living cells and/or the cells may be virally- or bacterially-infected cells such as but not limited to cells infected with cancer causing viruses or bacteria.

BRIEF DESCRIPTION OF THE DRAWINGS

FIGS. 1A-1B show a scheme of the processing of miR-21 hairpin precursors and its oncogenic function. Arrows indicate sites of nuclease cleavage. FIGS. 1C-1D display the sequence-based design of monomeric (1) and dimeric (2) compounds targeting the pre-miR-21 three-dimensional structure via Inforna. FIG. 1E shows compound 2 (FIGS. 2A-2C) decreased miR-21 and increased pre-miR-21 levels in MDA-MB-231 cells. FIG. 1F shows miRNA profiling of MDA-MB-231 cells treated with 1 or 2. Dotted lines represent an FDR of 1% and variance of $S_0(0.1)$. *, $p<0.05$; **, $p<0.01$ as tested by a two-tailed Student's t-test.

FIGS. 2A-2C show the compounds used in this study. FIG. 2A describes compounds that bind pre-miR-21 at the Dicer site to affect processing. FIG. 2B describes the active and inactive RNase L nuclease recruitment modules; an x-ray structure for compound 3 was solved and is shown in the ball and stick model. FIG. 2C describes the active, inactive, and negative control compounds assembled from RNase L recruitment and RNA-binding units that were used to study enzymatic cleavage of pre-miR-21.

FIG. 3A shows that Compound 5 dimerizes RNase L onto pre-miR-21 to enzymatically cleave it. FIG. 3B shows compounds 2, 5, and 7 decreased miR-21 levels in MDA-MB-231, however, only RNase L recruiting 5 decreased pre-miR-21 while 2 and 7 increased pre-miR-21 levels. FIG. 3C shows that diminished effects of 5 (50 nM) on pre-miR-21 were observed upon siRNA ablation of RNase L. FIG. 3D shows that co-treatment of 2 with 5 increased pre-miR-21 levels. FIG. 3E shows that co-immunoprecipitation of RNase L showed a ~3-fold increase in pre-miR-21 only with 5 (200 nM), while showing no enrichment of pre-miR-210. FIG. 3F shows RT-qPCR profiling of miRNAs in MDA-MB-231 with 2 (1000 nM) and 5 (50 nM) treatment exhibited high selectivity for miR-21. FIG. 3G shows the majority of downregulated proteins with 5-treatment were proliferative proteins, while the majority of upregulated proteins are anti-proliferative, as measured by global proteomics and pathway analysis. Dotted lines represent FDR of 1% and a group variance of $S_0(0.1)$. *, $p<0.05$; **, $p<0.01$ as tested by a two-tailed Student's t-test.

FIGS. 4A-4E show that compound 5 inhibits in vivo MDA-MB-231 invasion. FIG. 4A shows in vivo treatment of 5 (10 mg/kg, q.o.d., 6 weeks) decreased lung nodules (white nodules) stained with Bouin's solution. FIG. 4B shows hematoxylin and eosin (HE) staining of lung tissue from mice treated with 5 or vehicle. FIG. 4C shows lung nodule tissue treated with 5, but not vehicle, exhibited decreased mature miR-21 and FIG. 4D, pre-miR-21 expression, as measured by FISH probing. FIG. 4E shows that treatment with 5 increased PDCD4 levels in lung nodule tissue sections. *, $p<0.05$; **, $p<0.01$ as tested by a two-tailed Student's t-test.

FIG. 28A top panel shows secondary structures of 5' Cy5 labeled pre-miR-21 WT mimic used for MST binding analyses. Below, FIG. 28A shows representative binding isotherms of 1 and 2 to pre-miR-21 WT RNA. FIG. 28B, top panel shows secondary structures of 5' Cy5 labeled pre-miR-21 BP control with the A and U bulges base paired used for MST binding analyses. Below, FIG. 28B shows representative binding isotherms of 1 and 2 to pre-miR-21 BP RNA. No saturation of the binding isotherm was observed with the addition of 100 μM of compound. MST signal was normalized to the fluorescence signal of 1 to pre-miR-21 WT. Data represent mean±s.e.m. ($n\geq3$).

FIG. 29A on the left shows mapping gel of in vitro transcribed $^{32}P$ 5'-end labeled pre-miR-21 WT RNA. On the right shows quantification of Dicer protection of pre-miR-21 WT with 1 and 2 treatment. Protection with compound is observed at U23 (boxes marked with arrows) and U26 and U27 (unmarked boxes). FIG. 29B shows a mapping gel of in vitro transcribed $^{32}P$ 5'-end labeled pre-miR-21 BP RNA. On the right, FIG. 29B shows quantification of Dicer protection of pre-miR-21 BP with 1 and 2 treatment. Protection with compound is observed at U26 and U27 (indicated by boxes). Compounds were pre-incubated with the appropriate RNA and Dicer endonuclease was added for 1 h at RT. The products were resolved on a 15% PAGE gel. OH indicates hydrolysis ladder, which cleaves at every base; T1 indicates denaturing cleavage conditions with T1 endonuclease that cleaves after every G base; "(–) indicates untreated RNA; +/– Dicer indicates RNA with or without Dicer endonuclease, respectively; Vehicle indicates treatment with DMSO. Dashed lines indicate signal from untreated RNA. Data are expressed as mean±s.e.m. ($n\geq3$). *$p<0.05$, $p<0.01$, *$p<0.001$, as measured by a two-tailed Student t-test.

FIG. 30A shows that monomeric compound 1 inhibits mature miR-21-5p biogenesis and boosts levels of pre-miR-21 in MDA-MB-231 cells. FIG. 30B, top panel, shows a synthetic scheme of peptoid linker strategy to optimize the linker length between RNA-binding modules. Below, FIG. 30B shows screening of dimers was performed in HEK293T cells. Measuring mature miR-21-5p levels by RT-qPCR after treatment with 20 μM of 1 and dimers with varying linker lengths (n=1-6) indicated that n=2-4 worked the most effectively. FIG. 30C shows that linker lengths of n=3 and n=4 and 1 were tested in dose response, as previous studies have shown that n=3 or n=4 are the optimum length with the N-propyl peptoid linker to span the distance between the A and U bulges displayed in pre-miR-21[31]. The n=3 linker most significantly inhibited miR-21 levels as measured by RT-qPCR, and thus was selected as the optimal dimer 2. FIG. 30D shows the efficacy of dimeric compound 2 on mature miR-21-5p levels in various cancer cell line contexts. Dashed lines indicate relative RNA levels in untreated or vehicle samples. Data are expressed as mean±s.e.m. ($n\geq3$). *$p<0.05$, **$p<0.01$, as measured by a two-tailed Student t-test.

FIG. 31A shows an overlay of Volcano plots measuring the quantifiable miRNAs in MDA-MB-231 treated with 1 (10 μM), 2 (1 μM), or 5 (0.05 μM). In all cases, with an FDR of 1% and variance of $S_0(0.1)$ (dashed lines), miR-21 is the most significantly inhibited miRNA. FIG. 31B shows the Gini coefficient (GC), a measure of statistical dispersion, was applied as a measure of reactive selectivity. The Gini index has previously been applied as a measure of kinase selectivity with values closer to zero indicating little to no selectivity, while values closer to one indicating higher selectivity. That is, non-selective inhibitors, such as staurosporine have a GC of 0.150, while highly selective compounds that affect less than 10 kinases amongst the kinome, such as the selective PD184352 inhibitor, have a GC of 0.905[18]. Calculating the GC for 1, 2, and 5 at the indicated concentrations as applied to all miRNAs measured in the RT-qPCR profiling experiments results in GCs of 0.52, 0.68, and 0.84, indicating 5 has the highest selectivity. FIG. 31C shows an overlay of Volcano plots only displaying all quantifiable miRNA isoforms[33] that contain the same A and U bulge as miR-21. FIG. 31D shows the GC for 1 dropped to 0.31 indicated decreased selectivity amongst miR-21 isoforms. The GCs for 2 and 5 both slightly decreased to 0.65 and 0.78 indicating that these dimeric compounds maintain selectivity for miR-21 over other miRNA isoforms.

FIG. 32A shows the structures used for Chem-CLIP studies. Appendage of a chlorambucil nucleic acid cross-linking module and a biotin purification module gives the Chem-CLIP probe specific for miR-21, compound 8. Compound 9 is the control compound without any RNA-binding modules, which was synthesized previously[23]. FIG. 32B shows the schematic of Chem-CLIP pulldown to enrich target RNA and competitive Chem-CLIP (C-Chem-CLIP) where treatment with the parent monomer, 1, or dimer, 2, depletes pulldown of the target RNA since compounds compete for occupancy of the target sites. FIG. 32C shows the pulldown of $^{32}P$ 5'-end labeled pre-miR-21 WT RNA in vitro. 8 shows greater enrichment of the RNA compared to 9. FIG. 32D shows treatment of 8 (10 μM) in MDA-MB-231 cells shows an enrichment for the pre-miR-21 transcript compared to no enrichment by 9 (10 μM), as measured by RT-qPCR. FIG. 32E shows that enrichment is depleted upon competing off with parent monomer, 1, and dimer, 2, compounds. Dashed line indicates relative fold enrichment levels in before pulldown samples. Values below this line indicate less enriched (depleted) levels of measured miRNA after pulldown. Data are expressed as mean±s.e.m. (n≥3). $*p<0.05$, $**p<0.01$, as measured by a two-tailed Student t-test.

FIG. 33A shows 2 appended to the nucleic acid cleaving natural product bleomycin A5 (dashed line) yields compound 10, which enables pre-miR-21 cleavage. FIG. 33B shows small molecule nucleic acid profiling by cleavage applied to RNA (Ribo-SNAP) was performed in vitro. Mapping of $^{32}P$ 5'-end labeled pri-miR-21 RNA with a dose responsive treatment of 10 indicated the compound induced an RT stop at the indicated sites (boxes). FIG. 33C shows four different RT stop regions were mapped in vitro as indicated by the boxes in the pre-miR-21 secondary structure. All RT stop sites were proximal to the predicted binding sites of 2 (A bulge, U bulge and hairpin region), suggesting the selective binding of the dimer in vitro. FIG. 33D shows quantification of RT stops induced in pre-miR-21 by 10 in vitro. The A, U, G and C sequencing ladders were generated by using a ratio of ddNTP/dNTP of 3:1. The "Fe" lane indicates the addition of iron without compound addition, while "(−)" represents untreated RNA. $**p<0.01$, as measured by a two-tailed Student t-test.

FIG. 34A shows treatment of MDA-MB-231 cells with the parent dimer, 2, or the parent dimer appended with Bleomycin A5, 10, decreases mature miR-21 levels, as measured by RT-qPCR. FIG. 34B shows treatment of MDA-MB-231 cells with 10 cleaved and decreased pre-miR-21 levels, while the parent dimer, 2, boosted levels of pre-miR 21, as measured by RT-qPCR. Dashed line represents vehicle control relative RNA abundance levels. $*p<0.05$, relative to vehicle values, as measured by a two-tailed Student t-test.

FIG. 35A displays a scheme of the amplification approach to identify small molecule binding sites via cleavage with 10. FIG. 35B shows analysis of sequencing data revealed the cleavage sites (indicated with an arrow in the pri-miR-21 secondary structure) relative to untreated samples; 57% of reads (12/21 reads) stop at the first C (5'); 14% of reads (3/21 reads) stop at the second A (3'); 29% of reads (6/21 reads) stop at the third A (3'). The cellular cleavage sites correspond to the first RT stop sites observed in vitro (FIGS. 33A-33D). FIG. 35C shows representative Sanger sequencing results from cDNA of the cleaved RNA. The cleavage site is indicated with a box.

FIG. 36A shows a scheme of PTEN 3' UTR luciferase reporter assay.[25,26] A luciferase reporter containing the 3' UTR of PTEN that presents the binding site corresponding to the seed sequence of mature miR-21-5p is transfected into cells. In mock transfected or scramble LNA (Scramble) treated cells, the luciferase signal is inhibited by basal levels of mature miR-21-5p. Upon compound treatment with 2 or a locked nucleic acid targeted for miR-21-5p (LNA-21), mature miR-21-5p levels is decreased, resulting in an increased luciferase signal. FIG. 36B shows treatment of 2 and LNA-21 increased PTEN luciferase signal by ~1.5-fold relative to the mock or scramble controls. FIG. 36C shows that treatment of 2 or 5 de-repress levels of PDCD4 protein in MDA-MB-231 cells, as measured by Western blotting, relative to β-actin. FIG. 36D shows quantification of PDCD4 de-repression with compound treatment. Dashed lines indicate levels of normalized PTEN luciferase signal in mock samples or relative PDCD4 expression in vehicle samples. $*p<0.05$, $**p<0.01$, as measured by a two-tailed Student t-test.

FIG. 37A shows representative images of invasion with and without compound treatment in various cell lines. FIG. 37B shows that compound treatment with LNA-21(100 nM) or 2 (1000 nM) into MDA-MB-231, MDA-LM2, A549, and A375 decreased the invasive phenotype. Dashed line indicates normalized invasion in vehicle treated samples. $*p<0.05$, $**p<0.01$, as measured by a two-tailed Student t-test.

FIG. 38A shows a scheme of the in vitro fluorescence recovery assay using a model RNA 5' end labeled with FAM and 3' end labeled with a Black Hole Quencher (BHQ)[15]. Upon dimerization by compound, RNase L will activate to cleave the model RNA and separate the BHQ, thus recovering the fluorescence of FAM. FIG. 38B shows structures of previously used small molecule RNase L recruiters C1 and C2[15]. FIGS. 38C-38D show compound structures of medicinal optimization based on the parent C1 (C1 series) and C2 (C2 series) used for the in vitro fluorescence recovery assay. FIG. 38E shows screening the fluorescence recovery of C1 and C2 derivative compounds at 130 μM using the model RNA construct. Compound C1-3 (3) showed increased activity compared to Parent C1 (circle) and Parent C2 (triangle). Compound C1-4 (4, circle labeled "Inactive hit (4)") is structurally similar to 3, but was an inactive recruiter of RNase L. FIG. 38F shows the dose-responsive measurements of Parent C1, Parent C2, 3 (C1-3), and 4 (C1-4), revealed 3 (C1-3) as the most active activator of RNase L.

FIG. 39A shows in vitro fluorescence cleavage using a pre-miR-21 labeled FRET sensor showed a dose responsive increase in cleavage with 5 treatment. FIG. 39B shows in vitro oligomerization of RNase L with 5 treatment. Dashed line indicates oligomerization in vehicle samples. FIG. 39C shows gel mapping of labeled pre-miR-21 WT RNA with 5 and RNase L treatment. Cleavage was observed at U27, G25, C23, and G21, which are indicated by boxes. $*p<0.05$, $**p<0.01$, as measured by a two-tailed Student t-test.

FIG. 40A shows inhibition of miR-21 in MDA-MB-231 with treatment of 2 (1000 nM) and 5 (50 nM) up to 96 h, as measured by RT-qPCR. FIG. 40B shows downregulation of miR-21 by inhibition of biogenesis through compound binding to the Dicer site (2), by pre-miR-21 cleavage through bleomycin (10), and by enzymatic cleavage through RNase L recruitment (5) in MDA-MB-231 cells. FIG. 40C shows decreased mature miR-21 levels as indicated by RT-qPCR analysis indicated that targeting miR-21 with 5 is broadly applicable across cell lines. Dashed lines indicate relative RNA abundance in vehicle samples. *p<0.05, **p<0.01, as measured by a two-tailed Student t-test.

FIG. 41A shows compound structures of 25, RNase L recruiting module 3 appended to previously studied compound 26 that binds the Dicer site of pre-miR-210[31]. FIG. 41B demonstrates RT-qPCR analysis of pre-miR-210 expression in hypoxic MDA-MB-231 cells following 25-treatment. Compound 26 boosts levels of pre-miR-21. FIG. 41C displays RT-qPCR analysis of mature miR-210 expression in hypoxic MDA-MB-231 cells following 25-treatment. Compound 26 inhibits mature miR-210 levels by binding to the Dicer site in pre-miR-210 and inhibiting mature miR-210 biogenesis. Dashed lines indicate RNA abundance in vehicle samples. *p<0.05, **p<0.01, as measured by a two-tailed Student t-test.

FIG. 42A shows RT-qPCR was run to measure levels of mRNAs associated with the antiviral innate immune response upon treatment of MDA-MB-231 cells with compound 5 (50 nM) and transfection of 2'-5' $A_4$ (500 nM). No upregulation of these markers was observed with 5 treatment, while significant upregulation of Ifng, OAS1, RIG-I, and MDA5 was observed with transfection of 2'-5' $A_4$. Dashed lines indicate abundance of RNA in vehicle treated samples. FIG. 42B shows an ELISA of IFN-7 which indicated no activation of the innate antiviral immune response with 5 treatment. 2'-5' $A_4$ indicates transfection with 500 nM (positive control for antiviral RNase L-mediated innate immune response). FIG. 42C shows normalized IFN-7 indicates that protein levels (pg/mL) in vehicle treated samples are normalized to a value of 1. Dashed lines indicate abundance of protein in vehicle samples normalized to 1. *p<0.05, **p<0.01, as measured by a two-tailed Student t-test.

FIG. 44A shows significant decrease of invasion in MDA-MB-231 by 5 is ablated upon transient expression of pre-miR-21 (+pre-miR-21). FIG. 44B shows a similar decrease in invasion with 5 treatment is also observed in A375 and A549 cell lines. FIG. 44C shows MCF-10a, representative of healthy breast cells, only became invasive upon transient overexpression of pre-miR-21. Treatment with either LNA-21 or 5 decreased invasion induced by overexpression of pre-miR-21. Dashed lines indicate normalized invasion in vehicle samples. *p<0.05, **p<0.01, as measured by a two-tailed Student t-test.

FIG. 46A shows detection of 5 in mice plasma after treatment with 5 (i.p., 10 mg/kg) in C57BL/6 mice (n=3). FIG. 46B shows data for NOD/SCID mice i.v. tail vein injected with MDA-MB-231-Luc cells. Treatment of mice with 10 mg/kg of 5 started after 6 days of tumor cell injection. Over 42 days, 5 treatment did not cause significant weight changes compared to vehicle-treated mice. FIG. 46C shows histology of lung tissue with scrambled FISH probe (negative control LNA) showed little to no staining with vehicle and 5 treatment. Dashed line indicates normalized signal intensity in vehicle samples.

DETAILED DESCRIPTION

Figure 1A:
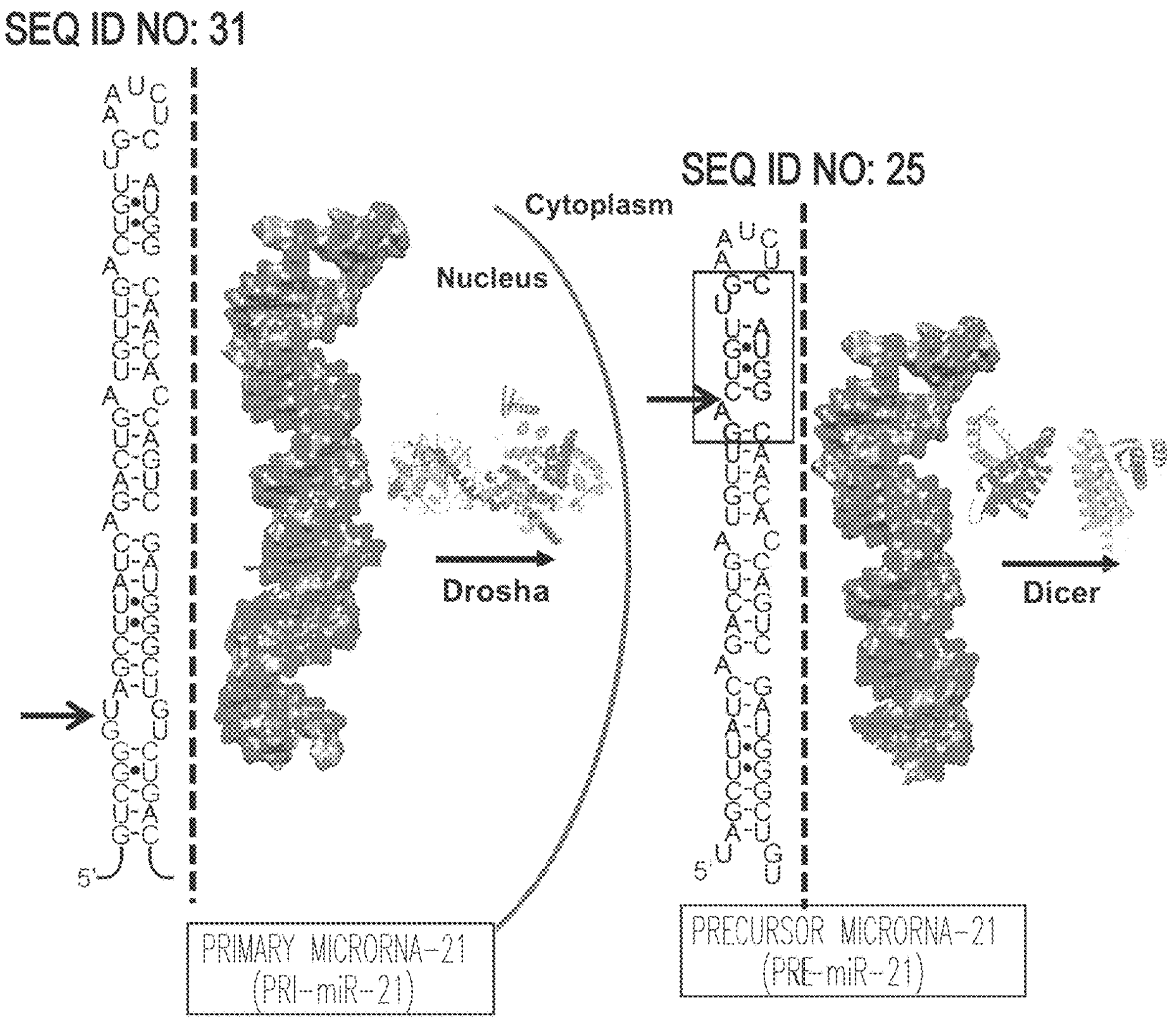
FIGS. 1A-1F. Rational Design of Small Molecules Targeting microRNA-21.
Figure 1B:
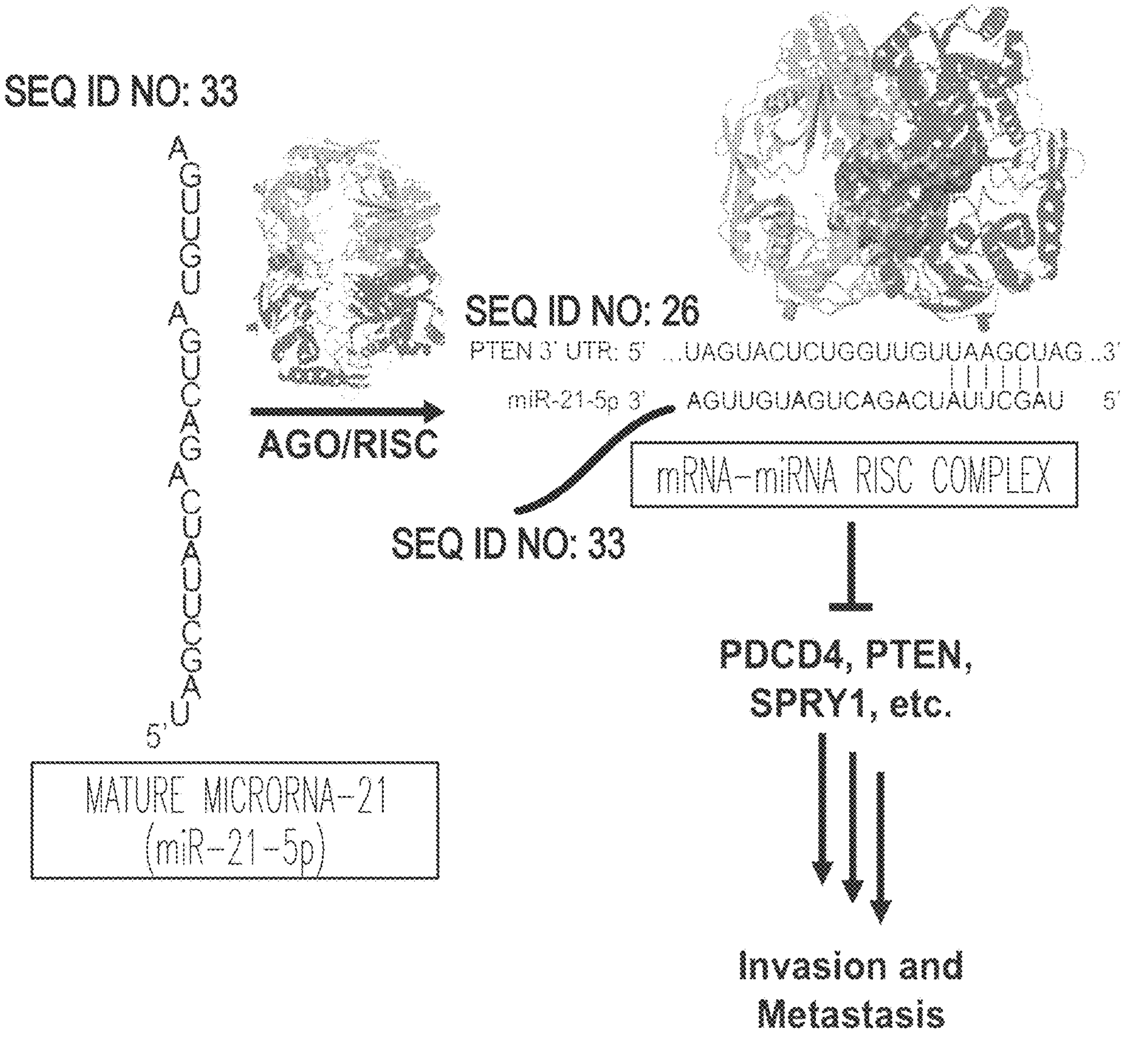
Figure 1C:
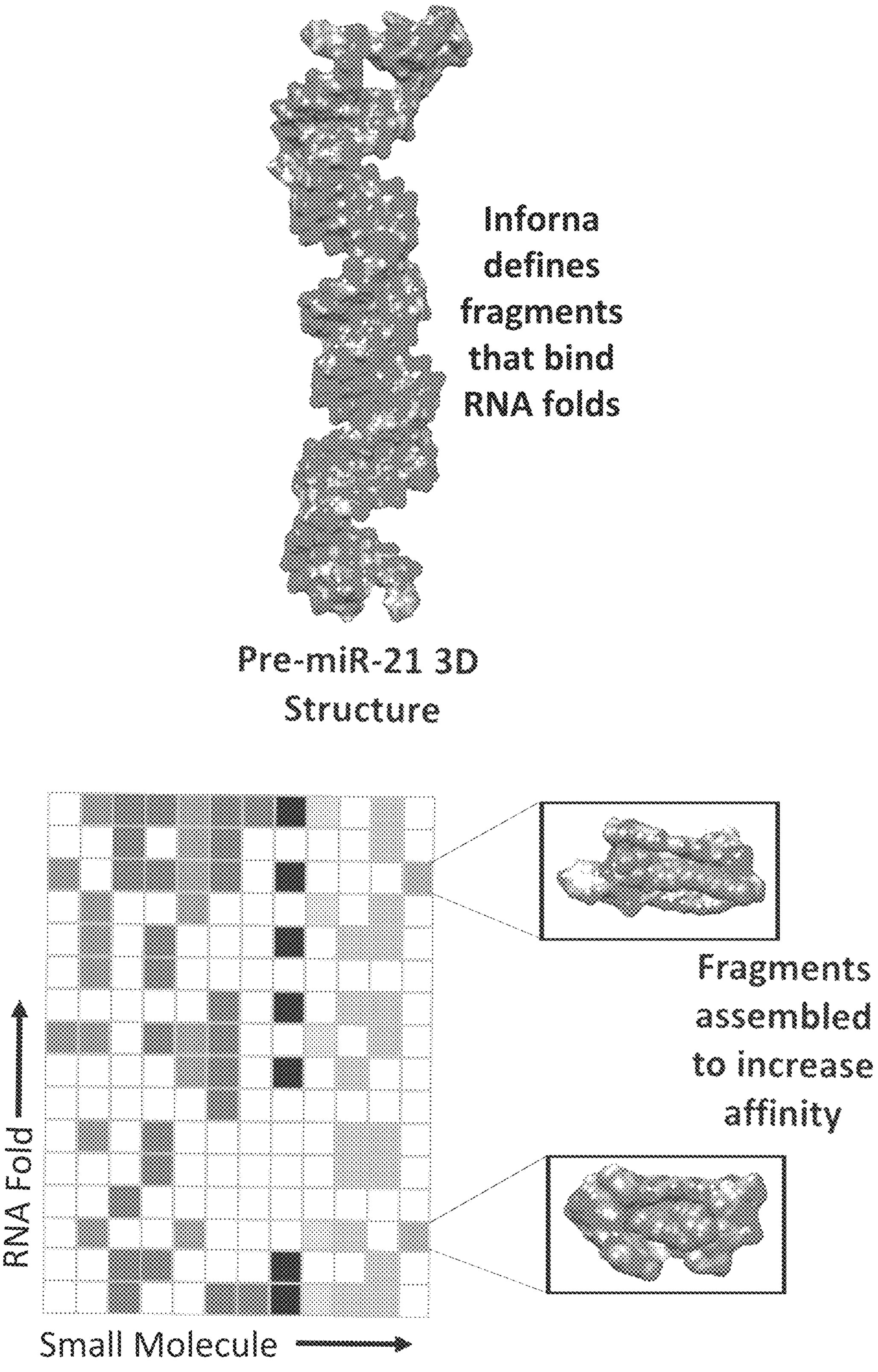
Figure 1D:
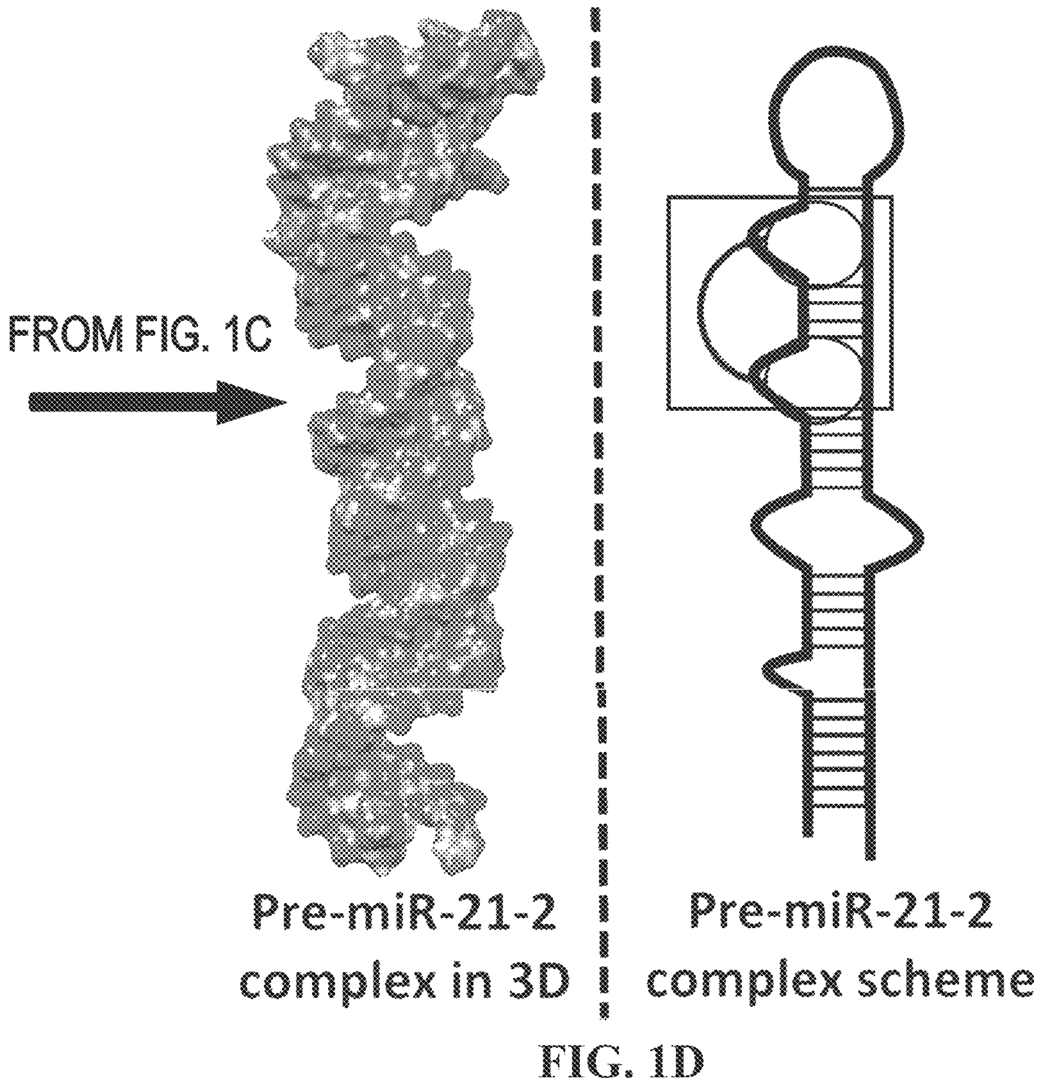

According to the present invention, embodiments of a pre-miR-21 RNA small molecule inhibitor were developed using a microarray protocol termed RIBOTAC and a sequence-based design approach termed Inforna, see Disney et al., *ACS Chemical Biology,* 2016, 11, 1720-1728 and "Scripps Research News" published May 22, 2018 "Novel RNA-Modifying Tool" Dr. Matthew Disney et al. The approach enabled the design small molecules that target the three-dimensional folds in pre-miR-21 RNA. This approach is depicted conceptually in FIGS. 1C-1D. Inforna uses the output of folded RNA structures that bind small molecules. The small molecule models are derived from a library-versus-library screening approach, see S. P. Velagapudi, S. M. Gallo, M. D. Disney, Sequence-based design of bioactive small molecules that target precursor microRNAs. *Nat. Chem. Biol.* 10, 291-297 (2014). This analysis identified a small molecule compound of Formula 1 for further investigation. Modules based on Formula 1 were then designed and assayed for their ability to arrest growth of neoplastic cells such as triple negative breast cancer cells (MDA-MB-231). These modules demonstrated a significant ability to arrest neoplastic cell growth. Additionally, the inhibitory activity of these modules toward the metastasis behavior of MDA-MD-231 cells implanted in mice was investigated and found to be successful.

Explanation of the methods and use of the RIBOTAC and Inforna protocols in connection with the development and identification of the small molecule compound embodiments according to the invention and the features of the small molecule compound embodiments of the invention are set out in the following sections.

Definitions

Unless defined otherwise, all technical and scientific terms used herein have the same meaning as commonly understood by a person of ordinary skill in the art.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

All average molecular weights of polymers are weight-average molecular weights, unless otherwise specified.

The term "may" in the context of this application means "is permitted to" or "is able to" and is a synonym for the term "can." The term "may" as used herein does not mean possibility or chance.

It is also to be understood that as used herein and in the appended claims, the singular forms "a," "an," and "the" include plural reference unless the context clearly dictates otherwise, for example, the term "X and/or Y" means "X" or "Y" or both "X" and "Y", and the letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and the right is reserved to revise the application or claims to refer specifically to any individual member or any subgroup of members of the Markush group.

The expression "effective amount", when used to describe therapy to an individual suffering from a disorder, refers to the amount of a drug, pharmaceutical agent or compound of the invention that will elicit the biological or medical response of a cell, tissue, system, animal or human that is being sought, for instance, by a researcher or clinician. Such responses include but are not limited to amelioration, inhibition or other action on a disorder, malcondition, disease, infection or other issue with or in the individual's tissues wherein the disorder, malcondition, disease and the like is active, wherein such inhibition or other action occurs to an extent sufficient to produce a beneficial therapeutic effect. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

An "analog" of a chemical structure, as the term is used herein, refers to a chemical structure that preserves substantial similarity with the parent structure, although it may not be readily derived synthetically from the parent structure. A related chemical structure that is readily derived synthetically from a parent chemical structure is referred to as a "derivative."

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

At various places in the present specification substituents of compounds of the invention are disclosed in groups or in ranges. It is specifically intended that the invention include each and every individual subcombination of the members of such groups and ranges. For example, the term "C1-C6 alkyl" is specifically intended to individually disclose methyl, ethyl, propyl, isopropyl, n-butyl, sec-butyl, isobutyl, etc. For a number qualified by the term "about", a variance of 2%, 5%, 10% or even 20% is within the ambit of the qualified number.

Standard abbreviations for chemical groups such as are well known in the art are used; e.g., Me=methyl, Et=ethyl, i-Pr=isopropyl, Bu=butyl, t-Bu=tert-butyl, Ph=phenyl, Bn=benzyl, Ac=acetyl, Bz=benzoyl, and the like.

"Azido" refers to an $N_3$ group. An "azide" can be an organic azide or can be a salt of the azide ($N_3^-$) anion. The term "nitro" refers to an $NO_2$ group bonded to an organic moiety. The term "nitroso" refers to an NO group bonded to an organic moiety. The term nitrate refers to an $ONO_2$ group bonded to an organic moiety or to a salt of the nitrate ($NO_3^-$) anion.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as $NH_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", *J. Pharm. Sci.* 66: 1-19.)

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula (I) compounds, for example in their purification by recrystallization. All of these salts may be prepared by conventional means from the corresponding compound according to Formula (I) by reacting, for example, the appropriate acid or base with the compound according to Formula (I). The term "pharmaceutically acceptable salts" refers to nontoxic inorganic or organic acid and/or base addition salts, see, for example, Lit et al., Salt Selection for Basic Drugs (1986), *Int J. Pharm.,* 33, 201-217, incorporated by reference herein.

"Alkyl" refers to straight, branched chain, or cyclic hydrocarbyl groups, e.g., "cycloalkyl," including from 1 to about 20 carbon atoms unless otherwise specified herein. Preferred alkyl groups can have from 1 to 10 carbon atoms or 1 to 6 carbon atoms. Exemplary alkyl includes straight chain alkyl groups such as methyl, ethyl, propyl, butyl, pentyl, hexyl, heptyl, octyl, nonyl, decyl, undecyl, dodecyl, and the like, and also includes branched chain isomers of straight chain alkyl groups, for example without limitation, $-CH(CH_3)_2$, $-CH(CH_3)(CH_2CH_3)$, $-CH(CH_2CH_3)_2$, $-C(CH_3)_3$, $-C(CH_2CH_3)_3$, $-CH_2CH(CH_3)_2$, $-CH_2CH(CH_3)(CH_2CH_3)$, $-CH_2CH(CH_2CH_3)_2$, $-CH_2C(CH_3)_3$, $-CH_2C(CH_2CH_3)_3$, $-CH(CH_3)CH(CH_3)(CH_2CH_3)$, $-CH_2CH_2CH(CH_3)_2$, $-CH_2CH_2CH(CH_3)(CH_2CH_3)$, $-CH_2CH_2CH(CH_2CH_3)_2$, $-CH_2CH_2C(CH_3)_3$, $-CH_2CH_2C(CH_2CH_3)_3$, $-CH(CH_3)CH_2CH(CH_3)_2$, $-CH(CH_3)CH(CH_3)CH(CH_3)_2$, and the like. Thus, alkyl groups include primary alkyl groups, secondary alkyl groups, and tertiary alkyl groups. An alkyl group can be unsubstituted or optionally substituted with one or more substituents as described herein below.

The phrase "substituted alkyl" refers to alkyl substituted at one or more positions, for example, 1, 2, 3, 4, 5, or even 6 positions, which substituents are attached at any available atom to produce a stable compound, with substitution as described herein. "Optionally substituted alkyl" refers to alkyl or substituted alkyl.

Each of the terms "halogen," "halide," and "halo" refers to —F, —Cl, —Br, or —I.

The term "alkenyl" refers to straight, branched chain, or cyclic hydrocarbyl groups, e.g., "cycloalkenyl," including from 2 to about 20 carbon atoms having 1-3, 1-2, or at least one carbon to carbon double bond. The term "cycloalkenyl" refers specifically to cyclic alkenyl, such as $C_3$-$C_6$-cycloalkenyl. An alkenyl group can be unsubstituted or optionally substituted with one or more substituents as described herein below.

"Substituted alkenyl" refers to alkenyl substituted at 1 or more, e.g., 1, 2, 3, 4, 5, or even 6 positions, which substituents are attached at any available atom to produce a stable compound, with substitution as described herein. "Optionally substituted alkenyl" refers to alkenyl or substituted alkenyl.

"Alkyne or "alkynyl" refers to a straight or branched chain unsaturated hydrocarbon having the indicated number of carbon atoms and at least one triple bond. Examples of a ($C_2$-$C_8$) alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below.

"Substituted alkynyl" refers to an alkynyl substituted at 1 or more, e.g., 1, 2, 3, 4, 5, or even 6 positions, which substituents are attached at any available atom to produce a stable compound, with substitution as described herein. "Optionally substituted alkynyl" refers to alkynyl or substituted alkynyl.

The term "alkoxy" refers to an —O-alkyl group having the indicated number of carbon atoms. For example, a ($C_1$-$C_6$) alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "carbocyclyl" refers to a monocyclic, bicyclic, tricyclic, or polycyclic, 3- to 14-membered ring system, which is either saturated, such as "cycloalkyl," or unsaturated, such as "cycloalkenyl." The carbocyclyl may be attached via any atom. Carbocyclyl, for instance, also contemplates fused rings wherein, for instance, a carbocyclyl is fused to an aryl or heteroaryl ring as defined herein. Representative examples of carbocyclyl include, but are not limited to cyclopropyl, cyclobutyl, cyclopentyl, cyclohexyl, cyclopropenyl, cyclobutenyl, cyclopentenyl, cyclohexenyl, phenyl, naphthyl, anthracyl, benzofuranyl, and benzothiophenyl. A carbocyclyl group can be unsubstituted or optionally substituted with one or more substituents as described herein below.

"Substituted carbocyclyl" refers to carbocyclyl substituted at 1 or more, e.g., 1, 2, 3, 4, 5, or even 6 positions (and in some cases 1 or 2), which substituents are attached at any available atom to produce a stable compound, with substitution as described herein. "Optionally substituted carbocyclyl" refers to carbocyclyl or substituted carbocyclyl.

"Aryl" when used alone or as part of another term means a carbocyclic aromatic group whether or not fused having the number of carbon atoms designated or if no number is designated, up to 14 carbon atoms, such as a $C_6$-$C_{14}$-aryl. Particular aryl groups are phenyl, naphthyl, biphenyl, phenanthrenyl, naphthacenyl, and the like (see e.g. *Lang's Handbook of Chemistry* (Dean, J. A., ed) 13th ed. Table 7-2 [1985]). A particular aryl is phenyl. "Aryl" also includes aromatic ring systems that are optionally fused with a carbocyclyl ring, as herein defined. An aryl group can be unsubstituted or optionally substituted with one or more substituents as described herein below.

A "substituted aryl" is an aryl that is independently substituted with one or more substituents attached at any available atom to produce a stable compound, wherein the substituents are as described herein. In some cases, the aryl is substituted with 1, 2, or 3 substituents. "Optionally substituted aryl" refers to aryl or substituted aryl.

The term "heteroatom" refers to N, O, and S. Inventive compounds that contain N or S atoms can be optionally oxidized to the corresponding N-oxide, sulfoxide, or sulfone compounds.

"Heteroaryl," alone or in combination with any other moiety described herein, refers to a monocyclic aromatic ring structure containing 5 to 10, such as 5 or 6 ring atoms, or a bicyclic aromatic group having 8 to 10 atoms, containing one or more, such as 1-4, 1-3, or 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or heteroatom is the point of attachment of the heteroaryl ring structure such that a stable compound is produced. Examples of heteroaryl groups include, but are not limited to, pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl. A heteroaryl group can be unsubstituted or optionally substituted with one or more substituents as described herein below.

A "substituted heteroaryl" is a heteroaryl that is independently substituted, unless indicated otherwise, with one or more, e.g., 1, 2, 3, 4 or 5, also 1, 2, or 3 substituents, also 1 substituent, attached at any available atom to produce a stable compound, wherein the substituents are as described herein. "Optionally substituted heteroaryl" refers to heteroaryl or substituted heteroaryl.

"Heterocycloalkyl" means a saturated or unsaturated non-aromatic monocyclic, bicyclic, tricyclic or polycyclic ring system that has from 3 to 14, such as 3 to 6, atoms in which from 1 to 3 carbon atoms in the ring are replaced by heteroatoms of O, S or N. A heterocycloalkyl is optionally fused with aryl or heteroaryl of 5-6 ring members, and includes oxidized S or N, such as sulfinyl, sulfonyl and N-oxide of a tertiary ring nitrogen. The point of attachment of the heterocycloalkyl ring is at a carbon or heteroatom such that a stable ring is retained. Examples of heterocycloalkyl groups include without limitation morpholino, tetrahydrofuranyl, dihydropyridinyl, piperidinyl, pyrrolidinyl, piperazinyl, dihydrobenzofuryl, and dihydroindolyl. A heterocycloalkyl group can be unsubstituted or optionally substituted with one or more substituents as described herein below.

"Optionally substituted heterocycloalkyl" denotes a heterocycloalkyl that is substituted with 1 to 3 substituents, e.g., 1, 2 or 3 substituents, attached at any available atom to produce a stable compound, wherein the substituents are as described herein.

The term "nitrile" or "cyano" can be used interchangeably and refer to a —CN group which is bound to a carbon atom of a heteroaryl ring, aryl ring and a heterocycloalkyl ring.

A "hydroxyl" or "hydroxy" refers to an —OH group.

Compounds described herein can exist in various isomeric forms, including configurational, geometric, and conformational isomers, including, for example, cis- or trans-conformations. The compounds may also exist in one or more tautomeric forms, including both single tautomers and mixtures of tautomers. The term "isomer" is intended to encompass all isomeric forms of a compound of this disclosure, including tautomeric forms of the compound. The compounds of the present disclosure may also exist in open-chain or cyclized forms. In some cases, one or more of the cyclized forms may result from the loss of water. The specific composition of the open-chain and cyclized forms may be dependent on how the compound is isolated, stored or administered. For example, the compound may exist primarily in an open-chained form under acidic conditions but cyclize under neutral conditions. All forms are included in the disclosure.

Some compounds described herein can have asymmetric centers and therefore exist in different enantiomeric and diastereomeric forms. A compound of the invention can be in the form of an optical isomer or a diastereomer. Accordingly, the disclosure encompasses compounds and their uses as described herein in the form of their optical isomers, diastereoisomers and mixtures thereof, including a racemic mixture. Optical isomers of the compounds of the disclosure can be obtained by known techniques such as asymmetric synthesis, chiral chromatography, simulated moving bed technology or via chemical separation of stereoisomers through the employment of optically active resolving agents.

Unless otherwise indicated, the term "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound. The stereoisomer as described above can be viewed as composition comprising two stereoisomers that are present in their respective weight percentages described herein.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

As used herein, and unless otherwise specified, the term "compound" is inclusive in that it encompasses a compound or a pharmaceutically acceptable salt, stereoisomer, and/or tautomer thereof. Thus, for instance, a compound of Formula I includes a pharmaceutically acceptable salt of a tautomer of the compound.

The terms "prevent," "preventing," and "prevention" refer to the prevention of the onset, recurrence, or spread of the disease in a patient resulting from the administration of a prophylactic or therapeutic agent.

A "patient" or "subject" includes an animal, such as a human, cow, horse, sheep, lamb, pig, chicken, turkey, quail, cat, dog, mouse, rat, rabbit or guinea pig. In accordance with some embodiments, the animal is a mammal such as a non-primate and a primate (e.g., monkey and human). In one embodiment, a patient is a human, such as a human infant, child, adolescent or adult.

The term "Nucleic acid", as used herein, is meant to refer to RNA and DNA.

"RNA" or "RNAs", as used herein, is meant to refer to ribonucleic acid molecules and oligomers. RNA includes mRNA, tRNA, rRNA, miRNA, siRNA, shRNA and the like.

"DNA", as used herein, is meant to refer to deoxyribonucleic acid molecules and oligomers.

The term "labeled-RNA", as used herein refer to RNA which have been modified to contain a radiolabel, a fluorescent tag, a chromogenic tag or other detectable probe. Labeled RNAs may be provided or prepared from a RNA library.

The term "RNA library", as used herein refer to a collection of RNA which may be screened in use of the present invention. Many institutions have RNA libraries and some may be commercially available. The RNA library includes a non-coding RNA library, a RNA motif library, a miRNA library, a viral RNA library, or any combination thereof. The RNA motif library may be an internal loop motif library, a hairpin loop motif library, a bulge motif library, a multi-branch loop motif library, a pseudoknot motif library, or any combination thereof.

The term "RNA motif", as used herein, is meant to refer to a targetable internal loop, hairpin loop, bulge, or other targetable RNA structural motifs. Examples of RNA motifs include symmetric internal loops, asymmetric internal loops, 1×1 internal loops, 1×2 internal loops, 1×3 internal loops, 2×2 internal loops, 2×3 internal loops, 2×4 internal loops, 3×3 internal loops, 3×4 internal loops, 4×4 internal loops, 4×5 internal loops, 5×5 internal loops, 1 base bulges, 2 base bulges, 3 base bulges, 4 base bulges, 5 base bulges, 4 base hairpin loops, 5 base hairpin loops, 6 base hairpin loops, 7 base hairpin loops, 8 base hairpin loops, 9 base hairpin loops, 10 base hairpin loops, multibranch loops, pseudoknots, etc. Examples of DNA motifs include symmetric internal loops, asymmetric internal loops, bulges, and hairpin loops. In some cases, the term "motif" includes RNA secondary structures generally, but also in cases may refer to a particular RNA structure that has already been identified.

"Chase oligonucleotides", as used herein, are meant to include oligonucleotides that are designed to ensure that a screened compound interacts with the RNA motif (i.e., with the RNA motif library's variable region) and not with those nucleic acid regions that do not vary from member to member (e.g., invariant stem regions, invariant hairpin loop regions, etc.). The design of such stem chase and hairpin oligonucleotides may depend on the sequences used in the nucleic acid regions that do not vary from member to member. Chase nucleotides may sometimes include DNA chase oligonucleotides (i.e., oligonucleotides that are meant to ensure that the interactions are RNA specific). Example of suitable DNA chase oligonucleotides include duplex AT decamers, duplex CG decamers, and combinations thereof. In certain embodiments, the one or more chase oligonucleotides includes stem chase oligonucleotides. In certain embodiments, the one or more chase oligonucleotides includes hairpin chase oligonucleotides. In certain embodiments, the one or more chase oligonucleotides includes DNA chase oligonucleotides. Combinations of these and other chase oligonucleotides can be employed, for example as in the case where the one or more chase oligonucleotides includes stem chase oligonucleotides, hairpin chase oligonucleotides, and DNA chase oligonucleotides.

The term "gel" as used herein, is meant to refer to a non-fluid colloidal network or polymer network that is expanded throughout its whole volume by a fluid. For example, the gel may, but is not required to, contain a covalently crosslinked polymer network; a polymer network formed through the physical aggregation of polymer chains, caused by hydrogen bonds, crystallization, helix formation, complexation, etc, that results in regions of local order acting as the network junction points; a polymer network formed through glassy junction points, e.g., one based on block copolymers. The gel may be a hydrogel.

The term "non-covalently adhered" or "adhered", as used herein, is meant to refer to compounds adhered closely to a discrete area of a gel without forming covalent linkages between the compound and the gel. Adherence may be via absorption, e.g., into a fluid component of the gel solvent system, or may be via adsorption, e.g., to a surface of the gel, or a combination thereof. As another example, adherence may be the result of, e.g., thermodynamic and/or kinetic stabilization, van der Waals interactions, electrostatic interactions, solvation, or combinations thereof. In some cases, adherence may be the result of hydrogen bonding. In some cases, adherence may be described functionally or empirically, for example, adherence may be described by compounds which exhibit minimal diffusion, such that the compounds remain within discrete locations on a microarray gel. As another example, adherence may be described by compounds which remain substantially adhered when the microgel is washed or incubated. Groups of compounds may be considered non-covalently adhered when, as examples, at least 70%, 80%, 90%, 95%, 99%, 99.5%, 99.9% are adhered to the gel without forming any covalent linkages. The above examples are not intended to limit the manner or extent that compounds adhere to the gel and are provided solely for illustrative purposes.

As used herein, non-covalently adhered does not include compounds which are coupled to the gel via a triazole linkage, e.g., formed via Huisgen cycloaddition of an azide and an alkyne. Adhered also does not include compounds which are spatially separated from the gel, such as where the gel has wells and compounds are dissolved or suspended in a solvent which is physically contained in the well. As another example, adhered does not include compounds which are contained with a discrete droplet which sits upon the gel but does not mix with the gel. For example, adhered does not include compounds which are immobilized as discrete droplets which are then contacted with the RNA motif library using aerosol deposition technology). Further, adhered does not include compounds which simply rest upon the microarray as a dry chemical microarray. For example, a dry chemical microarray has the disadvantage that, if subjected to washing, incubation, or both, the deposited compounds would mix or be removed completely from the discrete locations they were spotted to.

The term "binding interaction", as used herein, is meant to refer to binding or other stabilized association between a small molecule and an RNA molecule or RNA motif. The association can be thermodynamically stabilized or kinetically stabilized or both, and the interaction can be the result of covalent bonding, hydrogen bonding, van der Waals interactions, electrostatic interactions, or combinations of these and/or other types of interactions.

The term "drug-like compound" refers to small molecule compounds having characteristics typical of FDA-approved small molecule drugs. For example, the compounds may have, but are not required to have, one or more of the following characteristics, no more than 5 hydrogen bond donors, no more than 10 hydrogen bond acceptors, a molecular mass less than 500 g/mol, and an octanol-water partition coefficient log P not greater than 5. As another example, the compounds may have, but are not required to have, one or more of the following characteristics, no more than 3 hydrogen bond donors, no more than 3 hydrogen bond acceptors, a molecular mass less than 300 g/mol, and an octanol-water partition coefficient log P not greater than 3. As another example, the compound may be free of pharmacologically incompatible moieties. Other examples of drug-like compounds include small-molecule clinically-approved (e.g., FDA-approved) drugs and compounds which are derivatives thereof. A list of all FDA-approved drugs may be found at Drugs@FDA at accessdata.fda.gov/scripts/cder/daf/ or the FDA Orange Book which is incorporated by reference in its entirety.

RIBOTEC and INFORNA Microarray Methods

The embodiments of compounds of Formulas 1, 2, 5, and 20 of the present invention described below were developed by the microarray RIBOTAC small molecule library screening protocol and Inforna rapid identification program. See Scripps Research News, May 22, 2018 "Novel RNA-Modifying Tool" Dr. Matthew Disney et al. The RIBOTAC protocol provides a microarray comprising a substrate coated with a gel and a plurality of compounds that are non-covalently adhered to the gel at discrete locations. See also PCT/US2019/037762 filed Jun. 18, 2019 (hereinafter PCT '762) which is based upon U.S. Provisional Patent Application No. 62/686,834, filed Jun. 19, 2018, the disclosures of which are incorporated herein by reference. PCT '762 provides full details of these protocols and claims these methods, the protocols and claims of which are incorporated herein by reference as if fully and completely repeated here.

The identification of compound leads resulting from the RIBOTEC and INFORNA protocols may be initiated by populating a microarray investigation with pre-existing small molecules from academic, commercial, open source research institution and similar multiple compound libraries. These include a library of FDA-approved drugs, compounds used in phase I clinical trials, compounds used in phase II clinical trials, kinase inhibitors, topoisomerase inhibitors, mRNA splicing modulators, compounds predicted or known to have RNA-modulating activity, drug-like compounds, commercially-available bioactive compounds, or any combination thereof, and the compounds are unmodified therefrom.

The Microarray Gel

The microarray useful for RIBOTAC screening does not require that the arrayed compounds be subjected to immobilization chemistries. Thus, the compounds to be screened can be free of the functionalization which was previously required to couple and thus immobilize compounds to a microarray. As an example, the compounds of the microarray may be free of any, or all, of azide moieties, alkyne moieties, silyl chloride moieties, maleimide moieties, thiol moieties. Likewise, the compounds may comprise a variety of functional groups provided they are free of a functional group which would irreversible and covalently bind to the gel. For example, the microarray may be free of azide and some of the compounds may comprise an alkyne.

The multiple numbers of compounds ranging from minimums to large numbers ranging from two up to thousand or more and every integer number between may be adhered to the gel by being first deposited on the gel when the gel is partially dry and at least partially solvated so that the compounds may become incorporated into the gel. The gel may then be dried to result in a gel having compounds non-covalently adhered. The compounds may be adhered to the gel via absorption, e.g., into a fluid component of the gel solvent system. The compounds may be adhered to the gel via adsorption, e.g., to a surface of the gel. The compounds may exhibit minimal diffusion, such that the compounds remain within discrete locations on the microarray. The compounds may remain substantially adhered when the microgel is washed or incubated.

The gel of the microarray may comprise a polysaccharide, a polyacrylamide, agarose, separose, agar, polydextran and functional derivatives thereof. In various embodiments, the gel may be about 0.5% to about 5% (w/v) agarose gel.

The gel may be any shape and does not require, or may be free, of any particular molded structures or macroscopic architecture. In various embodiments, the microarray may retain sufficient solvent or moisture such that deposited compounds exhibit at least some degree of diffusion and/or some freedom of movement such that the compounds may interact with binding partners freely.

The substrate may be a rigid or semi-rigid body made of virtually any suitable, stable material including glass, polycarbonate, and the like.

The discrete locations on the gel may represent non-overlapping areas at which the deposited compounds are adhered. The discrete locations may be arranged in an array and may be each separated by at least 100 μm. The array may be a grid or other repeated pattern. In various embodiments, the microarray comprises a substrate coated with an agarose gel and the plurality of compounds are non-covalently adhered to the agarose gel at discrete locations. The discrete locations enable ready identification of the compounds post binding with RNA motifs.

Identification of Interactions Between Compounds And RNA

The microarray and the RIBOTEC protocol enable a method for evaluation of the extent to which RNA and RNA-mediated diseases may be modulated with small molecule compounds. The small molecule compound leads may be selected as described above. The microarray gel with these leads may be constructed as described above and in PCT '762. These methods for assaying leads having affinity for desired RNA may be probed using RNA motifs as described in the parallel library-versus-library screening approach which is dubbed two-dimensional combinatorial screening (2DCS). See Childs-Disney et al., ACS Chem. Biol. 2, 745-754 (2007); and Disney et al., J. Am. Chem. Soc. 130, 11185-11194 (2008).

These methods were used according to present invention to identify binding interactions between lead compound and RNA motifs that have commonality with pre-miR-21. The methods include the following steps.

1) Apply a plurality of labeled-RNAs and excess oligonucleotides to the microarray described herein.
2) Incubate the microarray to induce binding between labeled-RNAs and adhered compounds.
3) Wash the microarray with a buffer solution, remove excess buffer solution and dry the microarray.
4) Image the microarray to detect labeled-RNA which has bound to an adhered compound.
5) Characterize the bound RNA to identify the binding interaction.

Additional details for conducting the method to identify binding small molecules is provided in the above identified PCT application. In various embodiments, the method may comprise folding the labeled-RNAs and excess oligonucleotides, each separately, prior to applying the labeled-RNAs and excess oligonucleotides to the microarray.

The RNA identified by the RIBOTEC and INFORNA protocols may be an RNA motif which interacts with lead compounds. The RNA motif is a three-dimensional form of an RNA sequence that has commonality among many individual RNA sequences. While the RNA bases of these sequences may not be entirely identical, they typically will have substantial similarities. The RNA motif library may be an RNA internal loop library with symmetric loops, base bulge loops, hairpin loops, knot loops, multibranch loops and combinations thereof. The members may differ from one another (i) in the identity of the bases in the RNA internal loop and/or (ii) in the identity of the base pairs adjacent to the RNA internal loop (the so-called loop closing base pairs). Suitable RNA motif libraries can be prepared by conventional transcription techniques (e.g., those employing T7 RNA polymerase, as described, for example, in Milligan et al., "Synthesis of Small RNAs Using T7 RNA Polymerase," *Methods Enzymol.*, 180:51-62 (1989), which is hereby incorporated by reference) from DNA templates, such as DNA templates that are commercially available from Integrated DNA Technologies (Coralville, Iowa)).

In various embodiments, the plurality of small molecule compounds adhered to the microarray as described above can be contacted with the RNA library, or RNA motif library, by a variety of methods. For example, the RNA library can be dissolved or suspended in a suitable solvent, buffer, or buffer system, and the adhered compounds can be pre-equilibrated with a suitable hybridization buffer. The RNA library can then be applied to the adhered compounds, for example, by distributing the RNA library evenly over the array surface; and the adhered compounds and RNA library can be incubated with one another for a period of time and at a temperature effective for one or more members of the nucleic acid motif library to bind with the adhered compounds.

The bound RNA can be characterized according to the following steps, the details of which are provided in the above identified PCT '762. These steps include harvesting the bound RNA; performing reverse transcription on the harvested RNA; performing PCR amplification; and sequencing the amplified product.

The identity or identities of the small molecule compound bound to the RNA identified as described above is typically and usually determined by the discrete location of the small molecule compound on the gel of the microarray. Alternatively, the harvested RNA can be manipulated to include the bound small molecule compound. These two components can be separated and separately identified, the small molecule by ordinary chemistry spectrographic techniques and the RNA by the above amplification and sequencing technique. Additional steps can include incubating the plurality of compounds with one or more chase oligonucleotides such as stem chase oligonucleotides, hairpin chase oligonucleotides, DNA chase oligonucleotides, or any combination thereof. The chase oligonucleotides may include oligonucleotides that are designed to ensure that the compound interacts with the RNA motif (i.e., with the RNA motif library's variable region) and not with those nucleic acid regions that do not vary from member to member (e.g., invariant stem regions, invariant hairpin loop regions, etc.). The design of such stem chase and hairpin oligonucleotides may depend on the sequences used in the nucleic acid regions that do not vary from member to member.

These methods enable identification of small molecule compounds which interact with particular RNA motifs, such as motifs that have common properties among many RNA kinds and types. Since the nucleic acid sequences of many biologically important nucleic acid molecules are known, one can readily ascertain which biologically important nucleic acid molecules have the particular RNA motifs with which a particular compound interacts. Accordingly, small molecule compounds that bind or otherwise interact with biologically important RNAs can be identified and used to target such biologically important RNAs, for example, for diagnostic or therapeutic purposes.

As set out in the above identified PCT '762, the information regarding compound-RNA motif interactions derived using the methods can be assembled into a database. Such databases can then be used in methods for selecting, from a plurality of candidate compounds, one or more compounds that have increased likelihood of binding to an RNA having a particular RNA motif.

The method may further comprise additional analysis steps, such as inform and/or StARTs, which may be performed as described in U.S. Patent Application Publication No. 2016/0188791 A1, which is hereby incorporated by reference in its entirety.

In various embodiments, the method may further comprise an informa approach to identify compounds which target RNA as applied to human microRNA (miRNA) precursors. The inforna methods provide an expedited route to identify small molecules that target the RNA product of those genes. The inforna methods not only speed up drug discovery, but also more accurately identify drug candidates that have a higher likelihood of having useful activity. The inforna methods utilize and compare datasets of information, providing an output of which RNA structural secondary structures will likely bind to which small molecule. Those datasets include (a) a dataset of RNA secondary structures to be queried; and (b) a dataset of identified RNA motif-small molecule interactions (e.g., as identified by two-dimensional combinatorial screening (2DCS)). For example, Sequences of all miRNA precursors in the human transcriptome may be downloaded from miRBase (Griffiths-Jones et al., Nucleic Acids Res. 36, D154-158 (2008)) and their secondary structures predicted via RNAstructure (Mathews et al., Proc. Natl. Acad. Sci. U.S.A. 101, 7287-7292 (2004)). The secondary structural elements may be extracted from each query RNA and those secondary structures compared to a database of RNA motif-small molecule interactions identified by two-dimensional combinatorial screening (2DCS). Such a dataset can be generated, for example, by use of the microarray of the present invention in a two-dimensional combinatorial screening (2DCS) process. See, e.g., U.S. Patent Application Publication No. 2008/0188377 A1; Childs-Disney et al., *ACS Chem. Biol.* 2, 745-754 (2007); Disney et al., *J. Am. Chem. Soc.* 130, 11185-11194 (2008), each of which is hereby incorporated by reference in its entirety.

A dataset of RNA secondary structures to be queried can be generated from one or more RNA sequences alone. For example, RNA secondary structures can be identified as the lowest free energy secondary structures formed by an RNA as it folds back upon itself to form double-stranded regions as well as single-stranded loops and mismatched 'bubbles' in the double-stranded regions. Such low free energy secondary structures can be predicted by programs such as RNAstructure (Mathews et al., *Proc. Natl. Acad. Sci. U.S.A* 101, 7287-7292 (2004), which are specifically incorporated by reference in their entireties).

The output of RNA sequences and secondary structures that will likely bind to a small molecule can be further analyzed by other prediction processes and by chemical and biological assays (e.g., binding assays). For example, a StARTS statistical method can be used to further refine predictions. The StARTS method predicts the affinities and selectivities of RNA motif-small molecule interactions by comparing the rate of occurrence of small structural features (a guanine adjacent to an adenine, for example) in selected RNA motifs to its rate of occurrence in the entire RNA library. The StARTS method therefore facilitates identification of which RNA secondary structures and motifs are most unique or distinctive in populations of RNA molecules. StARTS is a statistical approach that can be paired with inforna to further evaluate the binding affinity of RNA secondary structures for the small molecule partner(s) identified by inforna. StARTS identifies features in RNA motifs that positively and negatively contribute to binding (see, Velagapudi et al., *Angew. Chem. Int. Ed. Engl.* 49, 3816-3818 (2010); Velagapudi et al., *J. Am. Chem. Soc.* 133, 10111-10118 (2011); Paul et al., *Nucleic Acids Res.* 37 (17): 5894-5907 (2009), each of which is incorporated by reference in its entirety).

In the StARTS approach, sequences of one or more RNA secondary structures identified as binding a small molecule are compiled, and the occurrence rate of each sequence feature in the RNA secondary structures may be compared to the occurrence rate of that feature in a larger population of RNA motifs. A sequence feature is any short RNA sequence (for example, a 5'GC step) that may or may not be different from the sequence features that are present in a larger population of RNA sequences. However, the sequence features are those sequences that are present in the population of RNA secondary structures that bind to a small molecule. By comparing these two populations, the relative enrichment for a specific feature in RNA secondary structure for binding to a small molecule can be computed. Thus, the StARTS method identifies which sequence features are more prevalent in a selected population of RNA sequences than in a larger population of RNA sequences.

The more distinctive sequence features may be assigned a statistical significance, or a Z-score and a corresponding two-tailed p-value. The Z scores can be determined by statistical analysis using a RNA Privileged Space Predictor (RNA-PSP) program that determines which features occur in the selected RNA secondary structures with greater than 95% confidence (see, Paul et al., *Nucleic Acids Res.* 37 (17): 5894-5907 (2009)). The confidence intervals are associated with a Z-score, where a larger value corresponds to a higher confidence level. Each RNA secondary structure can have multiple features that contribute to it being different from a larger population of RNA motifs and a sum of the Z-scores for all features in an RNA secondary structure can be computed (ΣZ) as an indicator of the total structural distinctiveness of an RNA motif.

To complete the StARTS analysis, the Z-scores can then plotted against the measured binding affinities of the RNA secondary structure for a compound, and this relationship can be fitted to an inverse first-order equation, which allows prediction of the affinity of a compound for a RNA library member.

These methods were used with libraries of various drug classes including kinase inhibitors, pre-mRNA splicing modulators, and topoisomerase inhibitors that bound RNA avidly. Lead molecules were identified. Structure-Activity-Relationships among the molecules and the binding indications with RNA motifs were identified. Additional small molecule compounds were identified and/or synthesized based upon these leads and SAR information. The microarray assays based on RIBOTEC and Inforna protocols were performed for the additional compounds and compound embodiments of Formula 1 were identified as having significant binding interaction with pre-miR-21 RNA.

Compounds

The Inforna screening and molecular design program (*ACS Chemical Biology* citation given above) for development of small molecules targeting structured RNAs provided compound embodiments of Formula 1, above, that bound the target pre-miR-21 RNA Dicer site selectively with a $K_d$ of 20 μM and inhibited in vitro Dicer processing to yield miR-21. The experimental details for the RNA binding property of Formula 1 are provided in the Examples section below. The compound embodiments of Formula 1 are derived from precursor Formula 1-P having an amino terminus bonded to $R^{16}$ as hydrogen, an alkyl or acyl group. Precursor Formula 1-P also has a phenoxy terminus (hydroxyl group) which has $R^{15}$ as hydrogen or has $R^{15}$ as a functional group for further modification. Preparation of $R^{15}$ as a functional group may be accomplished through a modification compound such as an ω-iodo alkanoic compound with a protected carboxyl group. Coupling such an alkanoic compound with Formula 1-P with $R^{15}$ as hydrogen, i.e., the phenoxy group, will provide a protected acyl alkyl group such as Pr—OOC—$(CH_2)_r$— as $R^{15}$ of Formula 1-P wherein Pr is a carboxy protection group and r is an integer of 2 to 6. The carboxy protection group may be combined with a diamine or an azidoalkyl amine to provide Formula 1-P with $R^{15}$ as the group $R^9C(=O)—(CH_2)_r$ and $R^{16}$ as hydrogen or methyl. This combination is Formula 1.

Formula 1-P

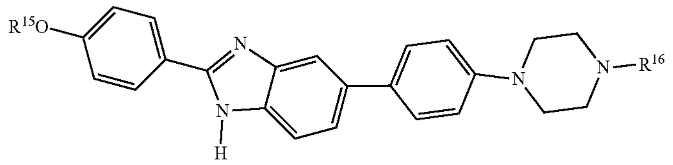

Formula 1

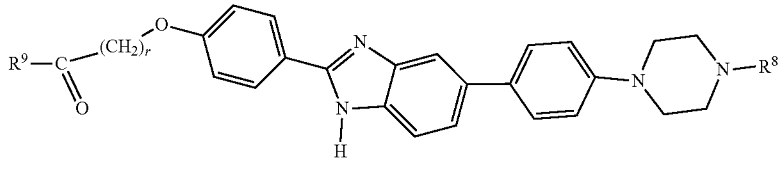

To optimize Compound Formula 1 for avidity, the RNA folds in all miR precursors in the human transcriptome were compared to pre-miR-21. See FIGS. 31A-31D. Several miR precursors display the A bulge motif of pre-miR-21 yet no other targets contained it and the adjacent U bulge of pre-miR-21. However, compound Formula 1 bound to both sites and assembly of a dimer of Formula 1 to target both sites in a single compound afforded the compound of Formula 2.

Formula 2

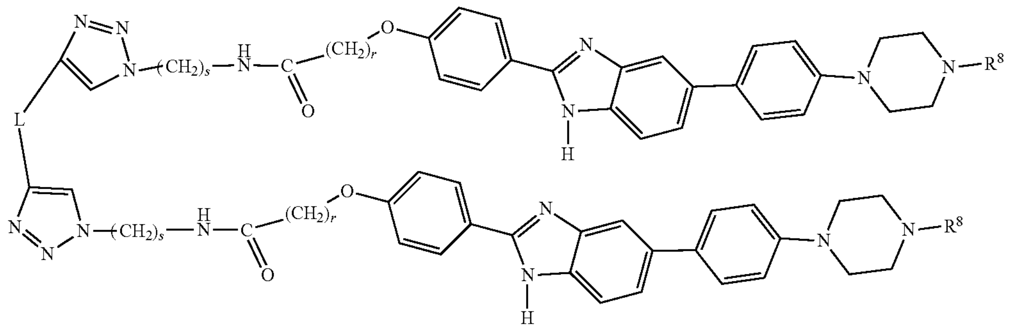

Figure 28A:
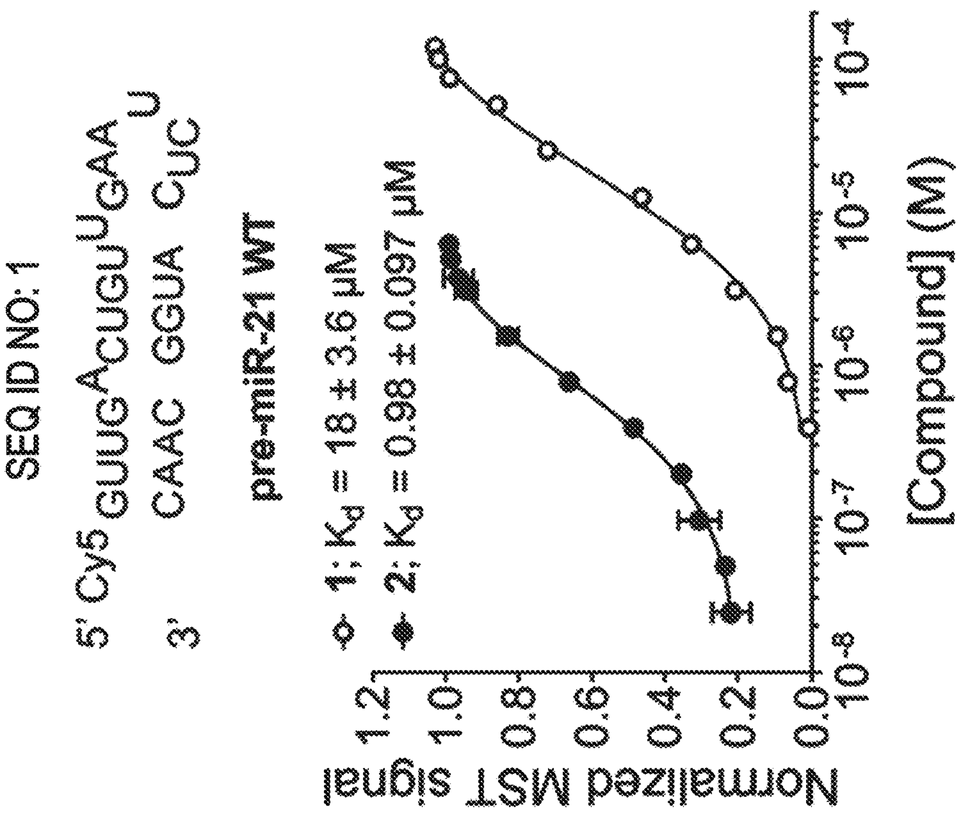
FIGS. 28A-28B. Microscale thermophoresis (MST) binding affinity analysis of formulas 1 and 2 in vitro.
Figure 28B:
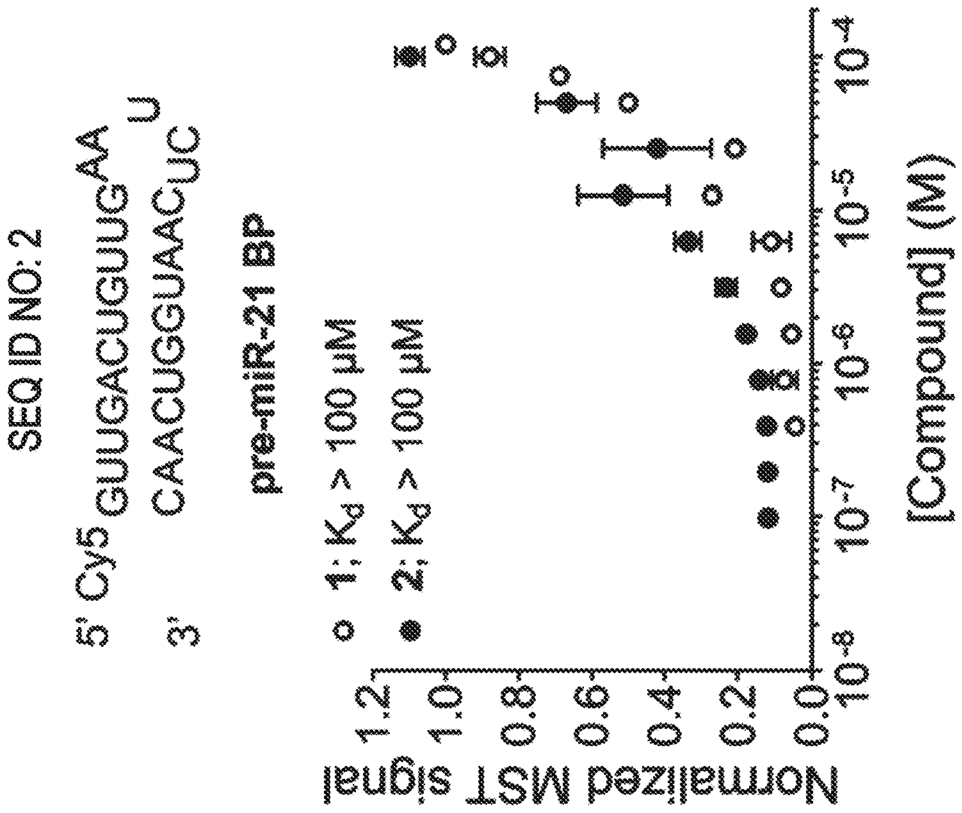
Figure 29A:
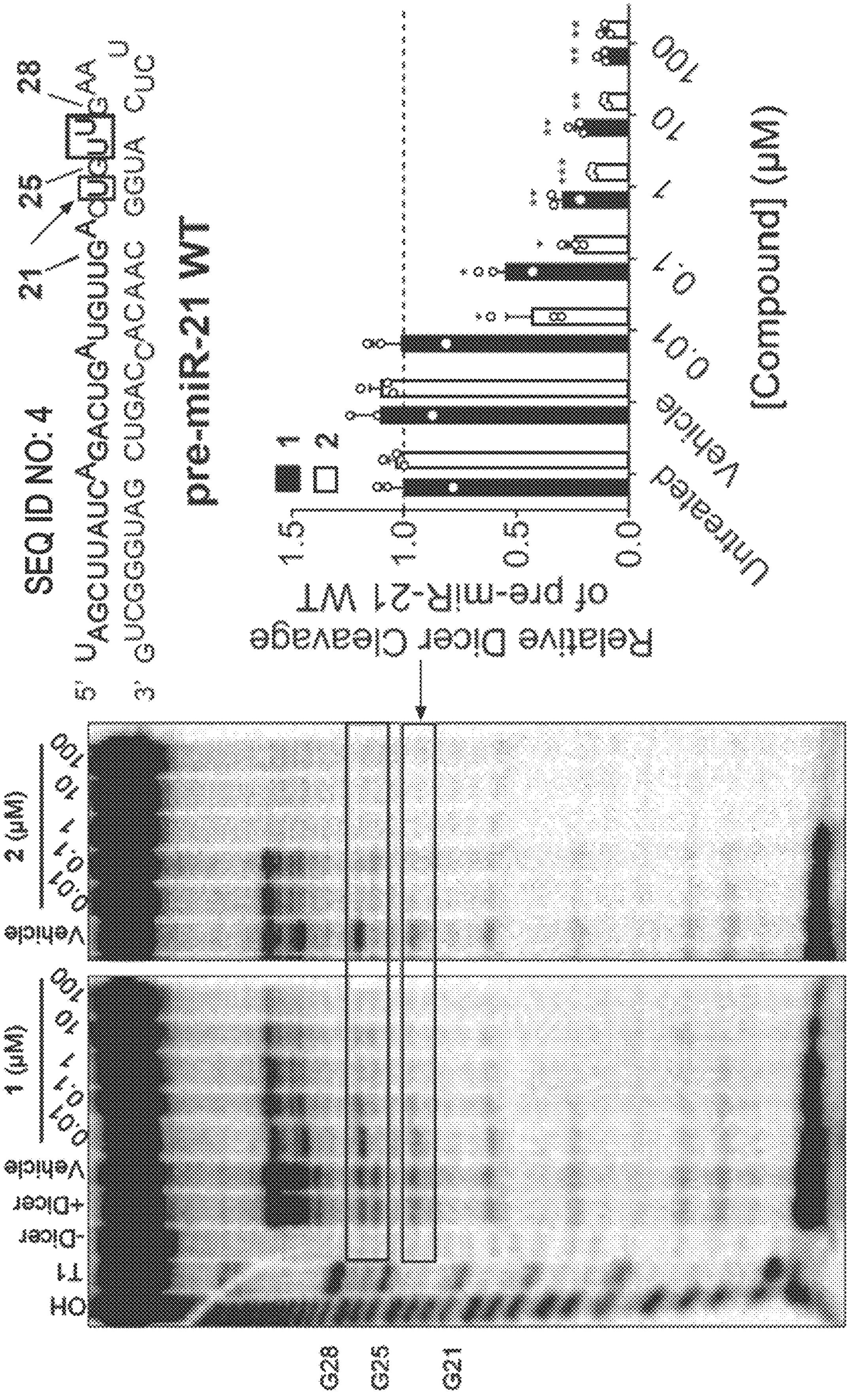
FIGS. 29A-29B. In vitro Dicer inhibition assay of formulas 1 and 2.
Figure 29B:
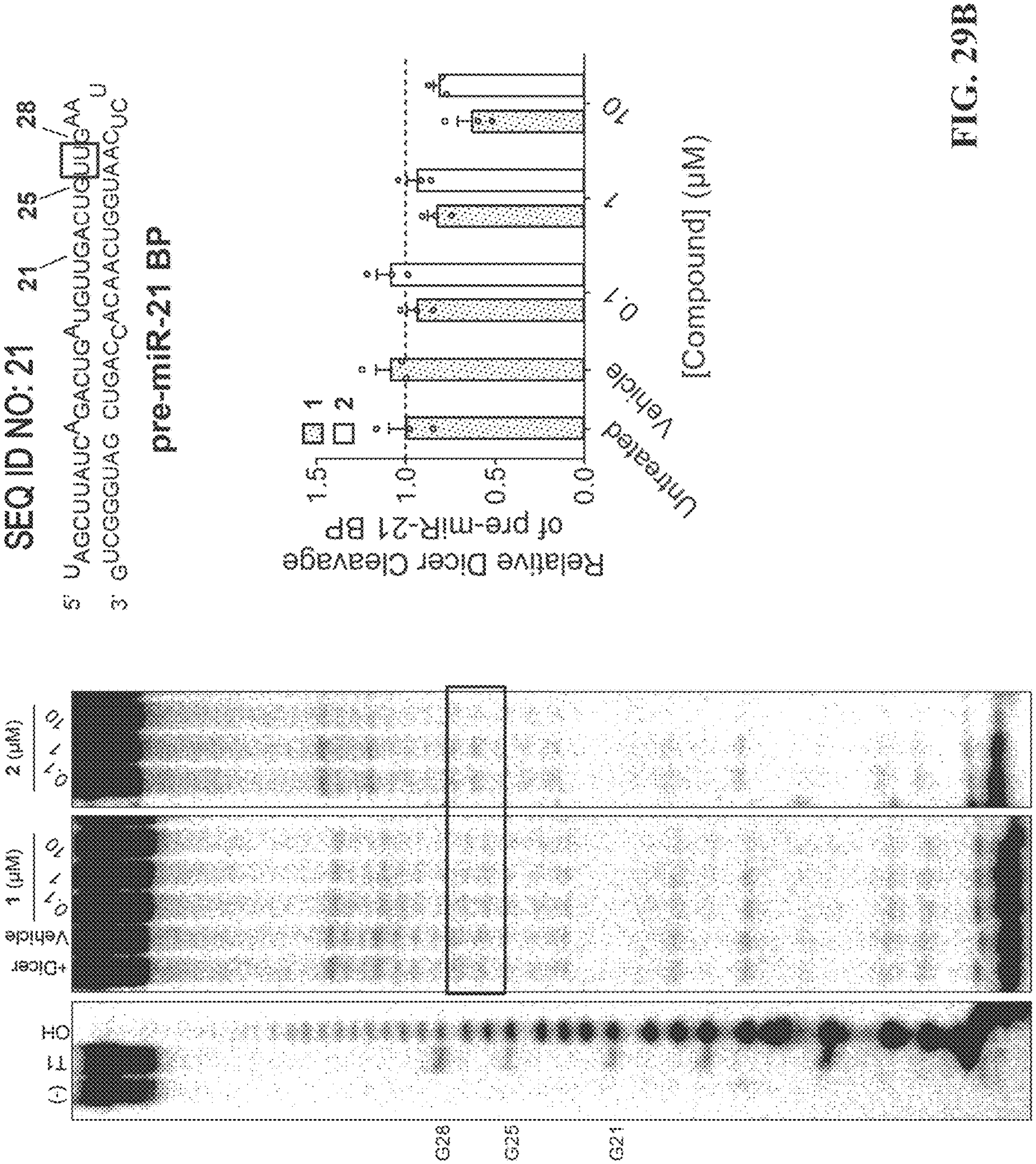
Figure 30A:
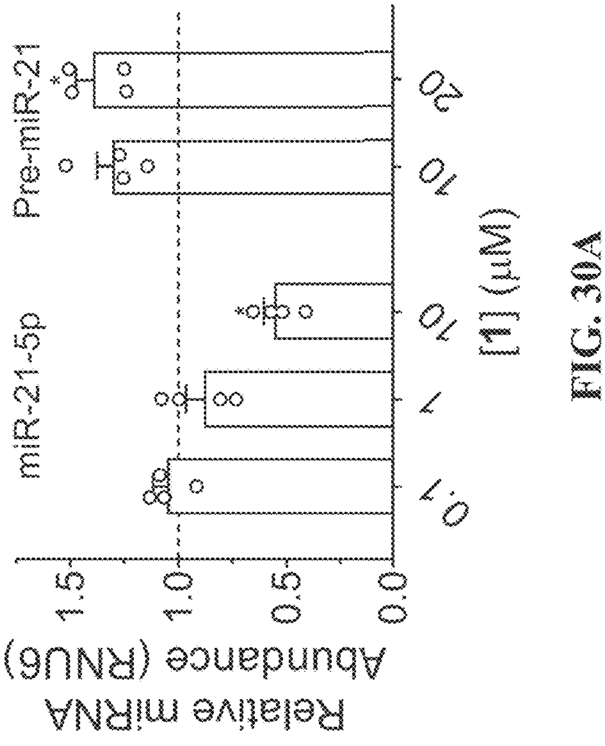
FIGS. 30A-30D. On-target effects of formulas 1 and 2 in cells.
Figure 30B:
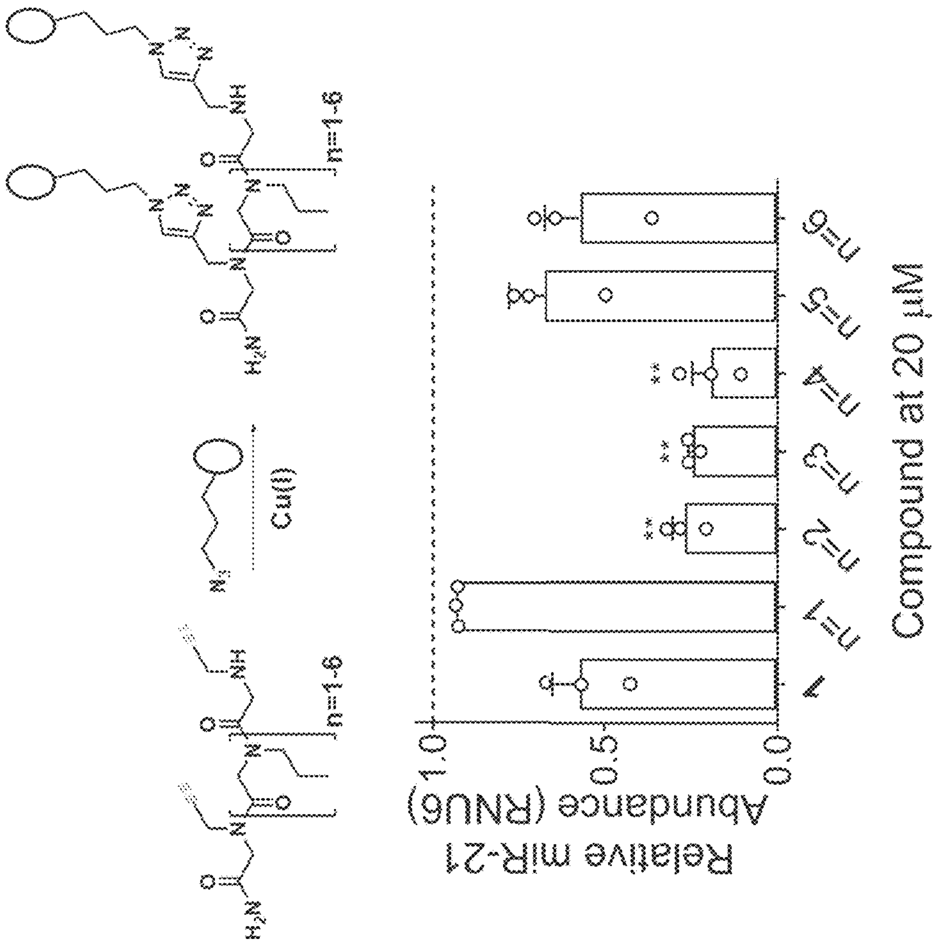
Figure 30D:
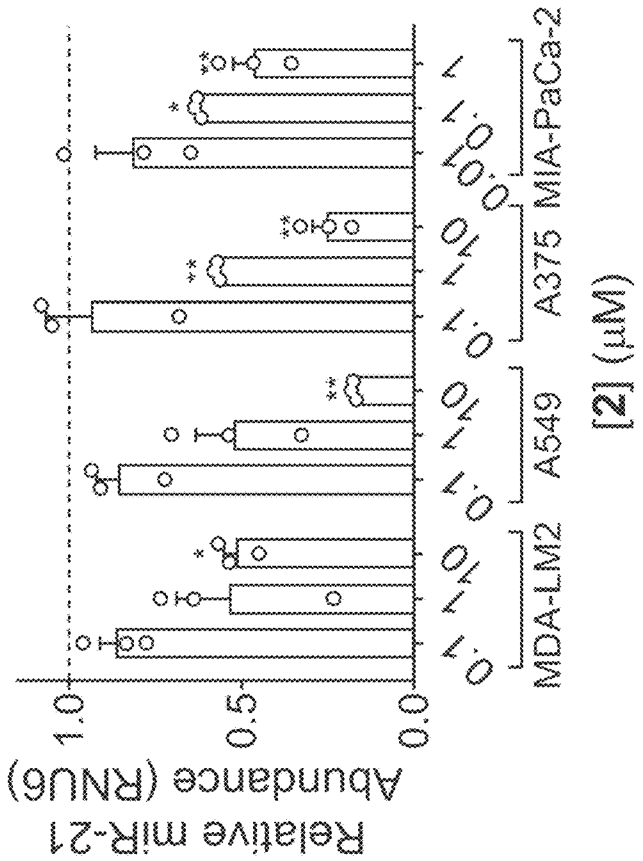
Figure 30C:
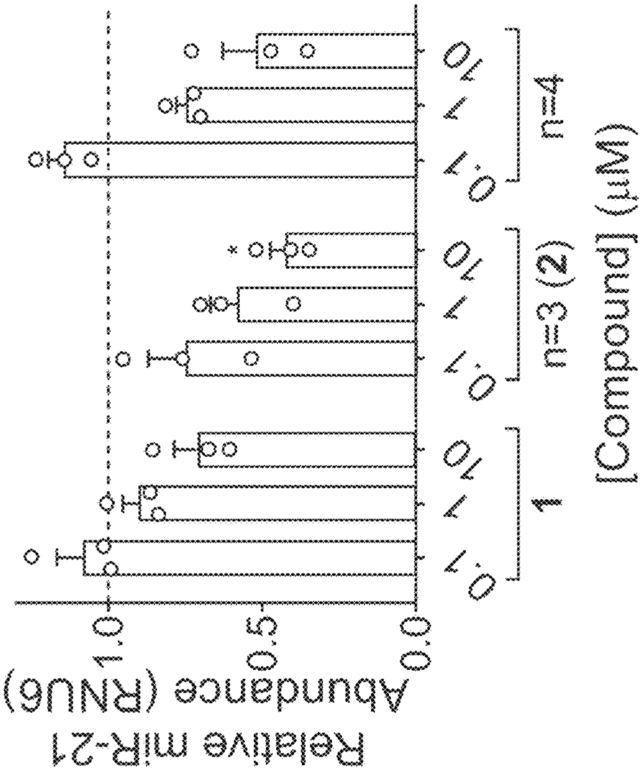
Figure 31A:
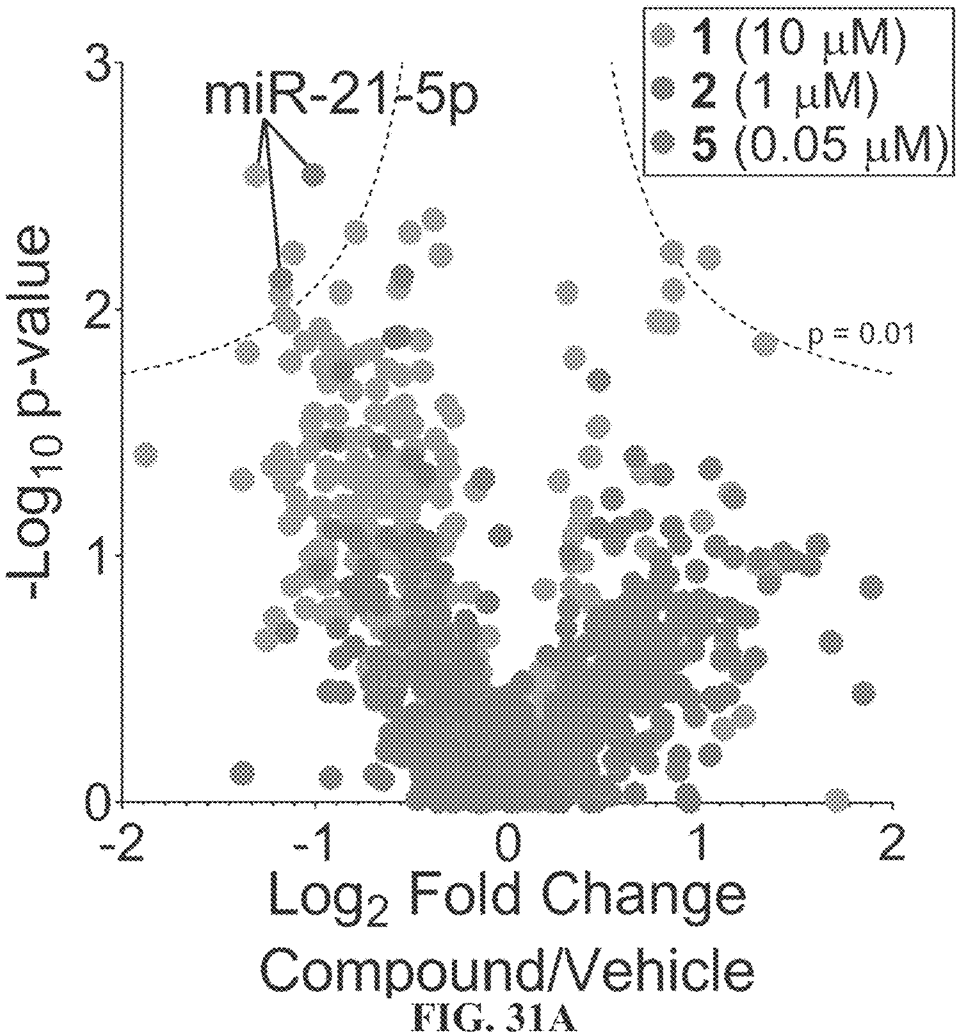
FIGS. 31A-31D. Analyzing the selectivity of compounds targeting miR-21.
Figure 31B:
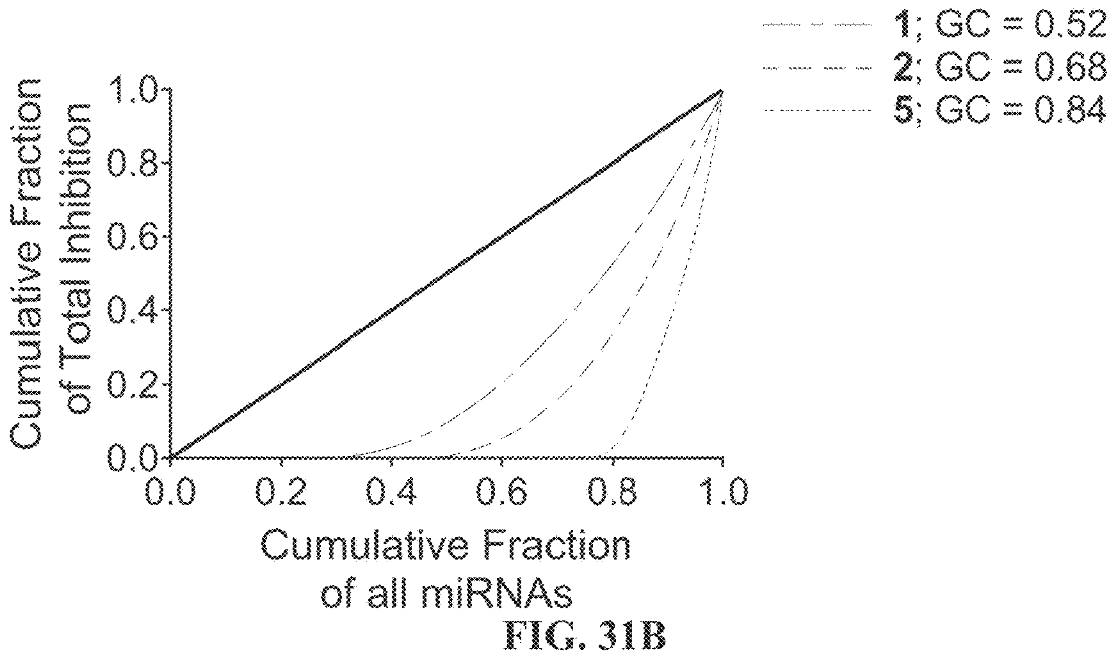
Figure 31C:
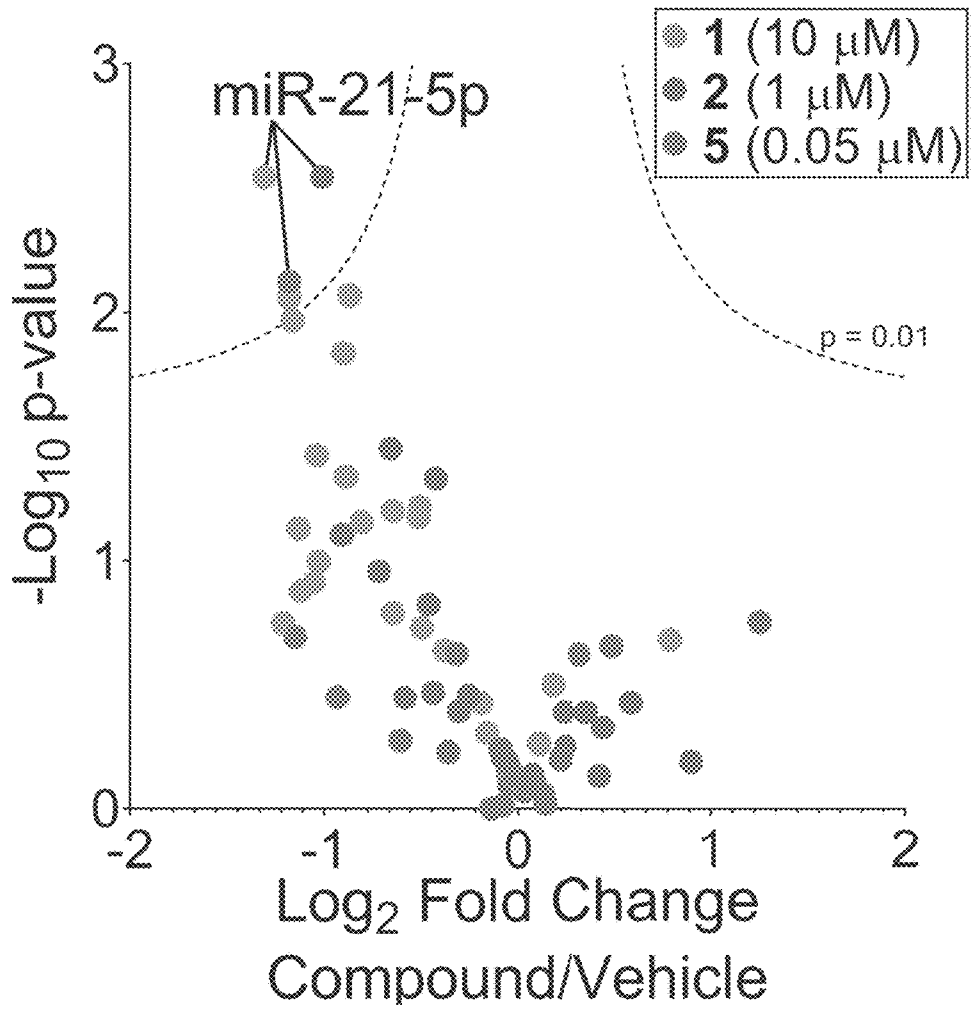
Figure 31D:
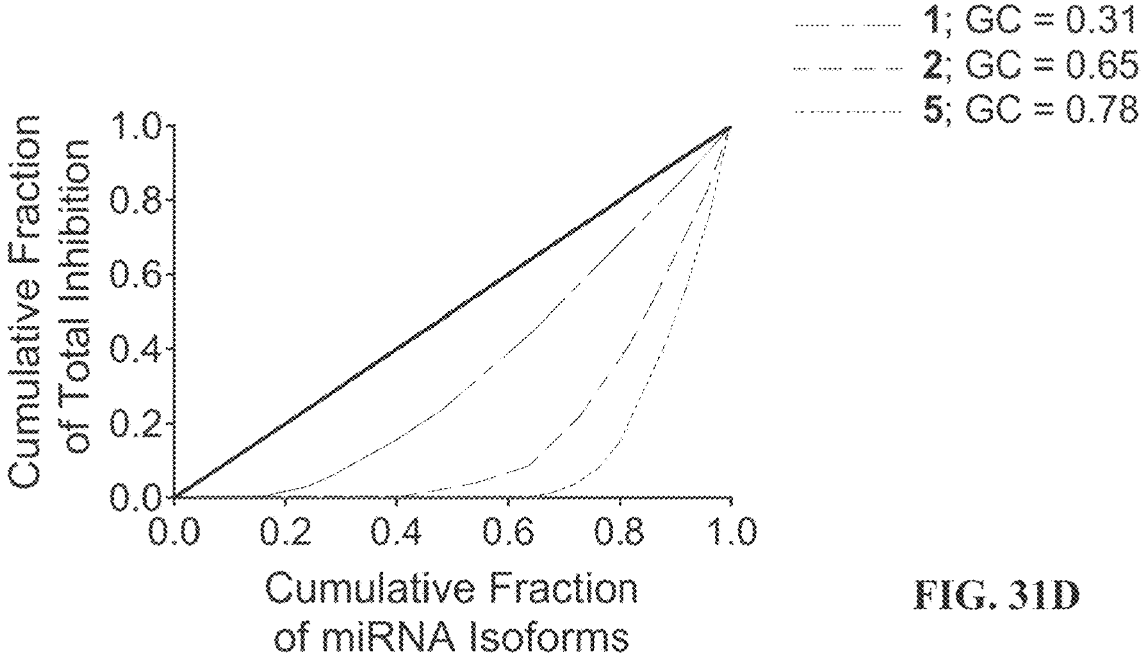
Figure 32A:
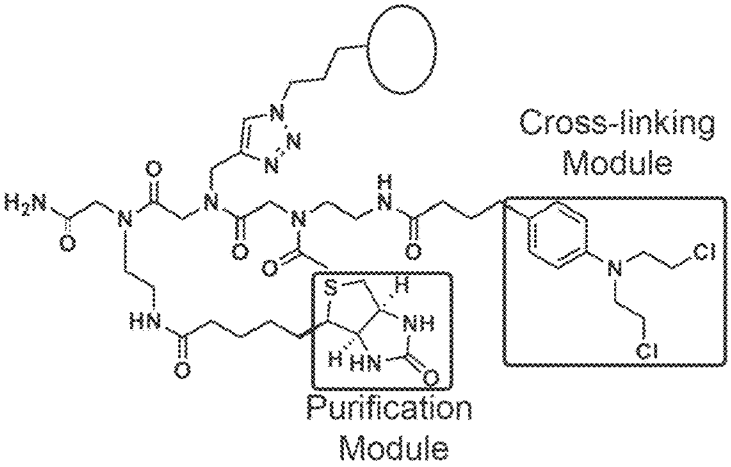
FIGS. 32A-32E. Chemical cross-linking and isolation by pull-down (Chem-CLIP) analysis using compounds 8 and 9.
Figure 32A:
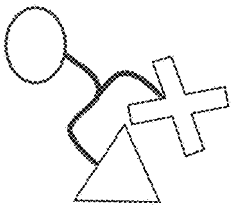
Figure 32A:
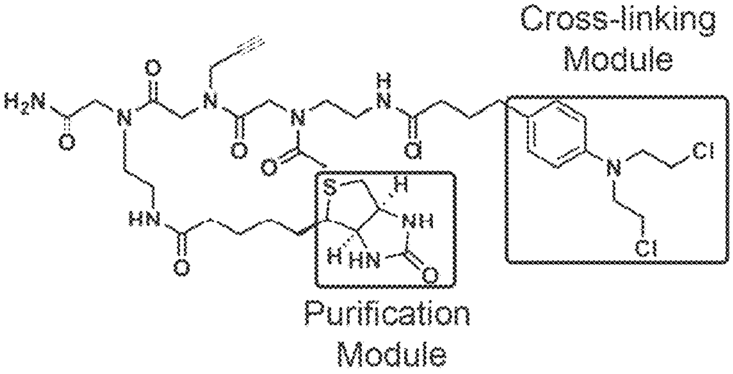
Figure 32A:
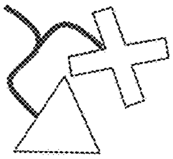
Figure 32B:
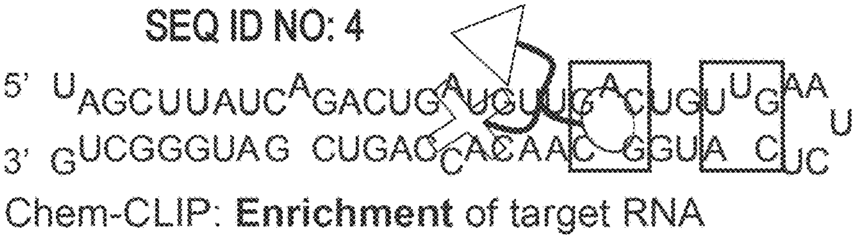
Figure 32B:
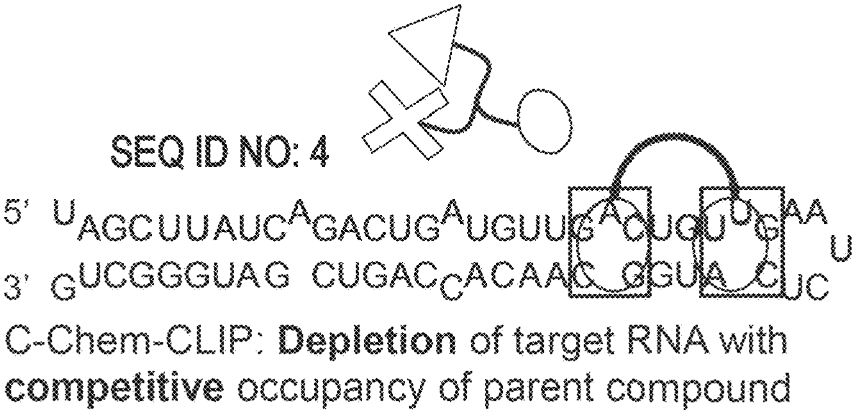
Figure 32C:
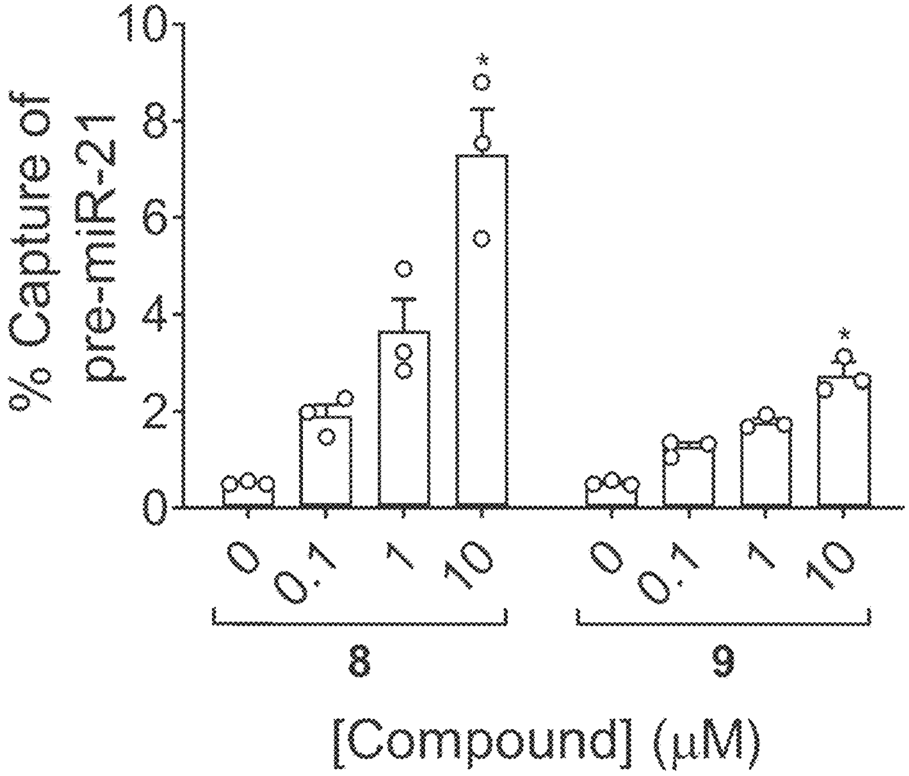
Figure 32D:
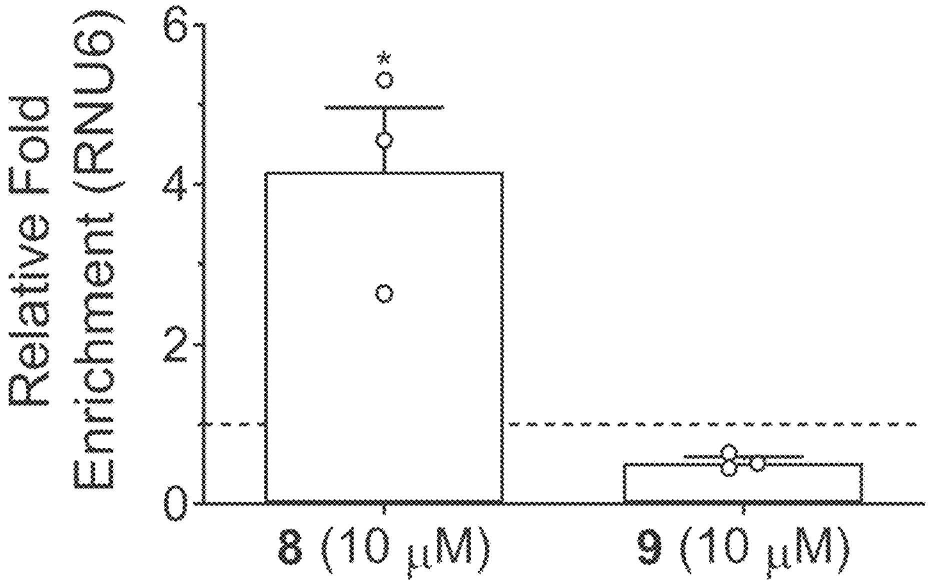
Figure 32E:
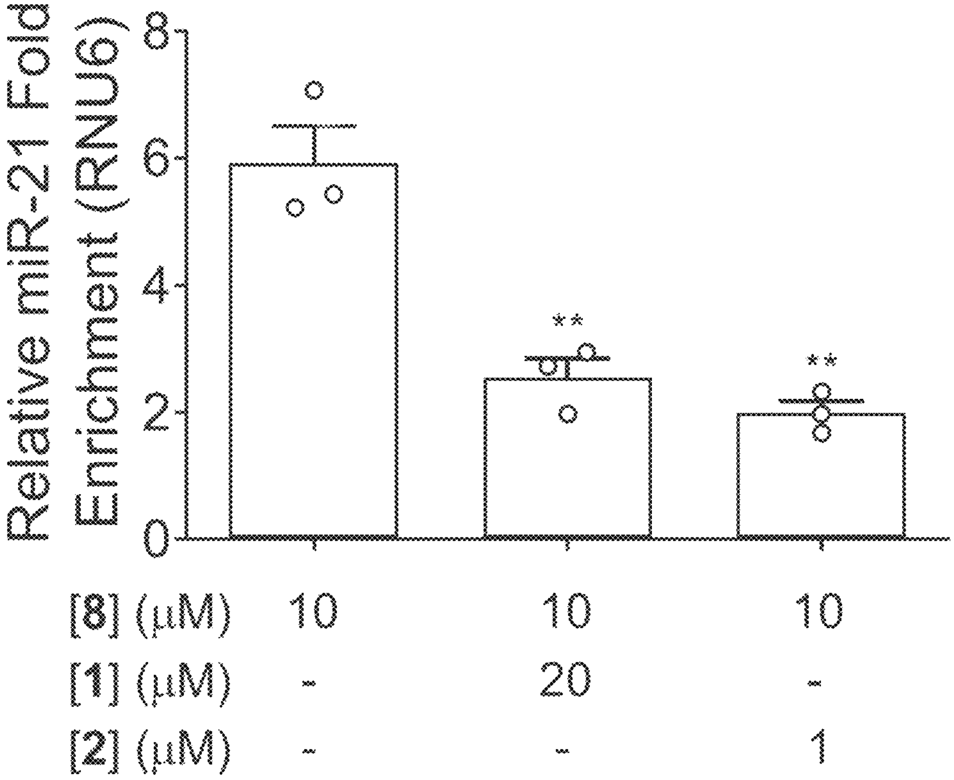
Figure 33A:
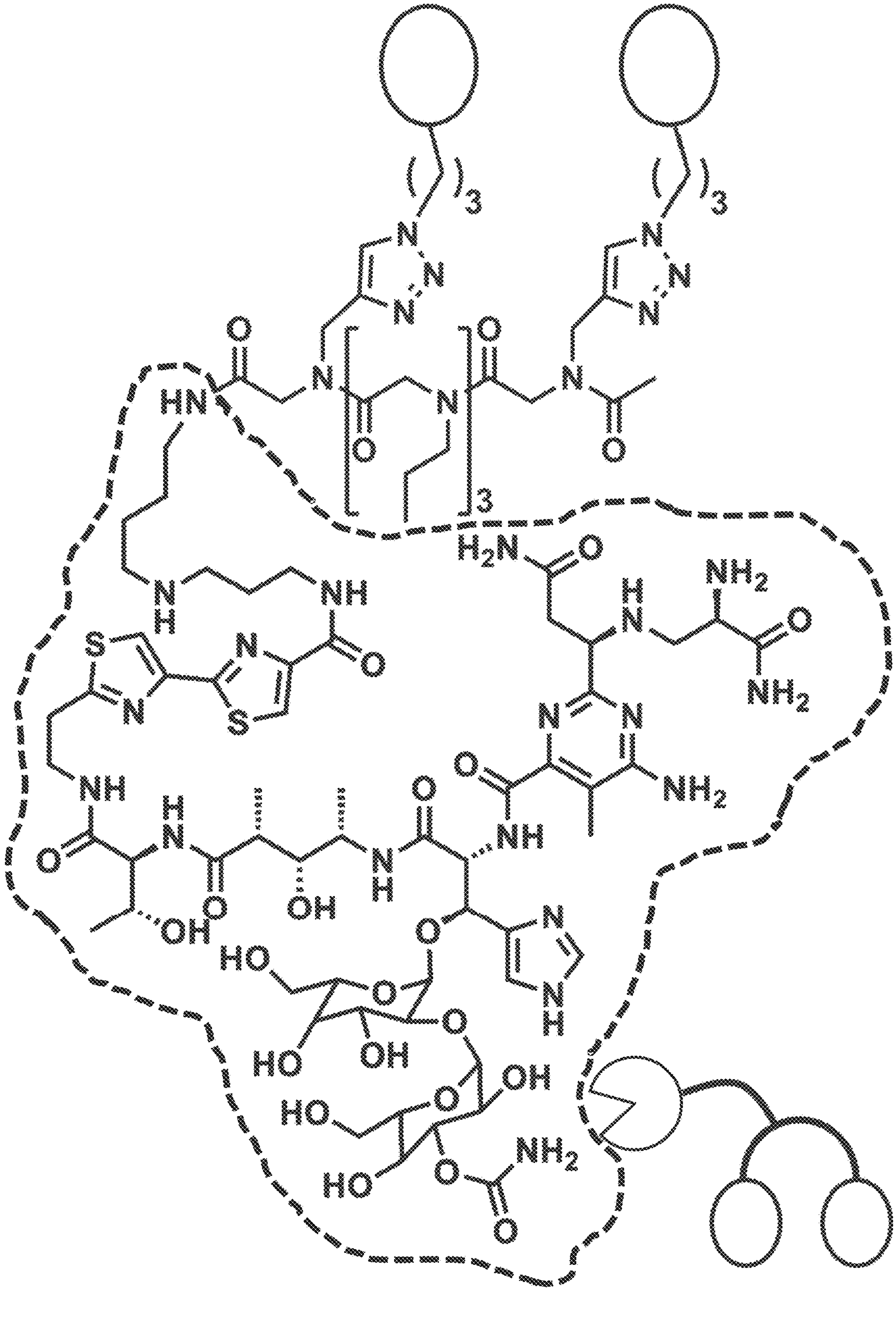
FIGS. 33A-33D. Parent dimer appended with Bleomycin A5 cleavage module (10) maps the pre-miR-21 binding site in vitro.
Figure 33B:
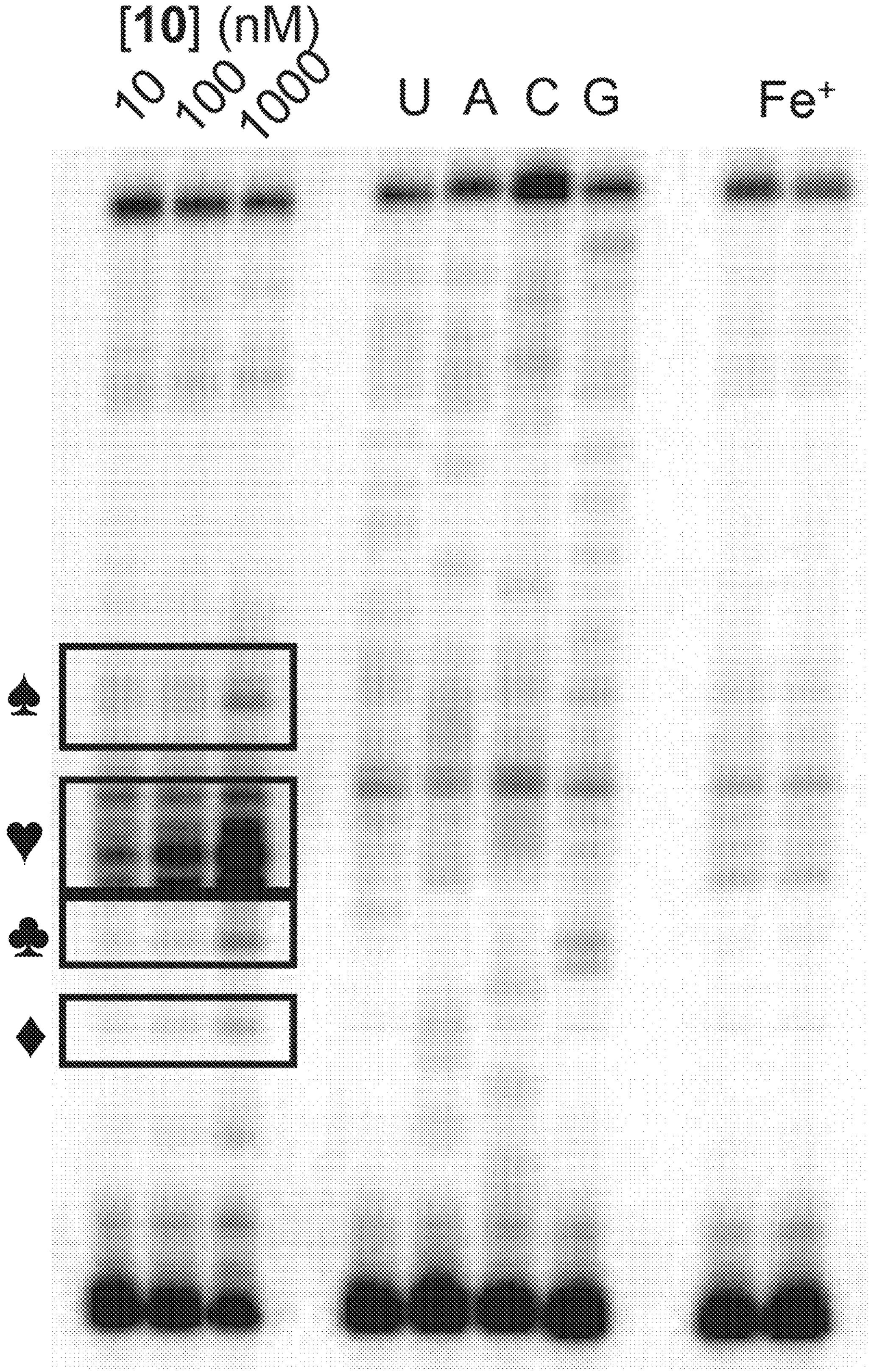
Figure 33C:
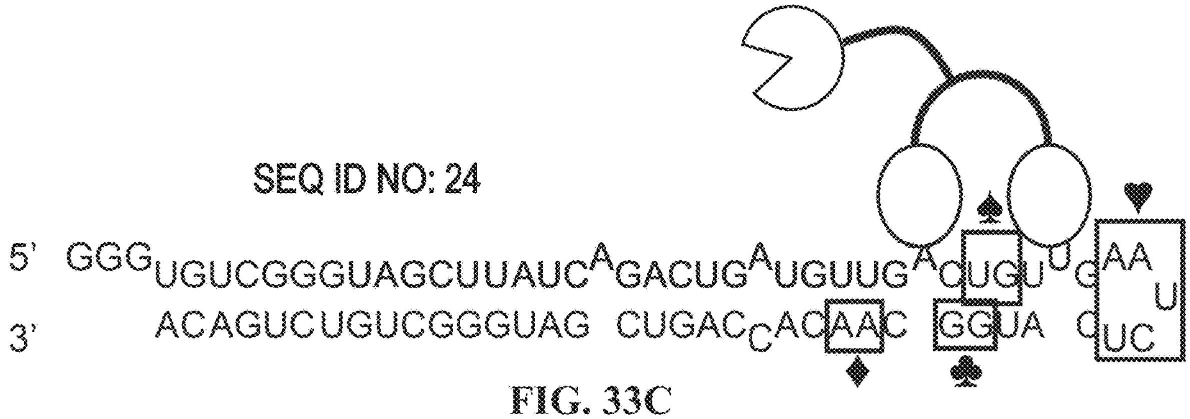
Figure 33D:
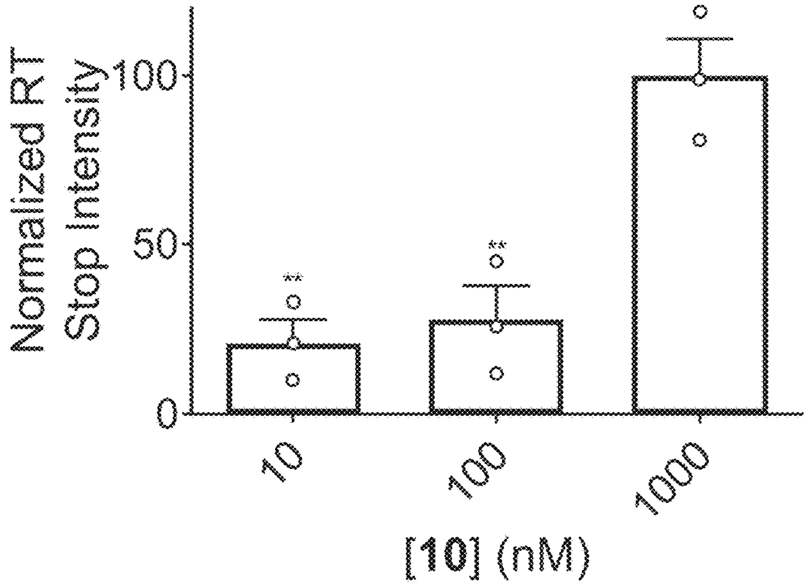
Figure 34A:
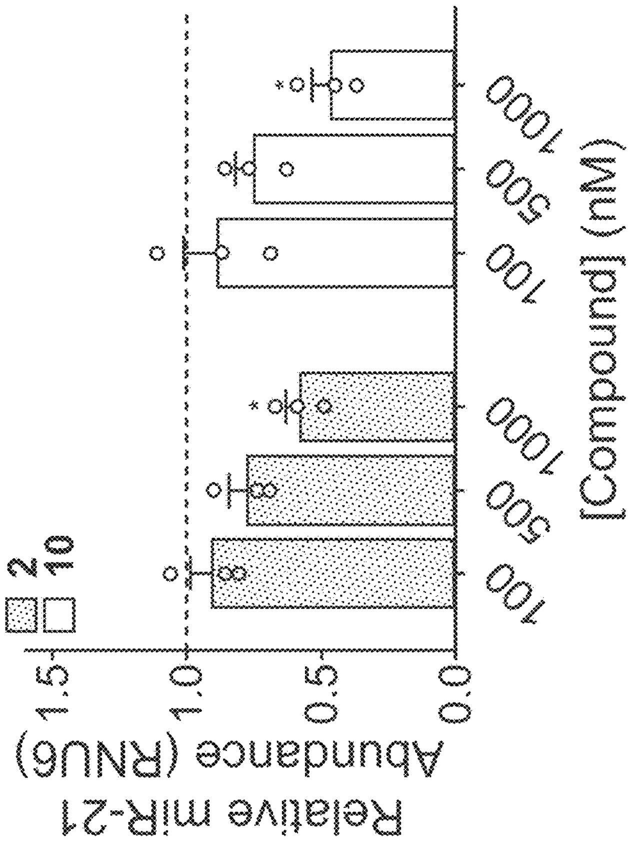
FIGS. 34A-34B. Cleavage of pre-miR-21 in MDA-MB-231 cells by compound 10.
Figure 34B:
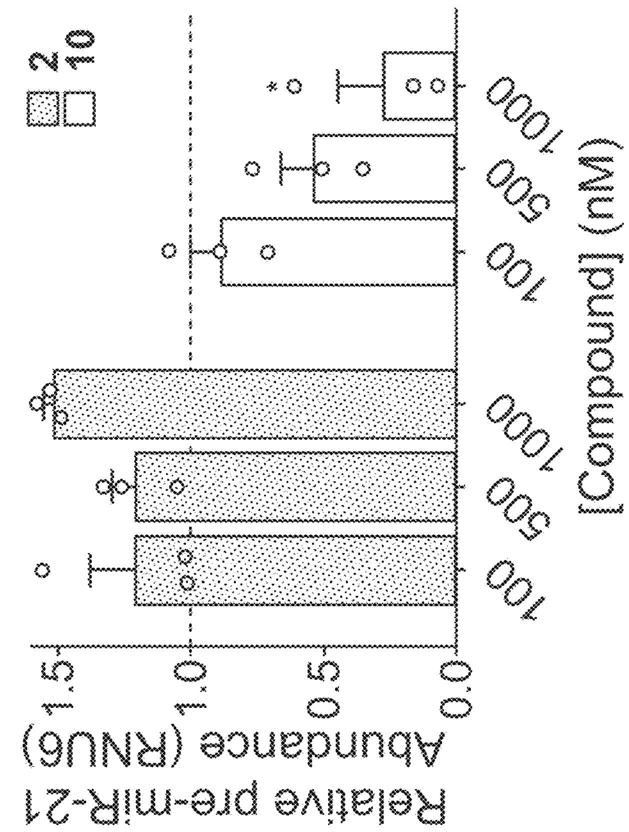
Figure 35A:
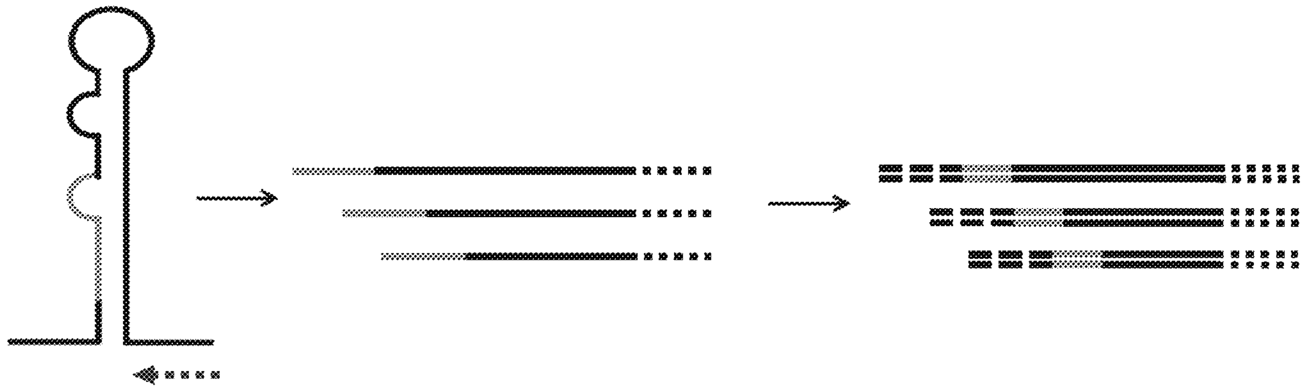
FIGS. 35A-35C. Ribo-SNAP by compound 10 in cells indicates small molecule binding sites via cleavage.
Figure 35B:
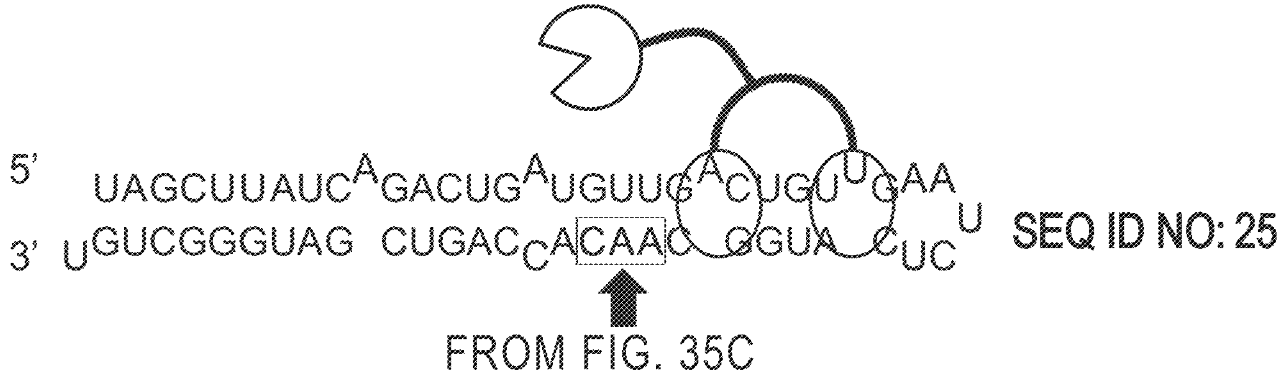
Figure 35C:
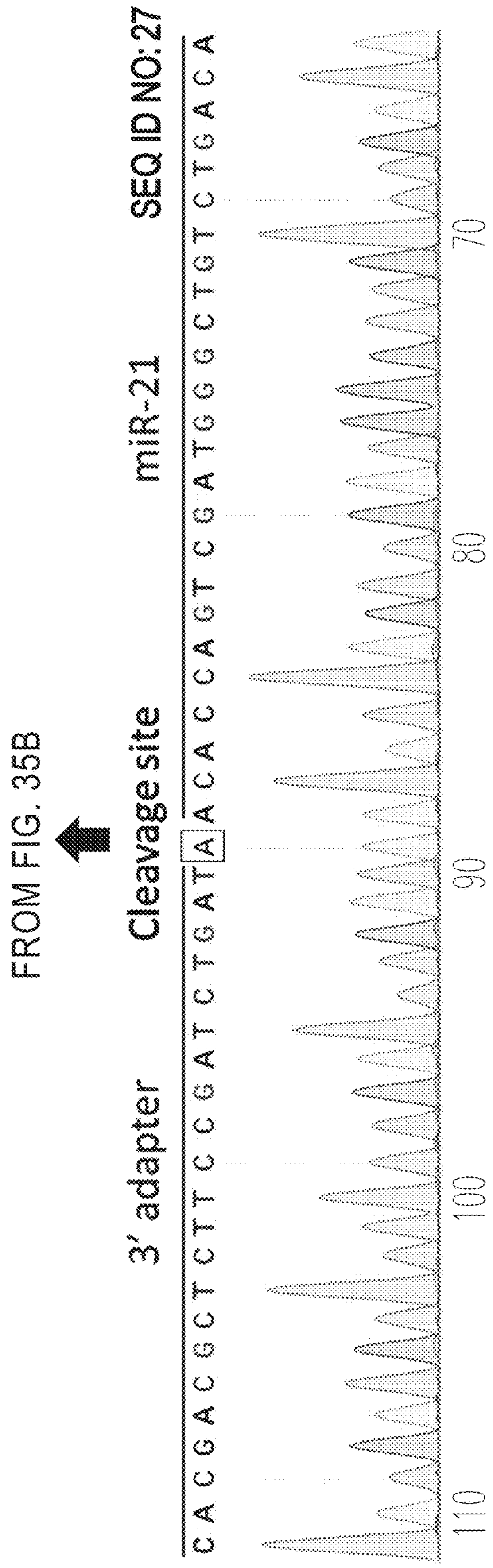
Figure 36A:
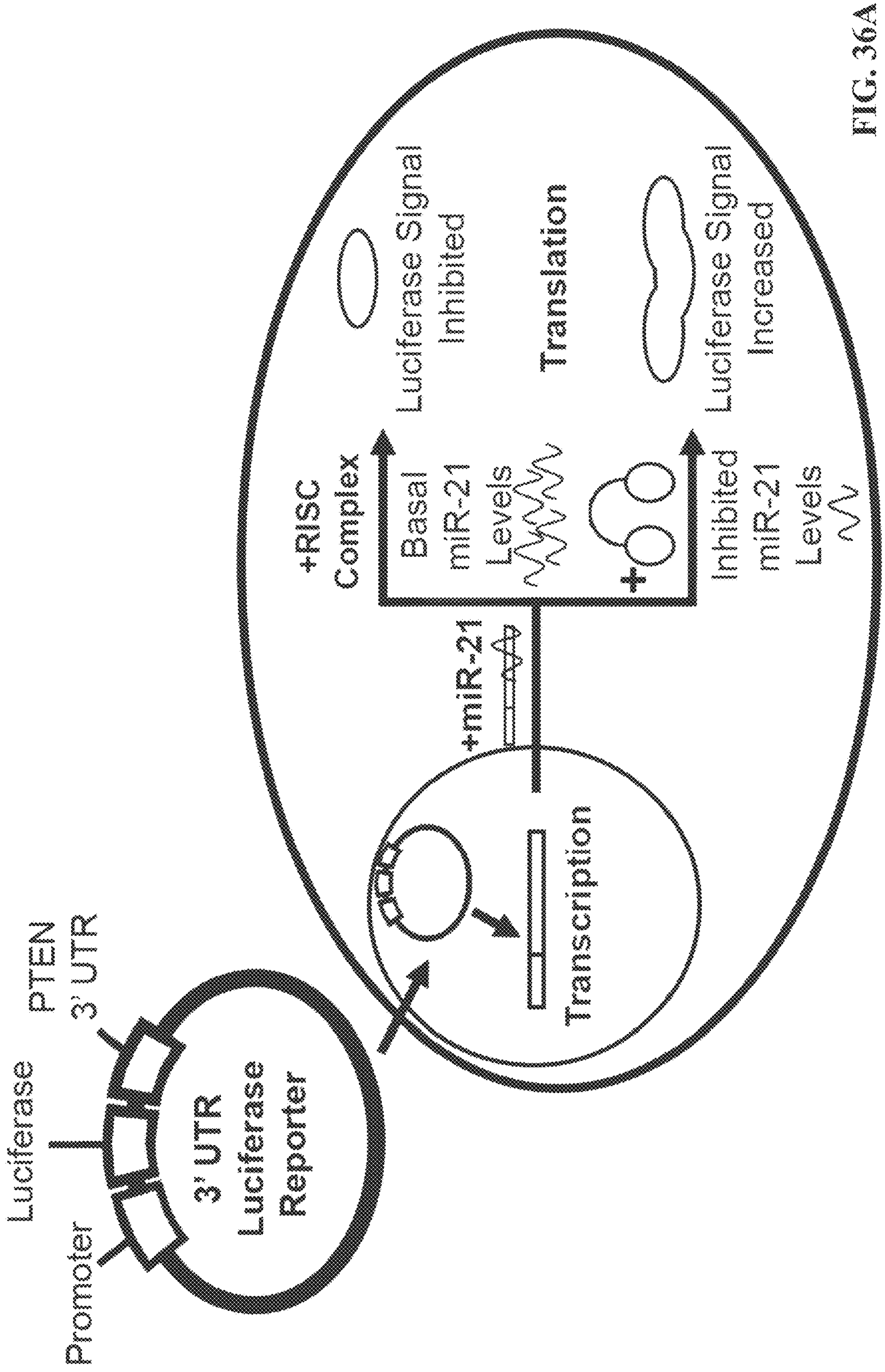
FIGS. 36A-36D. Effect of small molecule inhibition of mature miR-21 on downstream protein levels.
Figure 36C:
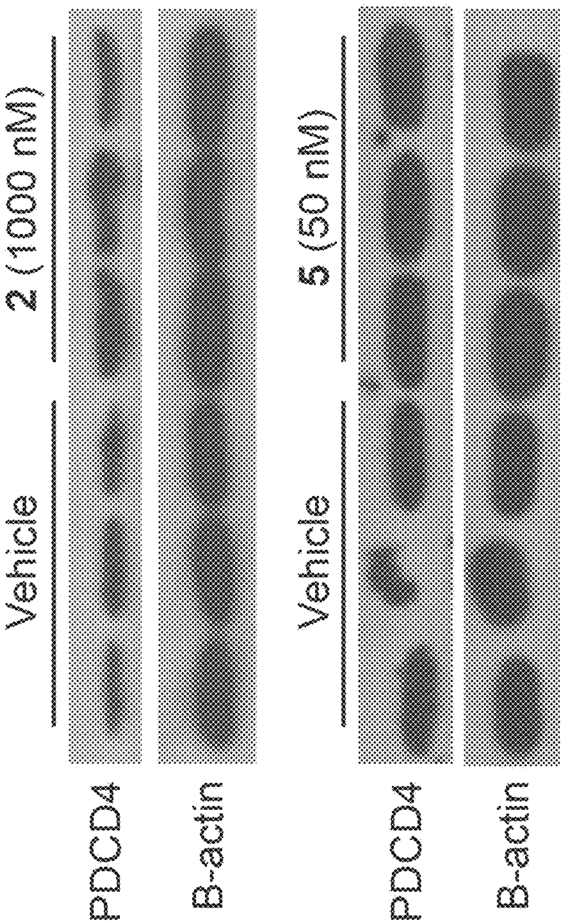
Figure 36B:
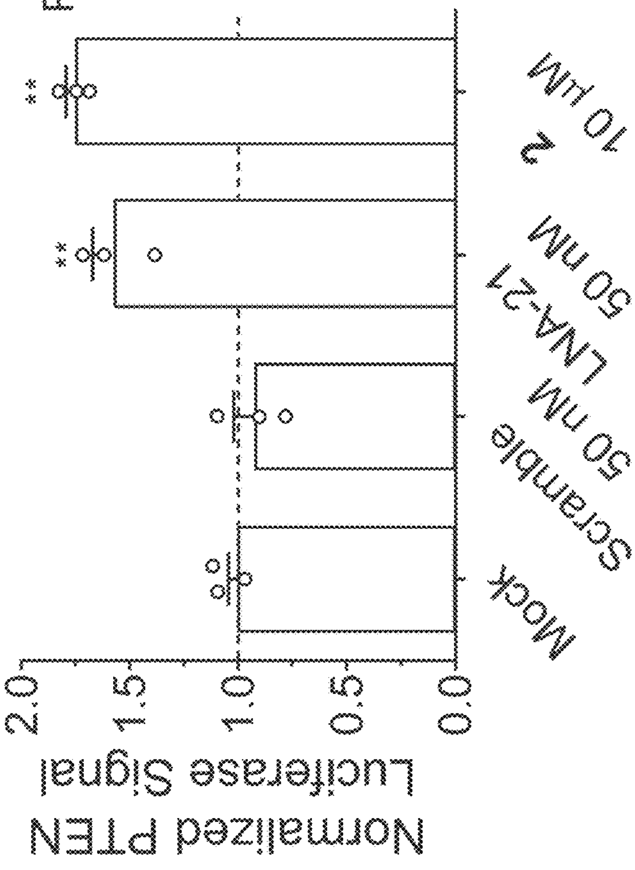
Figure 36D:
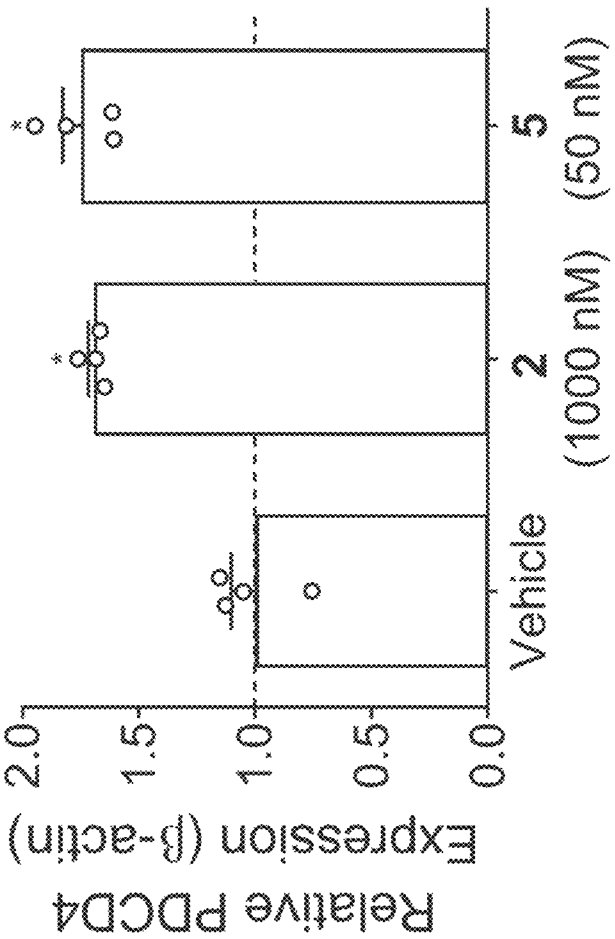

The designators r, s, $R^8$ and the ligand group L are the same as provided in the Summary. The compound of Formula 2 selectively binds pre-miR-21 with a 20-fold enhancement over the compound of Formula 1. See the examples section, FIGS. 28A-28B.

Dimerization of the compound embodiments of Formula I with $R^9$ as an azidoalkyl amino group and $R^8$ as methyl may be accomplished with a polyamino acid ligand L such as a polyglycine derivative of from 3 to 8 glycine residues. The polyamino acid ligand L may be modified at the nitrogens of its terminal glycine moieties by substitution of those nitrogens with alkynyl groups of the formula $$—(CH_2)_t—C≡CH$$

wherein designator t is an integer of 1 to 4. The dimerization with a polyamino acid derivative ligand L based on glycine afforded embodiments of the compound of Formula 2.

To accomplish the dimerization with a polyamino acid ligand L such as a polyglycine ligand with the appropriate alkynyl groups, the amine and carboxyl termini may be protected or modified as amide groups. The copper catalyzed addition of the azido group of the above described Formula 1 to the alkynyl group of such a ligand L will produce the connecting triazole moieties of the dimer of Formula 2 (Huisgen cycloaddition). Depending on the number of glycine groups of the ligand, binding strength with an RNA model of pre-miR-21 may be varied from moderate to strong. These results are provided in the following examples section.

Preferably, embodiments of the precursor of polyglycine derivative L of Formula 2 are the ligand Precursor Formula 20 wherein X is hydrogen, hydroxyl or amino, Y is oxygen or —NH—, designator n is an integer of 1 to 4, designator o is zero or 1, designator p is an integer of 1 to 6, $R^{10}$ is alkyl of 1 to 4 carbons, $R^{11}$ is hydrogen or acetyl. In this depiction of Formula 20, the numbers and letters 2, n, o, 10, p and 11 are to be considered the same as the subscripts of Formula 20 of the foregoing Summary.

Formula 20

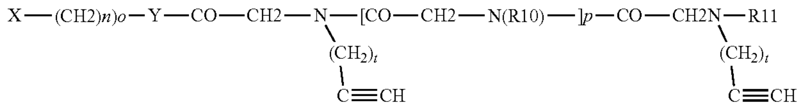

Formula 20 can be combined with the azide form of Formula 1 (Huisgen cycloaddition) to provide Formula 2 given above. For Formula 2, ligand L is Formula L-1 wherein Nr, EG, Y, My $R^{10}$ and $R^{11}$ are the same as given in the foregoing summary. The group Nr-$((EG)_m$-$(CH_2)_n)_o$— may be added to Formula 20 with Y as OH or $NH_2$ and o as zero for Formula 20 by its precondensation or postcondensation with a polyethylene glycol or polypropylene glycol carrying the Nr group and its opposite terminus bound to an alkylenyl diol or aminoalkylenyl alcohol. The result substitutes Nr-$(EG)_m$ onto X as hydroxyl or amino and the designator o as other than zero.

Nr-$((EG)_m$-$(CH_2)_n)_o$—Y—CO—$CH_2$—N(My)-[CO—$CH_2$—N($R^{10}$)—$]_p$—CO—$CH_2$N(My)-$R^{11}$ Formula L-1

When Nr is Formula C-1 and appropriate choice of the other designators and substituents is made, the result is Formula 5. Formula 5 is a preferred version of Formula 2 and provides significant binding strength with pre-miR-21.

Biology

In addition to the investigation of the binding capacity of embodiments of compounds of Formulas 1 and 2 with in vitro forms of pre-miR-21, the inhibition capacity of these compounds was investigated by whole cell assay. Triple negative breast cancer cells (MDA-MB-231) were treated with Formula 1 (embodiment with $R^8$ as methyl and $R^9$ as azidopropylamino, 10 μM) and inhibited miR-21 production by 50%, while the levels of pre-miR-21 were increased by 1.3-fold, as expected for a compound that acts by inhibiting Dicer processing. See FIGS. 30A-30D. Full miR profiling showed that this embodiment of Formula 1 was modestly selective, see FIG. 1F.

Figure 1E:
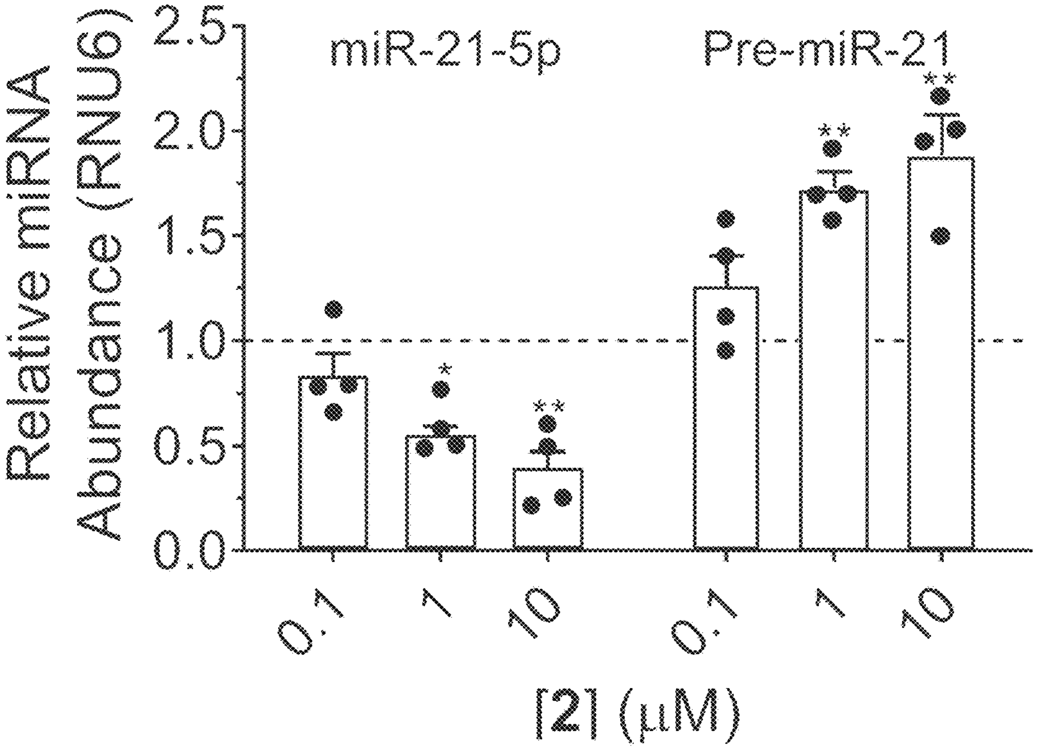
Figure 1F:
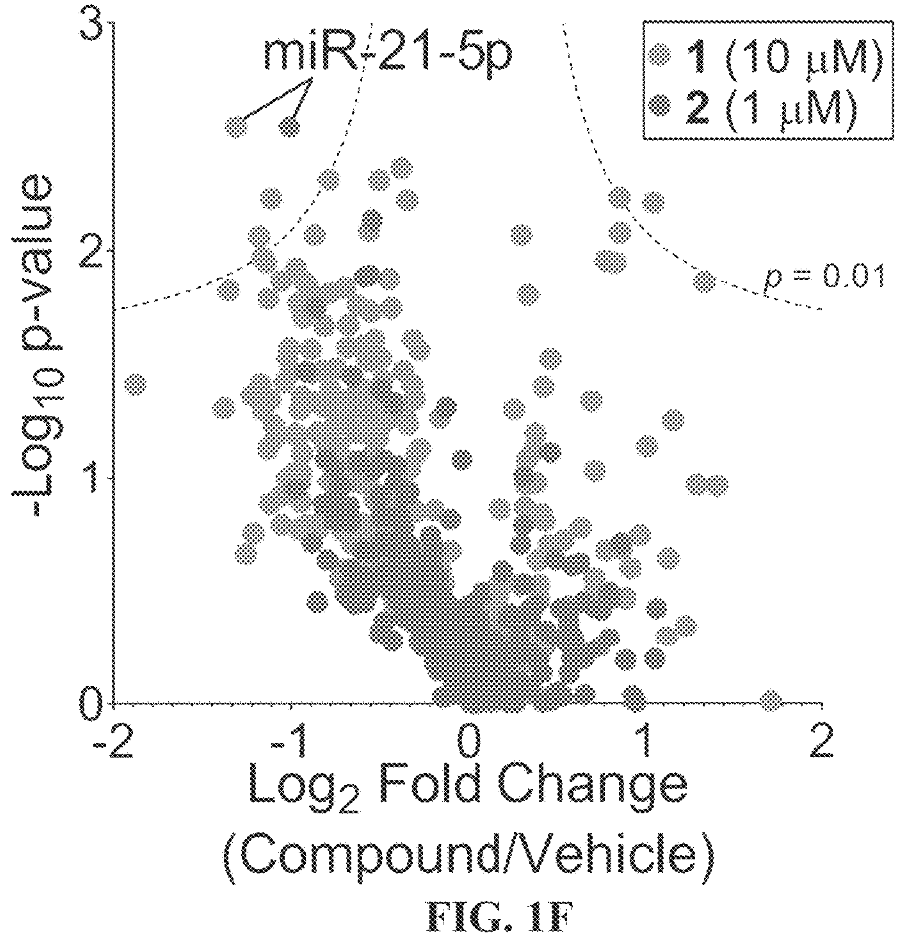

The biological assay of compound Formula 2 with respect to pre-miR-21 in vitro and in MDA-MB-231 cells demonstrated that the compound of Formula 2 affected pre-miR-21 in cells with an $IC_{50}$ of 1 μM. An increase in the levels of pre-miR-21 supported inhibition of biogenesis as a mode of action (FIG. 1E). Full miR profiling showed that Formula 2 only significantly affected miR-21, as expected based on the design strategy (FIG. 1F).

The binding of the compound of Formula 2 with pre-miR-21 was confirmed by using Chemical Cross-Linking and Isolation by Pulldown (Chem-CLIP) a strategy that utilizes a proximity-based reaction to cross-link compounds to their cellular targets. Cells were treated with both the active Chem-CLIP and inactive Chem-CLIP control probe without RNA binding modules, see FIGS. 32A-32E. The active compound selectively enriched levels of pre-miR-21 by ~2.5-fold at 10 μM FIGS. 32A-32E. Subsequently, Competitive Chem-CLIP (C-Chem-CLIP) was used to assess the relative occupancy of Formulas 1 and 2 to pre-miR-21 in MDA-MB-231 cells. Compound Formula 2 was 20-fold more potent in occupying pre-miR-21 in cells than Formula 1, the predicted difference based on the reactive affinity with compounds having similar cellular permeability, FIGS. 32A-32E. The cellular binding sites of Formula 2 to pre-miR-21 were mapped by conjugating Formula 2 to a bleomycin RNA cleaving module and showed that, as expected, the cleavage site is proximal to the designed binding site, FIGS. 33A-35C.

Figure 37A:
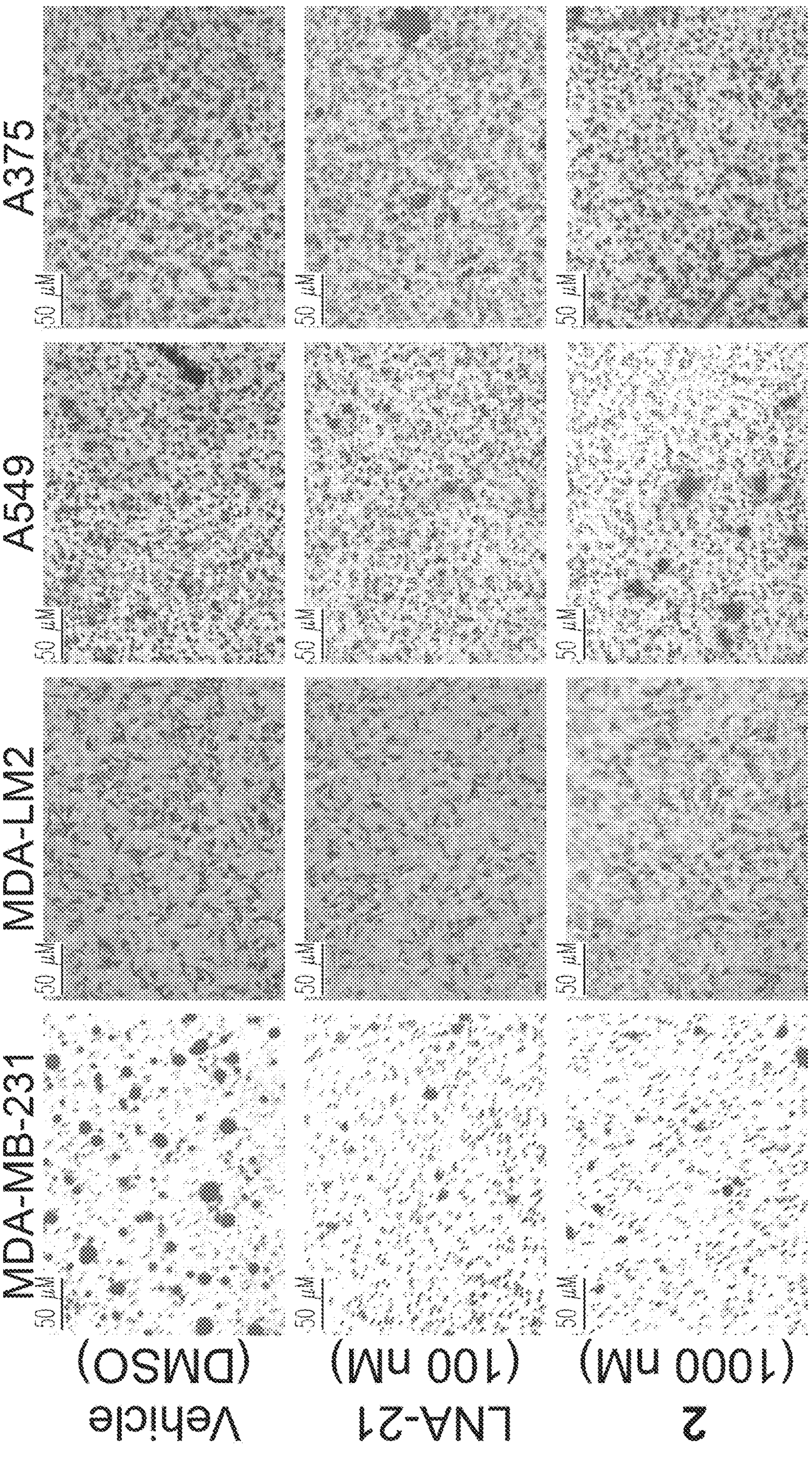
FIG. 37A-37B. Application of formula 2 in various cell lines inhibits invasive phenotype by decreasing mature miR-21 levels.
Figure 37B:
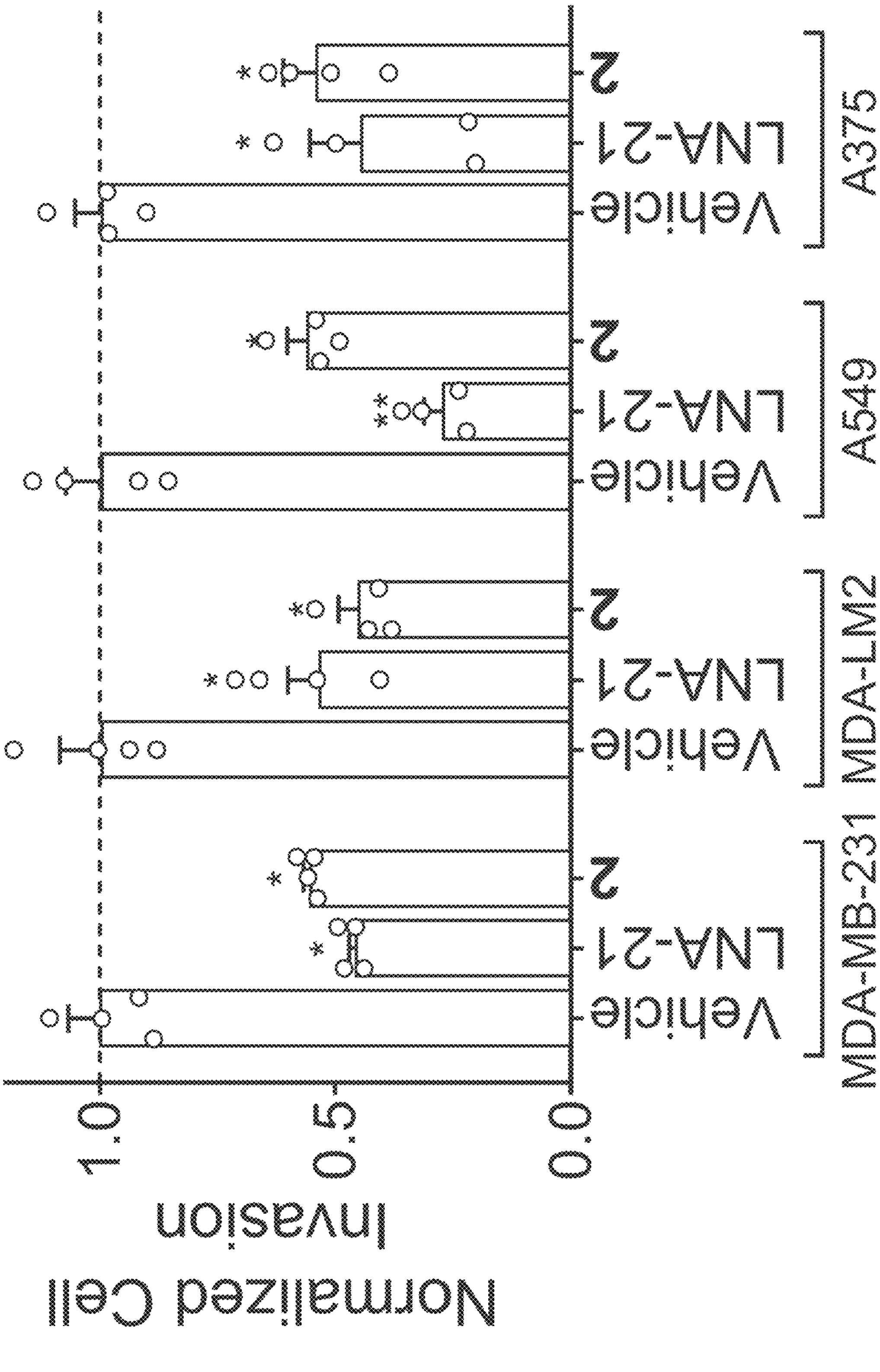
Figure 38A:
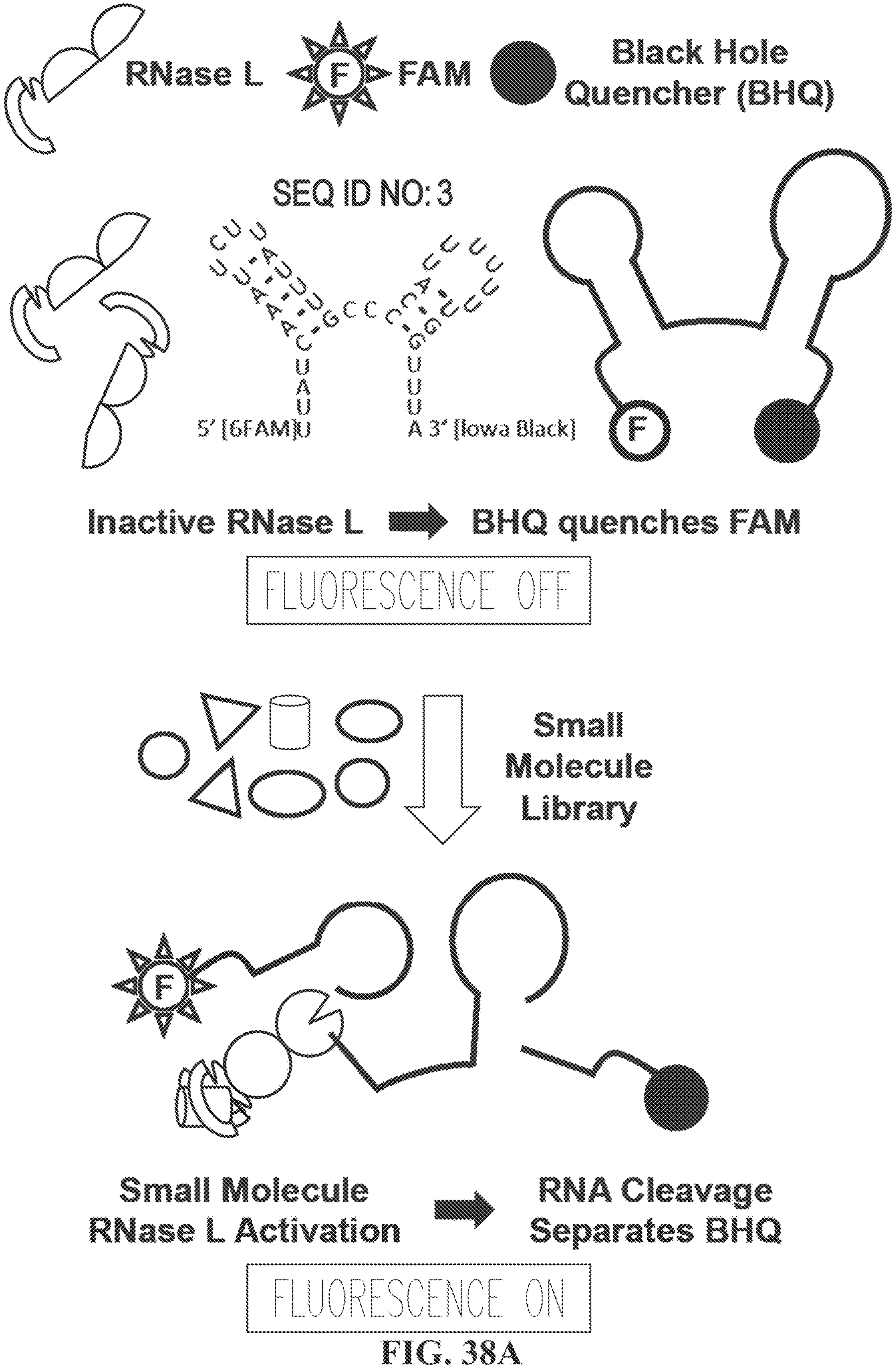
FIGS. 38A-38F. Screening of small molecules to identify C1-3 (3) as an RNase L recruitment module.
Figure 38B:
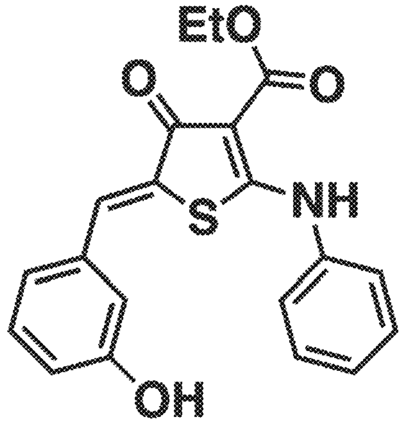
Figure 38B:
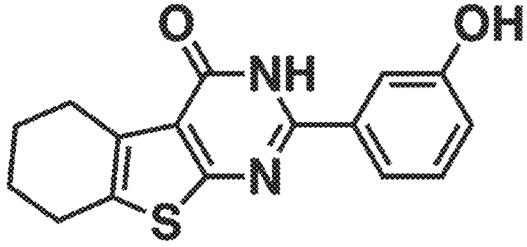
Figure 38C:
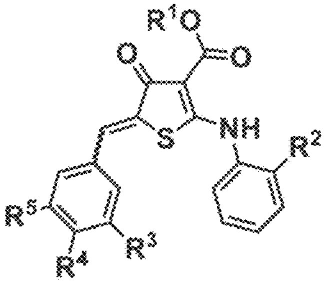
Figure 38D:
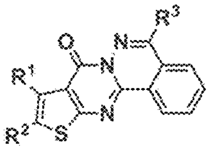
Figure 38D:
Figure 38D:
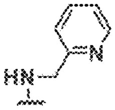
Figure 38D:
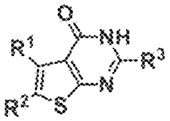
Figure 38D:
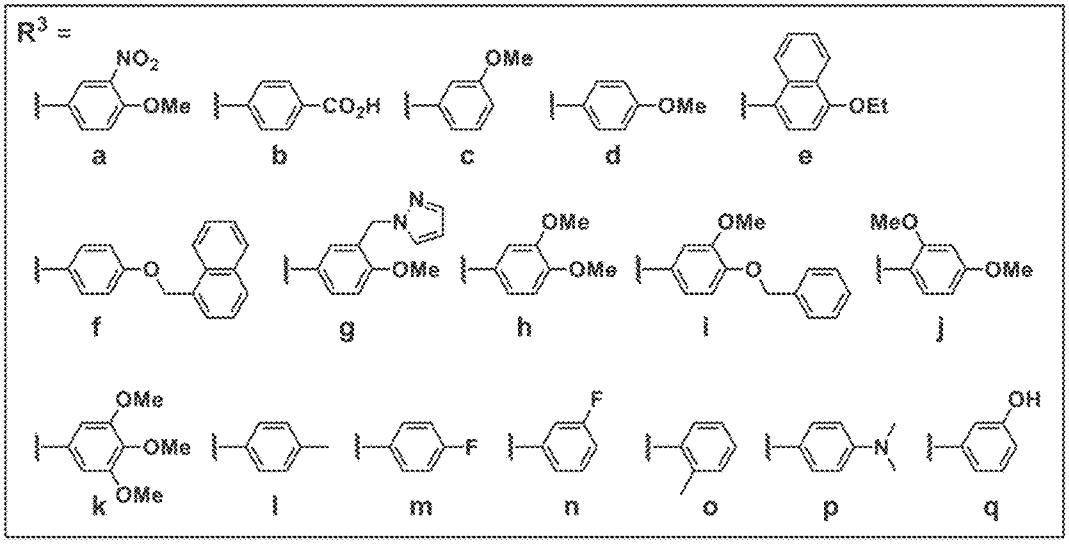
Figure 38E:
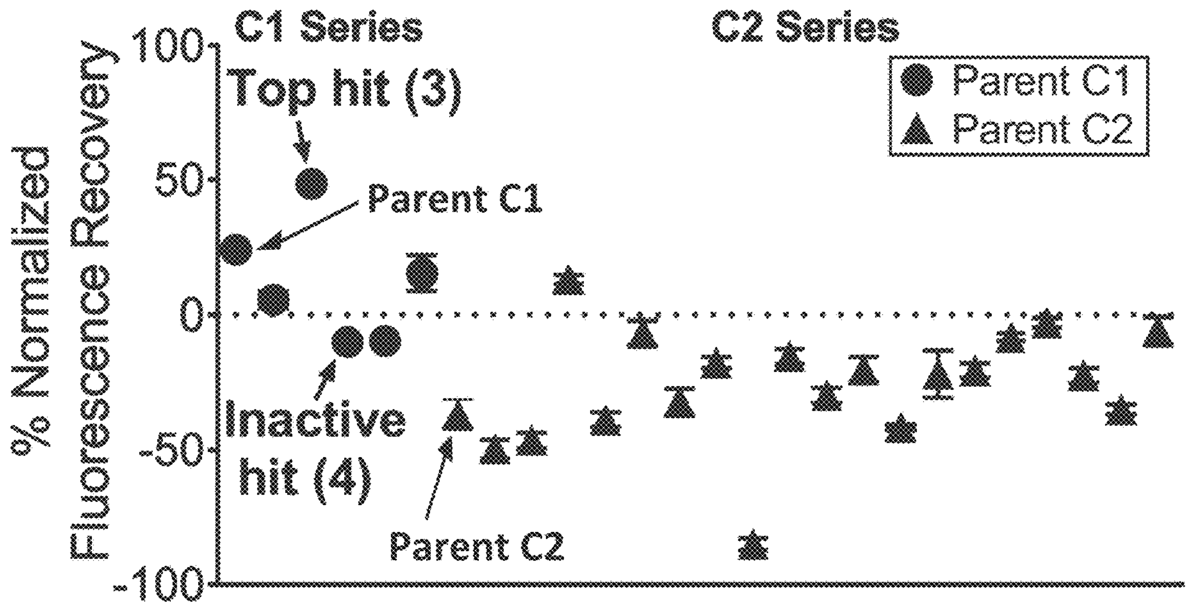
Figure 38F:
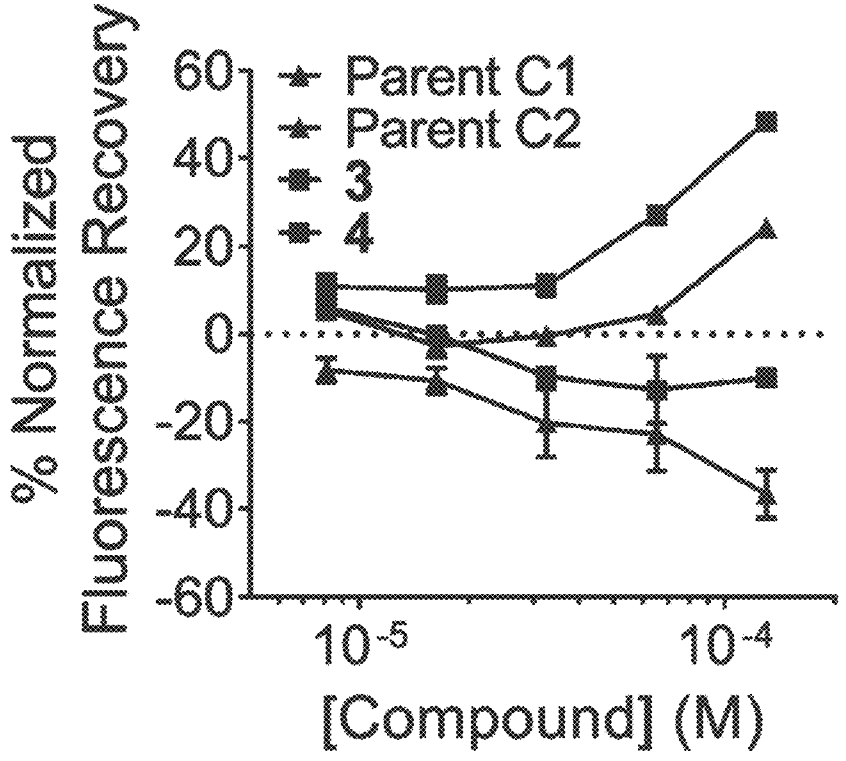
Figure 39A:
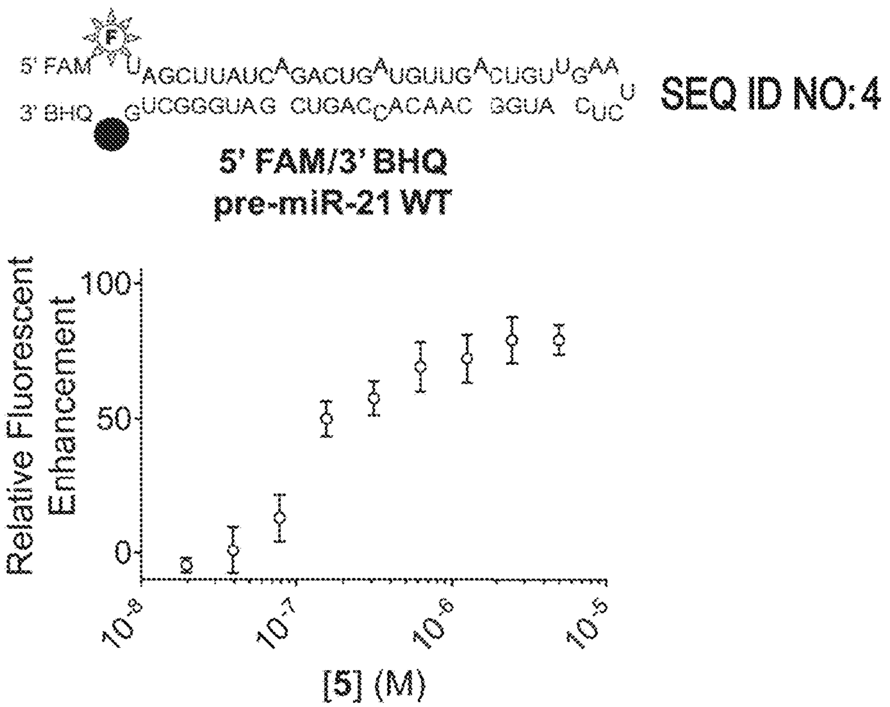
FIGS. 39A-39C. In vitro characterization of formula 2 appended with compound 3 (5).
Figure 39B:
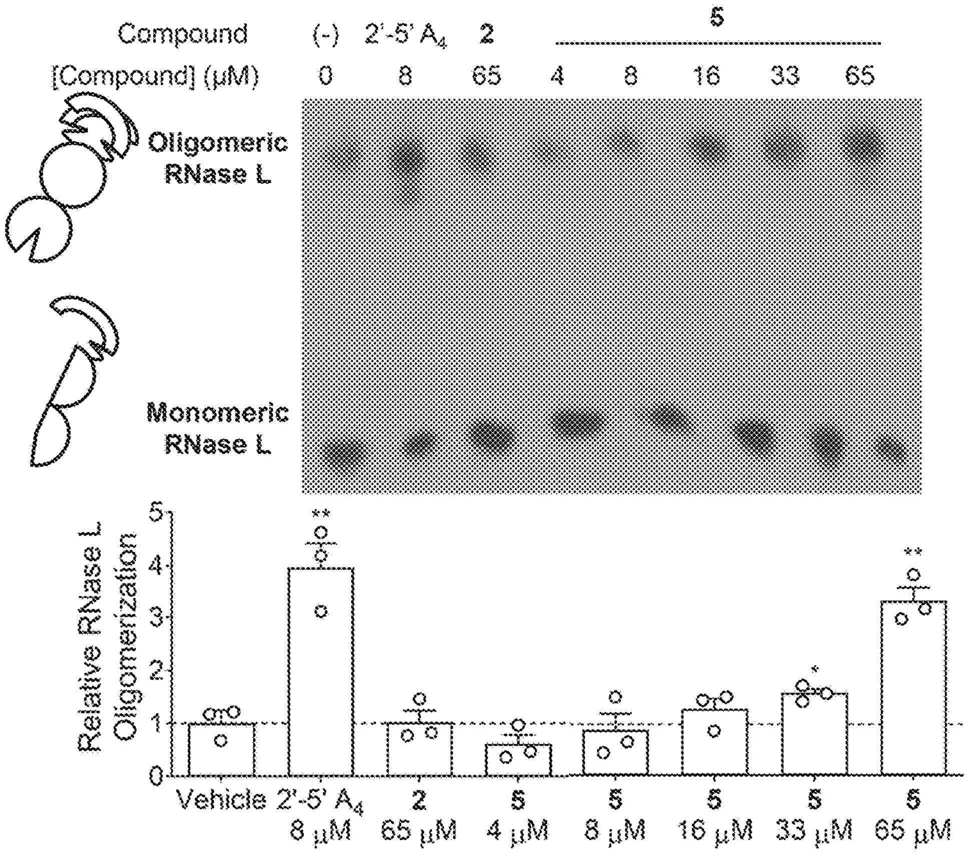
Figure 39C:
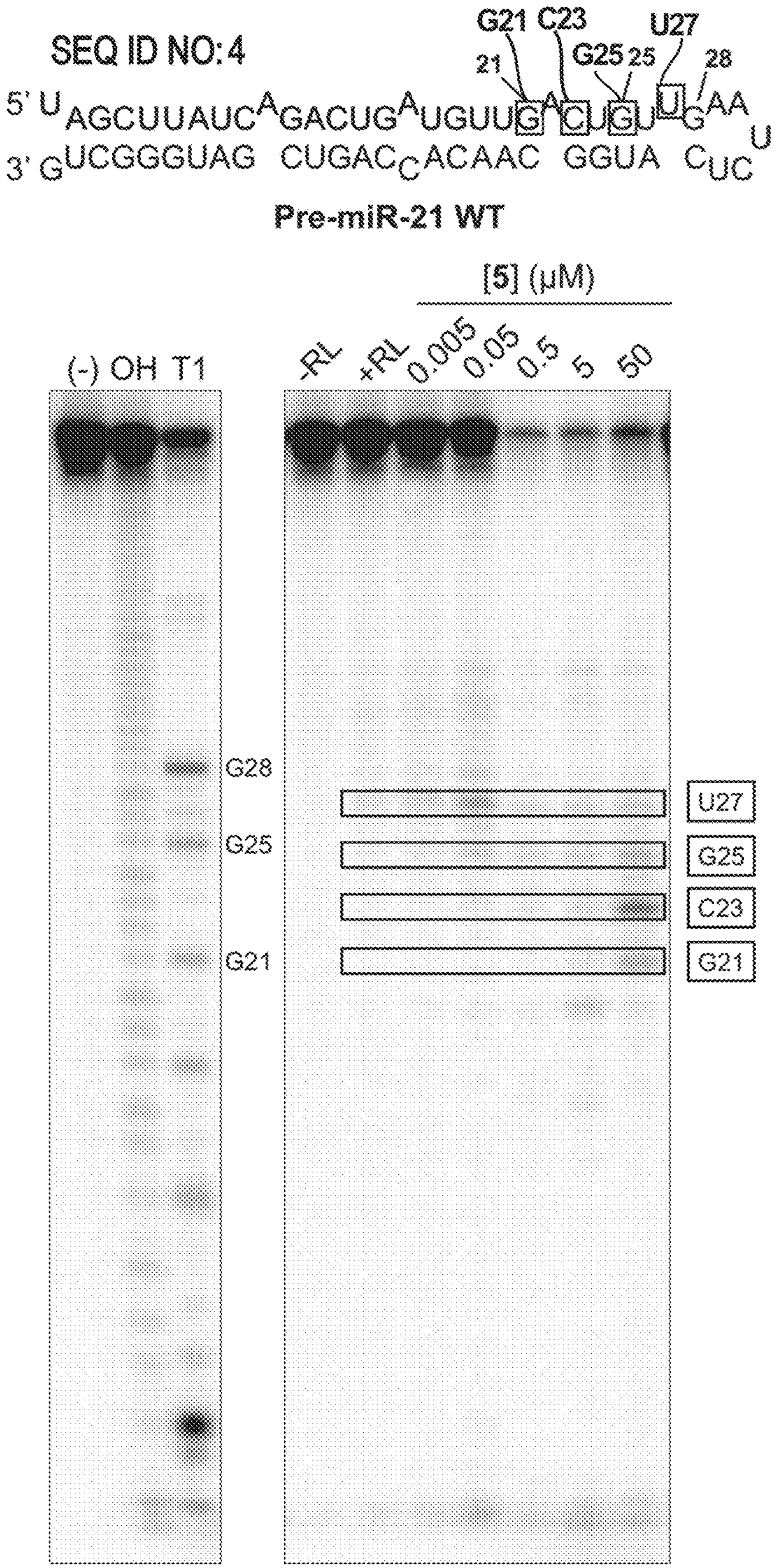

The ability of the compound of Formula 2 to engage programmed cell death or PCD was also investigated. Proteins that are translationally repressed by miR-21 include programmed cell death protein 4 (PDCD4) and phosphatase and tensin homolog (PTEN). Treatment of MDA-MB-231 cells with the compound of Formula 2 increased the levels of PDCD4 and PTEN by ~50% at 1 μM and 10 μM, respectively, FIGS. 36A-36D. As miR-21 inhibition affects the invasive and metastatic properties of MDA-MB-231 cells, invasion assays were used to evaluate phenotype modulation. Treatment with the compound of Formula 2 inhibited the invasive properties of MDA-MB-231, FIGS. 37A-37B), thus indicating a treatment for metastasis. The biological effect of the compound of Formula 2 was also studied in several other cancer cell model types and in all cases the compound of Formula 2 silenced miR-21 and modulated a miR-21-associated invasive phenotype, FIGS. 30A-30D, FIGS. 37A-37B.

Nuclease Degradation of Pre-MiR-21

Naturally, 2'-5'-linked oligoadenylates (2'-5' A) dimerize and activate RNase L. See M. G. Costales, Y. Matsumoto, S. P. Velagapudi, M. D. Disney, Small molecule targeted recruitment of a nuclease to RNA. *J. Am. Chem. Soc.* 140, 6741-6744 (2018). In addition to oligoadenylates, several model styrenyl thiophenyl and thiophenylpyrimidinyl heterocycles have been identified as substitutes for 2'-5' A to modestly activate this process. See C. S. Thakur, B. K. Jha, B. Dong, J. Das Gupta, K. M. Silverman, H. Mao, H. Sawai, A. O. Nakamura, A. K. Banerjee, A. Gudkov, R. H. Silverman, Small-molecule activators of RNase L with broad-spectrum antiviral activity. *Proc. Natl. Acad. Sci. U.S.A.* 104, 9585-9590 (2007).

Based on this information, study and structural revision of the model heterocycles were made to produce an appropriately activating heterocycle model. The result was a styrenyl thiophenyl compound of Formula C1 in which $R^3$ is hydroxyl, $R^4$ is methoxy and $R^5$ is hydrogen. This styrenyl thiophenyl compound was found to bind to inactive monomeric RNase L and dimerize it into an active nuclease. It was also found that Formula C1 with $R^3$ as methoxy, $R^4$ as hydroxyl and $R^5$ as hydrogen does not provide appropriate activation of RNase L and Formula C1 with $R^3$ as hydroxyl and both of $R^4$ and $R^5$ as hydrogen provided only minimal activation of RNase L. The model studied included Formula C1 with $R^1$ as alkyl of 1 to 3 carbons, $R^2$ as hydrogen or fluoro, $R^3$ as hydrogen, hydroxyl or methoxy, $R^4$ as hydrogen, hydroxy, methoxy or dimethylamino and $R^5$ is hydrogen, hydroxy or methoxy.

Formula C1

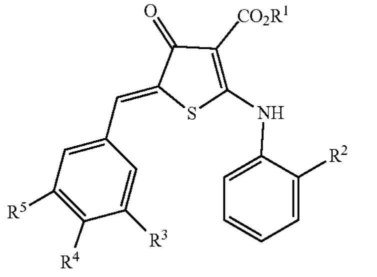

The styrenyl thiophenyl compound of Formula C-1 with $R^3$ as hydroxyl, $R^4$ as methoxy and $R^5$ as hydrogen was conjugated at its $R^4$ position to the compound of Formulas 1 and 2. The conjugation improves the potency of compounds of Formulas 1 and 2. The conjugation enables the conjugate to recruit RNase L to induce enzymatic cleavage of pre-miR-21. Conjugation with the compound of Formula 2 provides Formula 2 with Nu as Formula C1, and an embodiment of this conjugation is the compound of Formula 5 set out in the Summary; FIGS. 2A-2C, FIG. 3A, FIGS. 38A-38F, FIGS. 39A-39C.

cells as one mole of Formula 5 cleaves 26 moles of pre-miR-21 (SI Appendix Table S1). This value is consistent with the enhancement in potency of 5 versus 2. Significantly decreased miR-21 levels were also observed with a single Formula 5

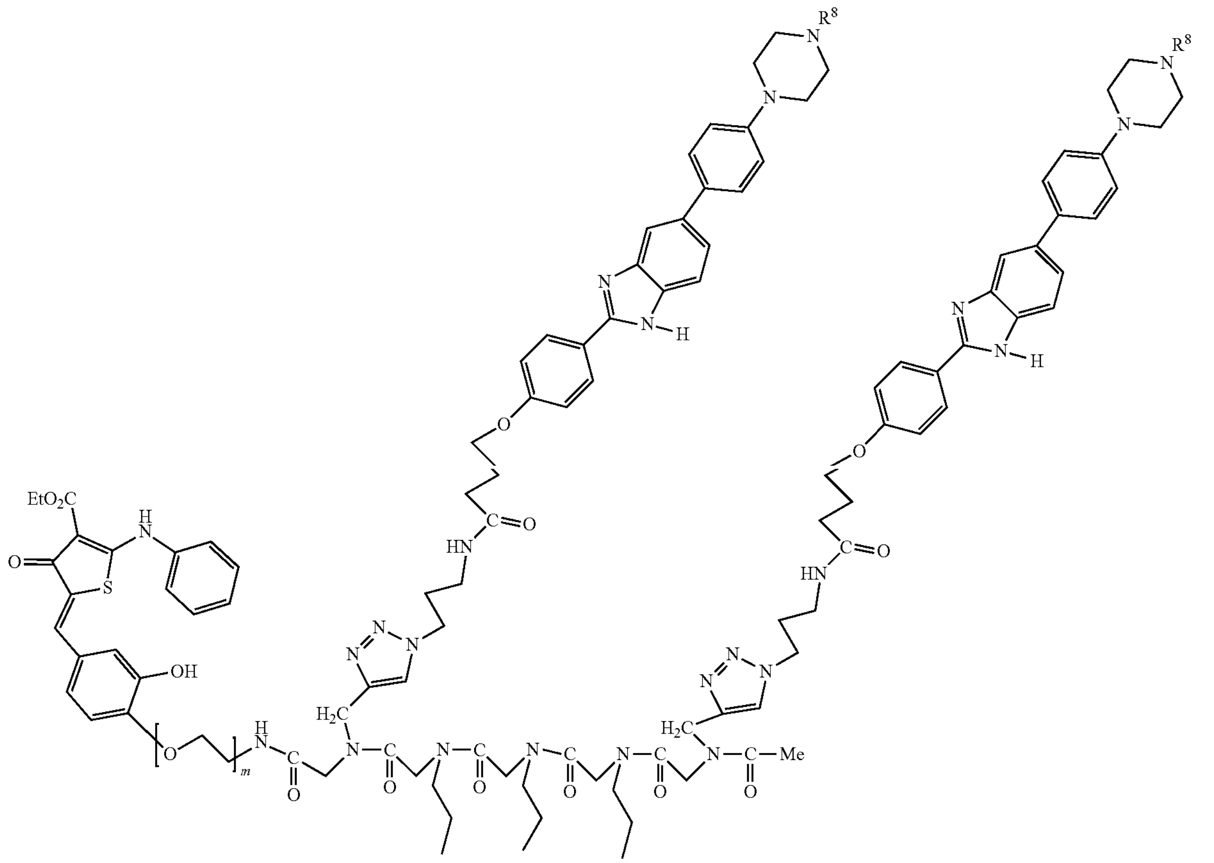

Figure 2A:
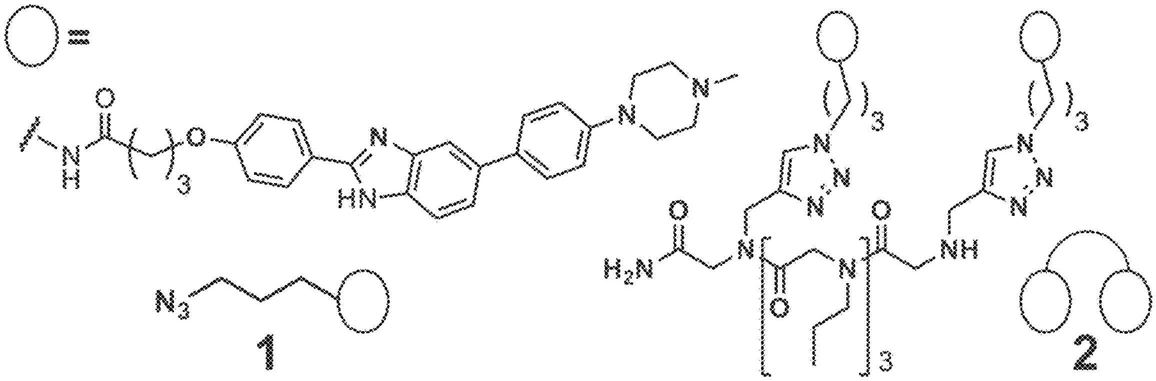
FIGS. 2A-2C. Small Molecules Produced by Design Strategy, FIGS. 1A-1F.
Figure 2B:
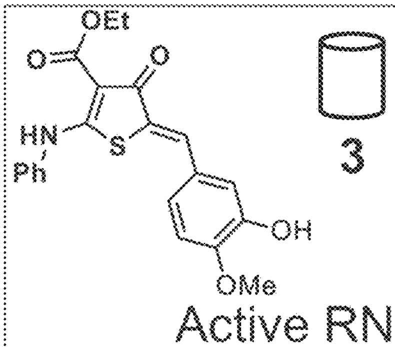
Figure 2B:
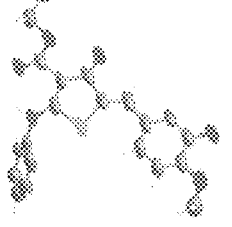
Figure 2B:
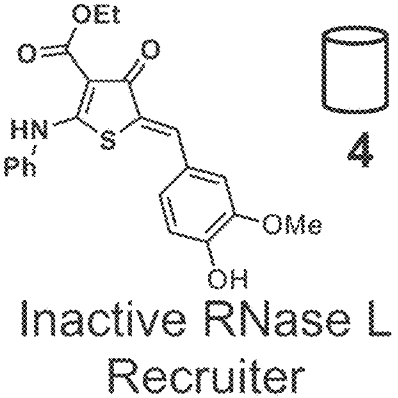
Figure 2C:
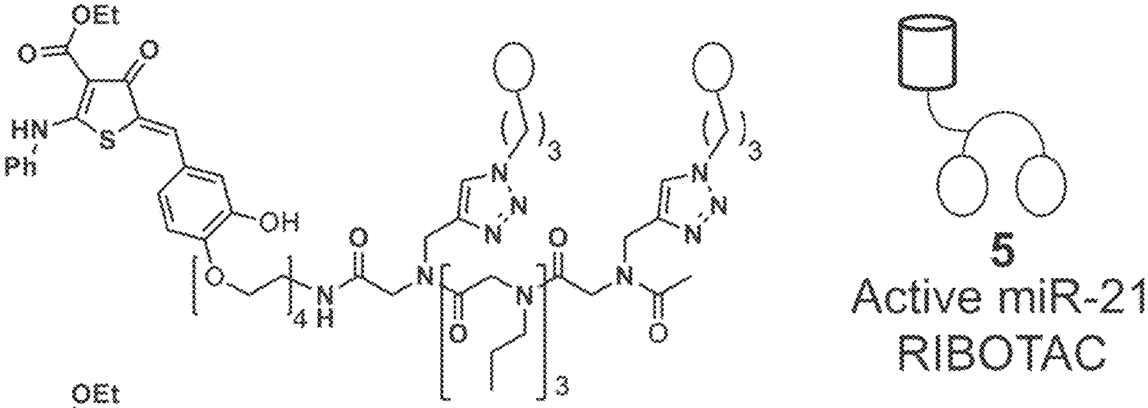
Figure 2C:
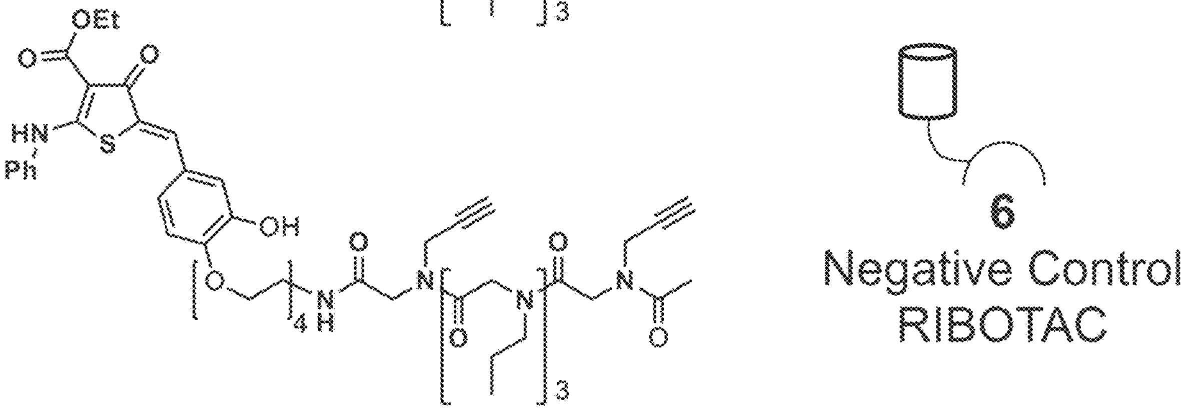
Figure 2C:
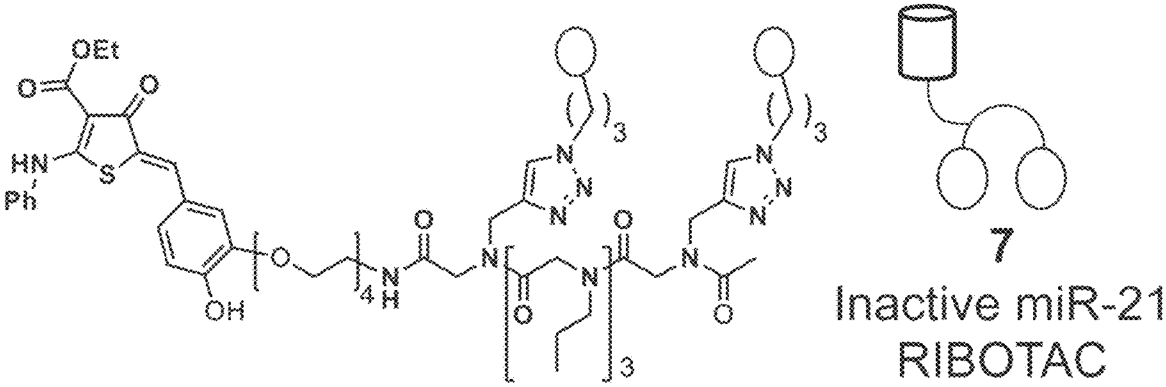

Additionally, an inactive RNase L recruiting compound (Formula 4) was identified with chemical substitutions of Formula C-1 including $R^3$ as methoxy, $R^4$ as hydroxyl and $R^5$ as hydrogen. (FIGS. 2A-2C). Control compound Formula 6, which is the active RNase L recruiter without the miR-21-binding modules in 2, and compound 7, which is 2 appended to inactive recruiter 4, were also synthesized and studied. See the examples section and FIGS. 2A-2C.

Figure 3A:
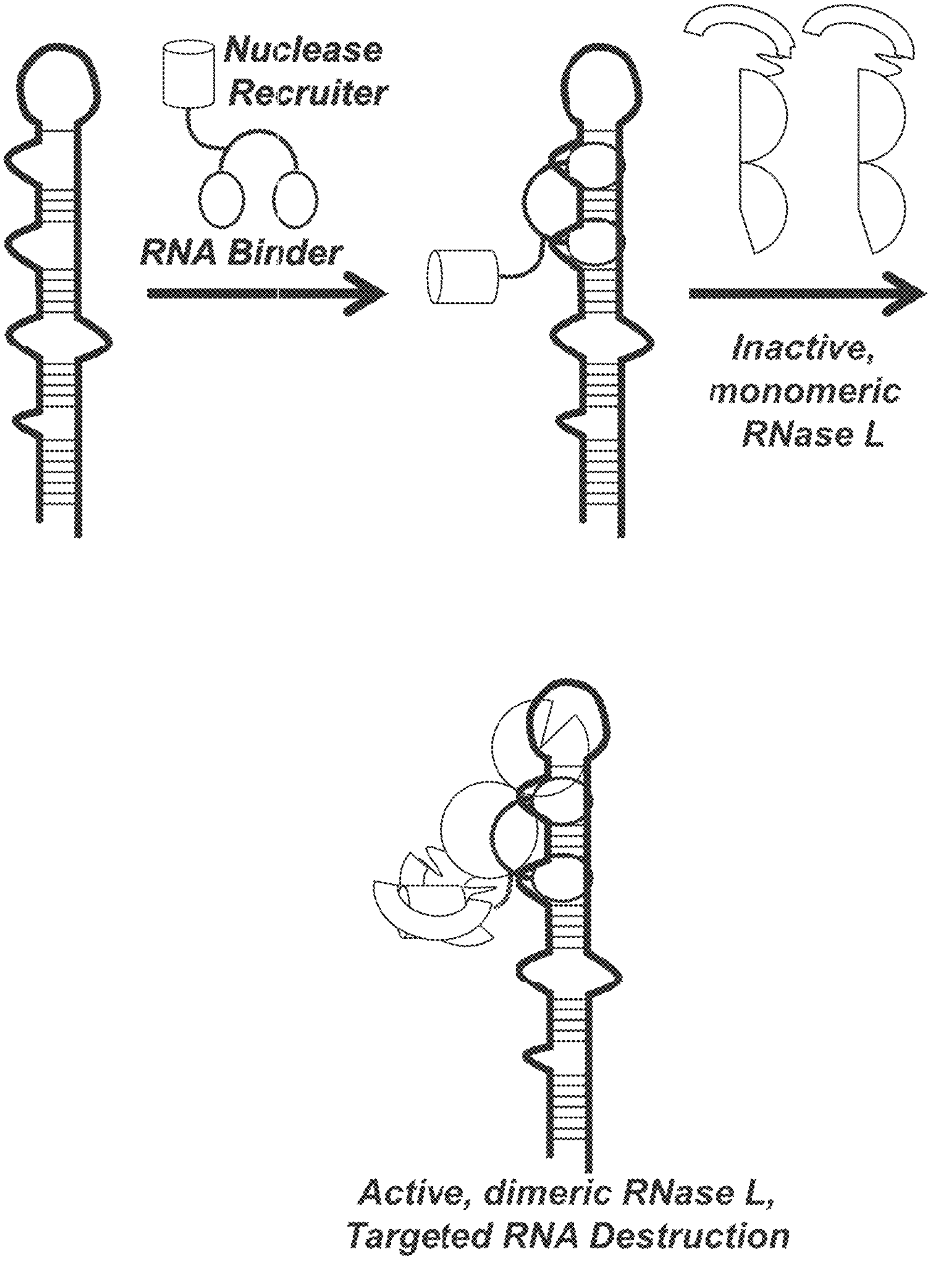
FIGS. 3A-3G. Selective cleavage of pre-miR-21 by a Small Molecule Recruiter of RNase L in MDA-MB-231 cells.
Figure 3B:
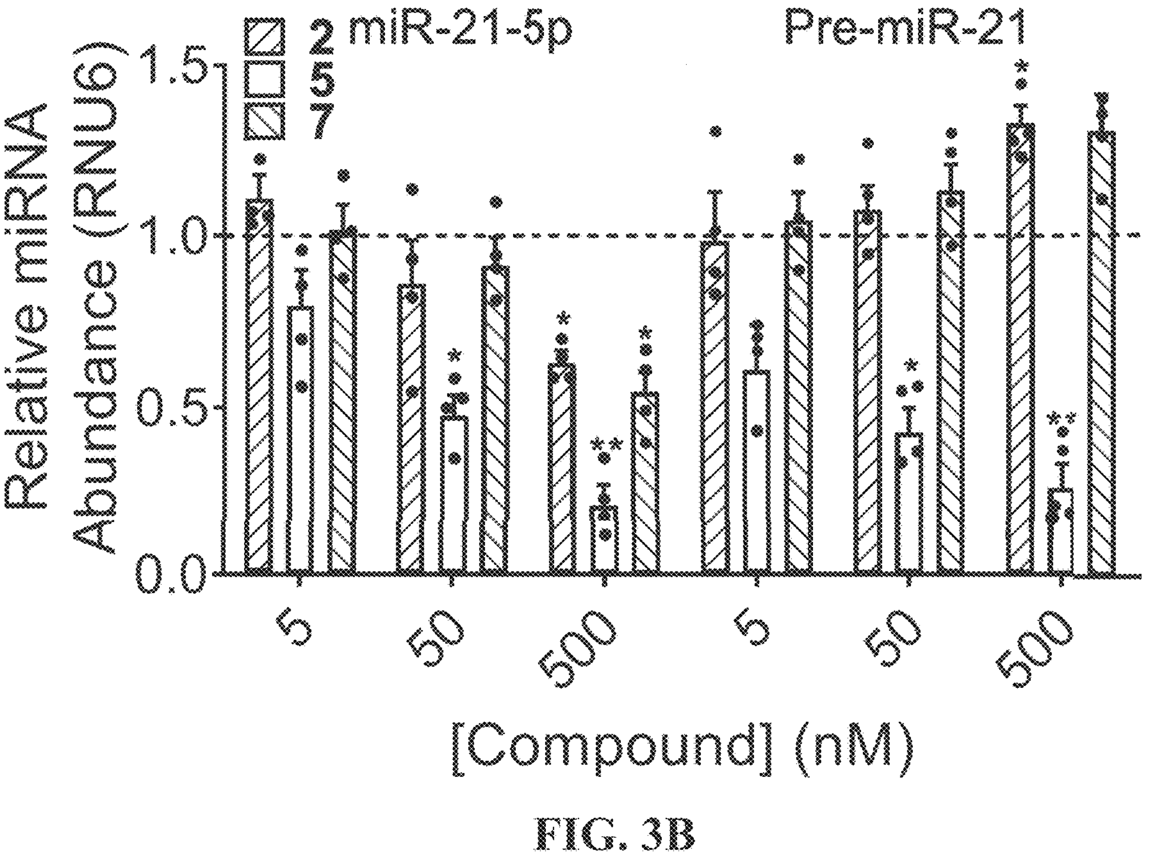
Figure 3C:
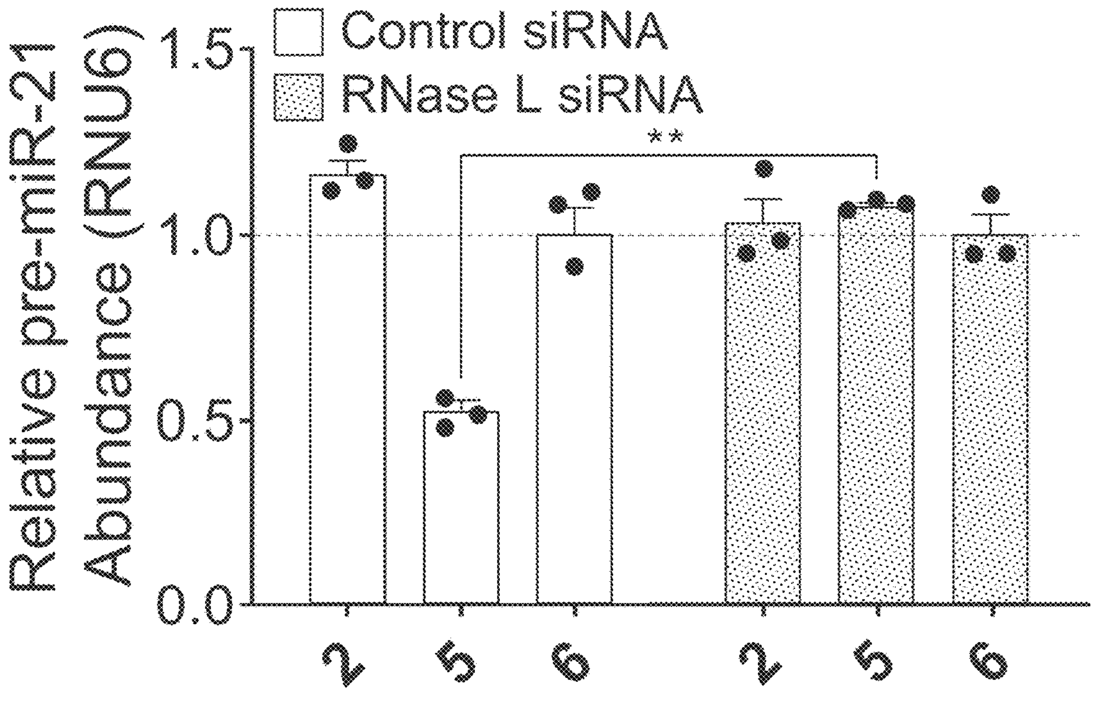
Figure 3D:
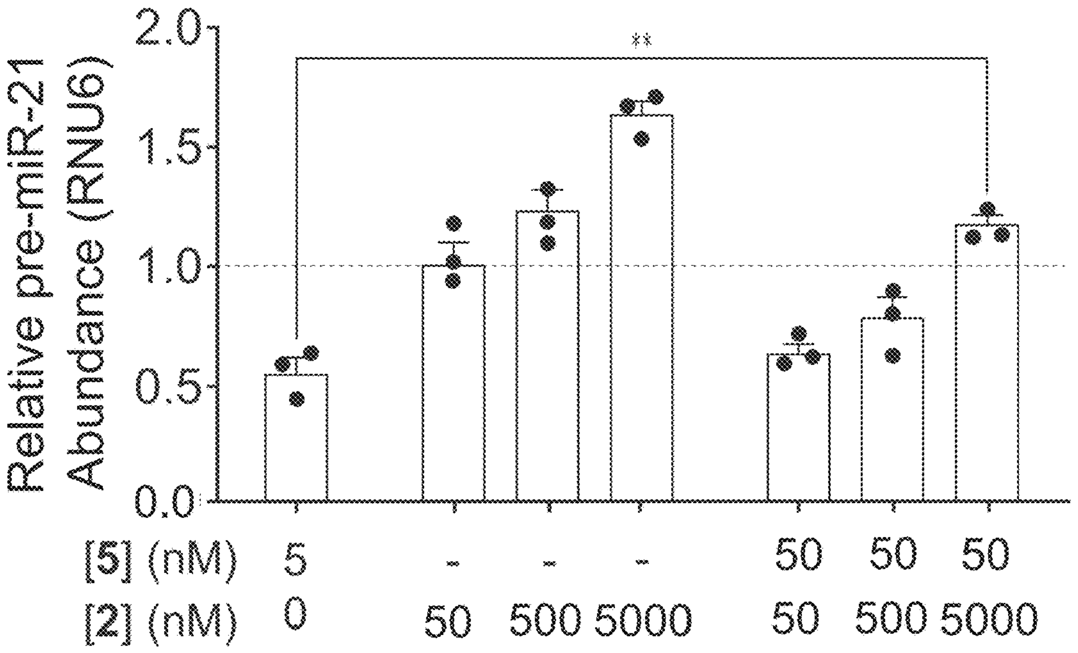
Figure 3E:
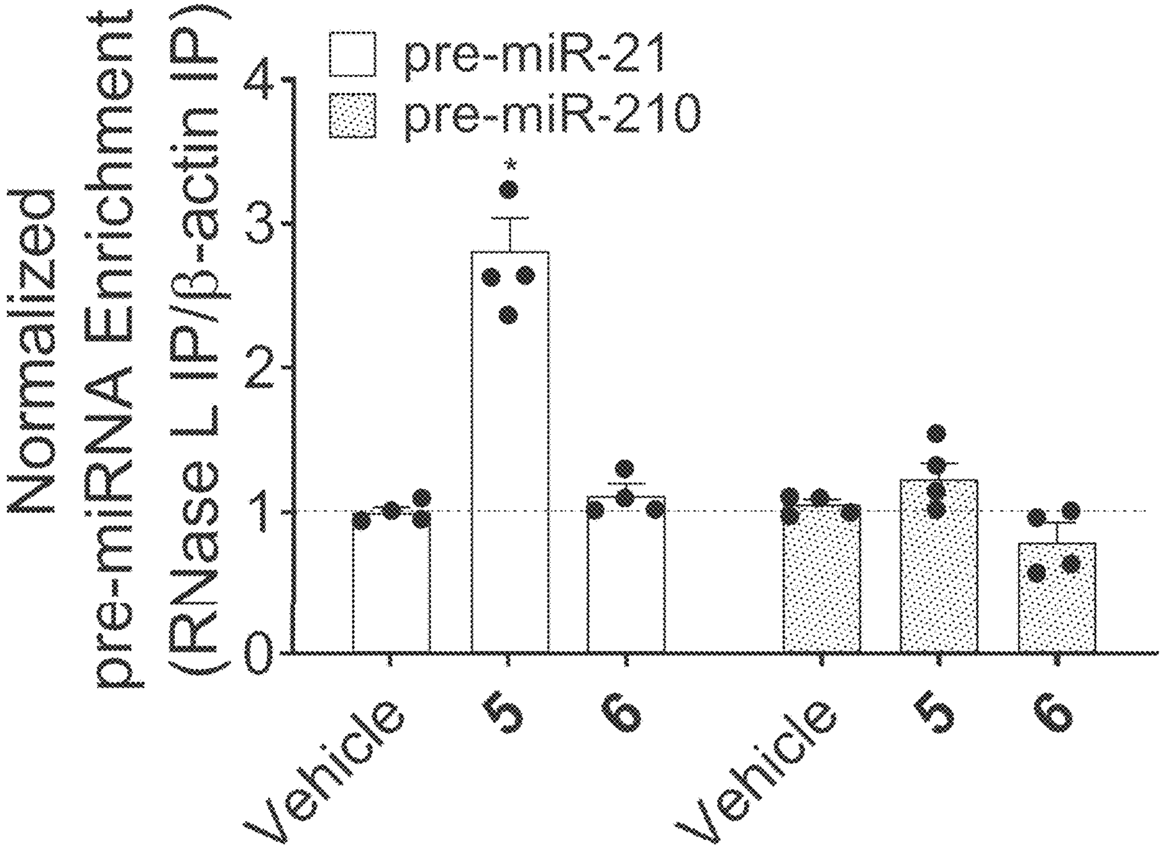
Figure 3F:
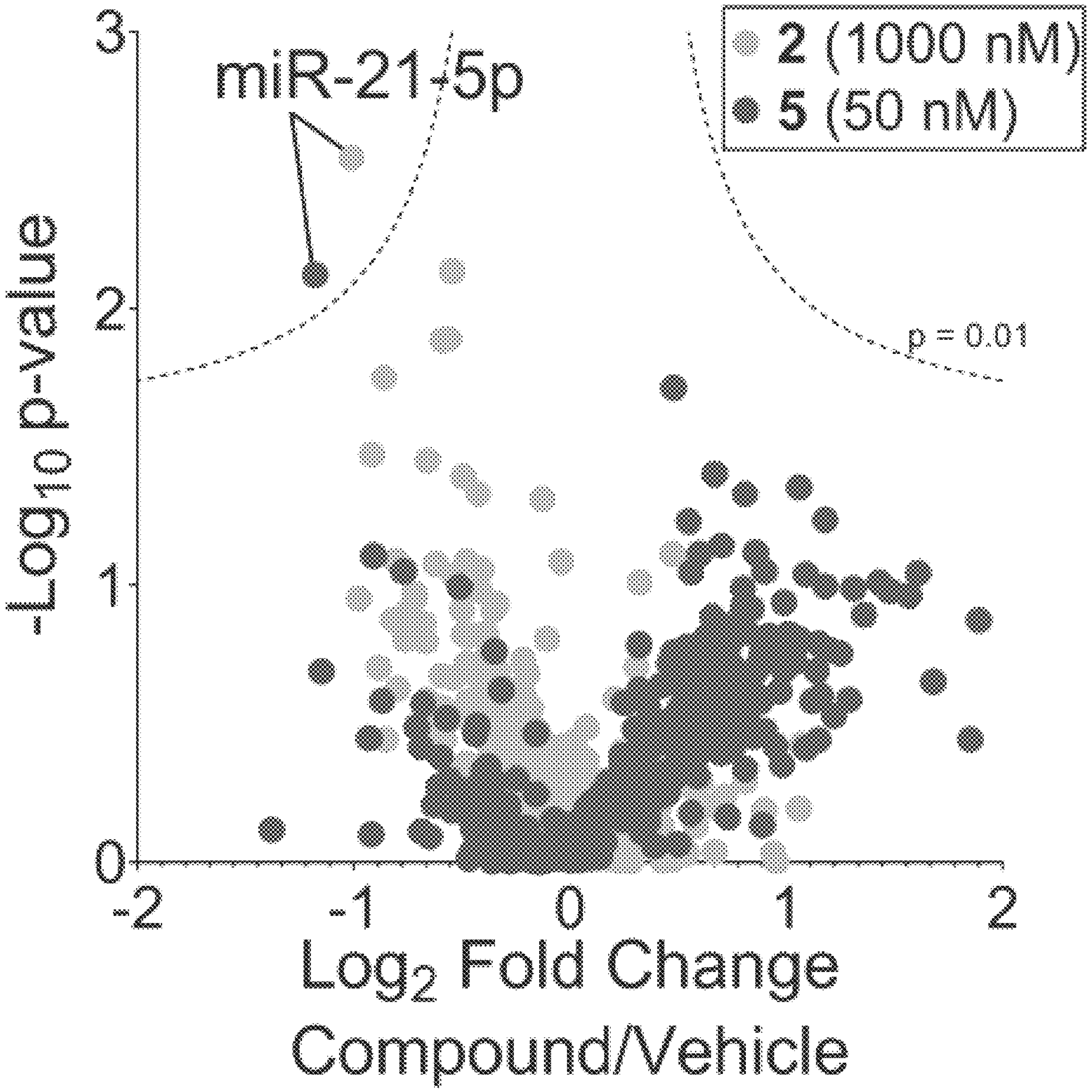

Application of Formula 5 to MDA-MB-231 cells showed 20-fold enhanced activity ($IC_{50}$~0.05 μM) for affecting miR-21 levels over parent 2 (FIG. 3*b*). Control compound Formula 7 did not have enhanced activity over Formula 2, while Formula 6 was inactive (FIGS. 3*b*, 3*c*). Levels of pre-miR-21 were diminished with Formula 5 as expected for a cleaving compound. To further support that Formula 5 directly cleaves pre-miR-21 via RNase L recruitment, it was demonstrated that: (i) siRNA ablation of RNase L decreased the ability of Formula 5 to cleave pre-miR-21 (FIG. 3*c*); (ii) addition of increasing amounts of Formula 2 to cells with constant amounts of Formula 5 competed away cleavage of pre-miR-21 as both bind to the same sites in pre-miR-21 (FIG. 3*d*); and, (iii) co-immunoprecipitation of RNase L from cells treated with Formula 5 yielded increased levels of pre-miR-21 in the enriched fraction (FIG. 3*e*).

Figure 40A:
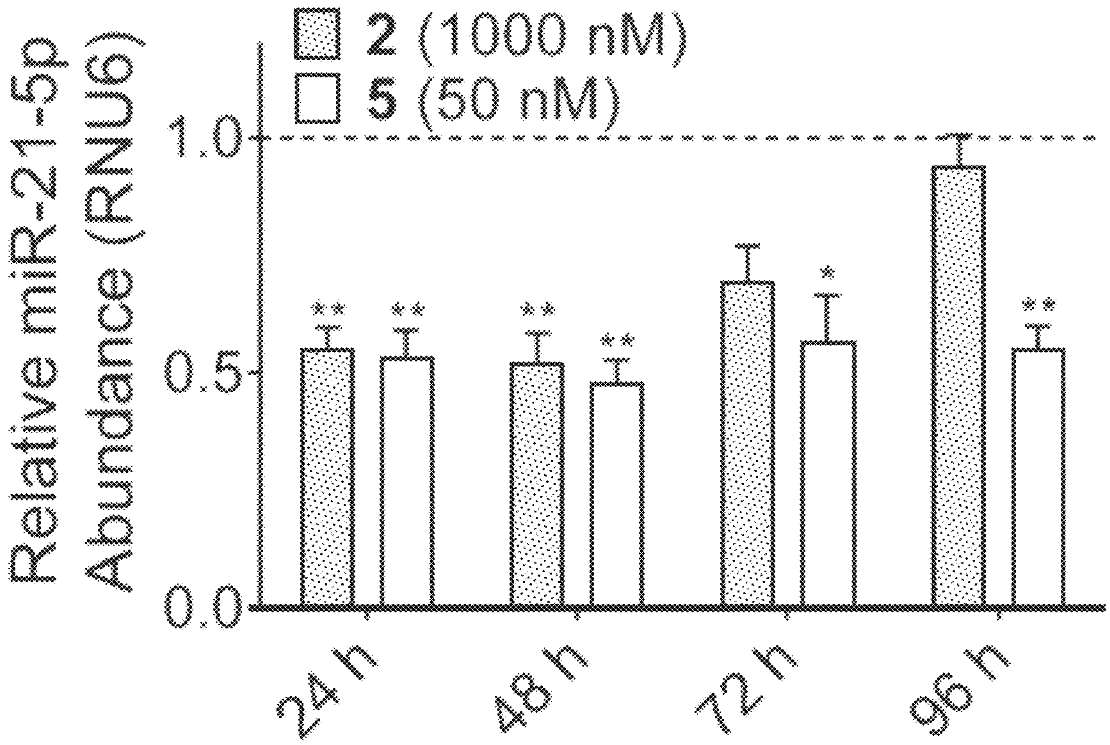
FIGS. 40A-40C. Efficacy of compounds targeting miR-21.
Figure 40B:
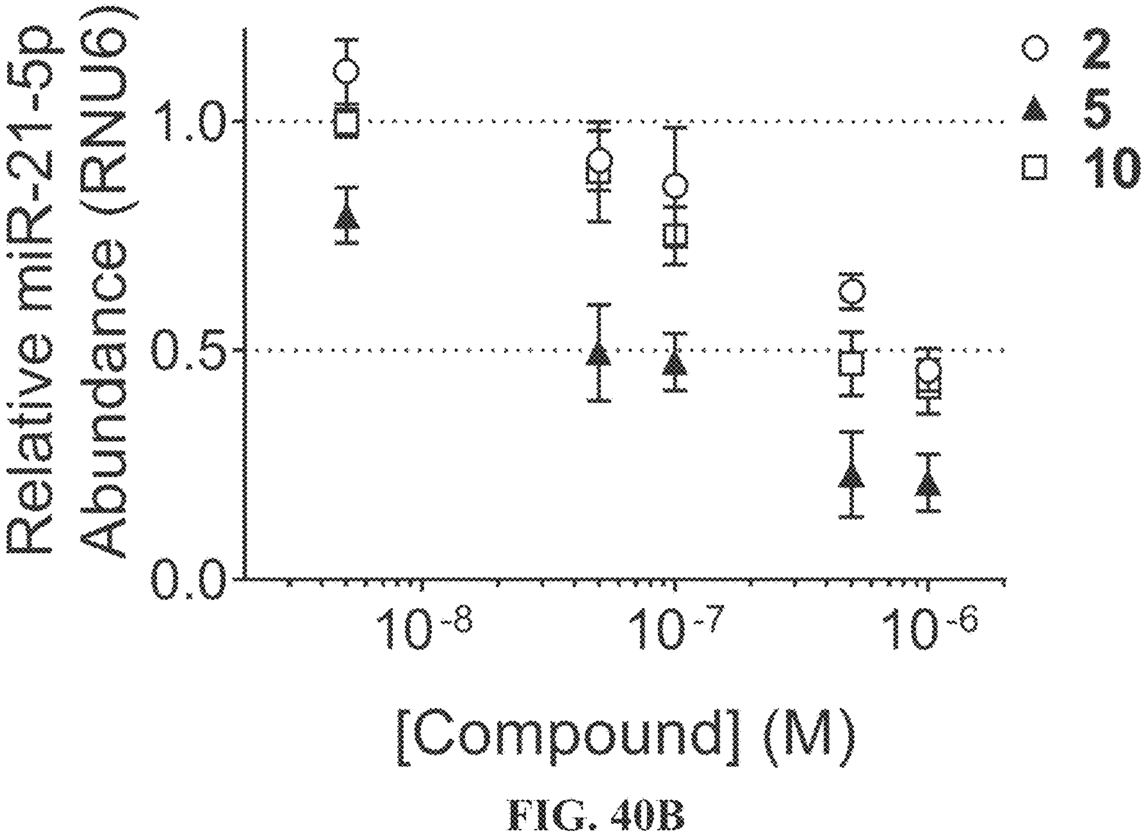
Figure 40C:
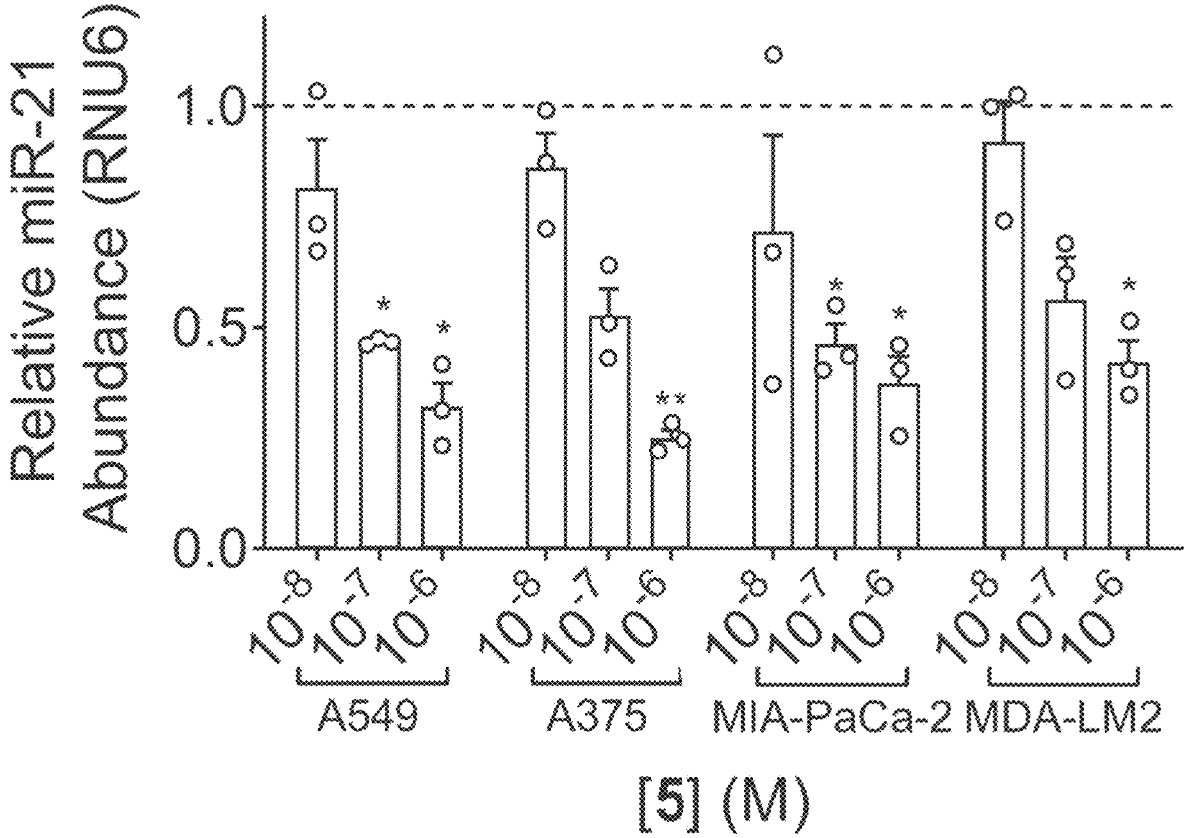

Further studies with Formula 5 showed that it sub-stoichiometrically cleaved pre-miR-21 in MDA-MB-231 dose of Formula 2 (1000 nM) and Formula 5 (50 nM) over a period of 48 h and 96 h, respectively, suggesting the more potent and long-lasting effect of the cleaving compound Formula 5, FIGS. 40A-40C.

Figure 41A:
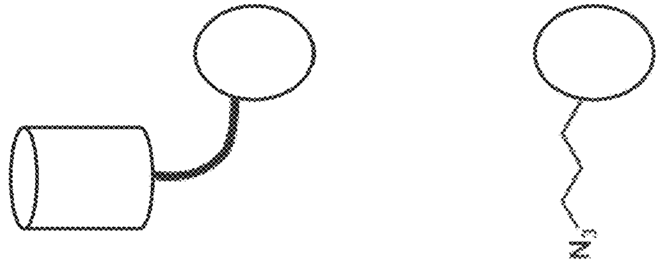
FIGS. 41A-41C. Cleavage of pre-miR-210 with compound 25.
Figure 41A:
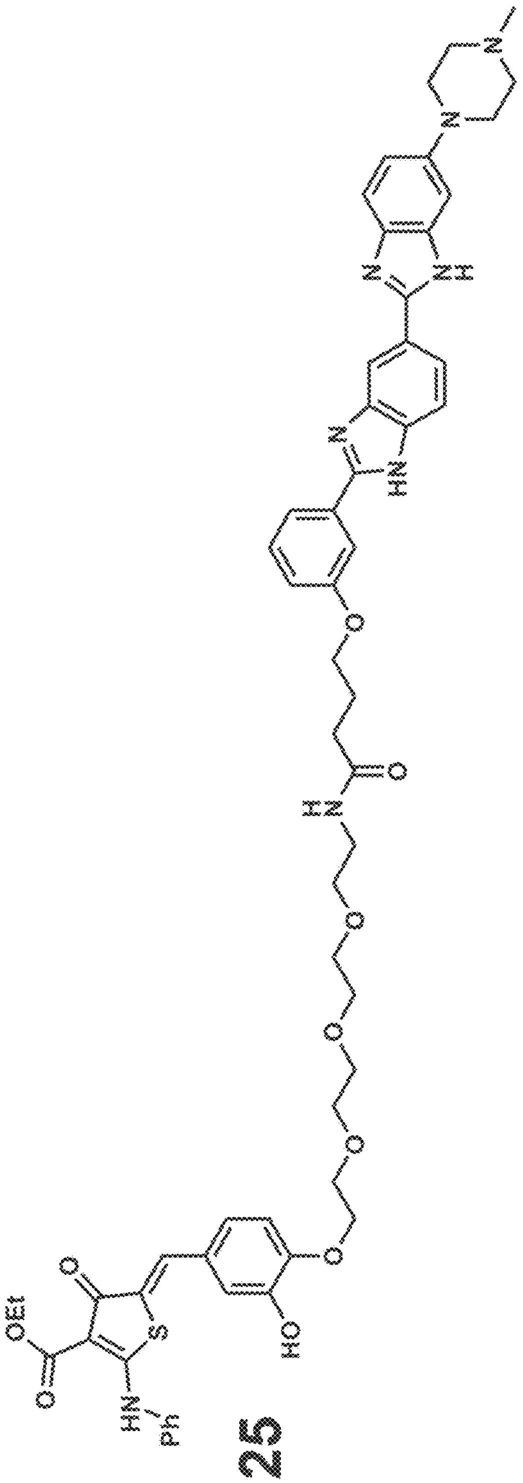
Figure 41A:
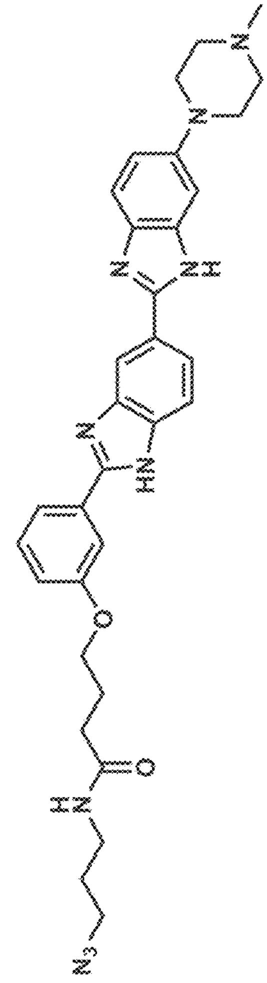
Figure 41C:
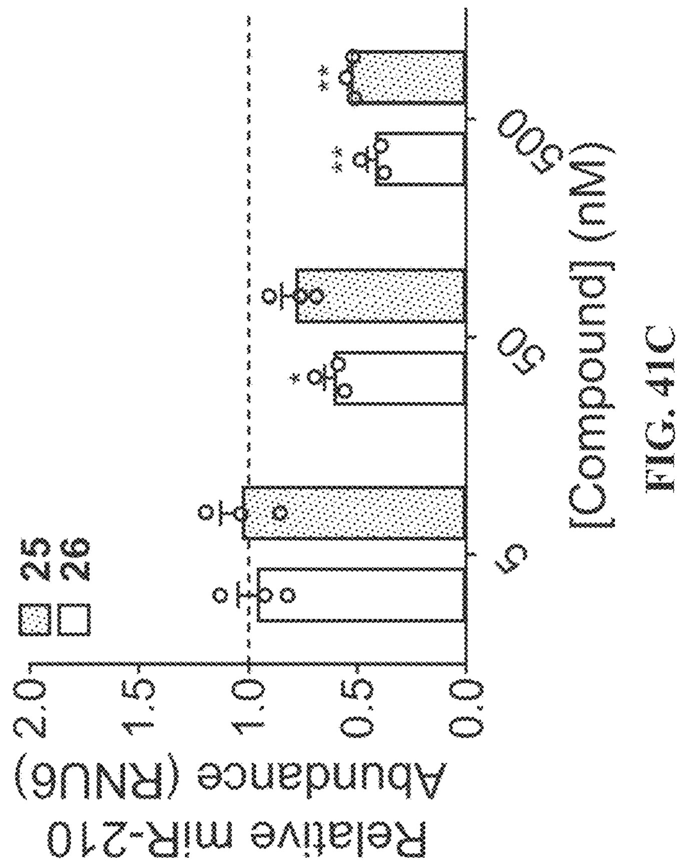
Figure 41B:
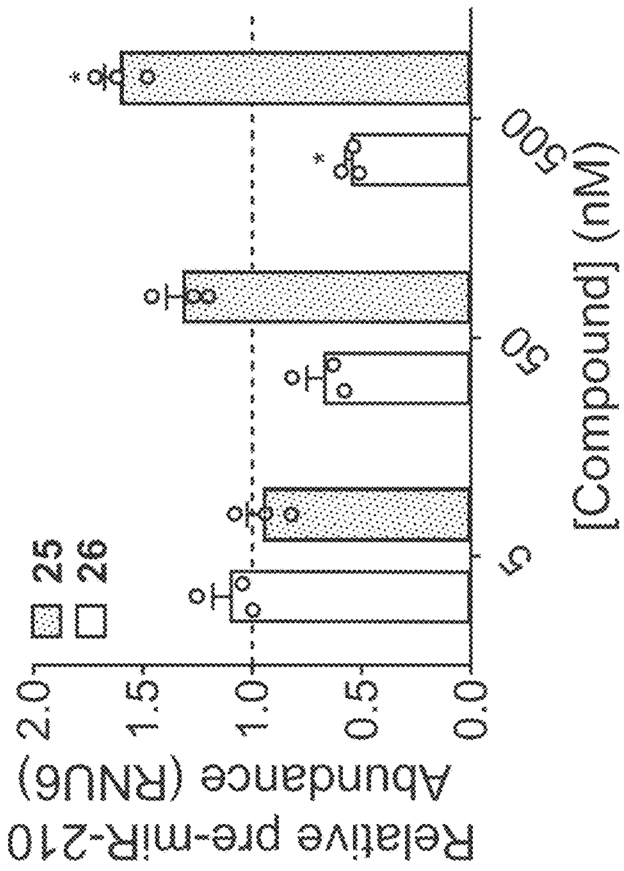
Figure 42B:
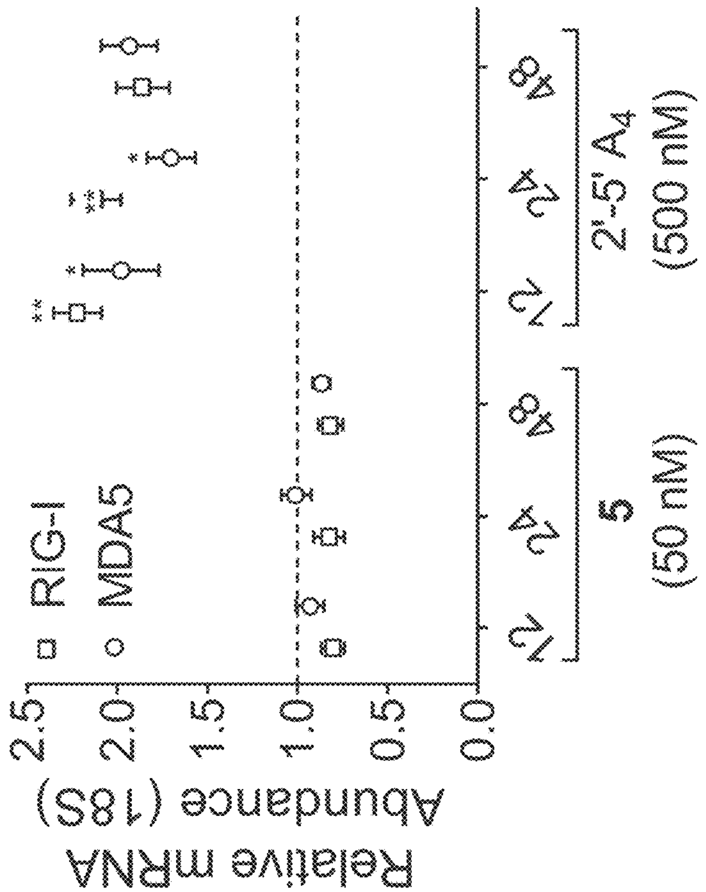
FIGS. 42A-42C. Innate immune response with compound 5 treatment.
Figure 42A:
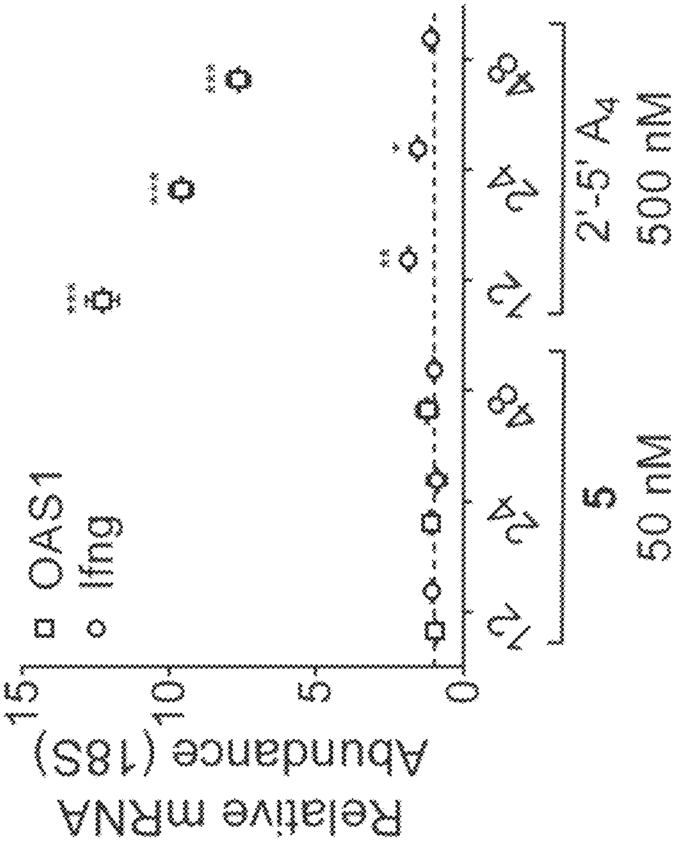
Figure 42C:
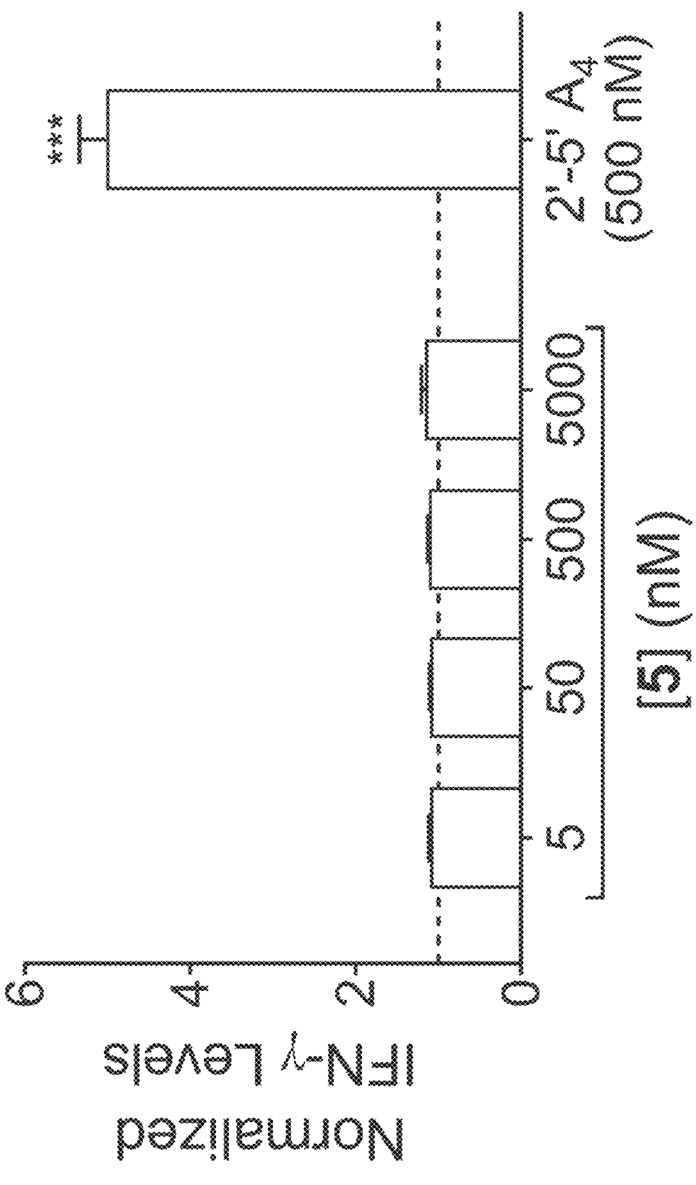

To assess the difference between enzymatic cleavage mediated by RNase L and non-enzymatic cleavage mediated by bleomycin, the effect of Formula 5 and a bleomycin conjugate of 2 were tested in MDA-MB-231 cells. Enzymatic cleavage was 10-fold more potent, FIGS. 40A-40C. In addition, cleavage by Formula 5 significantly inhibited miR-21 levels in various cancer cell lines, suggesting its broad applicability, FIGS. 40A-40C. To support that nuclease recruitment can be generally applicable, a compound was designed to recruit RNase L to cleave pre-miR-210. The results showed targeted cleavage as expected, FIGS. 41A-41C. As global RNase L activation is known to trigger antiviral and innate immune responses,[16] RT-qPCR and ELISA were used to measure modulation of innate immunity biomarkers. No significant changes were observed, demonstrating that 5 functions by local targeted recruitment of RNase L and not by general stimulation of the innate antiviral immune response, FIGS. 42A-42C.

Figure 43A:
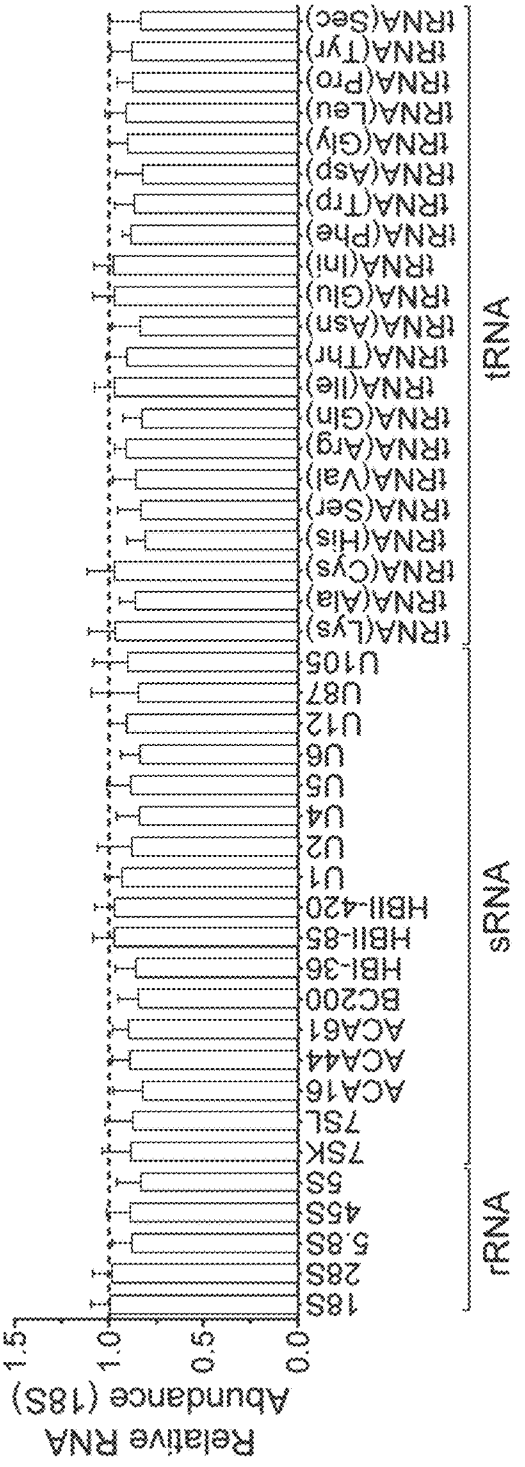
FIGS. 43A-43B. Cellular selectivity of compound 5 among abundant human RNAs. RT-qPCR profiling of highly abundant transcripts, including ribosomal (r)RNAs, small (s)RNAs, transfer (t)RNAs, and messenger (m)RNAs that span the diverse population of the transcriptome, with 5 treatment (50 nM) in MDA-MB-231 cells after 48 h. Dashed lines indicate abundance of RNA in vehicle treated samples.
Figure 43B:
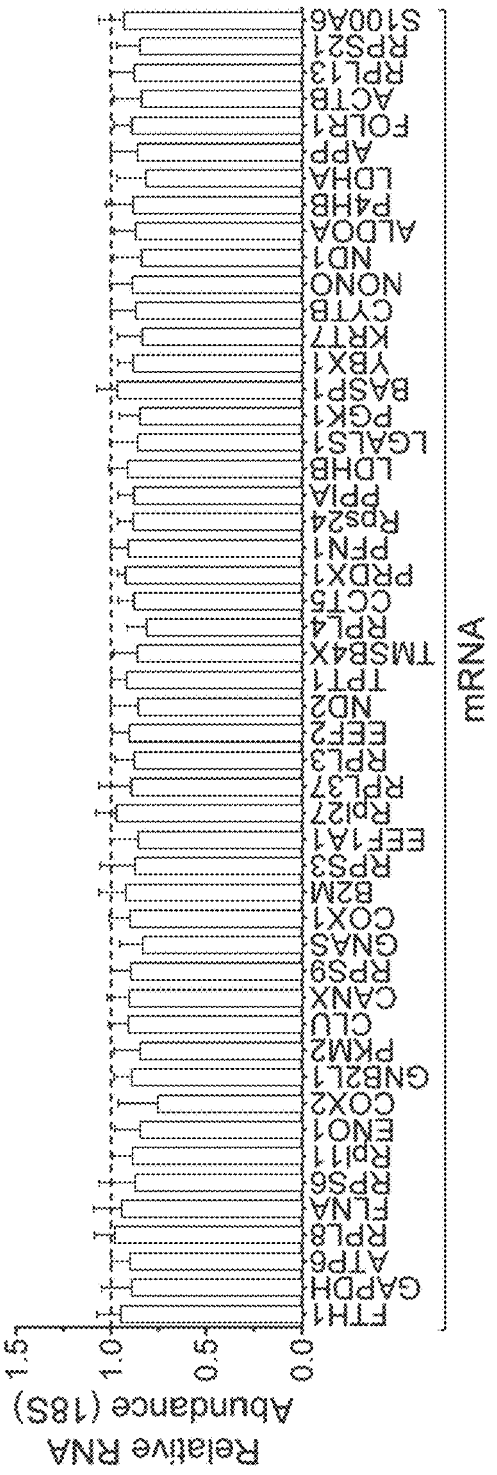

To quantify selectivity, cellular miR-inhibition profiles were used to calculate a Gini Coefficient (GC). A GC allows for selectivity to be scored in a single value; a GC of 0 indicates a non-selective compound while perfect selectivity has a GC of 1.0. See P. P. Graczyk, Gini coefficient: a new way to express selectivity of kinase inhibitors against a family of kinases. *J. Med. Chem.* 50, 5773-5779 (2007). For reference, GCs of protein kinase inhibitors with high selectivity (e.g. inhibits 1/85 kinases tested) have scores ranging from 0.65 to 0.91. Compounds of Formulas 1 and 2 have GCs of 0.52 and 0.68, respectively, demonstrating good selectivity, FIGS. 31A-31D). Importantly, an increase in selectivity was observed with nuclease recruiter Formula 5 (GC of 0.84) FIG. 3*f*, FIGS. 31A-31D. Additionally, compound Formula 5 showed no significant effects on a panel of highly abundant transcripts that span the diverse population of the transcriptome, further demonstrating its broad selectivity, FIGS. 43A-43B. Thus, nuclease recruitment does not diminish, but rather enhances potency and selectivity when compared to binders, and compounds designed to target RNA can be as selective as those that target proteins.

Figure 44A:
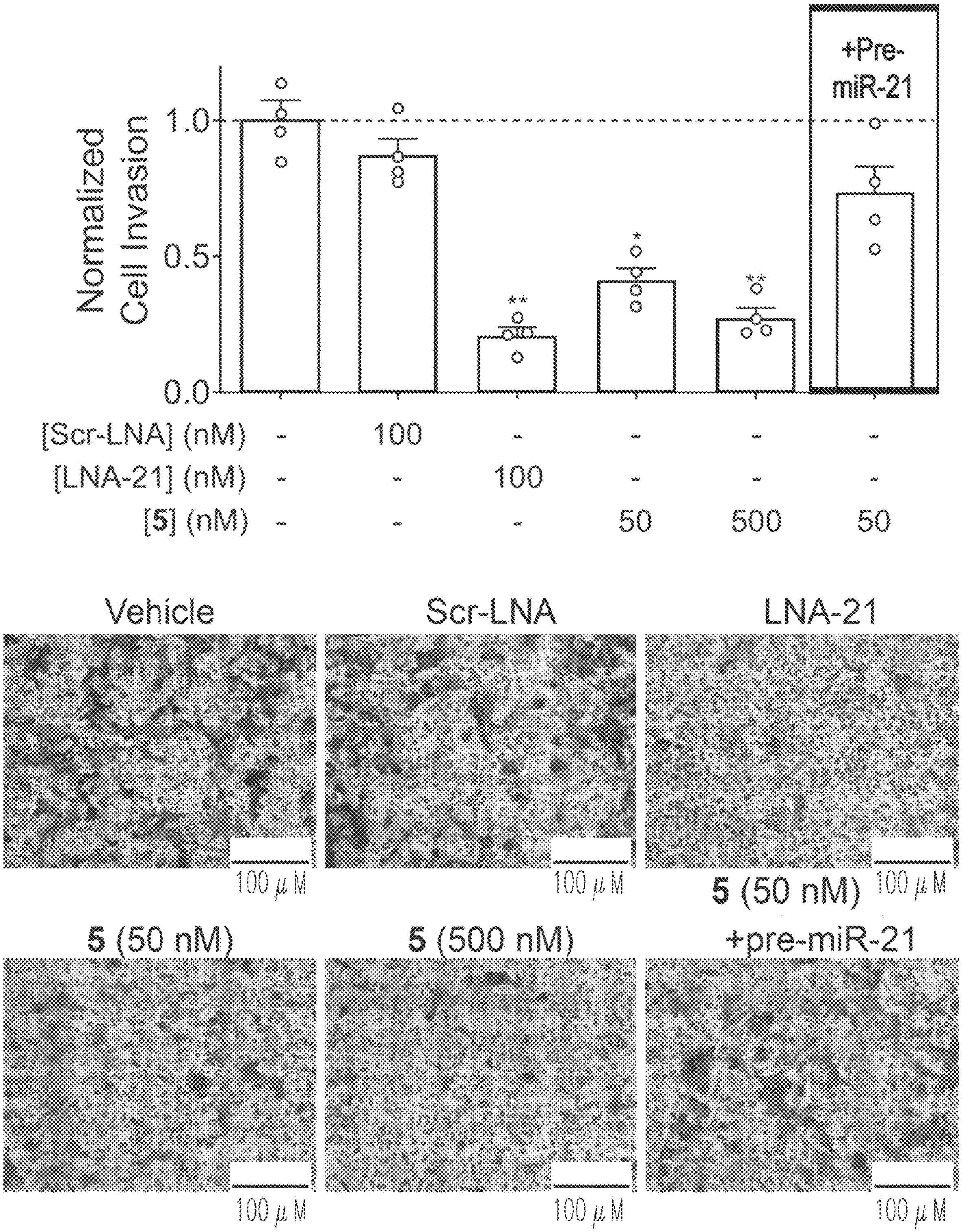
FIGS. 44A-44C. Decrease of invasive phenotype in multiple cell lines by compound 5.
Figure 44B:
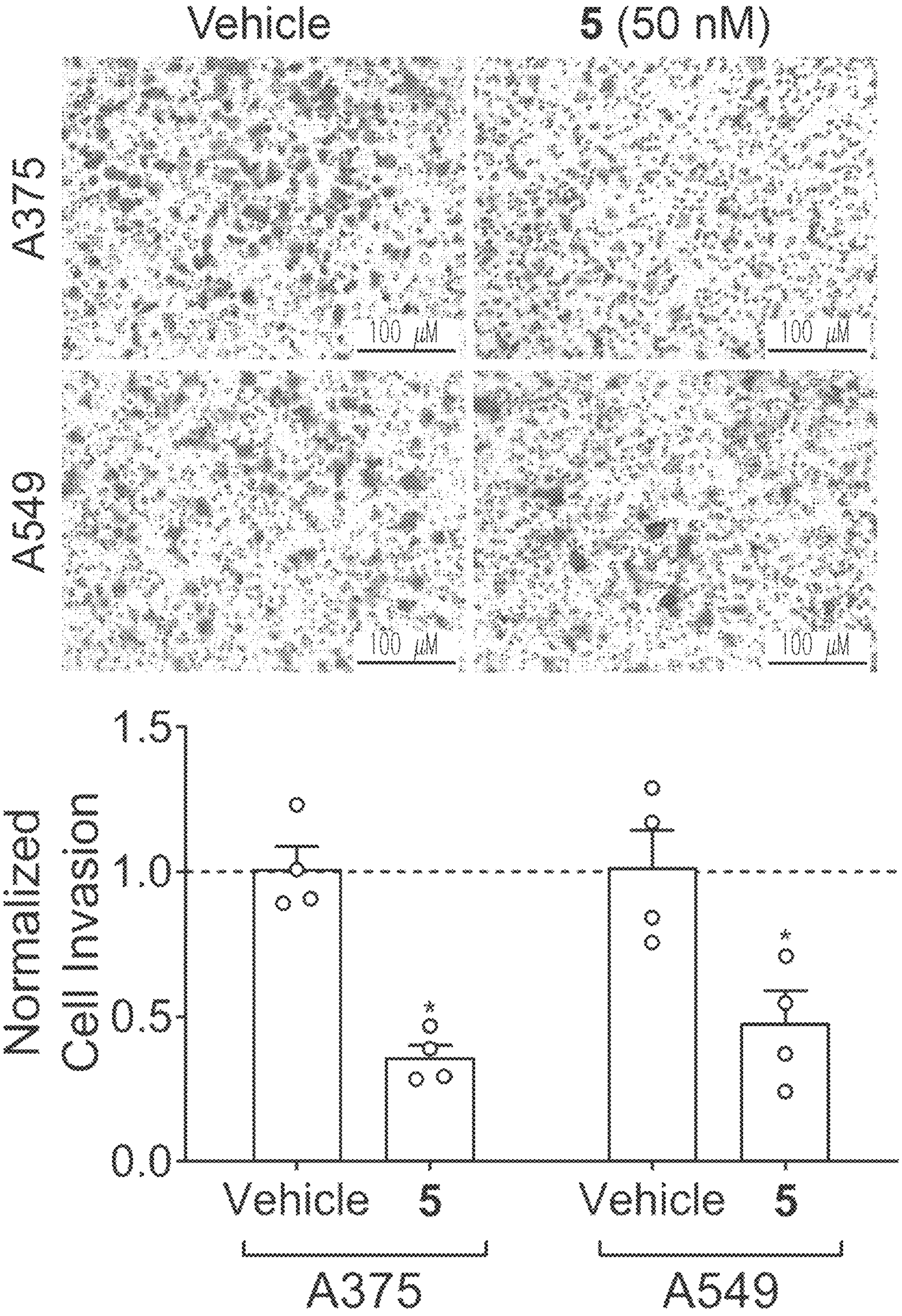
Figure 44C:
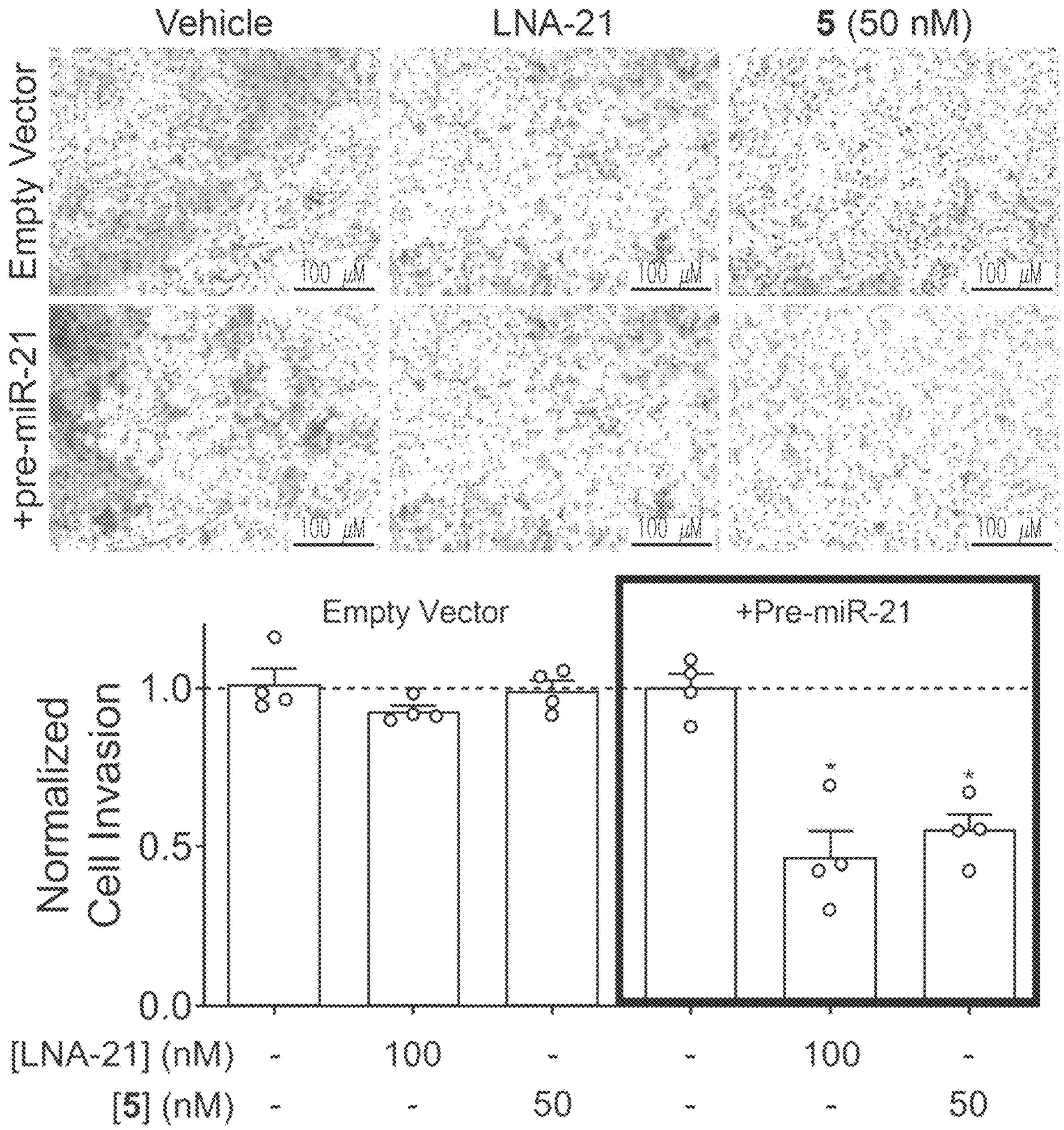

Since miR-21 stimulates an invasive phenotype in MDA-MB-231, the effect of Formula 5 on invasion was measured. Indeed, Formula 5 effectively inhibited invasion, FIGS. 44A-44C. To show that this effect in phenotype was due to targeting pre-miR-21, pre-miR-21 was transiently overexpressed, which ablated the inhibitory effect of Formula 5. Additionally, Formula 5 also decreased invasiveness broadly in melanoma and lung cancer cell lines, FIGS. 44A-44C. Further experiments to validate that Formula 5 affects a phenotype by inhibition of pre-miR-21 included testing its effect on MCF-10a, a cellular model of healthy breast that does not appreciably express pre-miR-21, and it had no effect on invasion. Transient transfection of pre-miR-21 into MCF-10a made the cell line invasive and application of Formula 5 to MCF-10a under these conditions inhibited invasion, FIGS. 44A-44C.

Figure 3G:
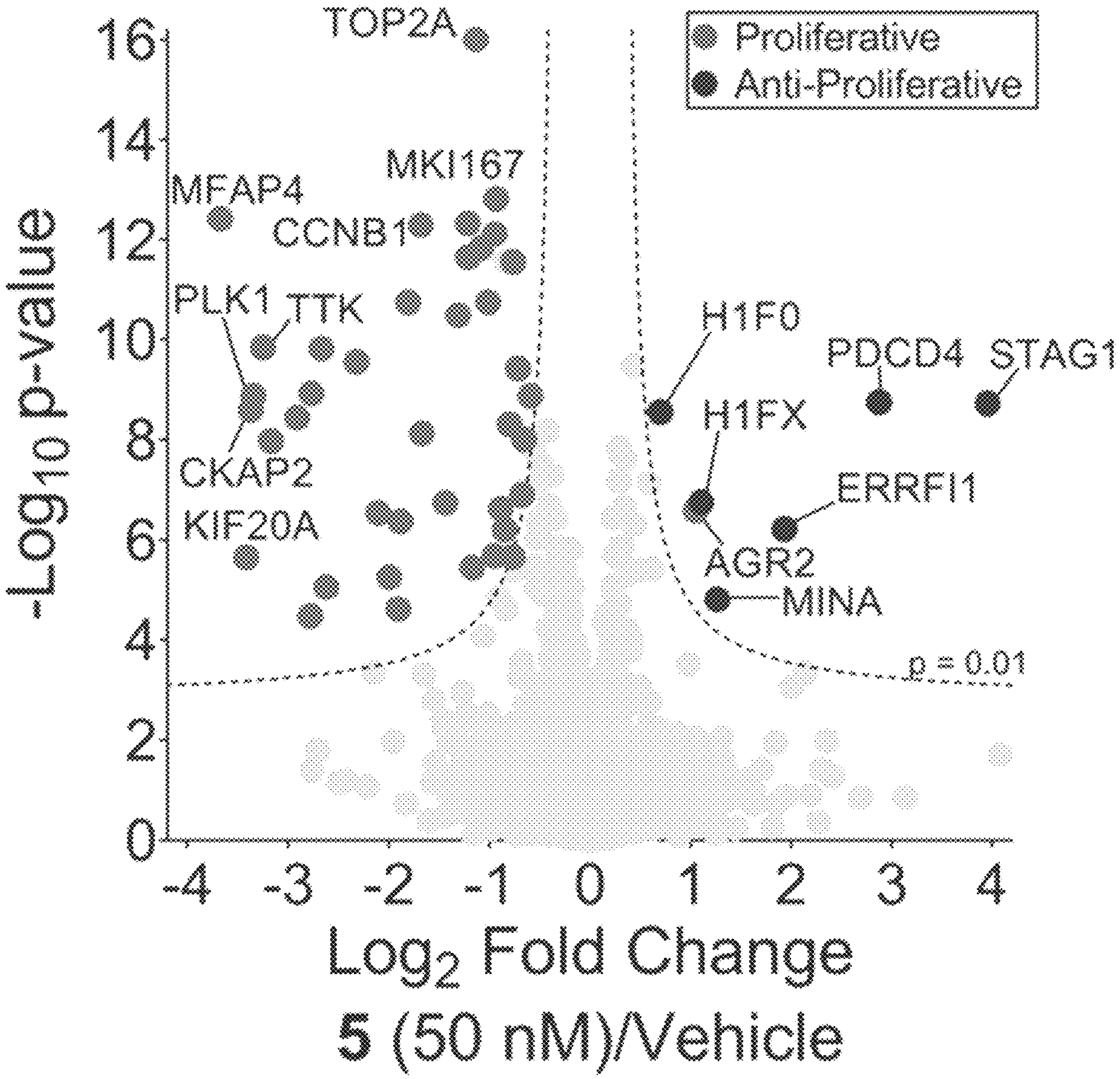
Figure 45:
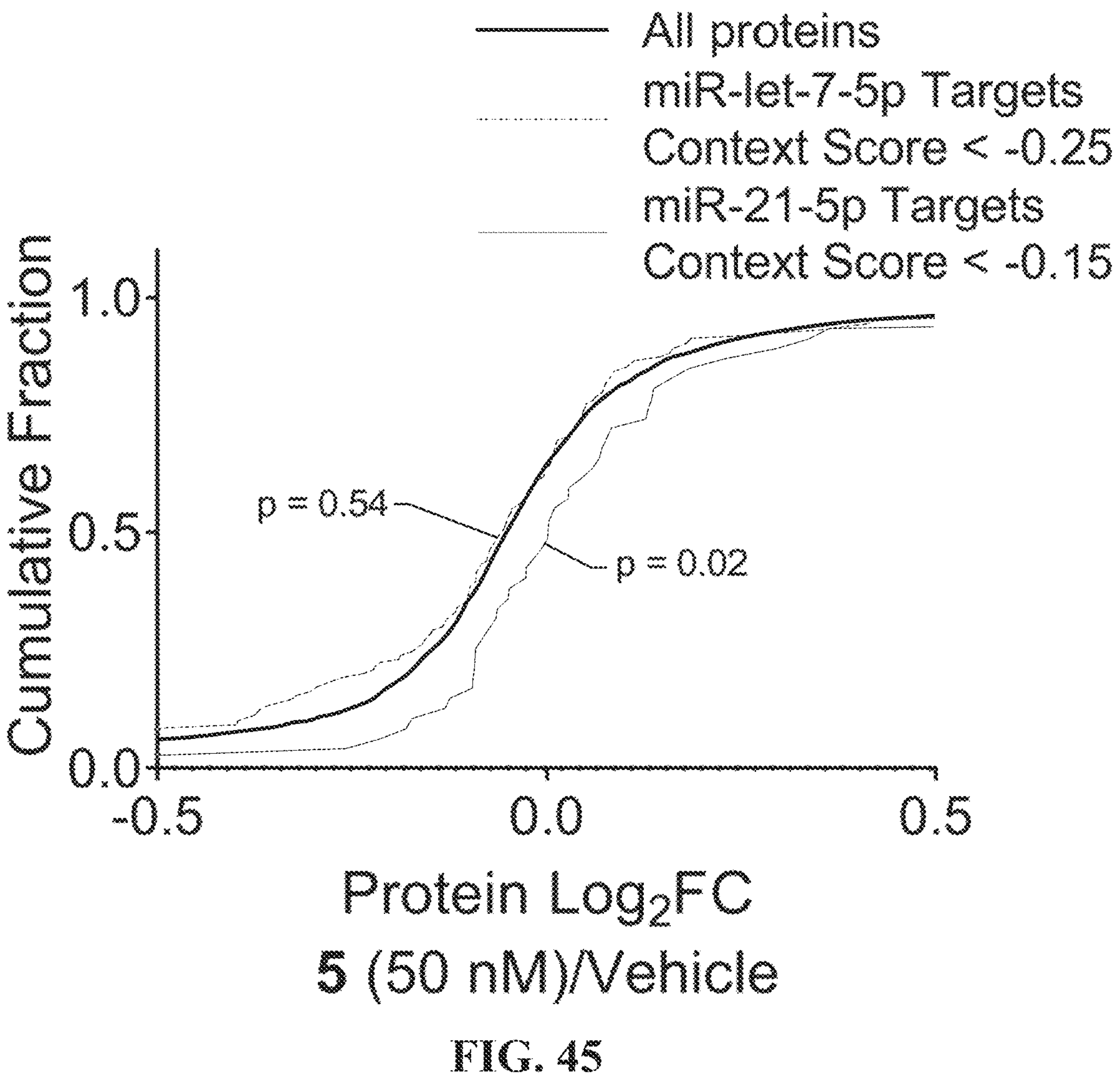
FIG. 45. On-target effects of compound 5 observed in global proteomics. TargetScanHuman v7.2 was used to predict downstream protein targets of miR-21-5p (n=382) and miR-let-7-5p (n=1207) containing conserved sites. Approximately 25% of miR-21-5p targets (95/382) and 20% of miR-let-7-5p targets (241/1207) were detectable in the global proteomics analysis. The top ~50% of predicted targets were used to calculate cumulative distributions, as represented by weighted context++ scores of <−0.25 or <−0.15 in miR-let-5p or miR-21-5p targets, respectively. The weighted context++ score represents the predicted efficacy of sites based on the sum of weighted contributions of various features (site type, local AU, minimum distance, 6/7/8-mer seed matches, etc.) between the miRNA and target gene[17]. Cumulative distribution plots of the fold change of proteins in 5-treated vs. vehicle-treated samples indicated a significant upregulation of only miR-21-5p targets, while no significant change was observed with miR-let-7-5p targets, relative to the cumulative distribution of all protein. Targets of miR-let-7-5p were used as comparison as it is a miR with similar expression levels as miR-21-5p in MDA-MB-231 cells. p values between distributions were calculated using a two-tailed Kolmogorov.

The effect of Formula 5 on the proteome of MBA-MB-231 cells was studied. Only 47 proteins of 4181 were significantly affected. The two most enhanced proteins were PDCD4, a direct target of miR-21, and STAG1, Cohesin subunit SA-1, which are involved in decreasing cellular proliferation and in protecting genome integrity, FIG. 3*g*. Pathway analysis of significantly modulated proteins found that Formula 5 affected pathways involved in cell division and proliferation and regulation of the cell cycle. Generally, proteins involved in genome stability were upregulated while oncogenes were downregulated. Importantly, the median log fold-change of predicted downstream protein targets of miR-21 (TargetScanHuman v7.2, V. Agarwal, G. W. Bell, J.-W. Nam, D. P. Bartel, Predicting effective microRNA target sites in mammalian mRNAs. *eLife* 4, e05005 (2015) following treatment by Formula 5 was significantly upregulated relative to all proteins, FIG. 45. In contrast, no significant shift was observed among the downstream protein targets of similarly expressed miR-let-7-5p, FIG. 45. Thus, effects on the proteome are selective and consistent with what would be expected upon miR-21 depletion.

Figure 4A:
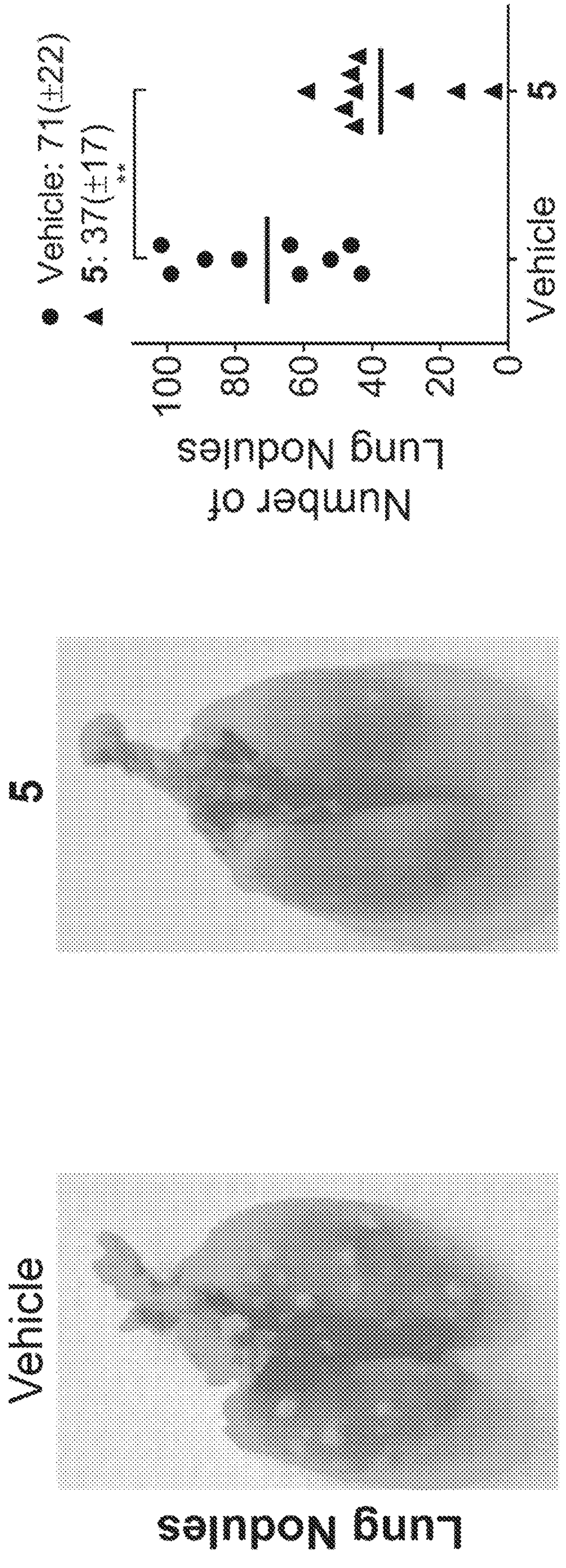
FIGS. 4A-4E. Inhibition of in vivo growth of cancer cells injected into Mouse.
Figure 4B:
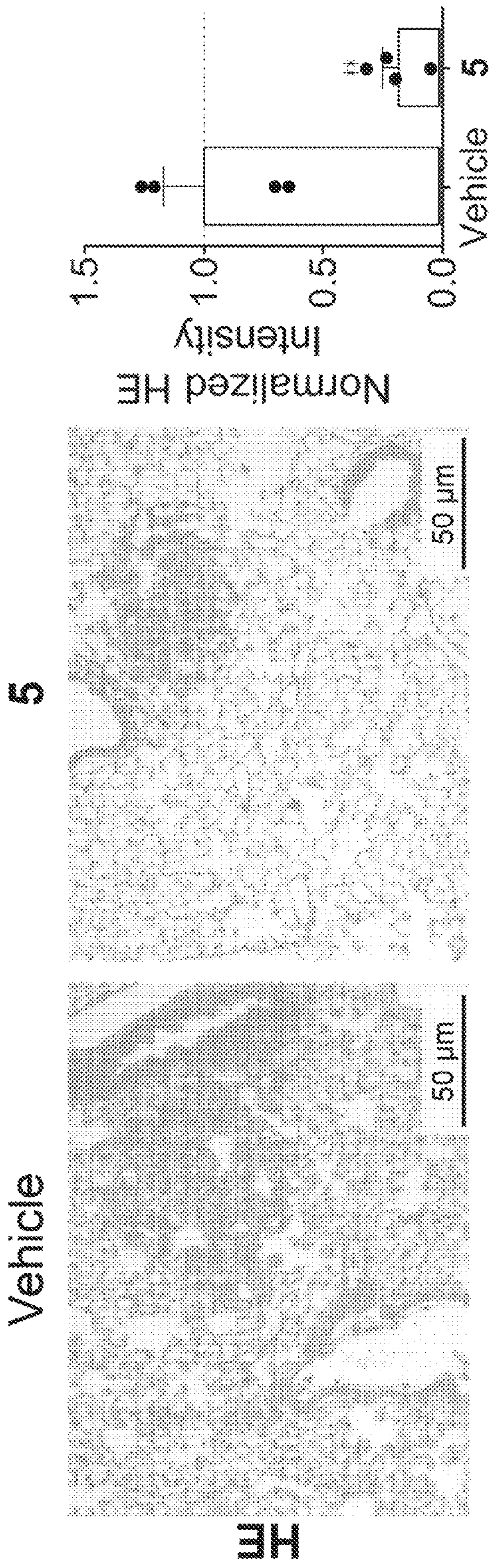
Figure 4C:
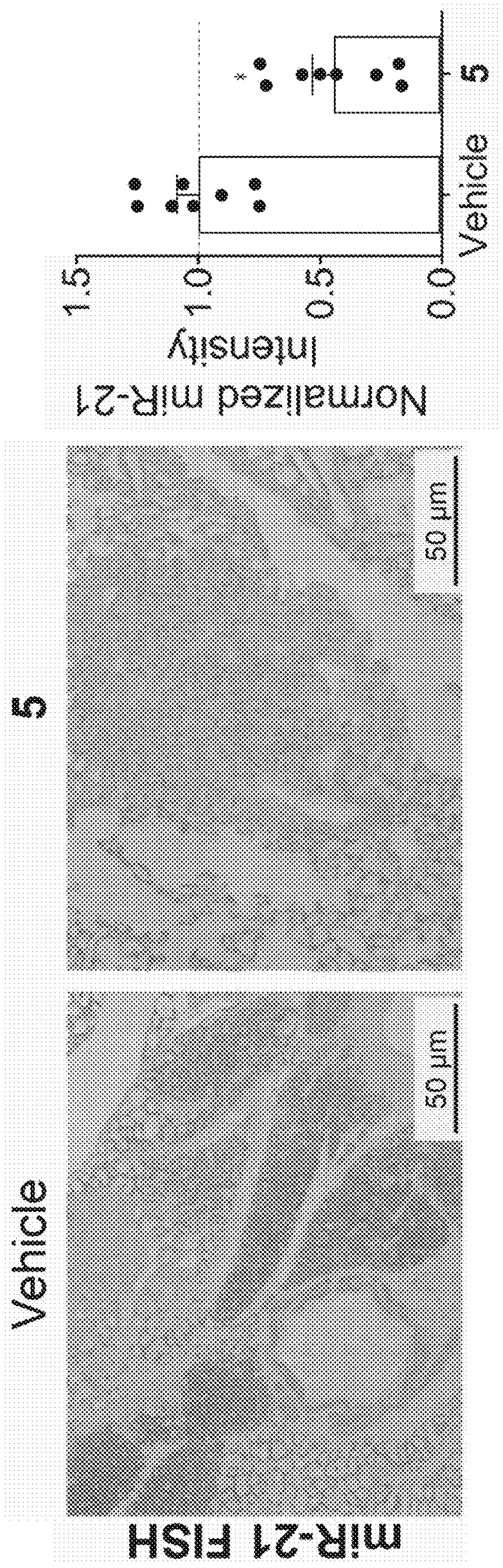
Figure 4D:
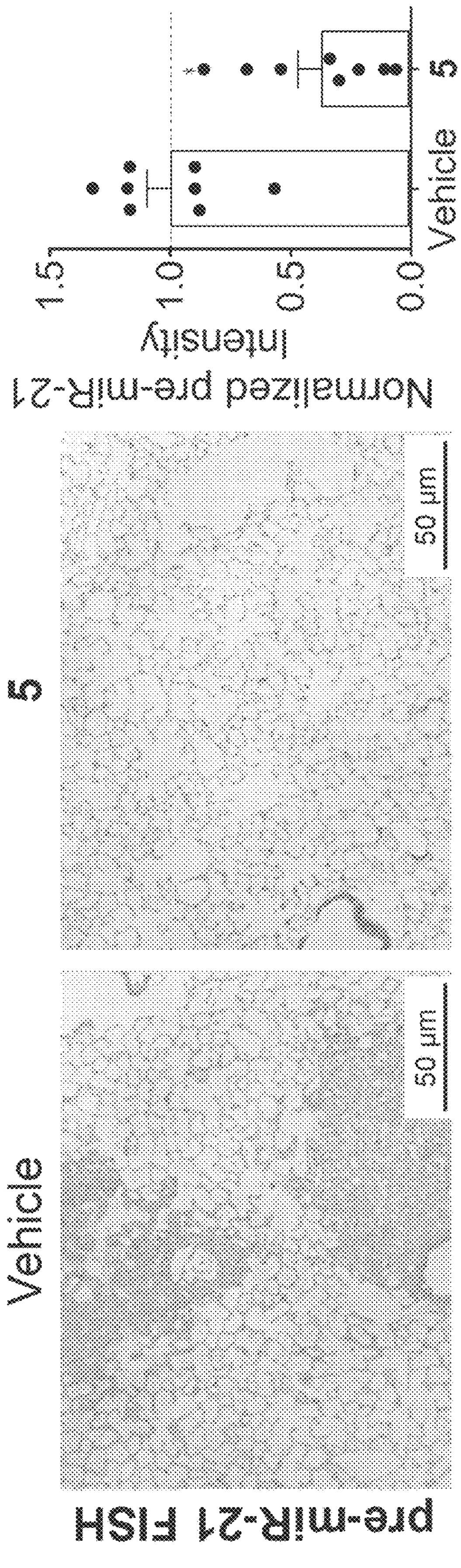
Figure 4E:
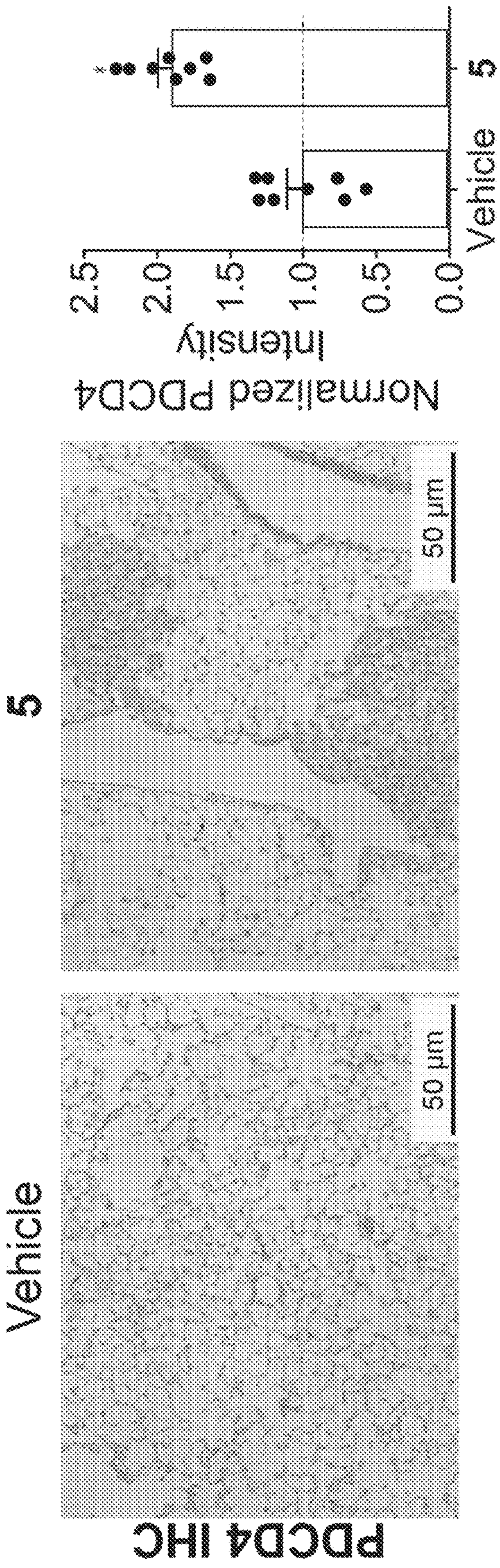
Figure 5A:
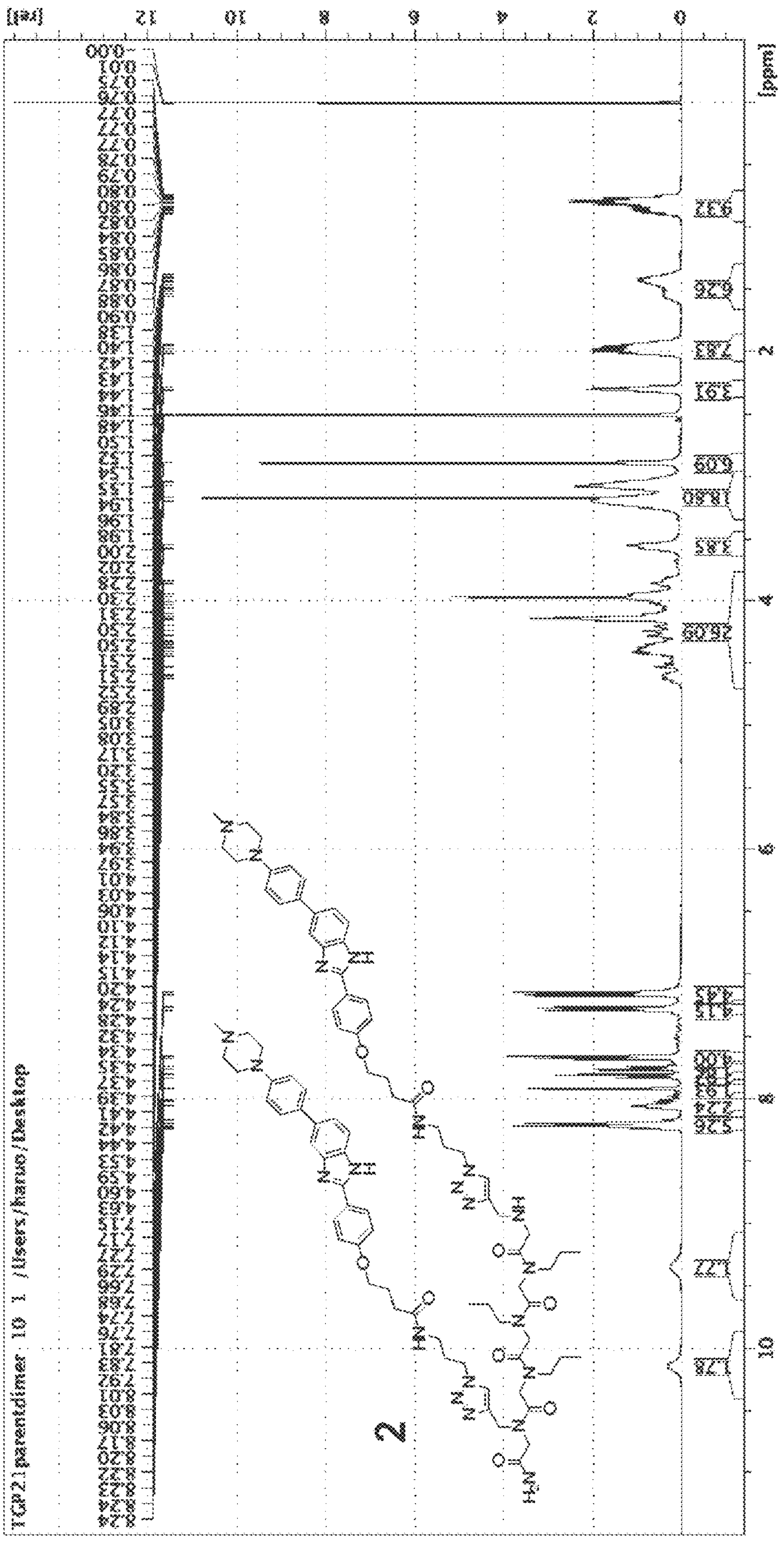
FIGS. 5A-5B. $^{1}H$ and $^{13}C$ NMR spectra of compound 2.
Figure 5B:
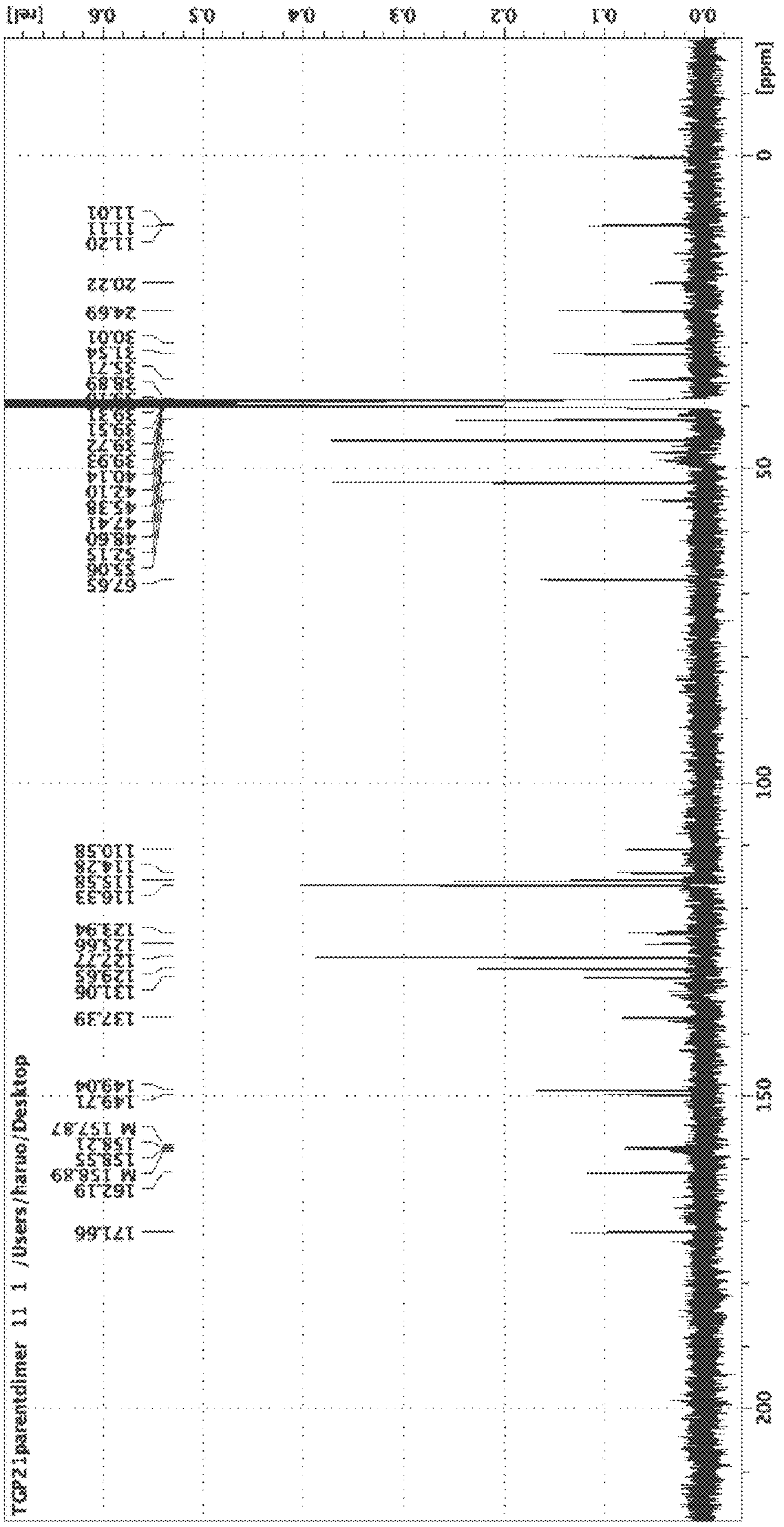
Figure 6A:
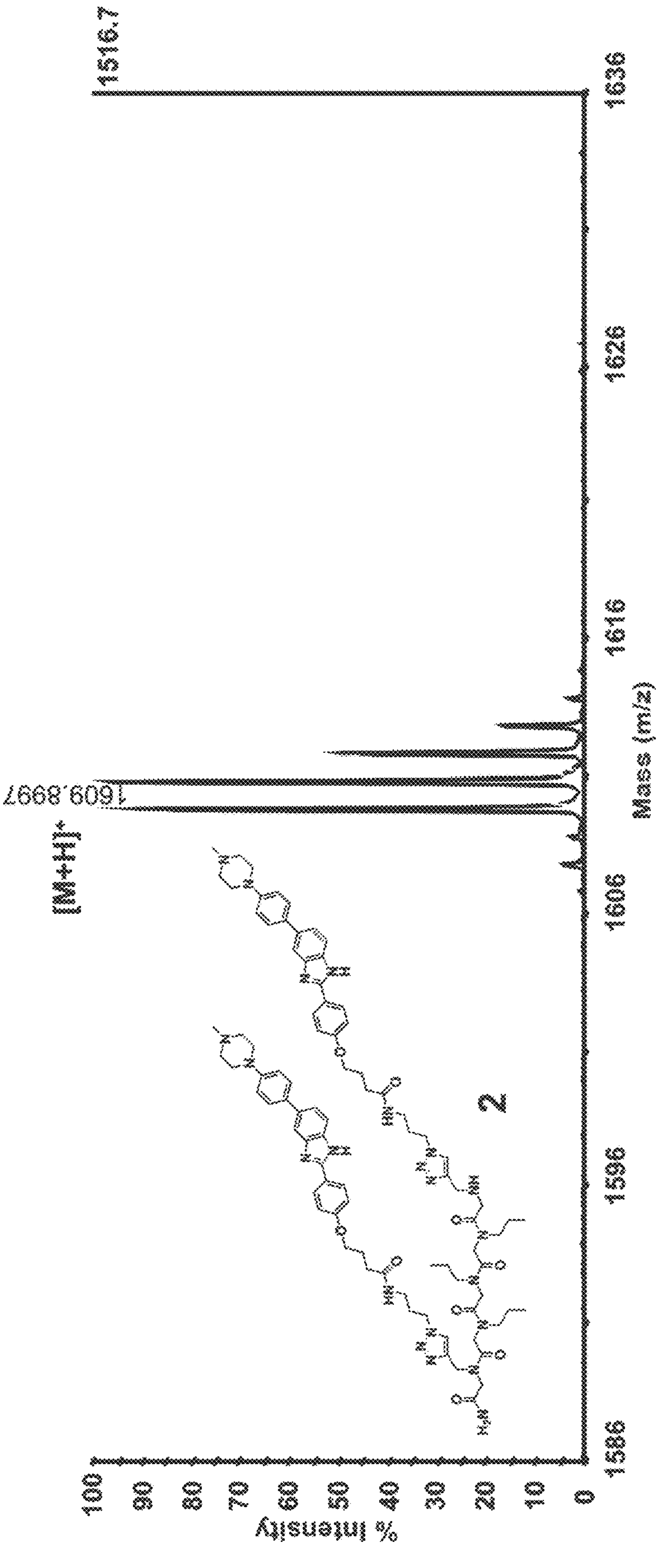
FIGS. 6A-6B. HR-MS of compound 2 by MALDI-TOF.
Figure 6B:
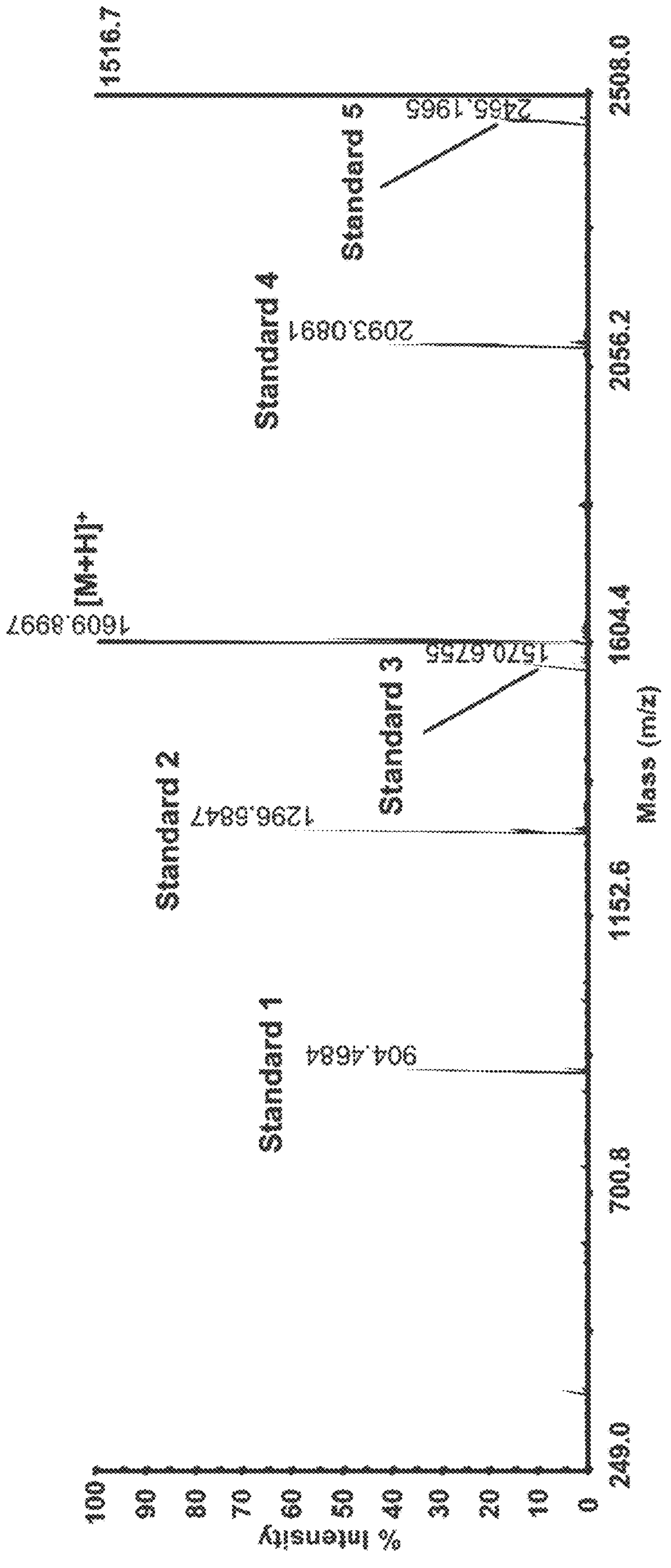
Figure 7A:
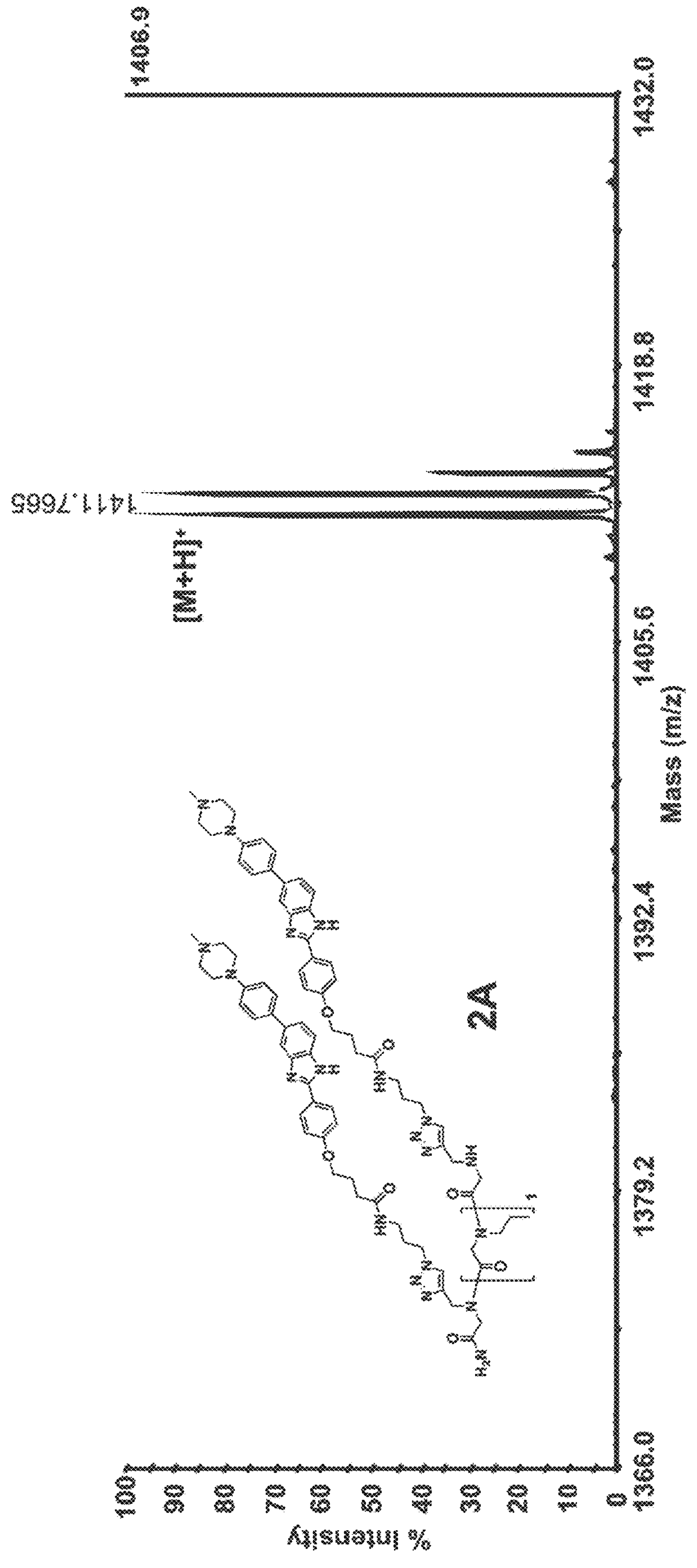
FIGS. 7A-7B. HR-MS of compound 2A by MALDI-TOF.
Figure 7B:
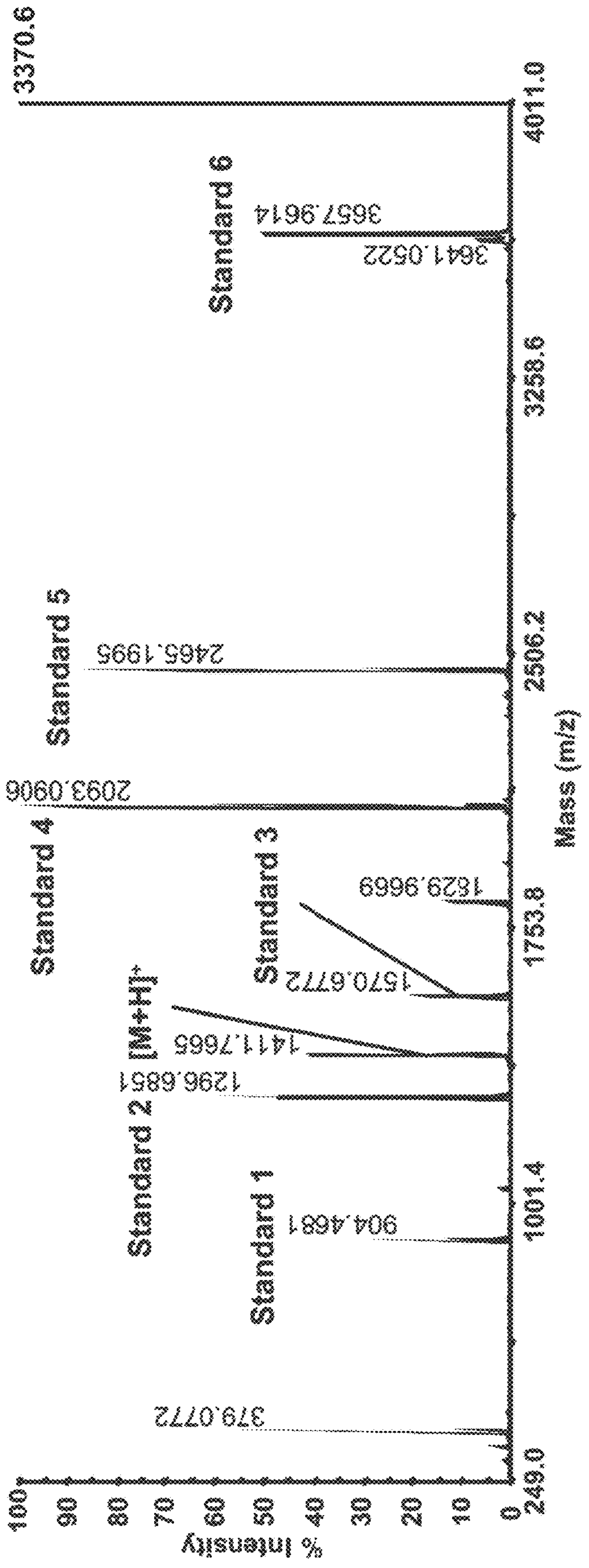
Figure 8A:
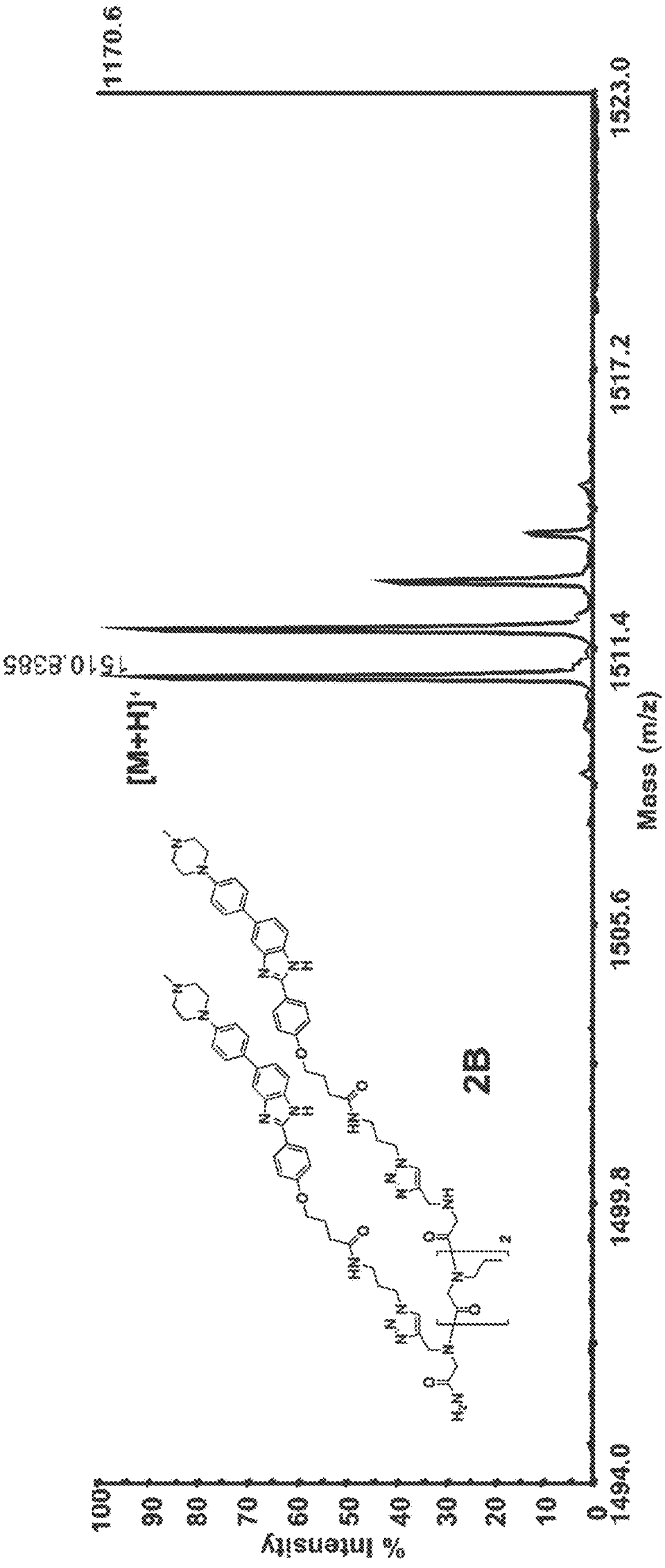
FIGS. 8A-8B. HR-MS of compound 2B by MALDI-TOF.
Figure 8B:
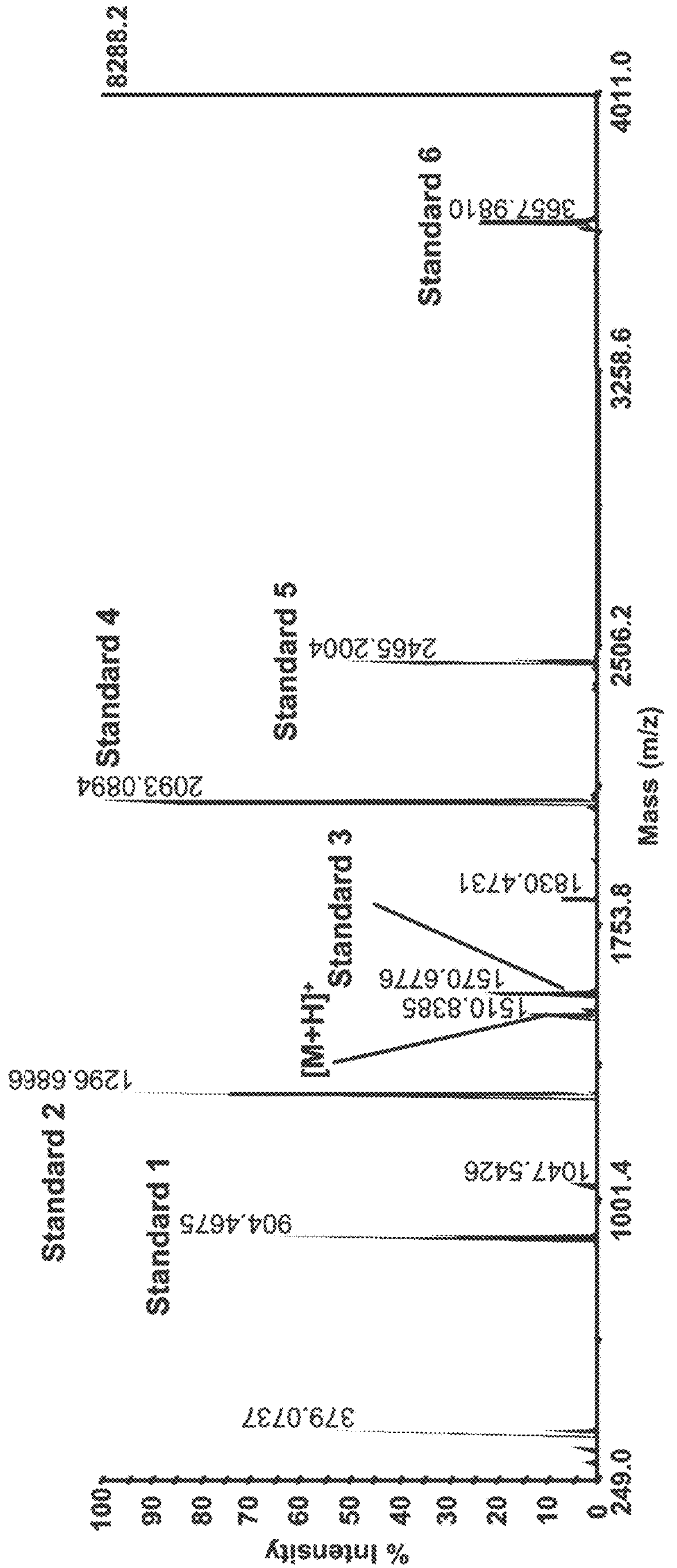
Figure 9A:
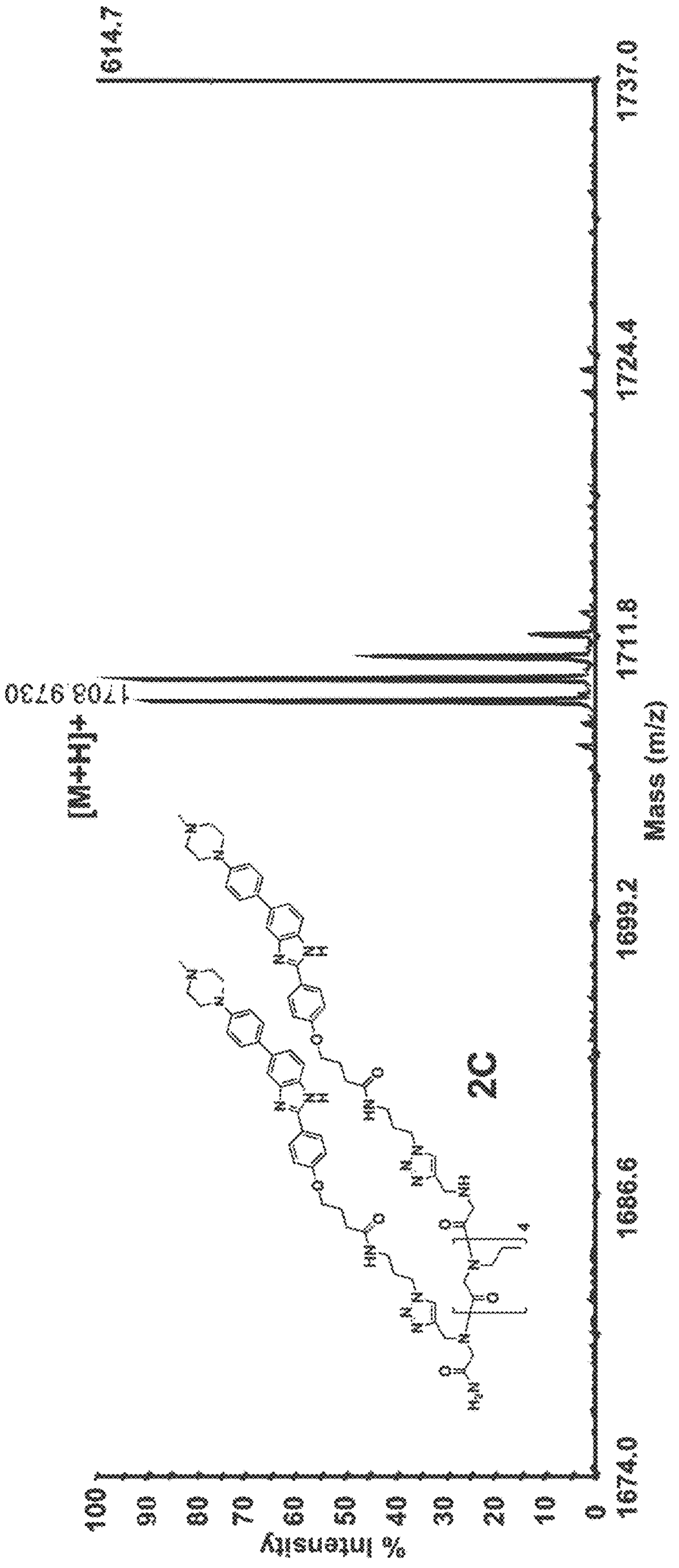
FIGS. 9A-9B. HR-MS of compound 2C by MALDI-TOF.
Figure 9B:
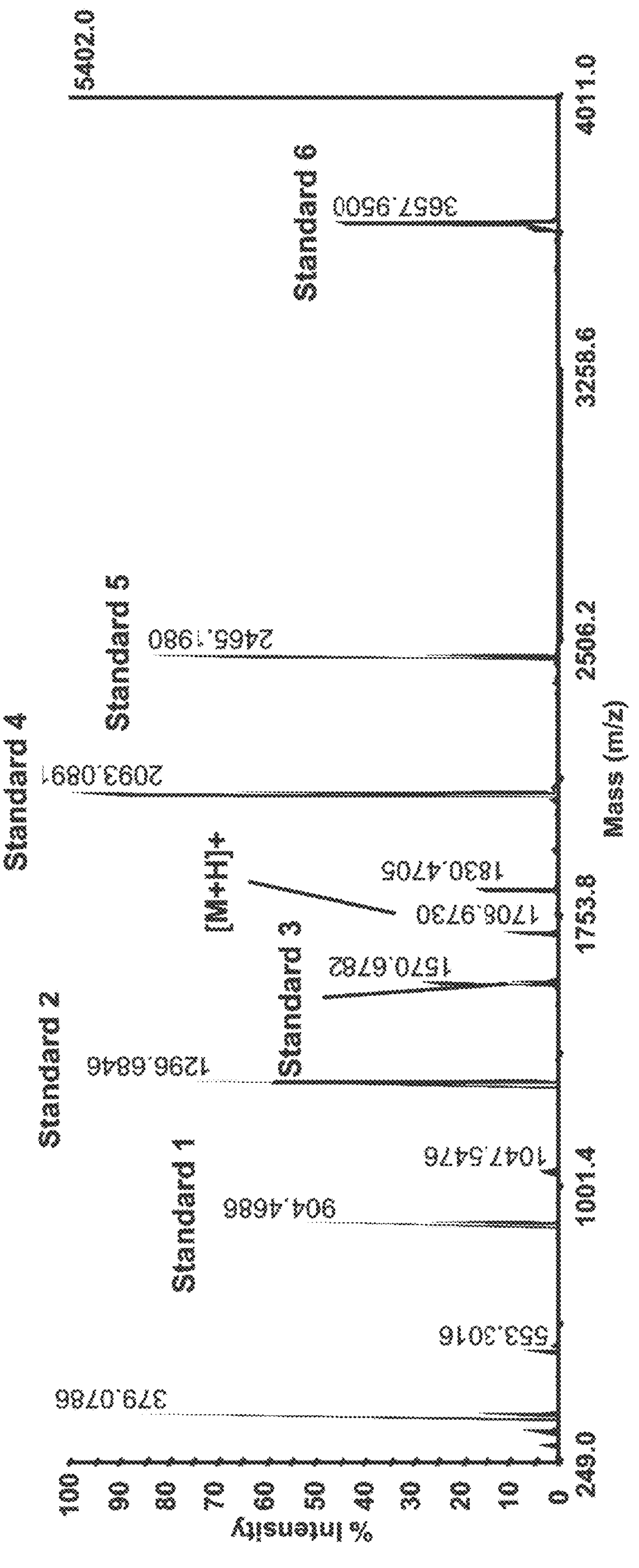
Figure 10A:
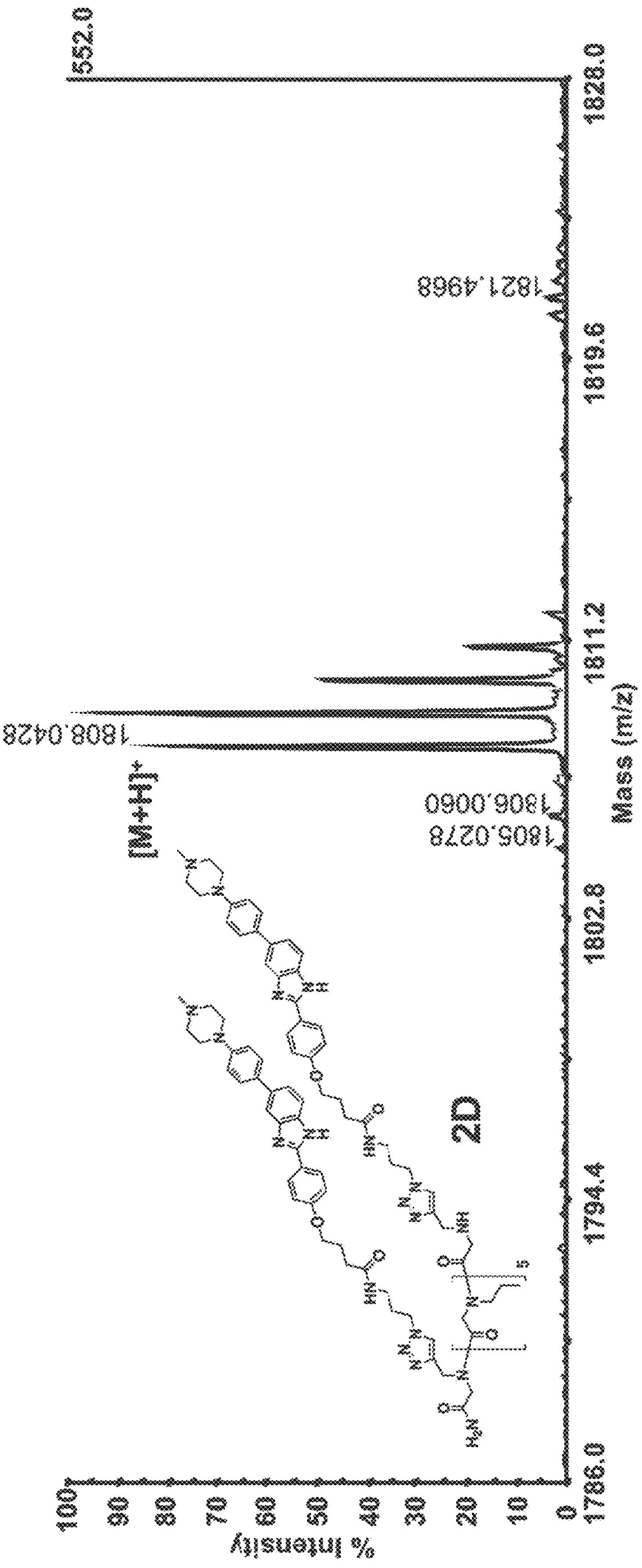
FIGS. 10A-10B. HR-MS of compound 2D by MALDI-TOF.
Figure 10B:
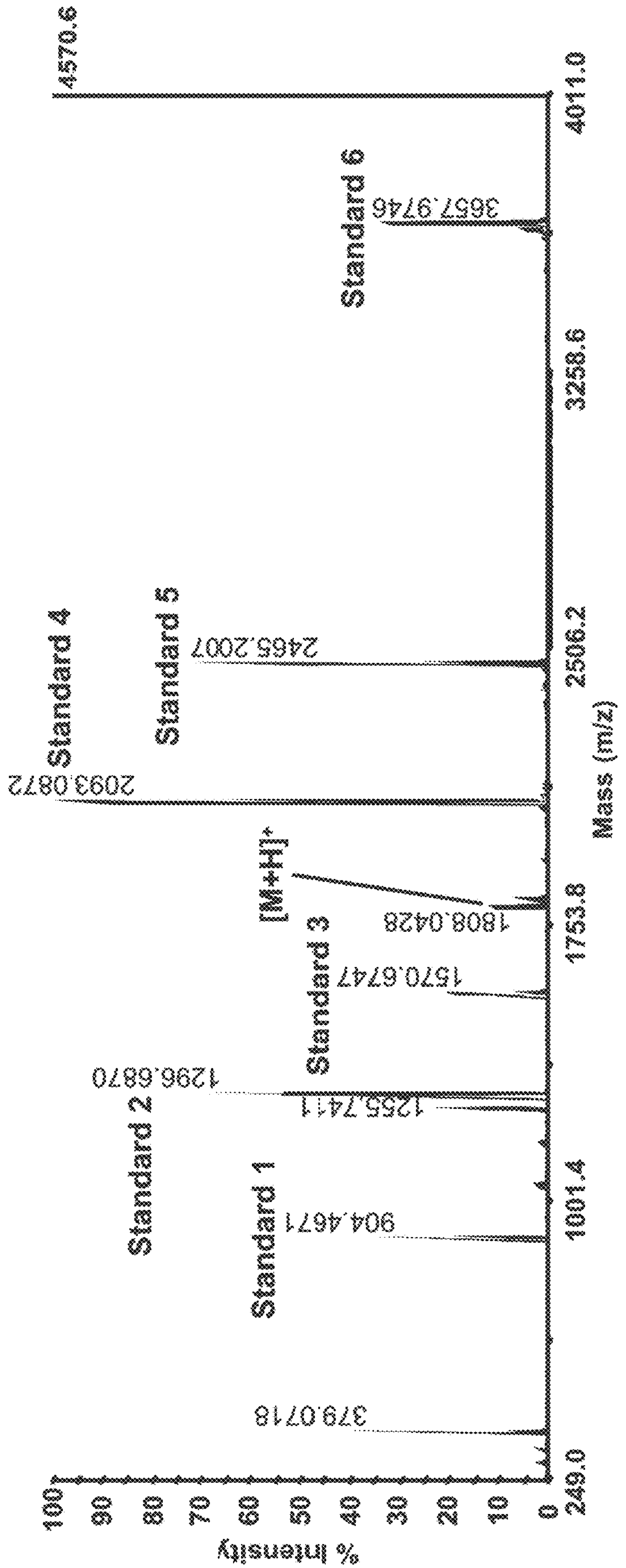
Figure 11A:
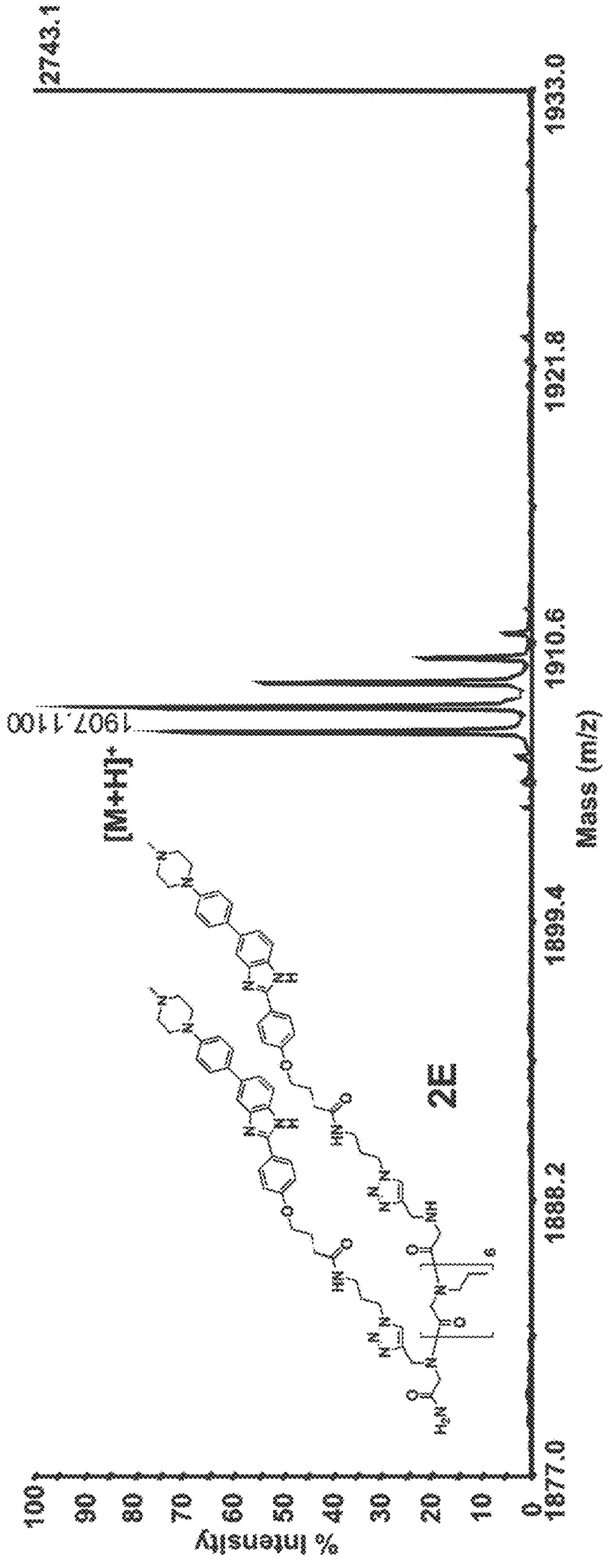
FIGS. 11A-11B. HR-MS of compound 2E by MALDI-TOF.
Figure 11B:
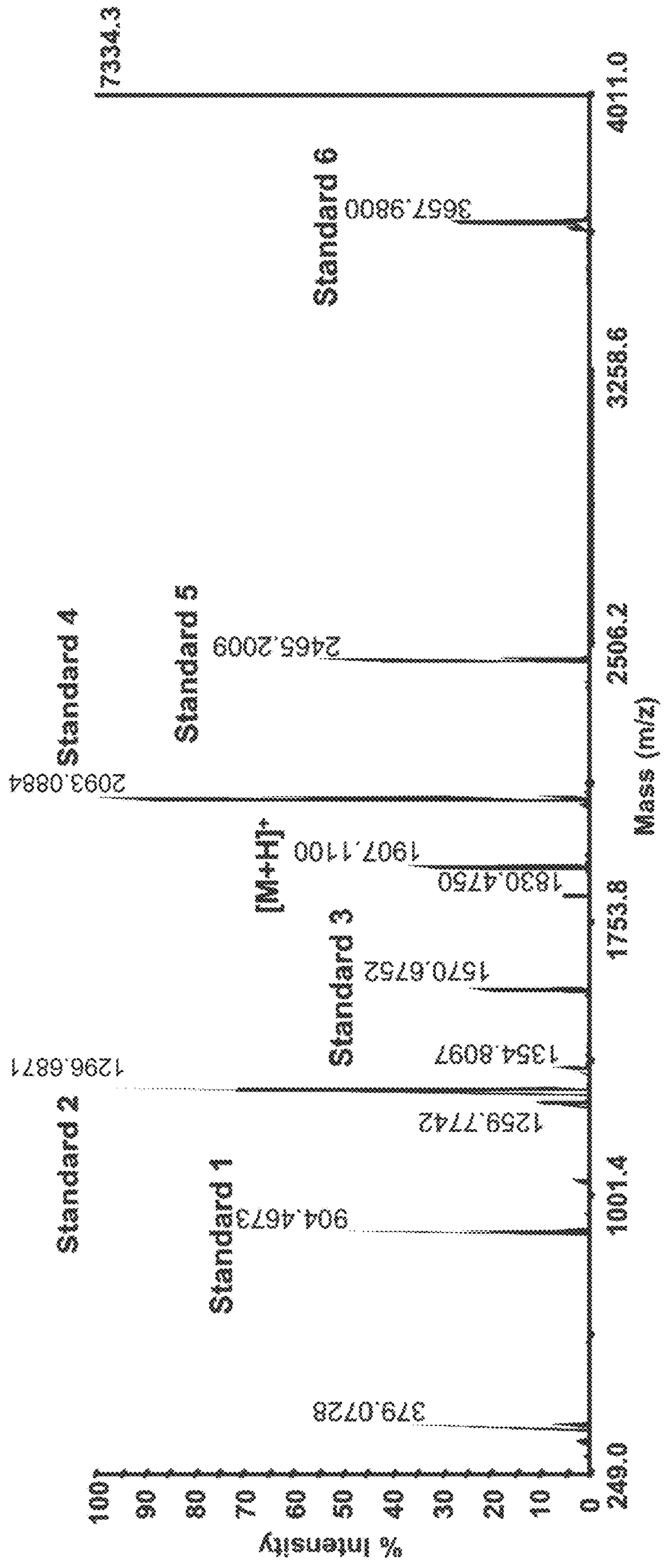
Figure 12A:
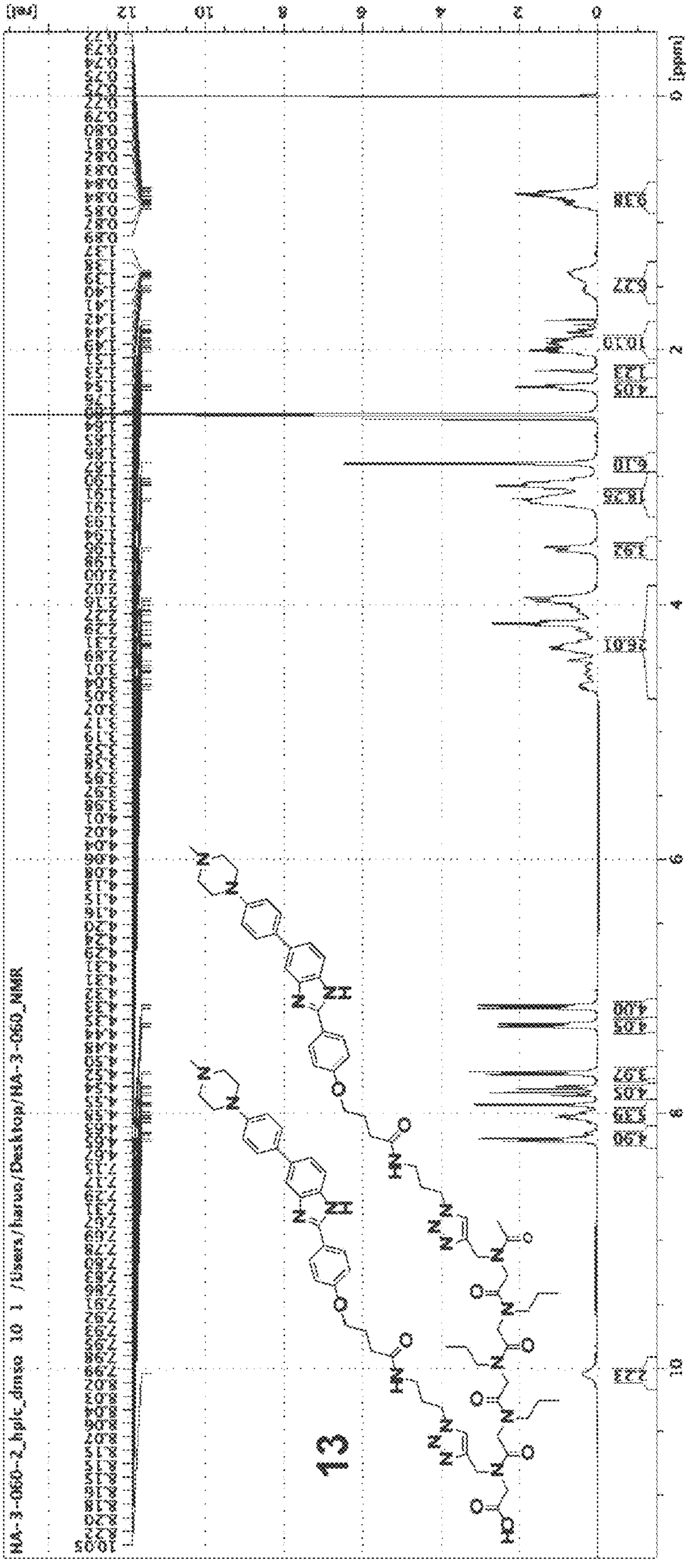
FIGS. 12A-12B. $^{1}H$ and $^{13}C$ NMR spectra of compound 13.
Figure 12B:
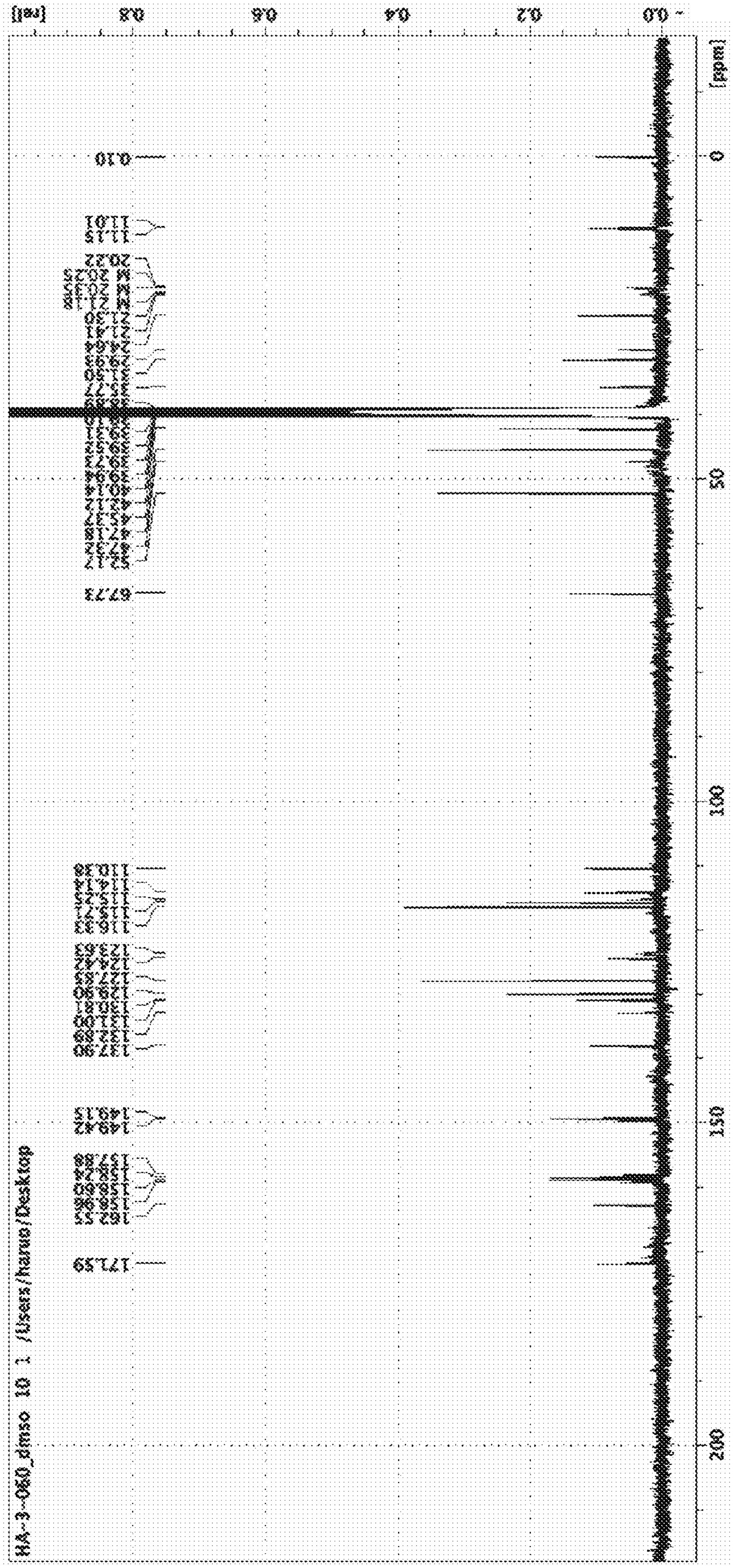
Figure 13A:
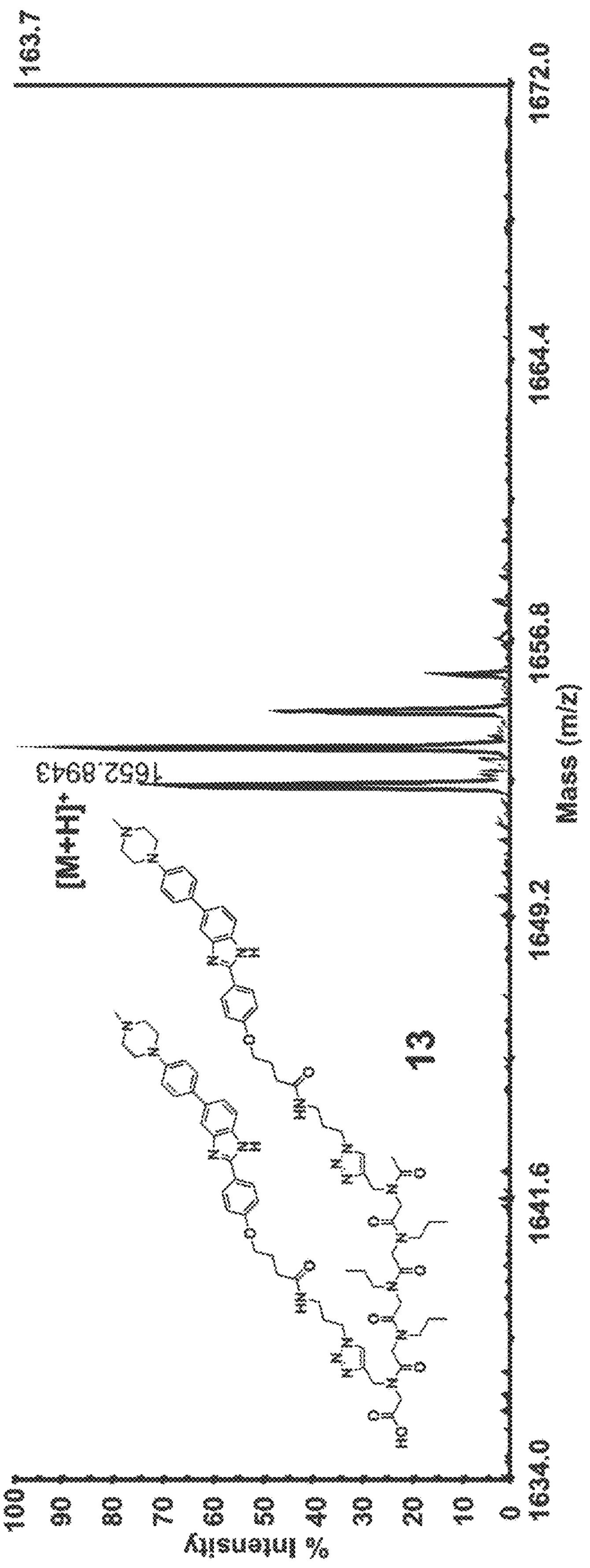
FIGS. 13A-13B. HR-MS of compound 13 by MALDI-TOF.
Figure 13B:
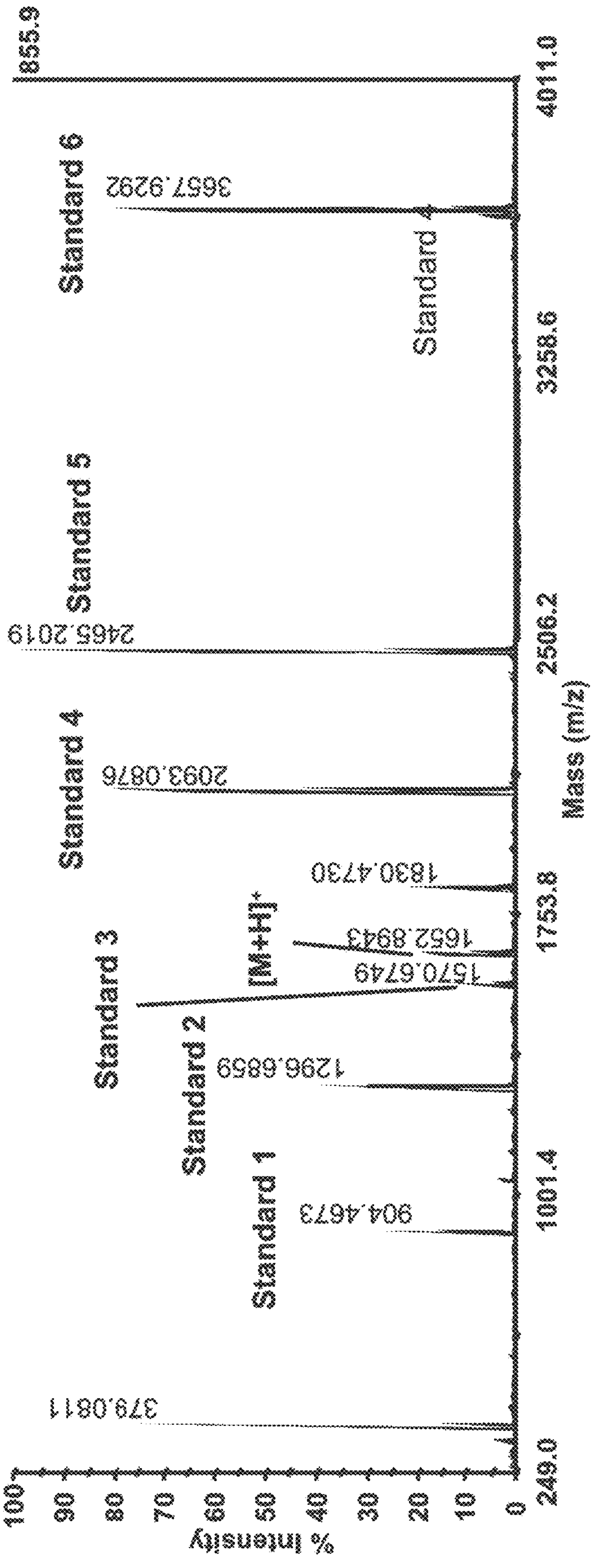
Figure 14A:
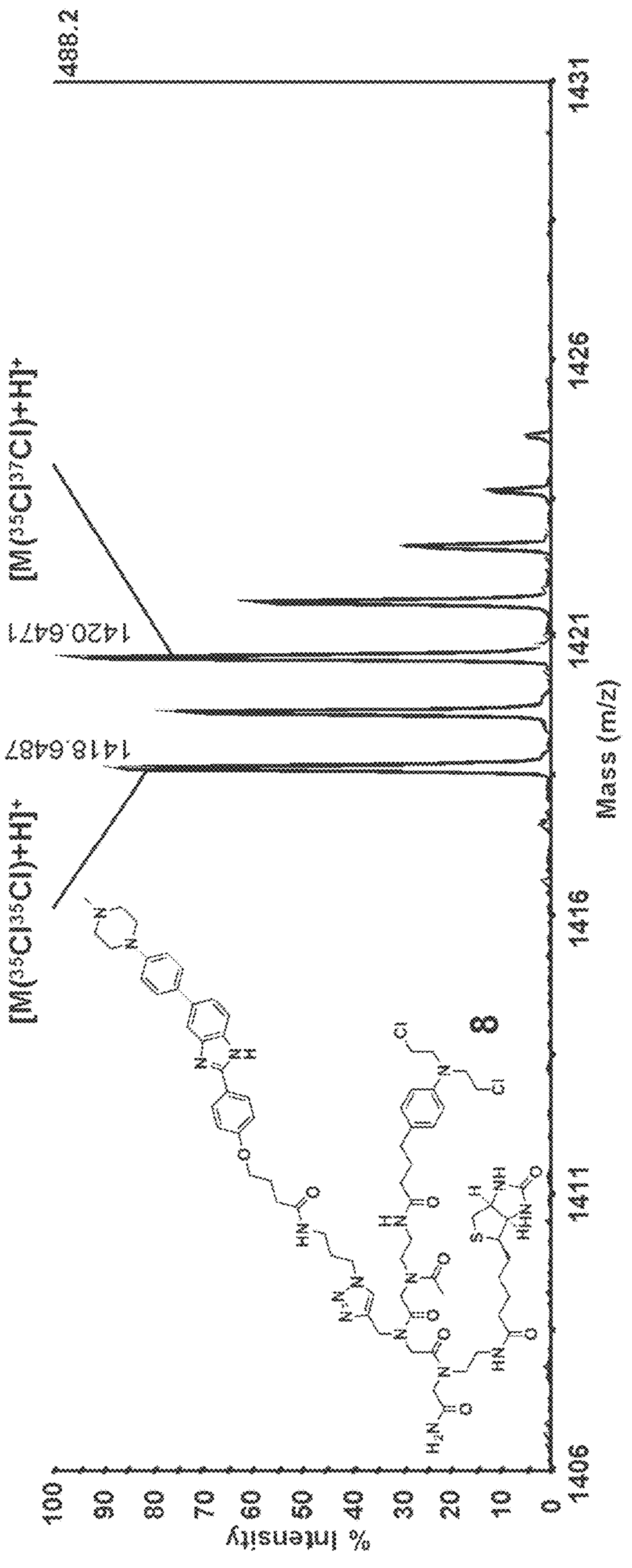
FIGS. 14A-14B. HR-MS of compound 8 by MALDI-TOF.
Figure 14B:
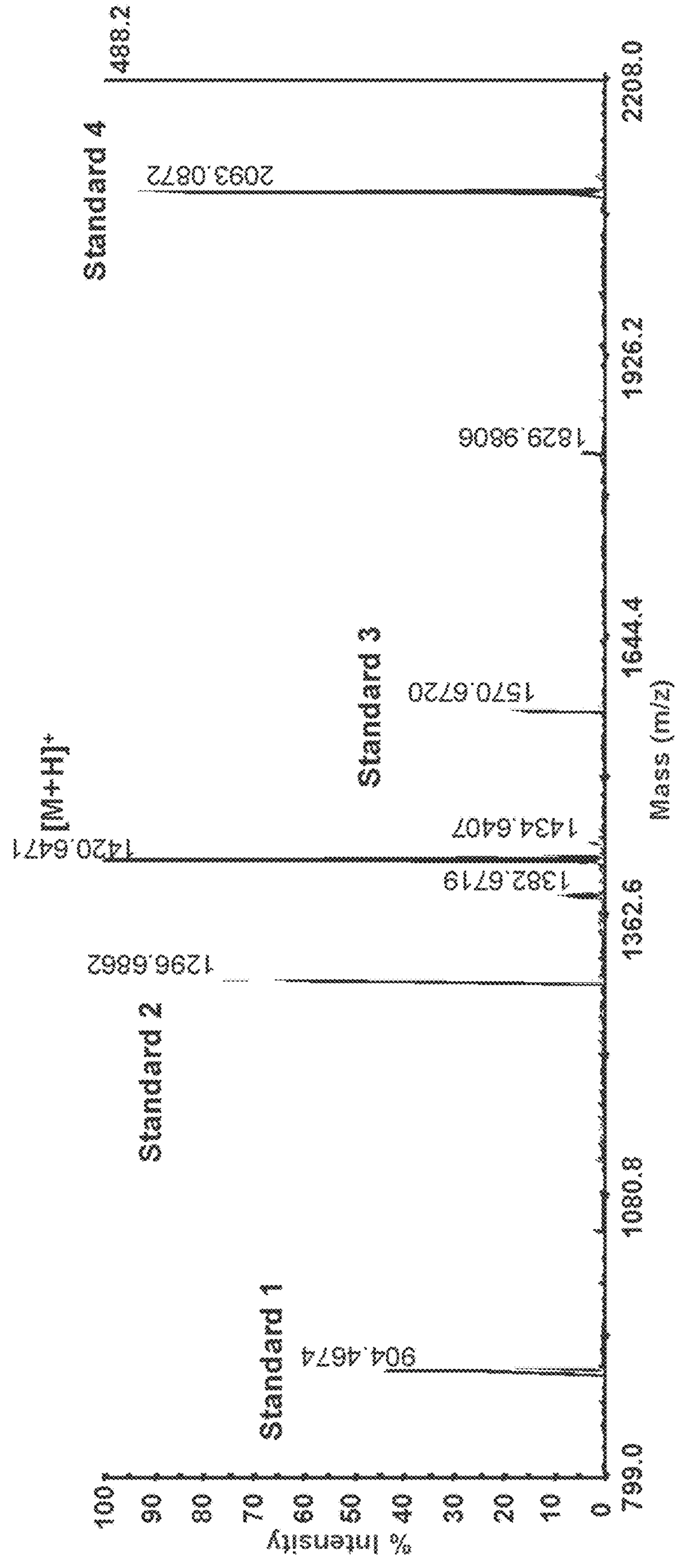
Figure 15A:
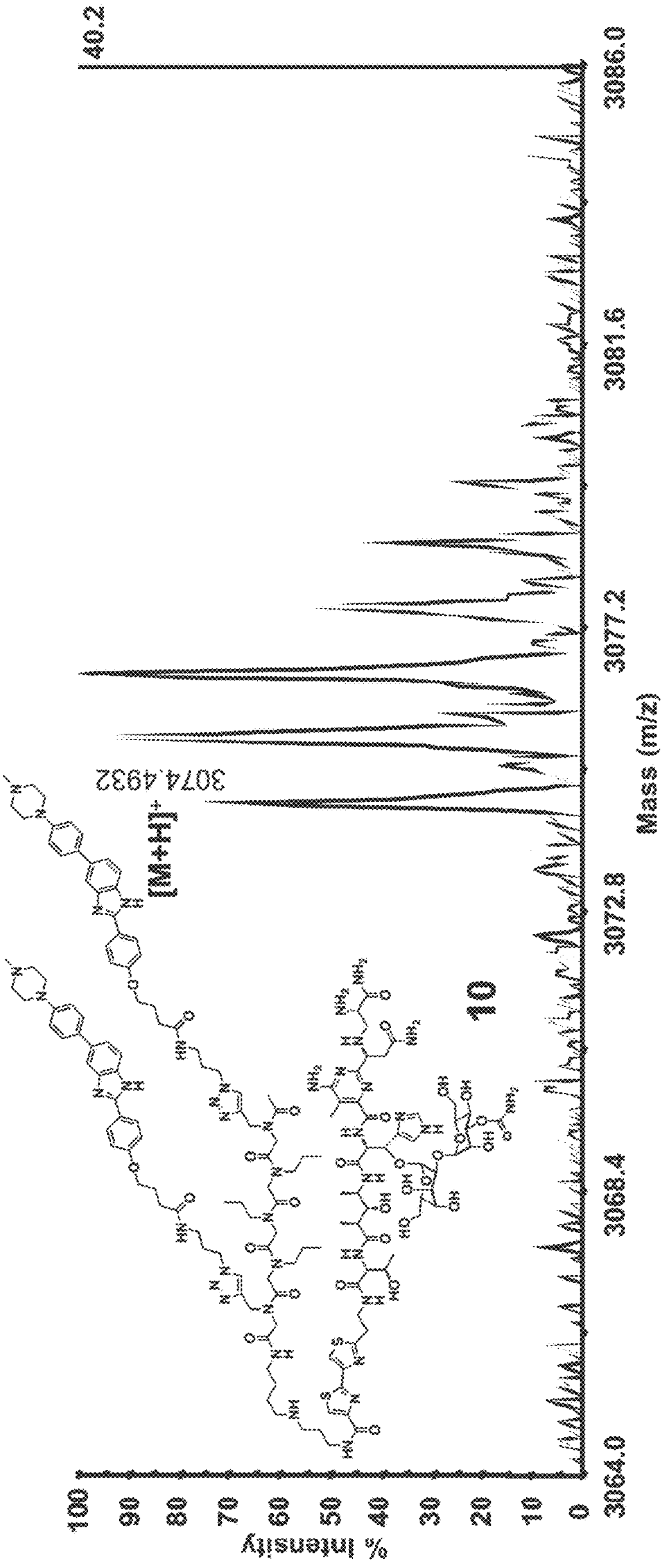
FIGS. 15A-15B. HR-MS of compound 10 by MALDI-TOF.
Figure 15B:
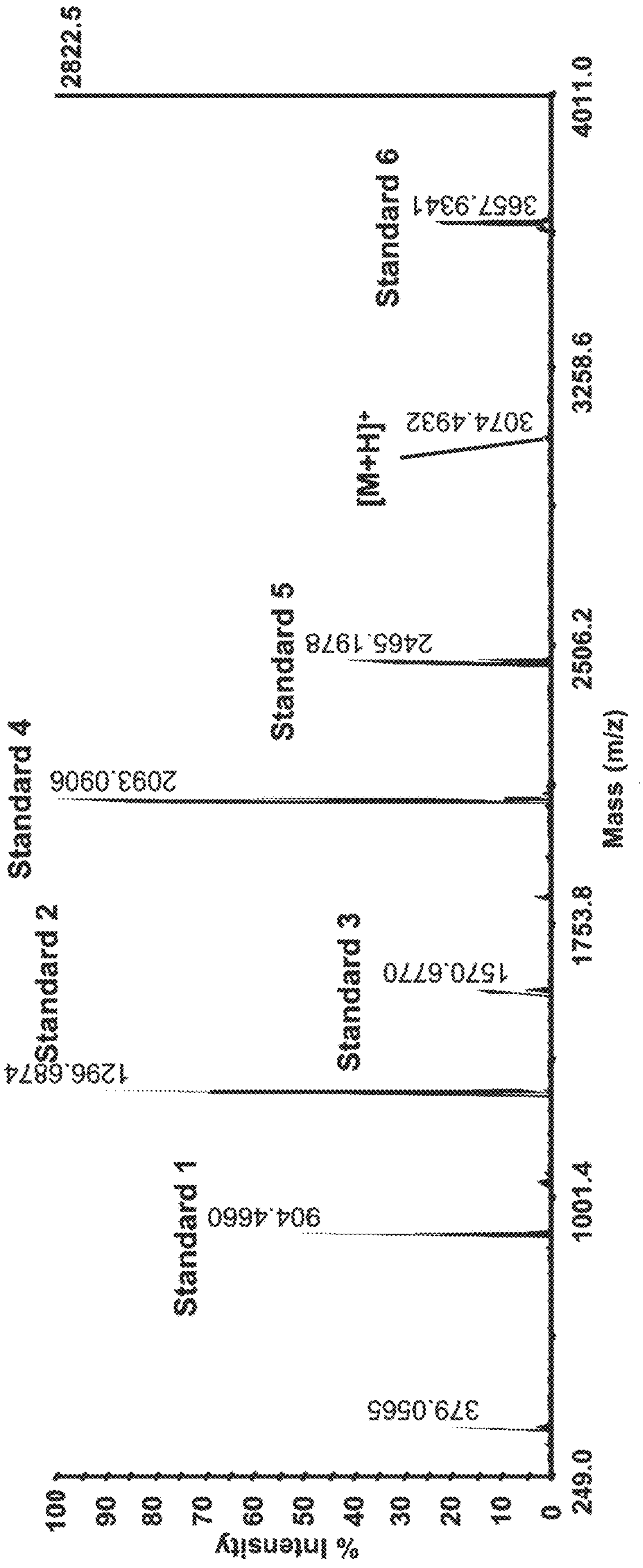
Figure 16A:
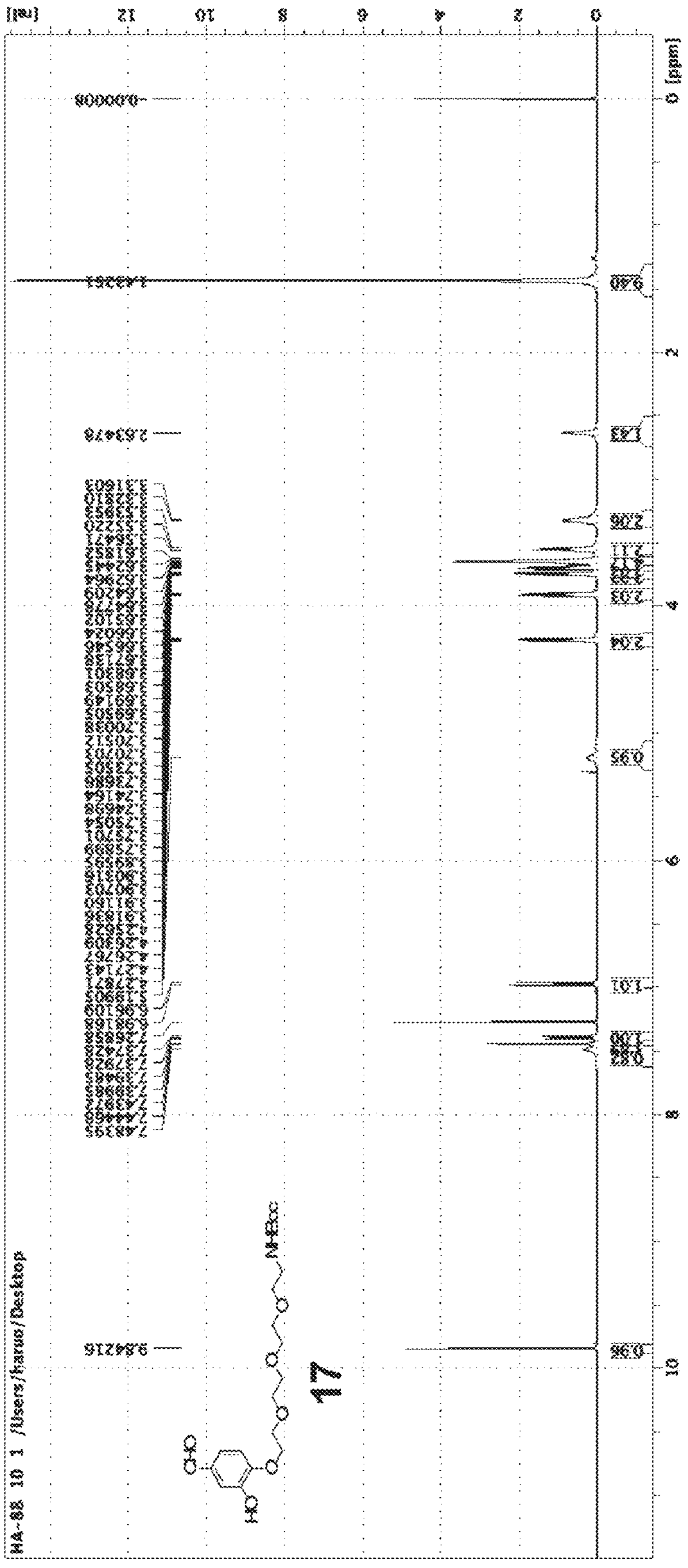
FIGS. 16A-16B. $^{1}H$ and $^{13}C$ NMR spectra of compound 17.
Figure 16B:
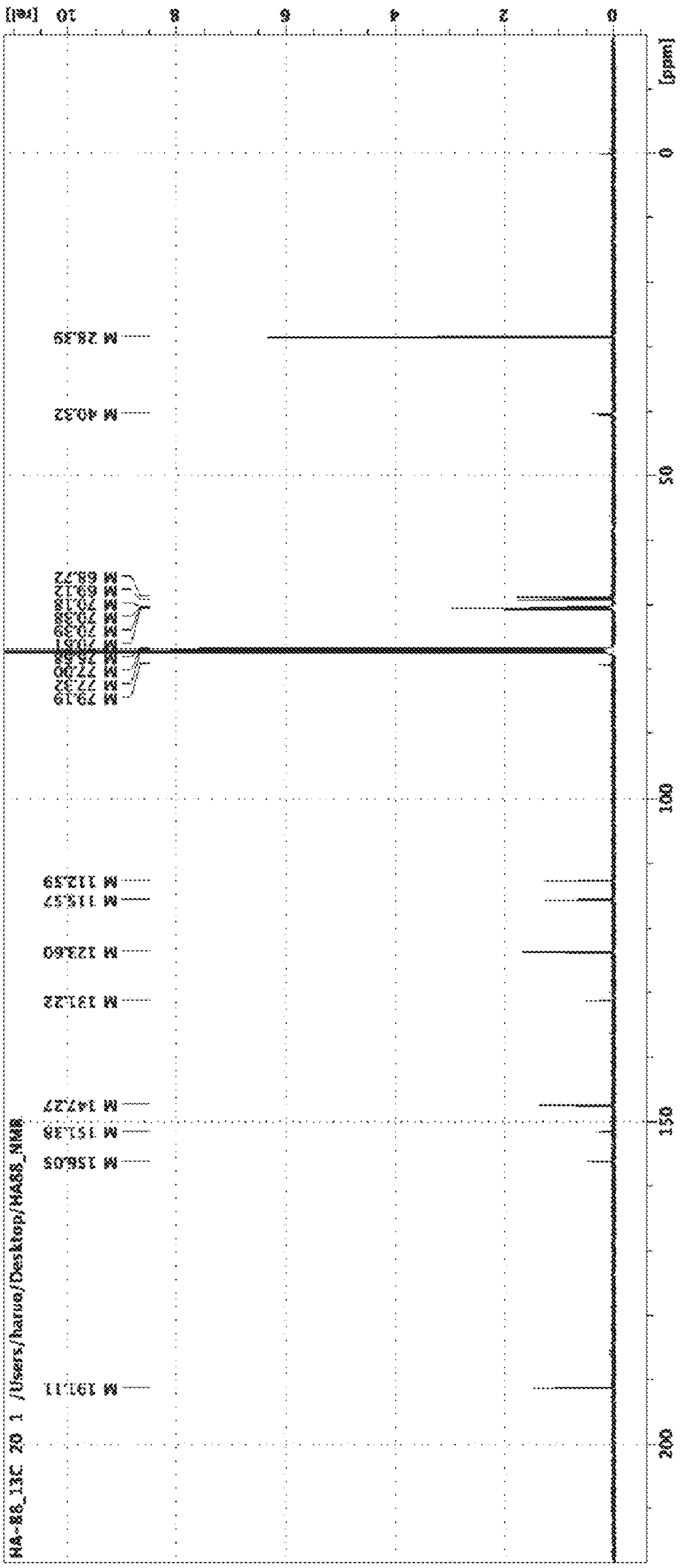
Figure 17A:
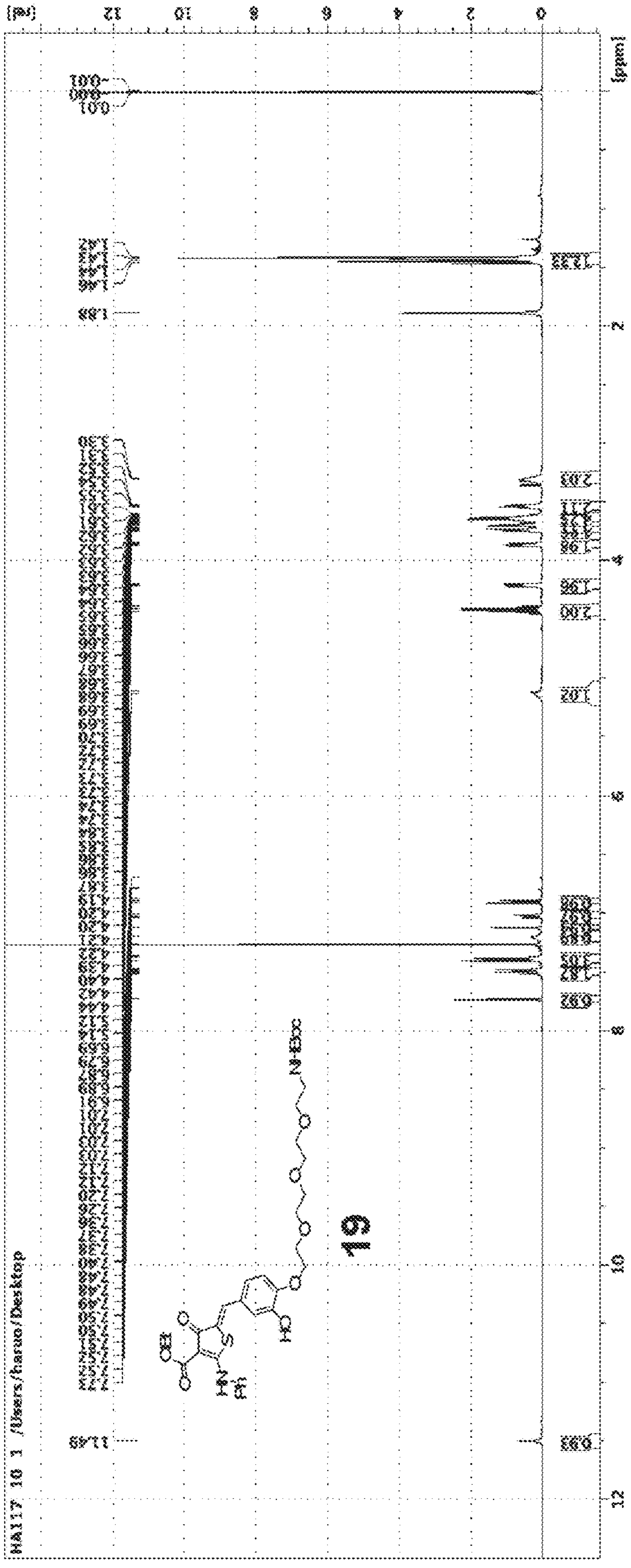
FIGS. 17A-17B. $^{1}H$ and $^{13}C$ NMR spectra of compound 19.
Figure 17B:
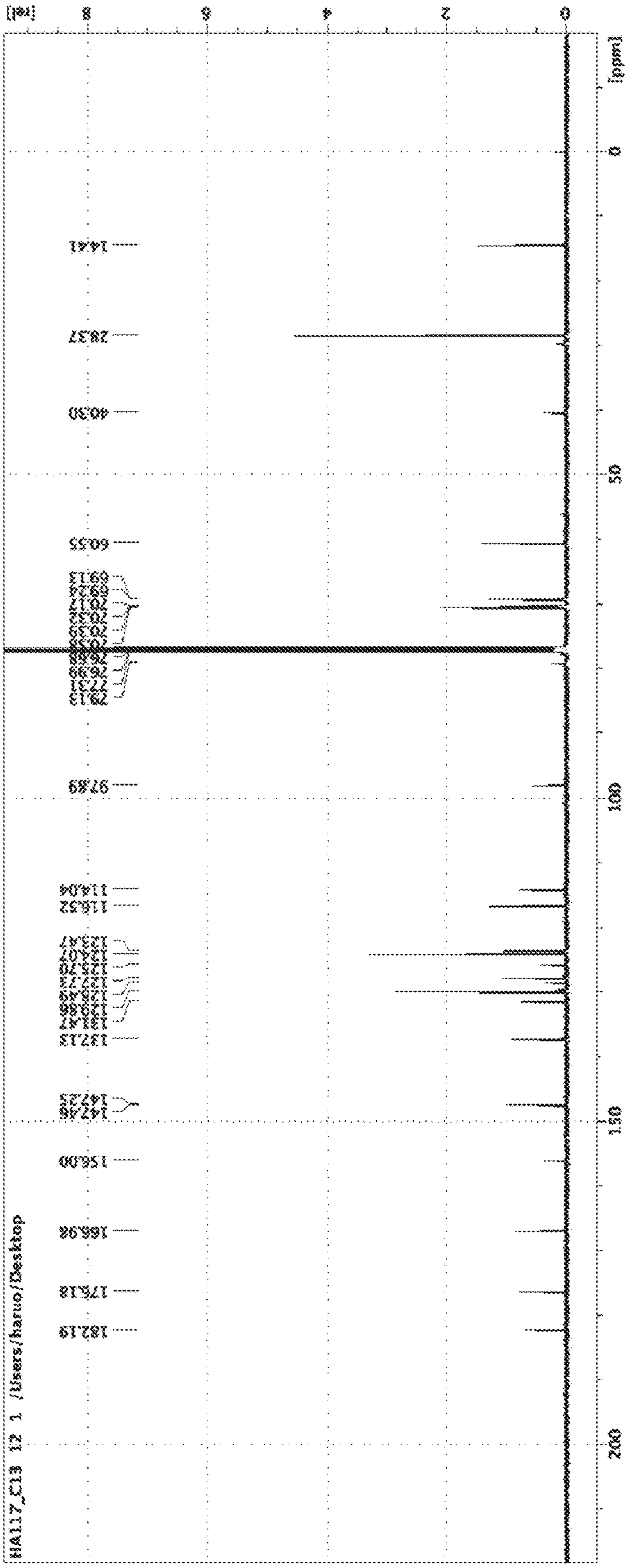
Figure 18A:
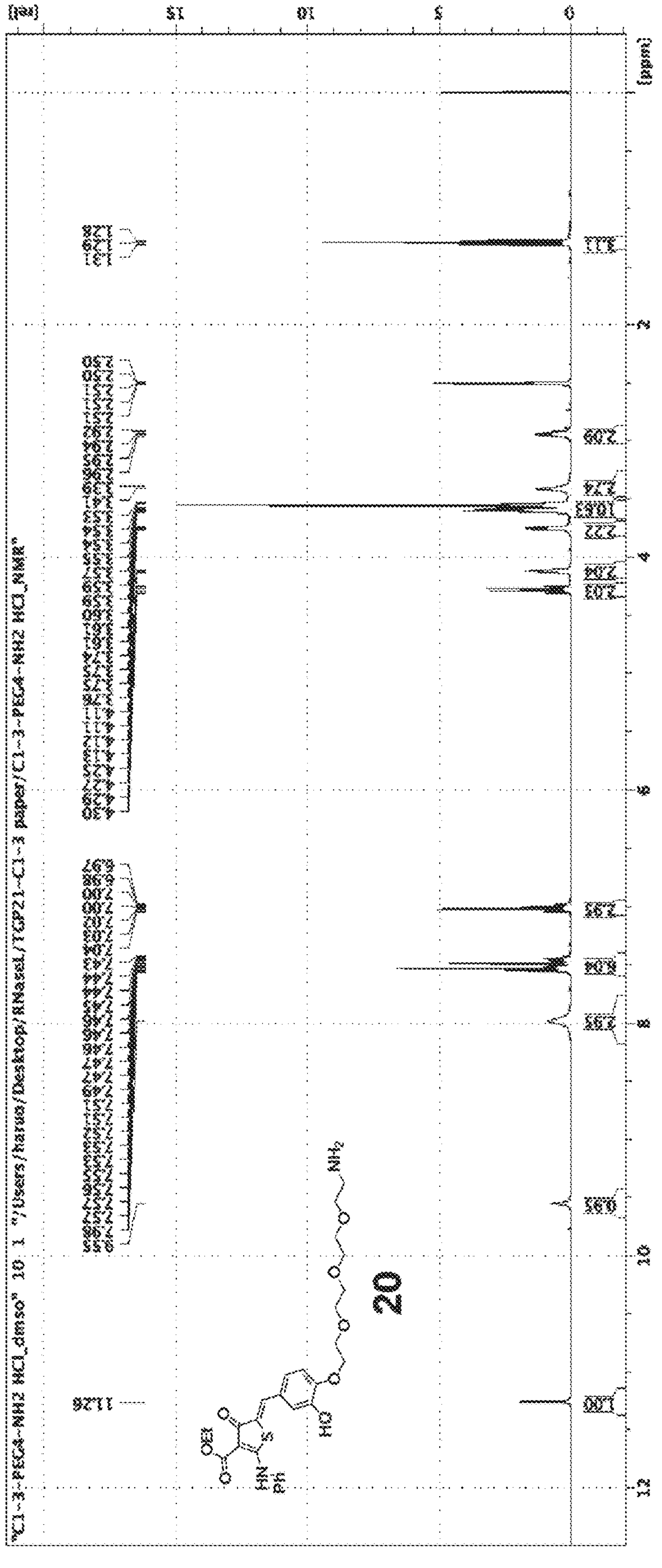
FIGS. 18A-18B. $^{1}H$ and $^{13}C$ NMR spectra of compound 20.
Figure 18B:
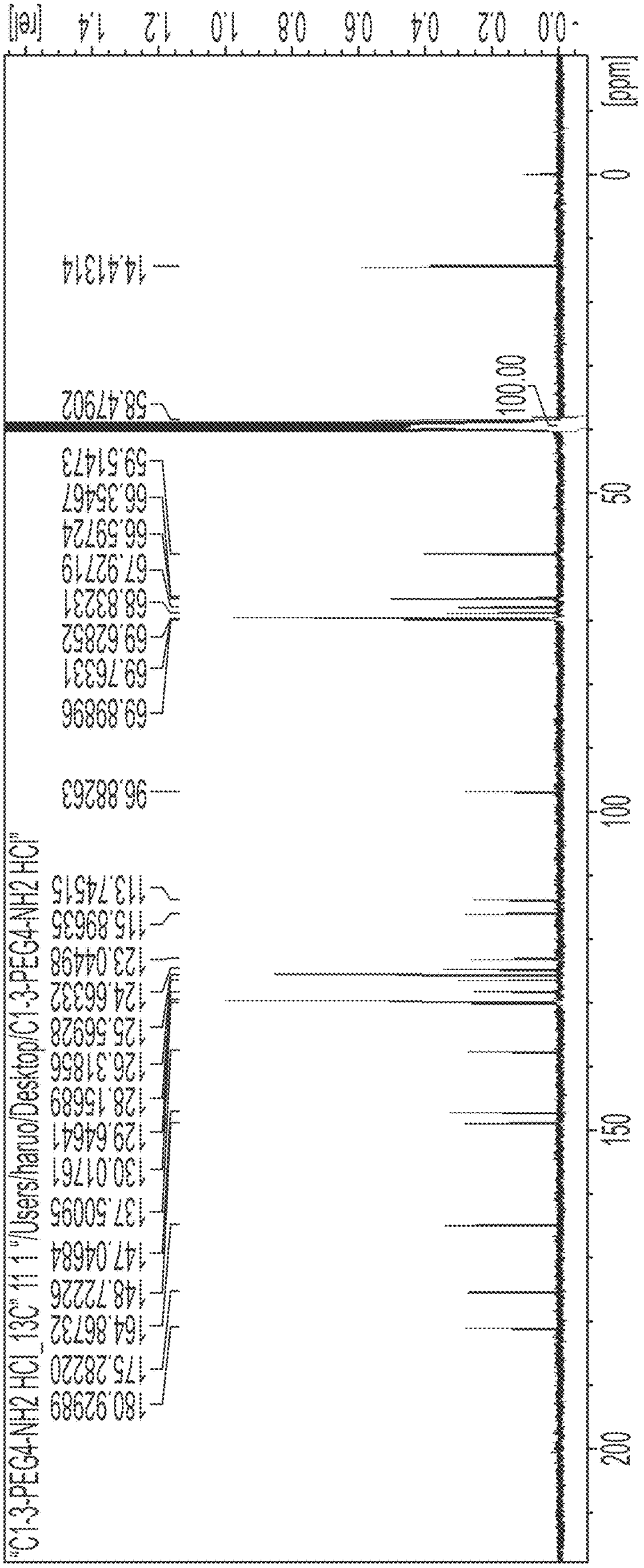
Figure 19A:
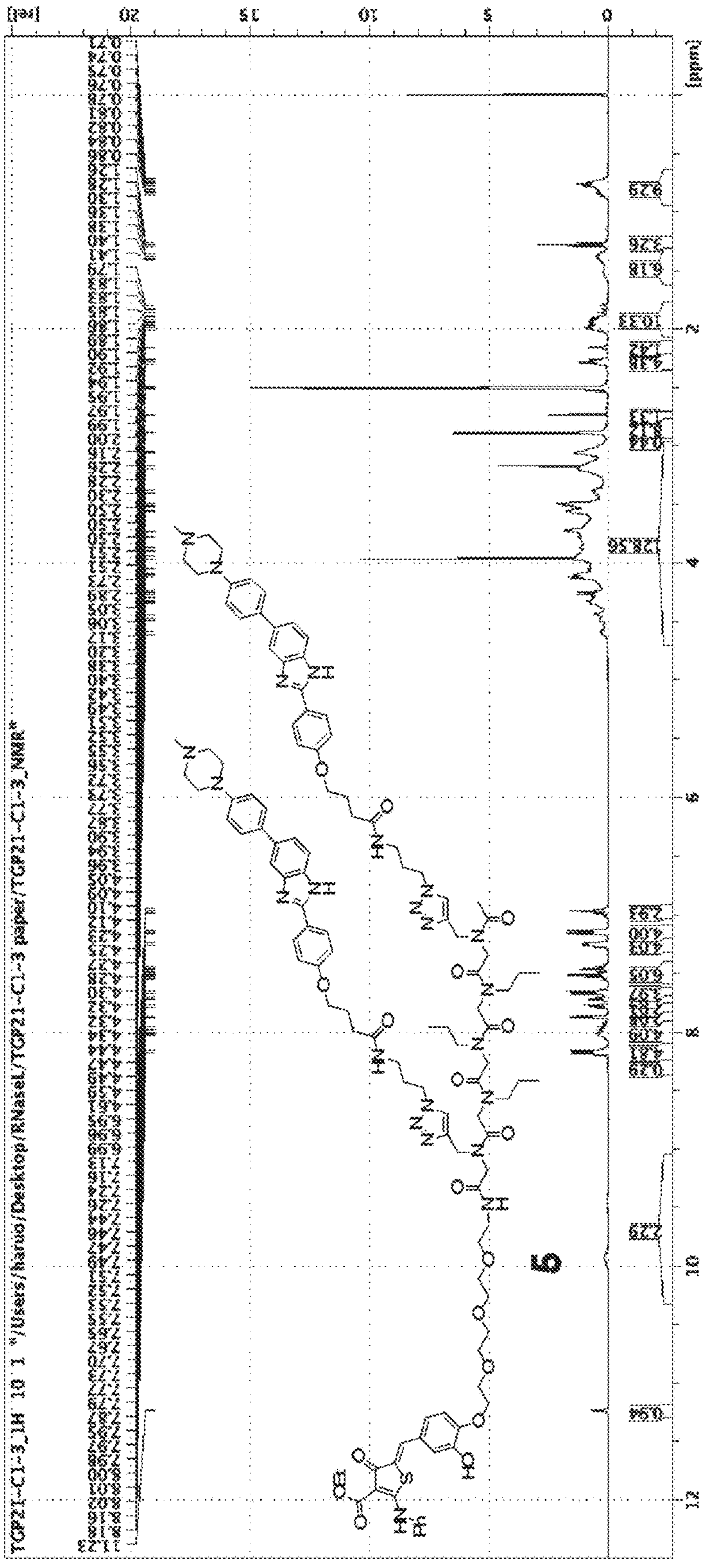
FIGS. 19A-19B. $^{1}H$ and $^{13}C$ NMR spectra of compound 5.
Figure 19B:
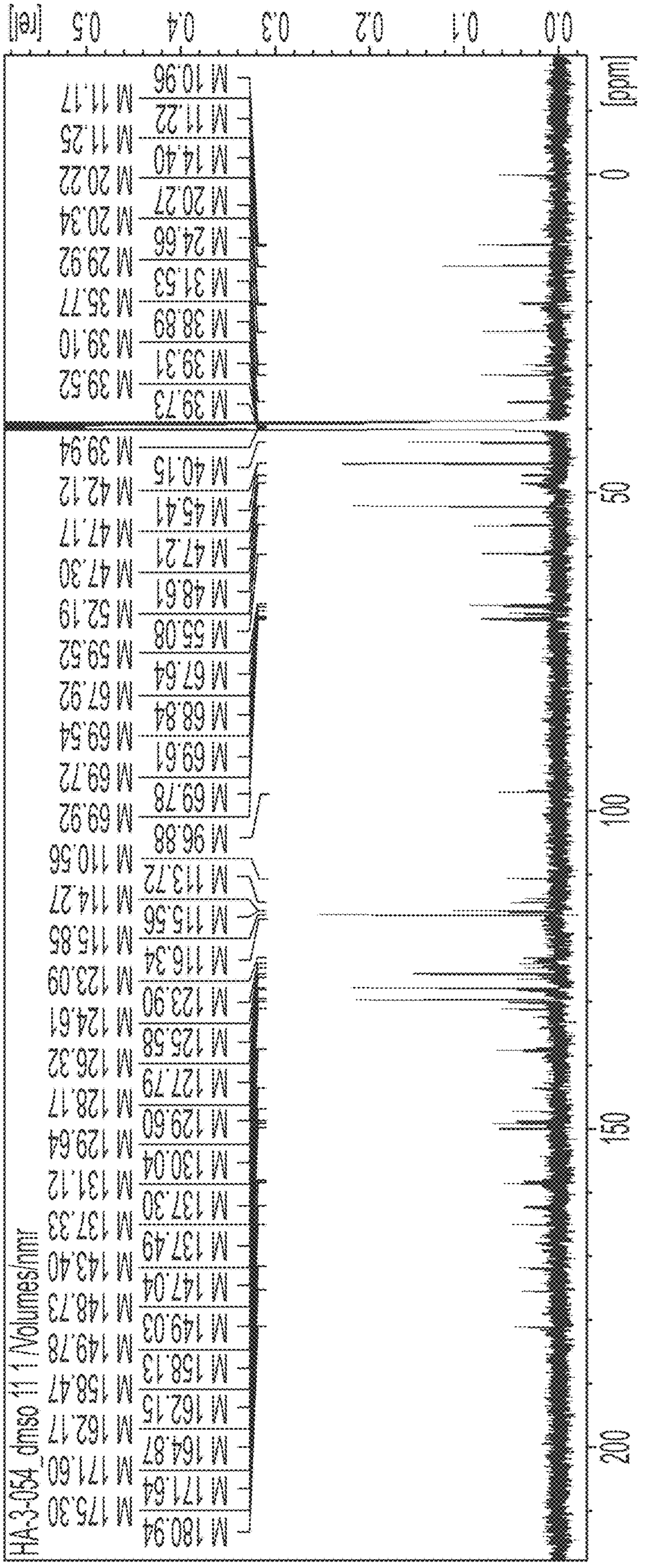
Figure 20A:
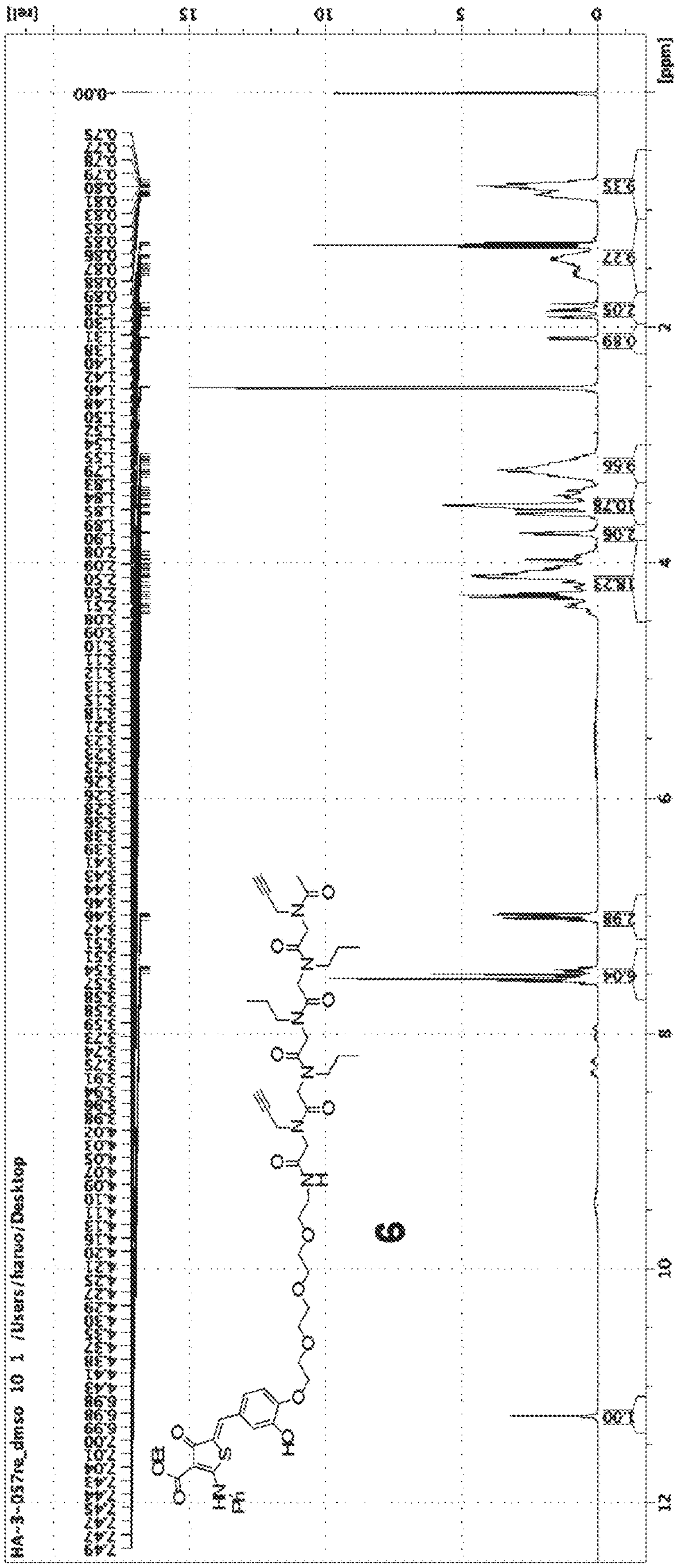
FIGS. 20A-20B. $^{1}H$ and $^{13}C$ NMR spectra of compound 6.
Figure 20B:
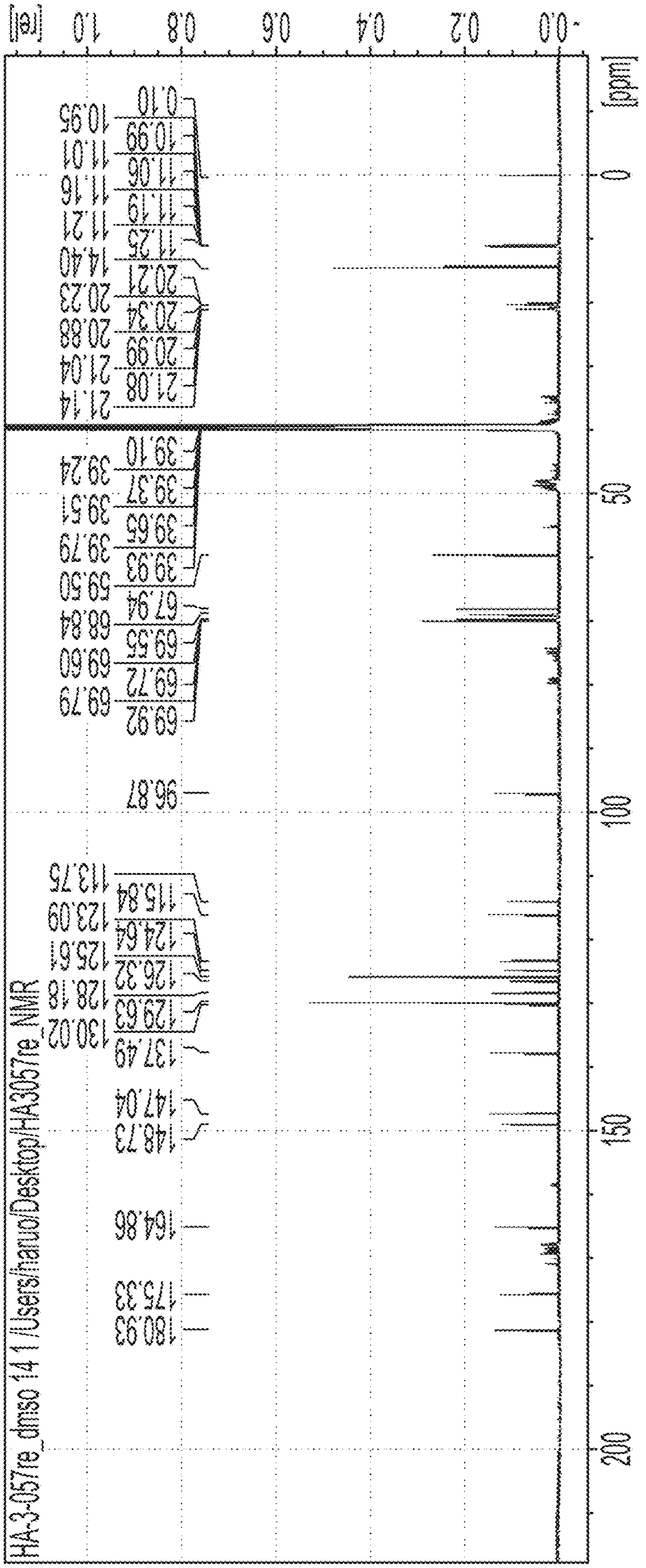
Figure 21A:
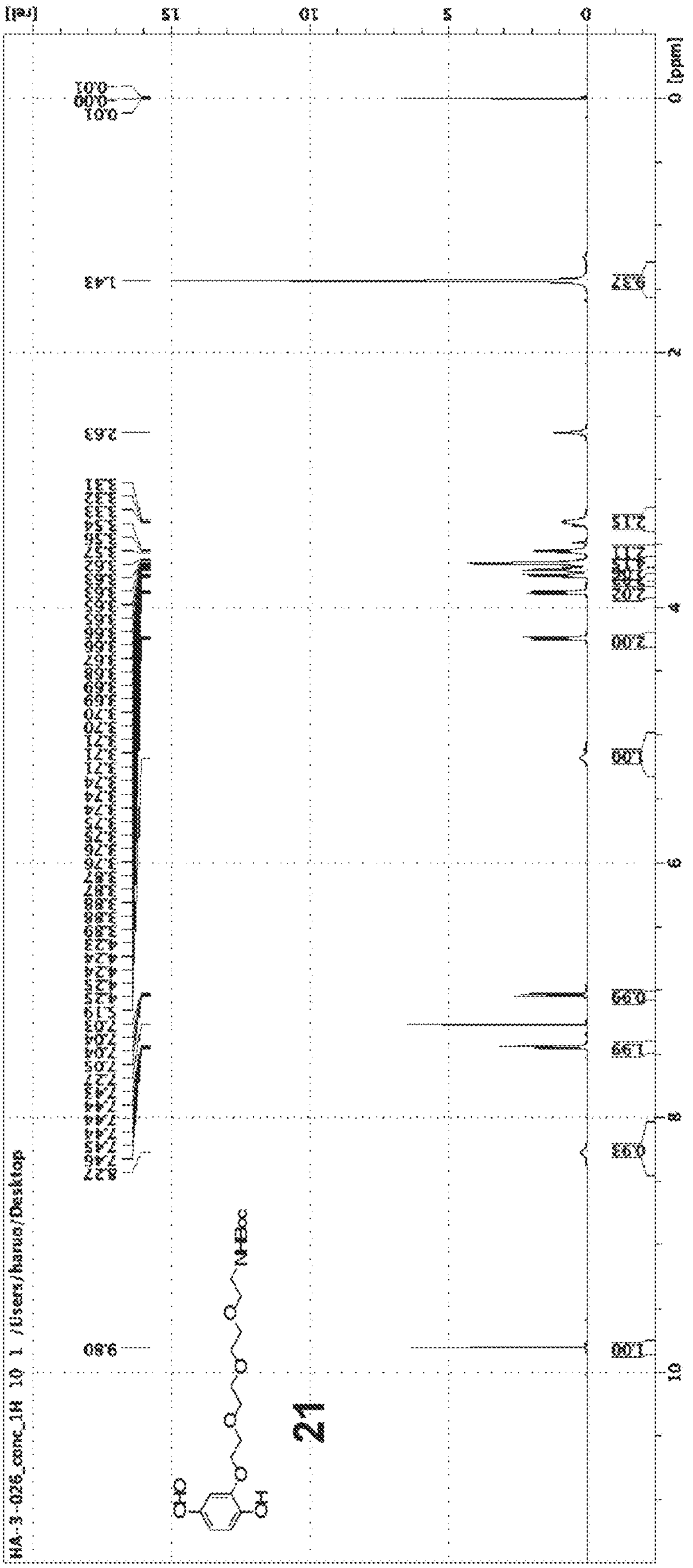
FIGS. 21A-21B. $^{1}H$ and $^{13}C$ NMR spectra of compound 21.
Figure 21B:
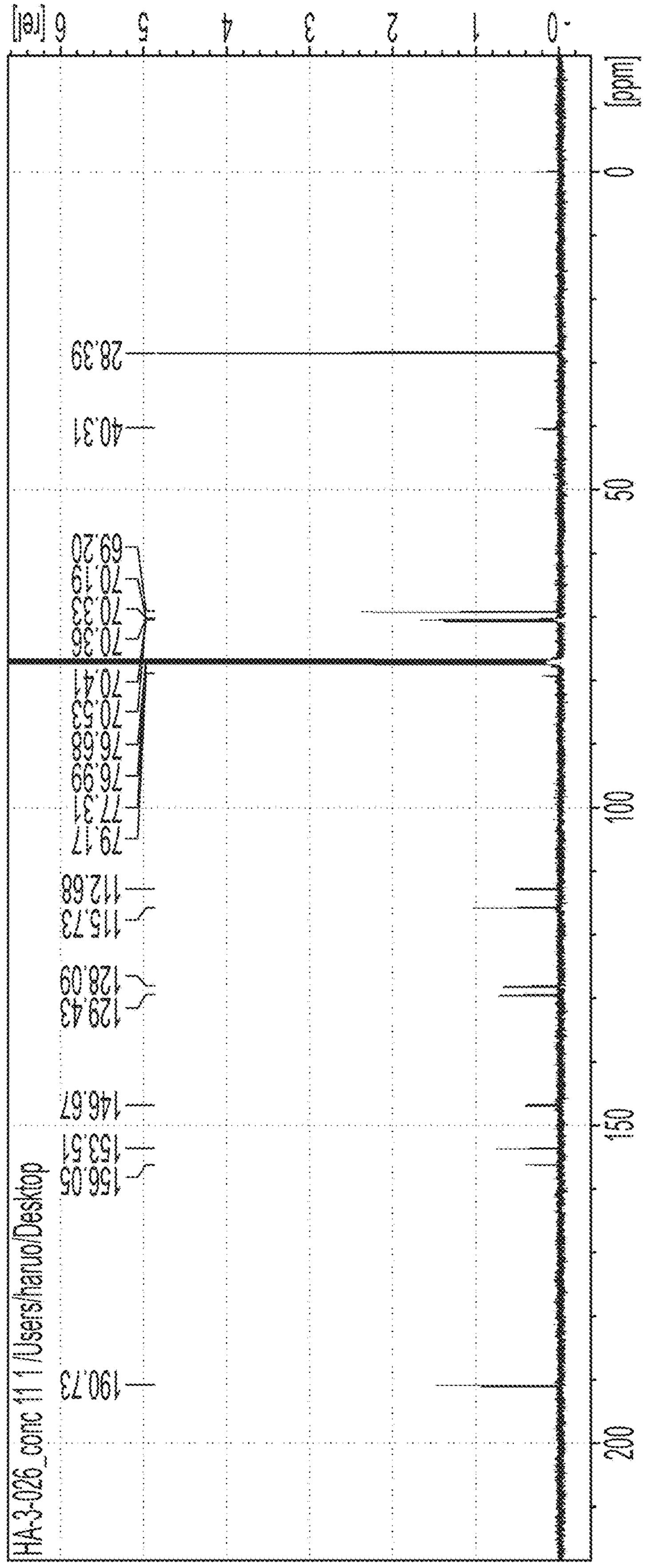
Figure 22A:
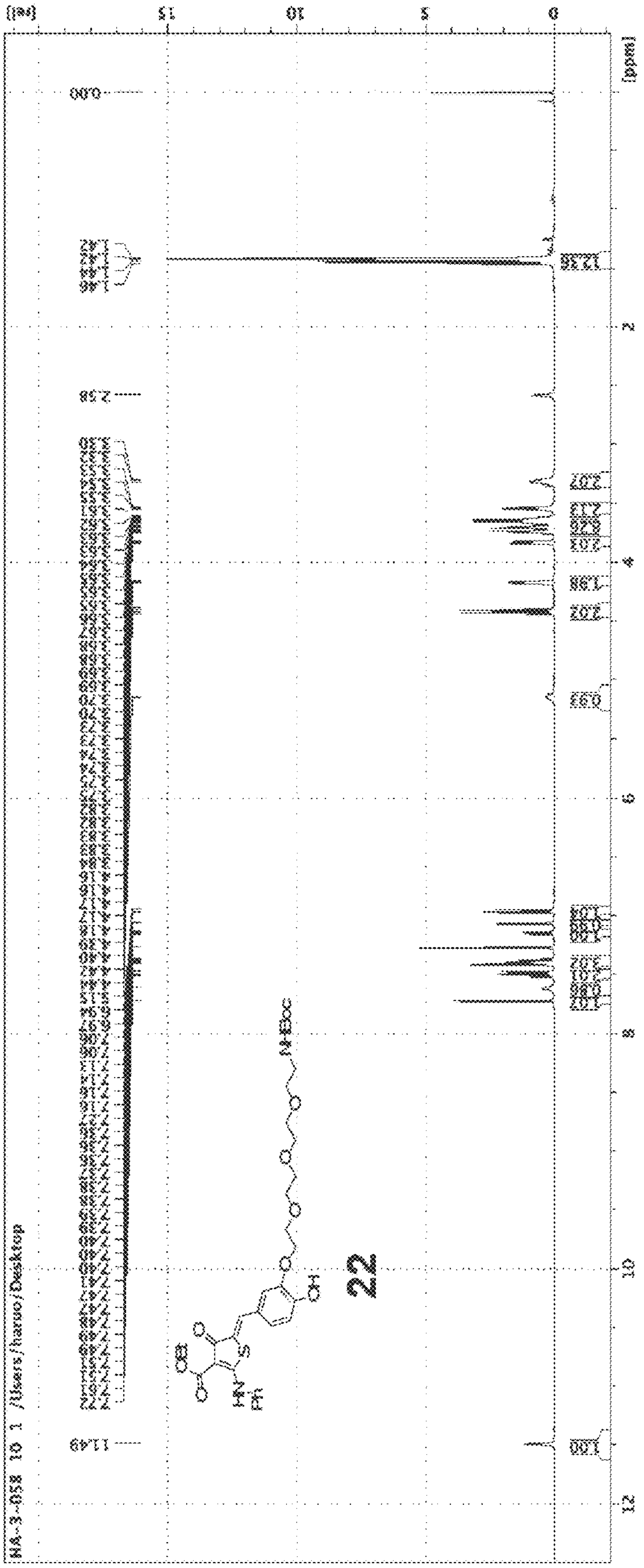
FIGS. 22A-22B. $^{1}H$ and $^{13}C$ NMR spectra of compound 22.
Figure 22B:
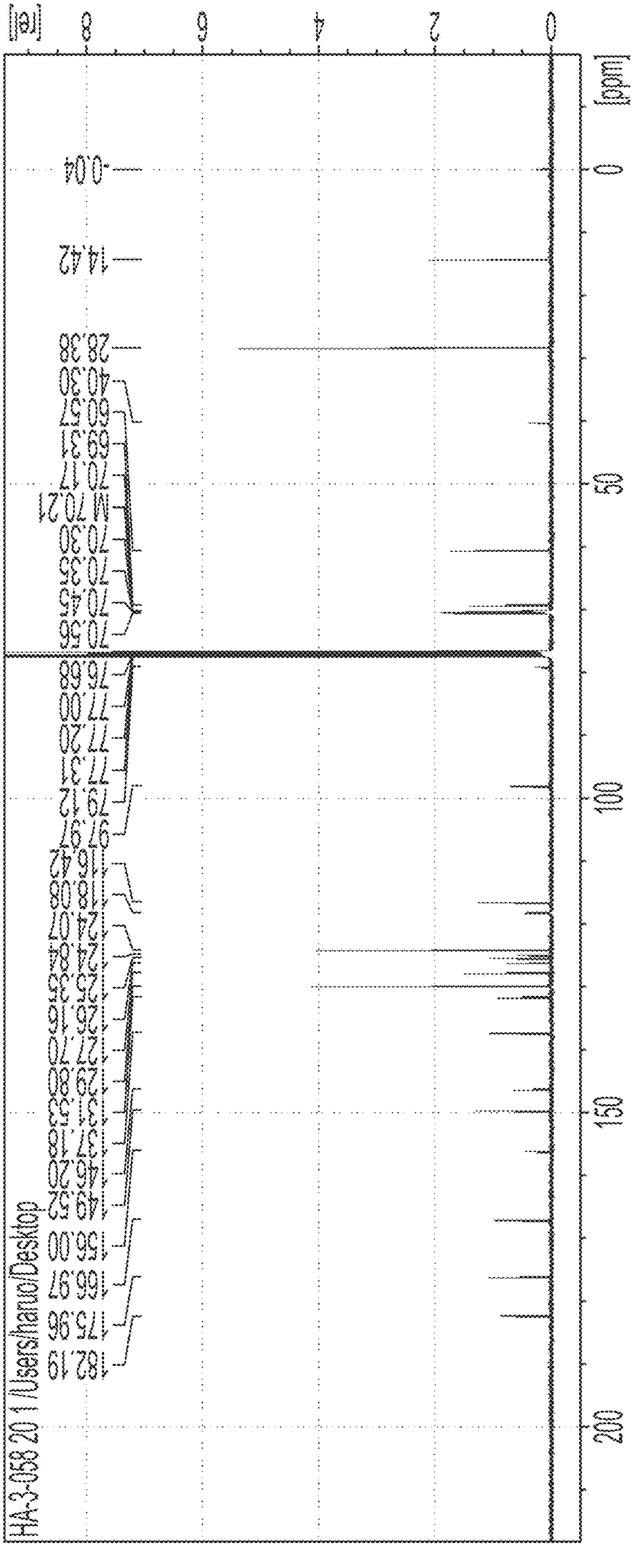
Figure 23A:
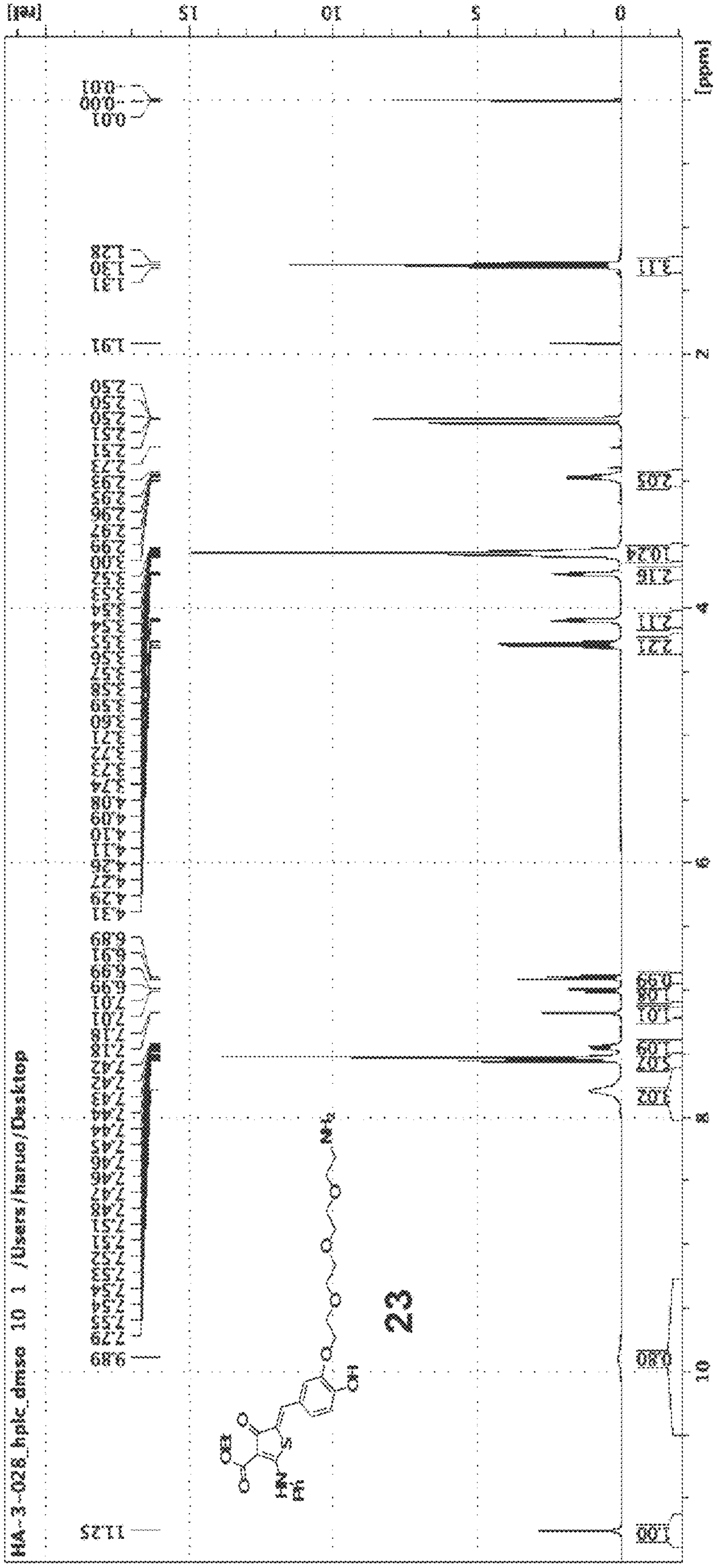
FIGS. 23A-23B. $^{1}H$ and $^{13}C$ NMR spectra of compound 23.
Figure 23B:
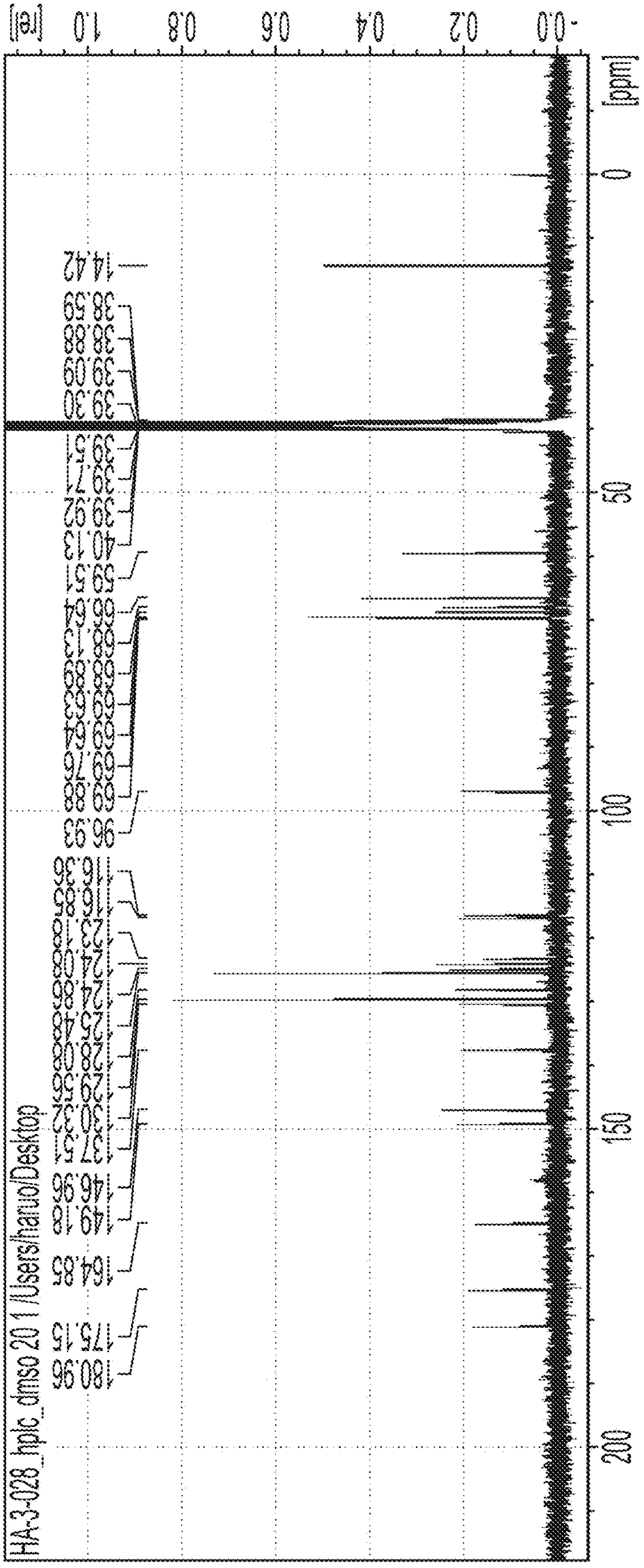
Figure 24A:
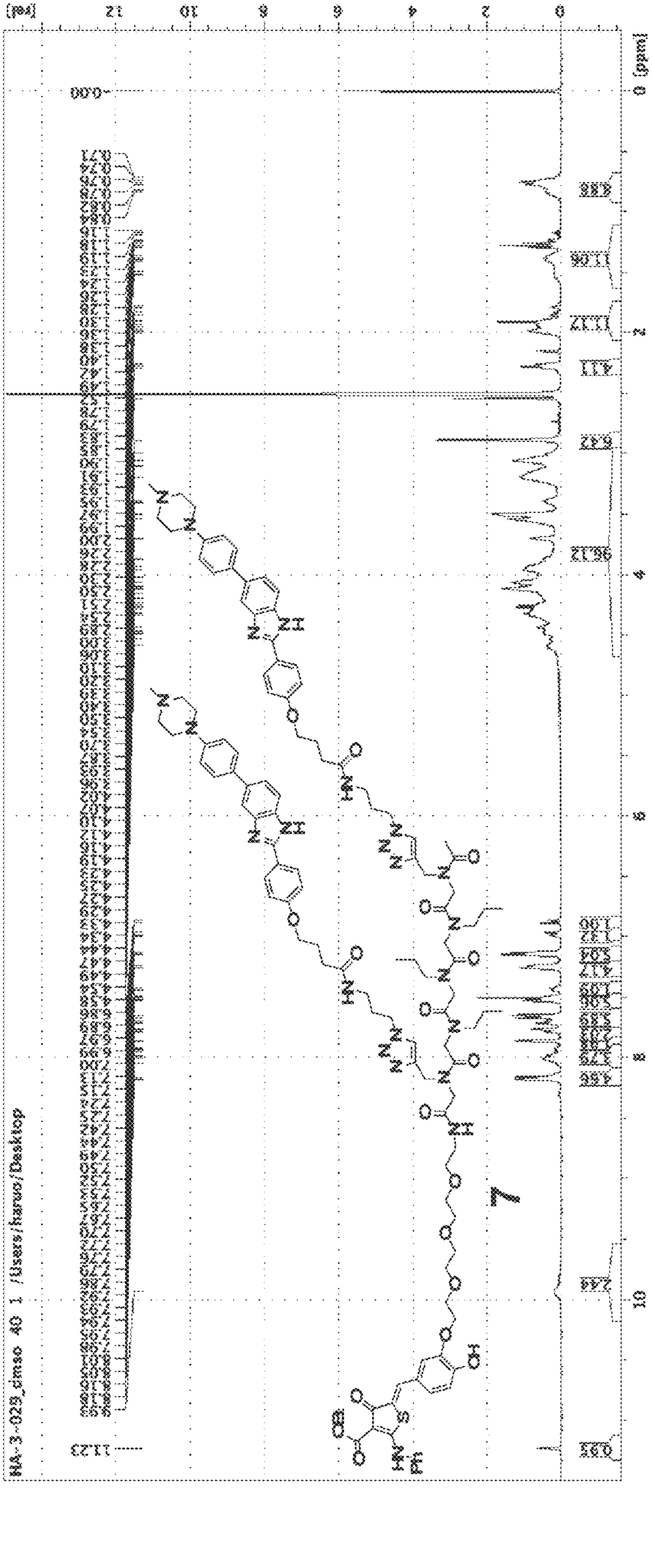
FIGS. 24A-24B. $^{1}H$ and $^{13}C$ NMR spectra of compound 7.
Figure 24B:
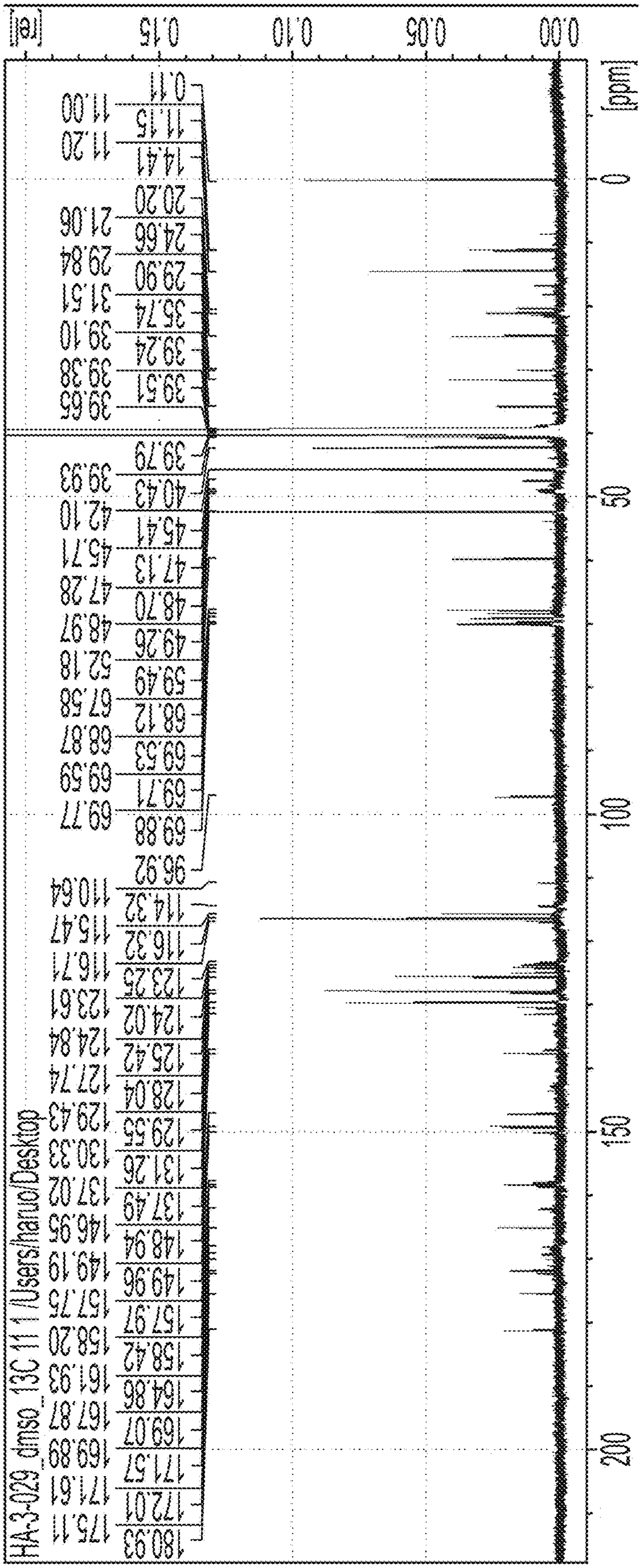
Figure 25A:
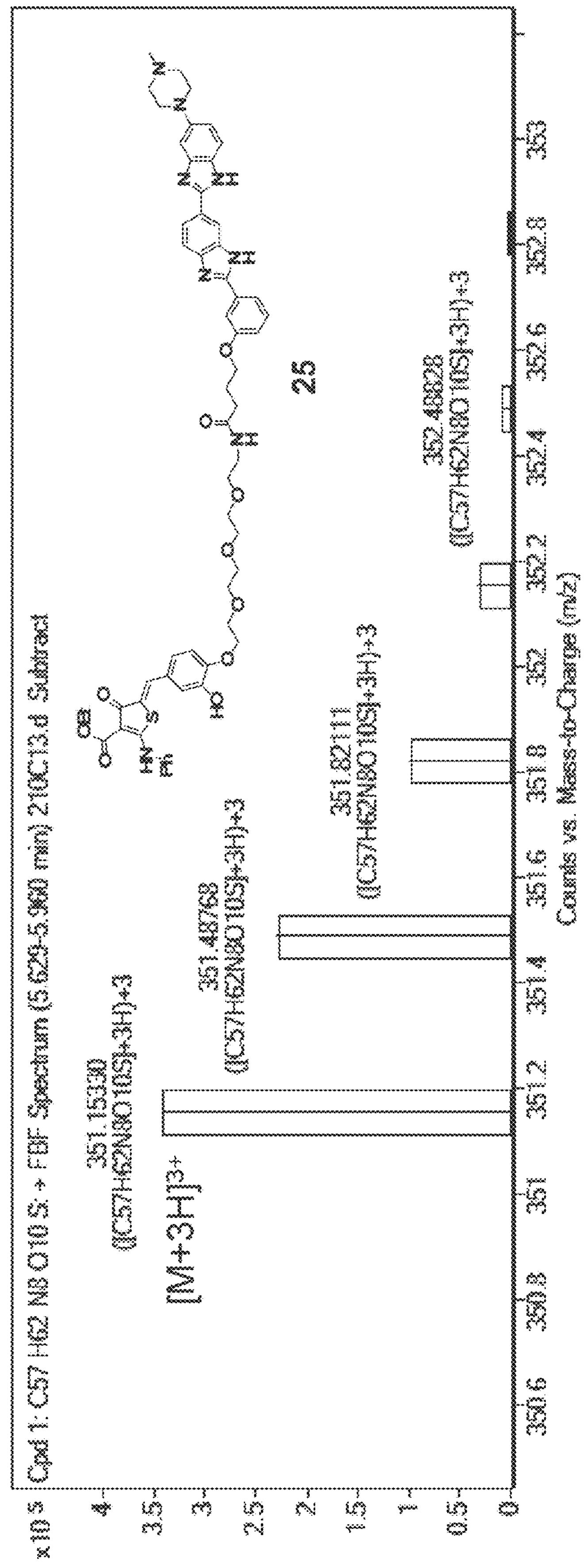
FIGS. 25A-25B. HR-MS of compound 25 by LC-MS (ESI-TOF).
Figure 25B:
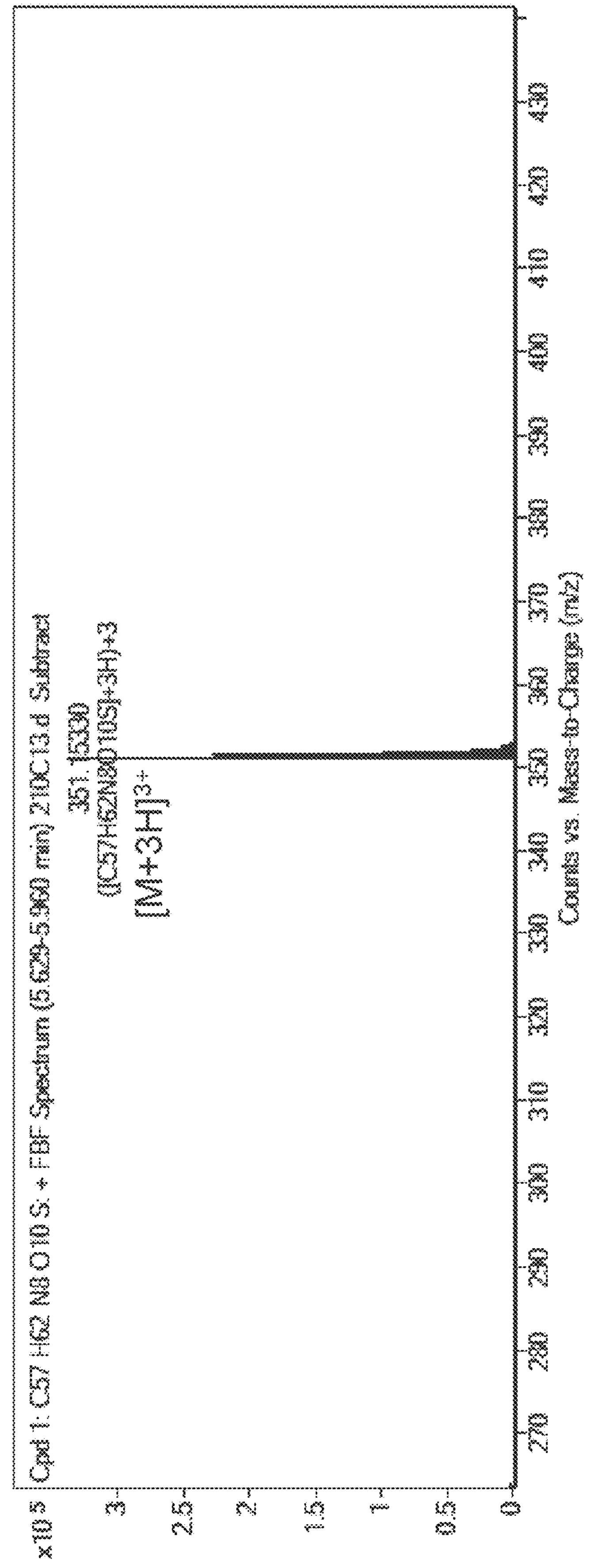
Figure 46A:
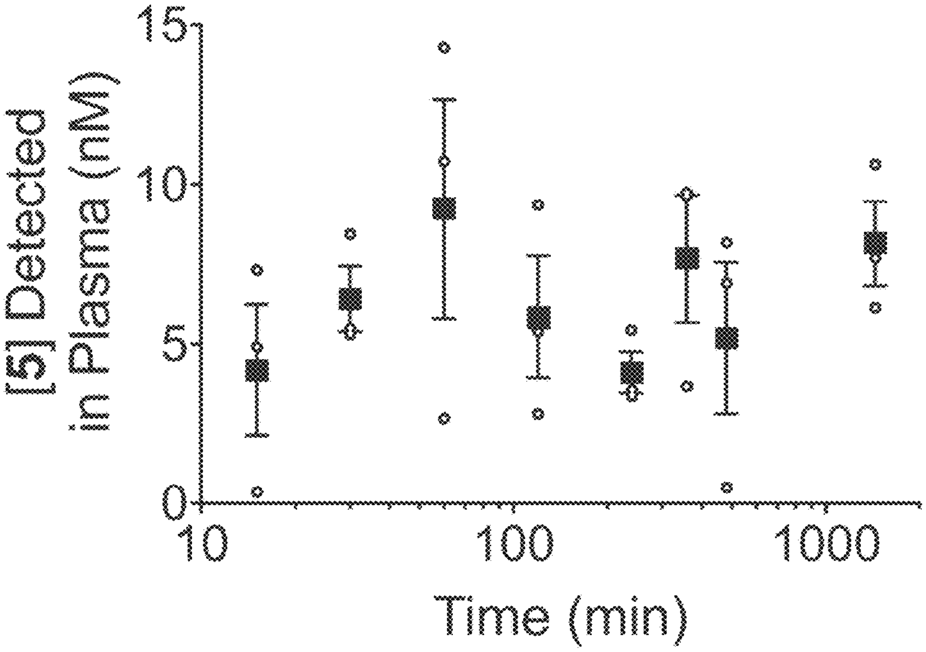
FIGS. 46A-46C. In vivo mouse weights and Scrambled FISH staining of lung nodules with 5 treatment.
Figure 46B:
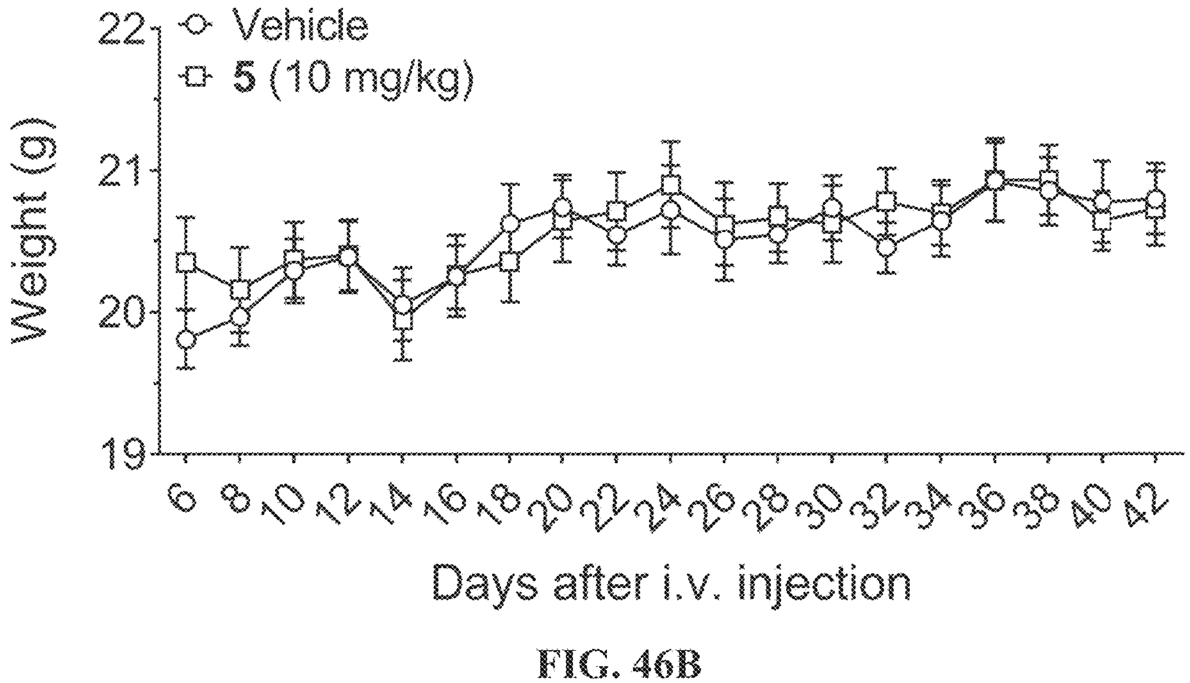
Figure 46C:
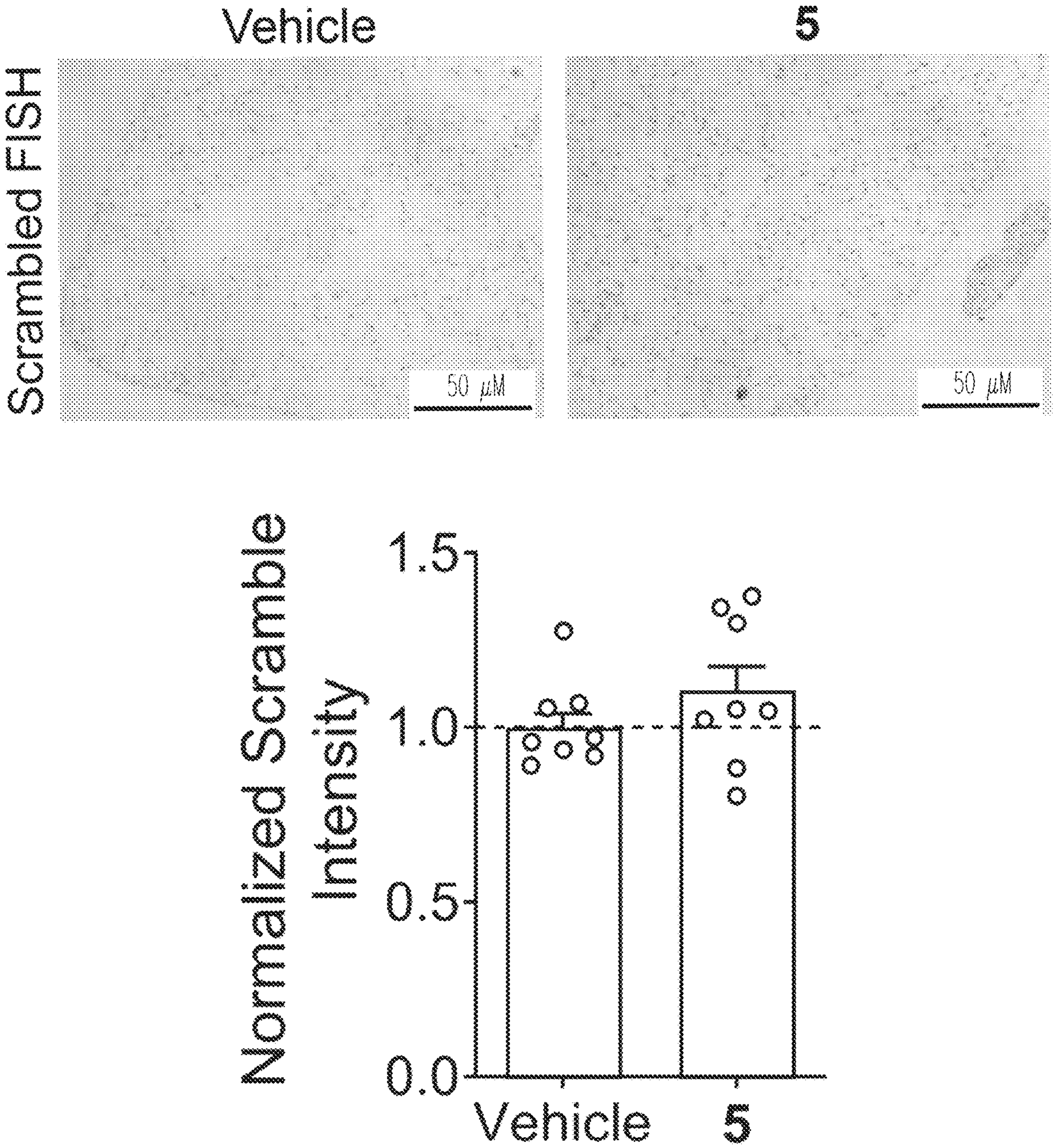
Figure 47A:
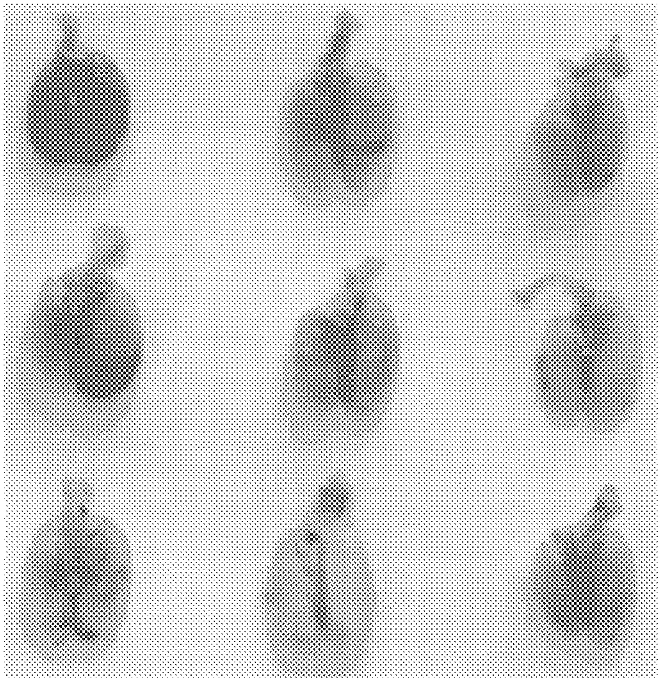
FIGS. 47A-47B. In vivo MDA-MB-231 lung nodule metastases with compound 5 treatment. Post-necropsy vehicle (10/10/80 DMSO/Tween-80/Water) and 5-treated PBS perfused lungs stained with Bouin's solution. Lung nodule metastases can be observed as white nodules on the surface of the lungs.
Figure 47B:
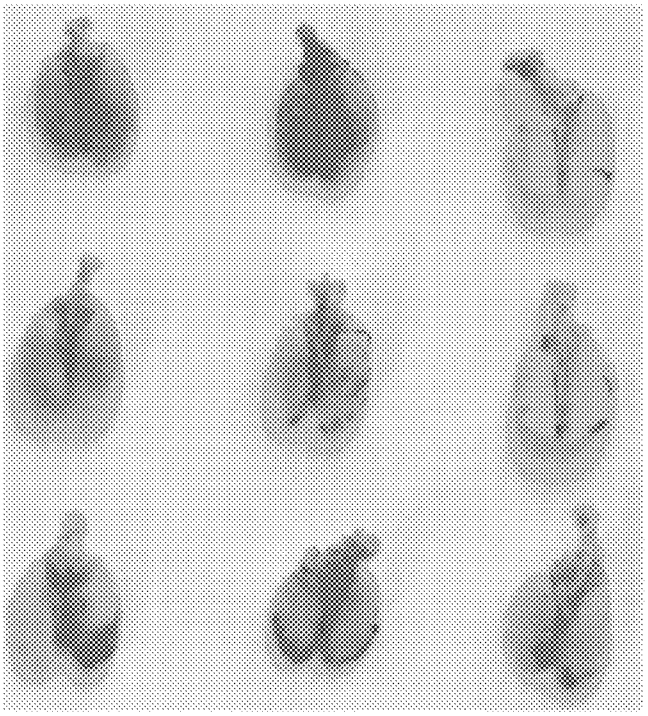

Intravenous delivery of MDA-MB-231 cells to mice is a model of breast cancer metastasis and metastatic behavior can be affected by inhibition of miR-21, S. Yang, J. J. Zhang, X.-Y. Huang, Mouse models for tumor metastasis. *Methods Mol. Biol.* 928, 221-228 (2012). Delivery of Formula 5 via intraperitoneal injection (10 mg/kg, q.o.d.) was well tolerated and maintained low nanomolar concentrations in mice, FIGS. 46A-46C. Compound treatment inhibited breast cancer metastasis to lung as evidenced by decreased lung nodules (FIG. 4*a*, FIGS. 47A-47B. Lung histological studies showed that Formula 5 decreased hematoxylin and eosin (HE) staining (FIG. 4*b*). To further validate the mode of action of Formula 5, miR-21 and pre-miR-21 levels were diminished, as expected, with no effect observed with scrambled controls, FIGS. 4*c*, 4*d*, FIGS. 47A-47B. Immunohistochemistry showed that Formula 5 stimulated an increase in PDCD4 protein expression (FIG. 4*e*). Thus, in a pre-clinical animal model Formula 5 modulates a miR-21-mediated pathway.

Mechanism of Action and Medical Treatment

In certain embodiments, the invention is directed to methods of inhibiting pre-miR-21. The compounds of Formulas 1, 2 and 5 of the invention for use in the methods disclosed herein bind to the active site of pre-miR-21. In certain such embodiments, the binding may be reversible or irreversible.

The compounds of the invention and their pharmaceutical compositions are capable of acting as "inhibitors" of pre-miR-21 which means that they are capable of blocking or reducing the expression of pre-miR-21, for example, inhibition of various activities of pre-miR-21. An inhibitor can act with competitive, uncompetitive, or noncompetitive inhibition. An inhibitor can bind reversibly or irreversibly, and therefore the term includes compounds that can cause nuclease degradation the structured RNA or it can cause a conformational change elsewhere on the structured RNA so as to prevent its function.

The compounds of the invention and their pharmaceutical compositions function as therapeutic agents in that they are capable of preventing, ameliorating, modifying and/or affecting a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The ability to prevent, ameliorate, modify and/or affect in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The compounds of the invention and their pharmaceutical compositions are capable of functioning prophylactically and/or therapeutically and include administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The compounds of the invention and their pharmaceutical compositions are capable of prophylactic and/or therapeutic treatments. If a compound or pharmaceutical composition is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof). As used herein, the term "treating" or "treatment" includes reversing, reducing, or arresting the symptoms, clinical signs, and underlying pathology of a condition in manner to improve or stabilize a subject's condition.

The compounds of the invention and their pharmaceutical compositions can be administered in "therapeutically effective amounts" with respect to the subject method of treatment. The therapeutically effective amount is an amount of the compound(s) in a pharmaceutical composition which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

Administration

Compounds of the invention and their pharmaceutical compositions prepared as described herein can be administered in various forms, depending on the disorder to be treated and the age, condition, and body weight of the patient, as is well known in the art. As is consistent, recommended and required by medical authorities and the governmental registration authority for pharmaceuticals, administration is ultimately provided under the guidance and prescription of an attending physician whose wisdom, experience and knowledge control patient treatment.

For example, where the compounds are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route or other similar transmucosal route, they may be formulated as drops or ointments.

These formulations for administration orally or by a transmucosal route can be prepared by conventional means, and if desired, the active ingredient may be mixed with any conventional additive or excipient, such as a binder, a disintegrating agent, a lubricant, a corrigent, a solubilizing agent, a suspension aid, an emulsifying agent, a coating agent, a cyclodextrin, and/or a buffer. Although the dosage will vary depending on the symptoms, age and body weight of the patient, the gender of the patient, the nature and severity of the disorder to be treated or prevented, the route of administration and the form of the drug, in general, a daily dosage of from 0.0001 to 2000 mg, preferably 0.001 to 1000 mg, more preferably 0.001 to 500 mg, especially more preferably 0.001 to 250 mg, most preferably 0.001 to 150 mg of the compound is recommended for an adult human patient, and this may be administered in a single dose or in divided doses. Alternatively, a daily dose can be given according to body weight such as 1 nanogram/kg (ng/kg) to 200 mg/kg, preferably 10 ng/kg to 100 mg/kg, more preferably 10 ng/kg to 10 mg/kg, most preferably 10 ng/kg to 1 mg/kg. The amount of active ingredient which can be combined with a carrier material to produce a single dosage form will generally be that amount of the compound which produces a therapeutic effect.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

The phrase "pharmaceutically acceptable" is employed herein to refer to those excipients, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutical Compositions Incorporating Compounds of Formulas 1, 2 and 5

The pharmaceutical compositions of the invention incorporate embodiments of a compounds of Formulas 1, 2 and 5 of the invention and a pharmaceutically acceptable carrier. The inventive compositions and their pharmaceutical compositions can be administered orally, topically, parenterally, by inhalation or spray or rectally in dosage unit formulations. The term parenteral is described in detail below. The nature of the pharmaceutical carrier and the dose of the compounds of Formulas 1, 2 and 5 depend upon the route of administration chosen, the effective dose for such a route and the wisdom and experience of the attending physician.

A "pharmaceutically acceptable carrier" is a pharmaceutically acceptable material, composition, or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted (3-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions. Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations suitable for oral administration may be in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of a compound of the invention as an active ingredient. A composition may also be administered as a bolus, electuary, or paste.

In solid dosage form for oral administration (capsules, tablets, pills, dragees, powders, granules, and the like), a compound of the invention is mixed with one or more pharmaceutically acceptable carriers, such as sodium citrate or dicalcium phosphate, and/or any of the following:

(1) fillers or extenders, such as starches, cyclodextrins, lactose, sucrose, glucose, mannitol, and/or silicic acid;
(2) binders, such as, for example, carboxymethylcellulose, alginates, gelatin, polyvinyl pyrrolidone, sucrose, and/or acacia;
(3) humectants, such as glycerol;
(4) disintegrating agents, such as agar-agar, calcium carbonate, potato or tapioca starch, alginic acid, certain silicates, and sodium carbonate;
(5) solution retarding agents, such as paraffin;
(6) absorption accelerators, such as quaternary ammonium compounds;
(7) wetting agents, such as, for example, acetyl alcohol and glycerol monostearate; (8) absorbents, such as kaolin and bentonite clay;
(9) lubricants, such a talc, calcium stearate, magnesium stearate, solid polyethylene glycols, sodium lauryl sulfate, and mixtures thereof; and
(10) coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered inhibitor(s) moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner.

Examples of embedding compositions which can be used include polymeric substances and waxes. A compound of the invention can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more inhibitor(s) with one or more suitable nonirritating excipients or carriers comprising, for example, cocoa butter, polyethylene glycol, a suppository wax or a salicylate, which is solid at room temperature, but liquid at body temperature and, therefore, will melt in the rectum or vaginal cavity and release the active agent.

Formulations which are suitable for vaginal administration also include pessaries, tampons, creams, gels, pastes, foams, or spray formulations containing such carriers as are known in the art to be appropriate.

Dosage forms for the topical or transdermal administration of an inhibitor(s) include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required.

The ointments, pastes, creams, and gels may contain, in addition to a compound of the invention, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to a compound of the invention, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

A compound of the invention can be alternatively administered by aerosol. This is accomplished by preparing an aqueous aerosol, liposomal preparation, or solid particles containing the composition. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of a compound of the invention together with conventional pharmaceutically acceptable carriers and stabilizers. The carriers and stabilizers vary with the requirements of the particular composition, but typically include nonionic surfactants (Tweens, Pluronics, sorbitan esters, lecithin, Cremophors), pharmaceutically acceptable co-solvents such as polyethylene glycol, innocuous proteins like serum albumin, oleic acid, amino acids such as glycine, buffers, salts, sugars, or sugar alcohols. Aerosols generally are prepared from isotonic solutions.

Transdermal patches have the added advantage of providing controlled delivery of a compound of the invention to the body. Such dosage forms can be made by dissolving or dispersing the agent in the proper medium. Absorption enhancers can also be used to increase the flux of the inhibitor(s) across the skin. The rate of such flux can be controlled by either providing a rate controlling membrane or dispersing the inhibitor(s) in a polymer matrix or gel.

Pharmaceutical compositions of this invention suitable for parenteral administration comprise one or more compounds of the invention in combination with one or more pharmaceutically acceptable sterile aqueous or nonaqueous solutions, dispersions, suspensions or emulsions, or sterile powders which may be reconstituted into sterile injectable solutions or dispersions just prior to isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a compound of the invention, it is desirable to slow the absorption of the compound from subcutaneous or intramuscular injection. For example, delayed absorption of a parenterally administered drug form is accomplished by dissolving or suspending the drug in an oil vehicle.

Injectable depot forms are made by forming microencapsule matrices of inhibitor(s) in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

The pharmaceutical compositions may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

The pharmaceutical compositions of the invention may be "systemically administered" "administered systemically," "peripherally administered" and "administered peripherally" meaning the administration of a ligand, drug, or other material other than directly into the central nervous system, such that it enters the patient's system and thus, is subject to metabolism and other like processes, for example, subcutaneous administration.

The compound(s) of the invention may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

Regardless of the route of administration selected, the compound(s) of the invention, which may be used in a suitable hydrated form, and/or the pharmaceutical compositions of the present invention, are formulated into pharmaceutically acceptable dosage forms by conventional methods known to those of skill in the art.

Actual dosage levels of the compound(s) of the invention in the pharmaceutical compositions of this invention may be varied so as to obtain an amount of the active ingredient which is effective to achieve the desired therapeutic response for a particular patient, composition, and mode of administration, without being toxic to the patient.

The concentration of a compound of the invention in a pharmaceutically acceptable mixture will vary depending on several factors, including the dosage of the compound to be administered, the pharmacokinetic characteristics of the compound(s) employed, and the route of administration.

In general, the compositions of this invention may be provided in an aqueous solution containing about 0.1-10% w/v of a compound disclosed herein, among other substances, for parenteral administration. Typical dose ranges are those given above and may preferably be from about 0.001 to about 500 mg/kg of body weight per day, given in 1-4 divided doses. Each divided dose may contain the same or different compounds of the invention. The dosage will be an effective amount depending on several factors including the overall health of a patient, and the formulation and route of administration of the selected compound(s).

Conjoint Therapy

Another aspect of the invention provides a conjoint therapy wherein one or more other therapeutic agents are administered with the compounds and compositions of the invention. Such conjoint treatment will achieve the same or similar treatment accounting for the additive effects of the conjoined therapeutic agents other than the compounds of the invention.

In certain embodiments, a compound of the invention can be conjointly administered with one or more proteasome inhibitor(s). In certain embodiments, a compound of the invention is conjointly administered with a chemotherapeutic. Suitable chemotherapeutics may include, natural products such as vinca alkaloids (i.e., vinblastine, vincristine, and vinorelbine), paclitaxel, epidipodophyllotoxins (i.e., etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates (busulfan), nitrosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine); aromatase inhibitors carboplatin), procarbazine, hydroxyurea, mitotane, aminoglutethimide; hormones (i.e. estrogen) and hormone agonists such as leutinizing hormone releasing hormone (LHRH) agonists (goserelin, leuprolide and triptorelin). Other chemotherapeutic agents may include mechlorethamine, camptothecin, ifosfamide, tamoxifen, raloxifene, gemcitabine, navelbine, or any analog or derivative variant of the foregoing.

In certain embodiments, a compound of the invention is conjointly administered with an immunotherapeutic agent. Suitable immunotherapeutic agents may include, but are not limited to, cyclosporine, thalidomide, and monoclonal antibodies. The monoclonal antibodies can be either naked or conjugated such as rituximab, tositumomab, alemtuzumab, epratuzumab, ibritumomab tiuxetan, gemtuzumab ozogamicin, bevacizumab, cetuximab, erlotinib and trastuzumab.

Treatment of Cancer

Exemplary forms of cancer which may be treated by the methods of the invention using the compounds of Formulas 1, 2 and 5 of the invention and their pharmaceutical compositions include, but are not limited to, prostate cancer, bladder cancer, lung cancer (including either small cell or non-small cell cancer), colon cancer, kidney cancer, liver cancer, breast cancer, cervical cancer, endometrial or other uterine cancer, ovarian cancer, testicular cancer, cancer of the penis, cancer of the vagina, cancer of the urethra, gall bladder cancer, esophageal cancer, or pancreatic cancer.

Additional exemplary forms of cancer which may be treated by the methods of the invention include, but are not limited to, cancer of skeletal or smooth muscle, stomach cancer, cancer of the small intestine, cancer of the salivary gland, anal cancer, rectal cancer, thyroid cancer, parathyroid cancer, pituitary cancer, and nasopharyngeal cancer. Exceptional treatment of forms of cancer including lung cancer, breast cancer, pancreatic cancer and melanoma and metastasis thereof may be accomplished.

The compounds of the present invention and their salts and solvates, thereof, may be employed alone or in combination with other therapeutic agents (conjoint therapy described above) for the treatment of the diseases or conditions associated with inappropriate Pre-miR-21 activity.

In various embodiments, compounds of the invention may be used to treat neoplastic growth, angiogenesis, infection, inflammation, immune-related diseases, ischemia and reperfusion injury, multiple sclerosis, rheumatoid arthritis, neurodegenerative conditions, or psoriasis.

Malignant neoplastic growth may include cancer. Suitably, the present invention relates to a method for treating or lessening the severity of a cancer selected from: brain (gliomas), glioblastomas, breast, Wilm's tumor, Ewing's sarcoma, rhabdomyosarcoma, ependymoma, medulloblastoma, colon, head and neck, kidney, lung, liver, melanoma, ovarian, pancreatic, prostate, sarcoma, osteosarcoma, giant cell tumor of bone, thyroid, lymphoblastic T cell leukemia, chronic myelogenous leukemia, chronic lymphocytic leukemia, Hairy-cell leukemia, acute lymphoblastic leukemia, acute myelogenous leukemia, chronic neutrophilic leukemia, acute lymphoblastic T cell leukemia, plasmacytoma, immunoblastic large cell leukemia, mantle cell leukemia, multiple myeloma megakaryoblastic leukemia, multiple myeloma, acute megakaryocytic leukemia, promyelocytic leukemia, erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, lung cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

In various embodiments, the cancer is selected from brain cancer (gliomas), glioblastomas, breast cancer, colon cancer, head and neck cancer, kidney cancer, lung cancer, liver cancer, melanoma, ovarian cancer, pancreatic cancer, prostate cancer, sarcoma and thyroid cancer.

In various embodiments, the cancer is a solid tumor. In various embodiments, the cancer is selected from multiple myeloma, metastatic breast cancer, non-small cell lung cancer, prostate cancer, advanced colorectal cancer, ovarian or primary peritoneal carcinoma, hormone refractory prostate cancer, squamous cell carcinoma of the head and neck, metastatic pancreatic adenocarcinoma, gastroesophageal junction or stomach, or non-Hodgkin's lymphoma.

A method of using the compounds described herein for treating a disorder characterized by an inappropriate level of proteasome activity, or in which a reduction of the normal level of proteasome activity yields a clinical benefit. This disorder can include cancer or immune disorders characterized by excessive cell proliferation or cellular signaling.

Compounds of the invention may be used to treat cachexia and muscle-wasting diseases. Compounds of the invention may be used to treat such conditions wherein the condition is related to cancer, fever, muscle disuse (atrophy) and denervation, nerve injury, fasting, renal failure associated with acidosis, diabetes, and hepatic failure.

Compounds of the invention can be used to treat hyperproliferative conditions such as diabetic retinopathy, macular degeneration, diabetic nephropathy, glomerulosclerosis, IgA nephropathy, cirrhosis, biliary atresia, congestive heart failure, scleroderma, radiation-induced fibrosis, and lung fibrosis (idiopathic pulmonary fibrosis, collagen vascular disease, sarcoidosis, interstitial lung diseases and extrinsic lung disorders).

EXAMPLES

Preparation of RNase L-GST protein. The pGEX-4T-RNase L-GST plasmid was prepared as previously described[22] and kept in Storage Buffer (20 mM HEPES, pH 7.4, 70 mM NaCl, 2 mM $MgCl_2$).

Microscale Thermophoresis (MST) Binding Measurements. MST fluorescent measurements were performed on a Monolith NT.115 system (NanoTemper Technologies) using the fluorescence of a miR-21 hairpin (A+U Bulge): (5' Cy5-GUUGACUGUUGAAUCUCAUGGCAAC-3') (SEQ ID NO: 1) or a miR-21 base paired control (5' Cy5-GUUGACUGUUGAAUCUCAAUGGUCAAC-3') (SEQ ID NO: 2) which were purchased from IDT with RNase-free HPLC purification and used without further purification. The RNA (5 nM) was diluted in 1×MST Buffer (8 mM $Na2HPO_4$, 190 mM NaCl, 1 mM EDTA, and 0.05% (v/v) Tween-20) and folded by heating at 60° C. for 5 min, and slowly cooling to room temperature. Compounds 1 and 2 were diluted in 1×MST Buffer, followed by 1:3 dilutions in 1×MST Buffer containing 5 nM RNA. Samples were incubated for 30 min at room temperature and then loaded into premium-coated capillaries (NanoTemper Technologies). Fluorescence measurements (Ex: 605-645 nm, Em: 680-685 nm) were performed at 10% LED and 80% MST power, with a Laser-On time of 30 s and Laser-Off time of 5 s. The data were analyzed by thermophoresis analysis and fitted by the quadratic binding equation in MST analysis software (NanoTemper Technologies). Dissociation constants were then determined by curve fitting using a single-site model. Normalized MST signal was calculated by normalizing the fluorescent signals using the MST data of 1 binding to pre-miR-21 WT with the lowest signal as 0 and the highest fluorescent signal as 1.

In Vitro Fluorescent RNA Cleavage. A model RNA hairpin[15] labeled with a 5' 6-Fluorescein (6FAM) and 3' Black Hole Quencher (IQ4) (5' 6FAM-UUAUCAAAUUC-UUAUUUGCCCCAUUUUUUUGGUUUA-3' IQ4; 5' FAM/3' BHQ model RNA) (SEQ ID NO: 3) or a miR-21 Hairpin Precursor RNA labeled with a 5' 6-Fluorescein (6FAM) and 3' Black Hole Quencher (IQ4) (5' 6FAM-UAGCUUAUCAGACUGAUGUUGACUGUUG AAU-CUCAUGGCAACACCAGUCGAUGGGCUG-3' IQ4; 5' FAM/3' BHQ miR-21 Hairpin Precursor RNA) (SEQ ID NO: 4) was purchased from Chemgenes with HPLC purification. Solutions of RNA (100 nM) were folded at 65° C. for 5 min and slowly cooled to room temperature in 1×RNase L Buffer (25 mM Tris-HCl, pH 7.4, 100 mM KCl) without $MgCl_2$, β-mercaptoethanol or ATP. After folding, the RNA was supplemented with 10 mM $MgCl_2$, fresh 7 mM β-mercaptoethanol, and 50 μM of ATP. Next, 100 nM of RNase L, prepared as described previously[22], and various concentrations of screening compounds were prepared in 1×RNase L Buffer and added to the RNA. Alternatively, dilutions of 5, were prepared in 1×RNase L Buffer and added to the RNA. The samples were then transferred to Corning non-binding surface half area 96-well black plates. The samples were incubated at room temperature for 60 min after which the fluorescence intensity (Ex: 485 nm, Em: 525 nm) was measured using a SpectraMax M5 plate reader or Biotek FLx800 plate reader. The percentage change in fluorescence intensity, where enhancement of fluorescence intensity was indicative of RNA cleavage, was determined by calculating the percentage change in sample fluorescent signals relative to the untreated fluorescent signal ($F_i$, %). Signals were normalized ($F_{norm}$, %) by the value of the positive control molecule (10 or 100 nM 2'-5' $A_4$) using equations 1 (Eq. 1) and 2 (Eq. 2).

$$F_i\ (\text{compound}) = \frac{F\ (\text{compound}) - F\ (\text{vehicle})}{F\ (\text{vehicle})} \times 100 \quad \text{(Eq. 1)}$$

$$F_{norm}\ (\text{compound}) = \frac{F_i\ (\text{compound})}{F_i(2' - 5'A_4)} \times 100 \quad \text{(Eq. 2)}$$

In Vitro RNase L Oligomerization. An aliquot of RNase L (3 μM) in 1×RNase L Buffer was supplemented with 10 mM $MgCl_2$, fresh 7 mM β-mercaptoethanol, and 50 μM of ATP. RNase L oligomerization was performed as previously described[13] using dilutions of 2'-5' $A_4$ or compounds (2 or 5) prepared in 1×RNase L Buffer. A Western blot (described below) was run to resolve monomeric and oligomeric RNase L populations using RNase L primary antibody (1:5000 dilution; Cell Signaling Technology: D4B4J) overnight at 4° C. in 1×TBST containing 5% nonfat dry milk and 1:10000 anti-rabbit IgG horseradish peroxidase secondary antibody conjugate (Cell Signaling Technology: 7074S) in 1×TBST containing 5% nonfat dry milk for 2 h at room temperature.

PCR amplification & in vitro transcription. The DNA template for miR-21 primary transcript RNA (pri-miR-21) (5'-GTCGGGTAGCTTATCAGACTGATGTTGACTGTT-GAATC-TCATGGCAACACCAGTC-GATGGGCTGTCTGAC-3') (SEQ ID NO: 5) was purchased from IDT with standard desalting and used without further purification. This template was PCR amplified in 1×PCR Buffer (10 mM Tris, pH 9.0, 50 mM KCl, and 0.1% (v/v) Triton X-100), 2 μM forward primer (5'-TAATACGACTCACTATAGGTCGGGTAGCTTATC-3') (SEQ ID NO: 6), 2 μM reverse primer (5'-GTCA-GACAGCCCATCGAC-3') (SEQ ID NO: 7), 4.25 mM $MgCl_2$, 330 μM dNTPs, and 1 μL of Taq DNA polymerase in a 50 μL reaction. PCR cycling conditions were initial denaturing at 95° C. for 90 s, followed by 25 cycles of 95° C. for 30 s, 55° C. for 30 s, and 72° C. for 60 s.

The DNA template for the pre-miR-21 WT (wild type) (5'-TAGCTTATCAGACTGATGTTGACTGTTGAATCT-CATGGCAACACCAGTCGATGGG CTG-3') (SEQ ID NO: 8) and the DNA template for the pre-miR-21 BP (base paired) (5'-TAGCTTATCAGACTGATGTTGACTGTT-GAATCTCAATGGTCAACACCAGTCGATG GGCTG-3') (SEQ ID NO: 9) were purchased from IDT with standard desalting and used without further purification. These templates were PCR amplified in 1×PCR Buffer (10 mM Tris, pH 9.0, 50 mM KCl, and 0.1% (v/v) Triton X-100), 2 μM forward primer (5'-TAATACGACTCACTATAGTAGCT-TATCAGACTG-3') (SEQ ID NO: 10), 2 μM reverse primer (5'-CAGCCCATCGACTGG-3') (SEQ ID NO: 11), 4.25 mM $MgCl_2$, 330 μM dNTPs, and 1 μL of Taq DNA polymerase in a 50 μL reaction. PCR cycling conditions were initial denaturing at 95° C. for 90 s, followed by 25 cycles of 95° C. for 30 s, 50° C. for 30 s, and 72° C. for 60 s. RNA was in vitro transcribed and purified as previously described[5]. Extinction coefficients were calculated using the online IDT Oligo Analyzer Tool.

In vitro Dicer processing. The miR-21 precursor (pre-miR-21 WT) or mutated base paired miR-21 precursor (pre-miR-21 BP) were 5'-end labeled with [γ-$^{32}$P] ATP and T4 polynucleotide kinase as described previously[5]. After folding the RNA in 1×Reaction Buffer (Genlantis) by heating at 60° C. for 5 min and slowly cooling to room temperature, then supplementing with 1 mM ATP and 2.5 mM $MgCl_2$, the Dicer processing reaction was run as previously described[23] using Dicer enzyme (BPS Bioscience) at a concentration of 1.5 ng/μL. Cleavage products were resolved on a denaturing 15% polyacrylamide gel, which was imaged using a Molecular Dynamics Typhoon phosphorimager and quantified with Bio-Rad's QuantityOne software, normalizing to full length RNA.

In vitro Chemical Cross-linking and Isolation by Pull Down (Chem-CLIP) and Competitive Chemical Cross-linking and Isolation by Pull Down (C-Chem-CLIP). RPMI growth medium was heat inactivated at 95° C. for 15 min and then cooled to room temperature. Approximately 10,000 counts of $^{32}P$ 5'-end labeled miR-21 precursor hairpin RNA (pre-miR-21 WT) was folded in growth medium at 95° C. for 1 min. After cooling to room temperature, dilutions of Chem-CLIP probes 8 or 9[23] were added and incubated at 37° C. for 18 h. Alternatively, for C-Chem-CLIP, dilutions of competing non-cross-linking parent compounds, 1 or 2, were incubated with RNA for 1 h before addition of Chem-CLIP probe compounds. Streptavidin-agarose beads (Sigma-Aldrich) were then used to pulldown RNA. Samples were then washed with 1×PBS supplemented with 0.1% (v/v) Tween-20 and bound and unbound RNA radioactivity measured using a Beckman Coulter LS6500 Liquid Scintillation Counter as previously described[23].

In vitro Ribo-SNAP. The pri-miR-21 RNA (1 μM) was folded as described above. Dilutions of cleaver compounds (Bleomycin A5 or 10) were pre-activated by the addition of 1 eq $Fe^{2+}$ and added to the folded RNA in a total volume of 20 μL. After 30 min and 60 min, an additional equivalent of $Fe^{2+}$ was added and then the reaction mixtures were incubated at 37° C. overnight. After ethanol precipitation and quantification by Nanodrop, reverse transcription was performed using SuperScript™ III Reverse Transcriptase (ThermoFisher Scientific) per the manufacturer's protocol using a 5' $^{32}P$-labeled forward primer (~10,000 counts). The A, T, G and C sequencing ladders were generated by using a ratio of ddNTP/dNTP of 3:1. The RNA was digested by the addition of RNase A and RNase H and incubated at 37° C. for 30 min. Then, an equal volume of Loading Buffer (95% formaldehyde, 50 mM EDTA, 0.05% (w/v) bromophenol blue, 0.05% (w/v) xylene cyanol) was added to each reaction. The final mixture was resolved on a denaturing 15% polyacrylamide gel.

Cell culture compound treatment and transfection. For treatment with compounds, stocks in DMSO or water were diluted in growth media and added to cells for 24-72 h. For transfection of plasmid DNA to overexpress the miR-21 hairpin precursor in pcDNA3.1 (Addgene 21114) or pcDNA3-RNaseL (R. H. Silverman, Cleveland Clinic[24]) in 24-well plates, Lipofectamine 2000 was used according to the manufacturer's protocol. After transfection, the medium was removed and replaced with growth medium containing compound prepared as described above. For transfection of a control (Santa Cruz Biotechnology: sc-37007) or RNase L targeting siRNA (Santa Cruz Biotechnology: sc-45965), Lipofectamine RNAiMAX Reagent was used for transfection of oligonucleotides, including 2'-5' $A_4$, according to the manufacturer's protocol.

Cellular Chem-CLIP/C-Chem-CLIP. The MDA-MB-231 cells were grown to ~70% confluency as monolayers in 60 mm dishes. The cells were treated with Chem-CLIP compounds (8 or 9) and/or non-cross-linking competitors (1 or 2) for 48 h. Total RNA was extracted using a Quick-RNA MiniPrep Kit (Zymo Research) per the manufacturer's protocol. Approximately 20-30 μg of total RNA was then incubated with 100 μL of streptavidin-agarose beads (Sigma-Aldrich) and shaken for 1 h at room temperature. The solution was removed beads washed six times with 1×PBS. The RNA bound to beads was released, purified, and used for RT-qPCR as previously described[23]. Relative fold enrichment of the measured RNA before and after pulldown was measured using equation 3 (Eq. 3):

$$\text{Relative Fold Enrichment} = 2^{-(\Delta C_t \text{before pulldown} - \Delta C_t \text{after pulldown})} \quad \text{(Eq. 3)}$$

where "$\Delta C_t$ before pulldown" is the difference between the $C_t$ values for the RNA of interest and a housekeeping gene in total RNA from cells and "$\Delta C_t$ after pulldown" is the difference between the $C_t$ values for the RNA of interest and the same housekeeping gene in RNA after pulldown.

Ribo-SNAP-Map. The MDA-MB-231 cells were grown in 100 mm dishes to ~70% confluency and treated with cleaving compound (10) for 6 h. Total RNA was then extracted by treatment with TRIzol (ThermoFisher Scientific) and quantified by Nanodrop. Approximately 10 μg of total RNA was used for reverse transcription with a pri-miR-21 specific primer (5'-CAGACGTGTGCTCTTCC-GATCTGAGAACATTGGATATGGATGGTCA-3'; 2 pmol) (SEQ ID NO: 12) using Superscript III (SSIII; Life Technologies). Approximately of 10 μg RNA with 2 pmol of gene-specific primer and 1 μL 10 mM dNTP Mix in a total volume of 13 μL was incubated at 65° C. for 5 min and then placed in ice for 5 min. Next, 4 μL 5×First-Strand Buffer, 1 μL 0.1 M DTT, 1 μL RNaseOUT and 1 μL SuperScript™ III RT were added and the mixture was incubated at 50° C. for 1 h, followed by 85° C. for 10 min. After digestion with RNase A and RNase H, the remaining cDNA was purified using RNAClean XP beads (Beckman Coulter; 1.8 volumes of beads and 3 volumes of isopropanol).

The purified cDNA was ligated with a 3' adapter (5' Phosphate NNN-AGATCGGAAGAGCGTCGTGTAG-3' Biotin) (SEQ ID NO: 13) by T4 RNA ligase 1 (New England BioLabs; NEB) following the manufacturer's recommended protocol (2 μL 10×T4 RNA ligase buffer, 1 μL of 1 mM ATP, 10 μL 50% PEG 8000, 5 μL cDNA, 1 μL of 20 μM ssDNA adaptor, and 1 μL of T4 RNA ligase). Then, the cDNA ligated to the adaptor was purified with RNAClean XP beads as described above. PCR amplification was performed with the ligated cDNA by using Phusion polymerase (NEB) with cycling conditions of 98° C. for 20 s, 64° C. for 20 s and 72° C. for 90 s and the following forward (5'-CA-GACGTGTGCTCTTCCGATC-3') (SEQ ID NO: 14) and reverse (5'-CTACACGACGCTCTTCCGATCT-3') (SEQ ID NO: 15) primers. The PCR products were separated on a denaturing 15% polyacrylamide gel and the target band was excised from the gel and ethanol precipitated. The purified DNA was ligated into a vector using NEB's PCR Cloning Kit per the manufacturer's protocol. Antibiotic-resistant colonies were selected and subjected to Sanger sequencing by Genewiz. The cleavage sites and percentage were determined by comparing the cleaver treated samples and non-treated samples.

PTEN Luciferase Assay. The MDA-MB-231 cells were grown in 48-well plates to ~60% confluency and then transiently co-transfected with a Firefly luciferase plasmid encoding the 3' untranslated region (UTR) of PTEN[25] and a control Renilla luciferase plasmid using Lipofectamine 2000 per the manufacturer's protocol. At 5 h post-transfection, compounds diluted in growth medium were added to cells and then incubated for 48 h. Luciferase assays were completed using a previously described protocol[23,26]. Luminescence signal was measured on a Biotek Flx800 plate reader.

PDCD4 Western blot: The MDA-MB-231 cells were grown to ~60% confluency in 6-well plates. Cells were incubated with compounds diluted in growth media for 48 h. Total protein was extracted using M-PER Mammalian Protein Extraction Reagent (Pierce Biotechnology) supplemented with 1×Protease Inhibitor Cocktail III for Mammalian Cells (Research Products International Corp.) per the manufacturer's protocol. Total protein lysate was quantified using a Micro BCA Protein Assay Kit (Pierce Biotechnology). A 30 μg aliquot of total protein was resolved on a 10% Bis-Tris SDS-polyacrylamide gel, with a 5% stacking layer, and then transferred to a PVDF membrane. The membrane was then blocked in 5% (w/v) nonfat dry milk in 1×TBST for 1 h at room temperature. The membrane was then incubated with 1:2000 rabbit mAb PDCD4 primary antibody (Cell Signaling Technology: D29C6) in 1×TBST containing 5% nonfat dry milk overnight at 4° C. The membrane was washed five times for 5 min each with 1×TBST and then incubated with 1:5000 anti-rabbit IgG horseradish peroxidase secondary antibody conjugate (Cell Signaling Technology: 7074S) in 1×TBST containing 5% nonfat dry milk for 1 h at room temperature. After washing seven times for 5 min each with 1×TBST, protein levels were quantified by chemiluminescence using a SuperSignal West Pico Chemiluminescent Substrate (Pierce Biotechnology) per the manufacturer's recommendations. The membrane was stripped with 1×Stripping Buffer (200 mM glycine, pH 2.2, 1% Tween-20 and 0.1% SDS) two times for 5 min each, followed by washing 3 times in 1×TBST. Then, the membrane was blocked and probed for β-actin following the same procedure described above using 1:5000 mouse β-actin primary antibody (Cell Signaling Technology: 8H10D10). The membrane was washed five times with 1×TBST and incubated with 1:10000 anti-mouse IgG horseradish-peroxidase secondary antibody conjugate (Cell Signaling Technology: 7076S). After washing seven times with 1×TBST for 5 min each, protein levels were quantified as described above. ImageJ software was used to quantify band intensities.

Measurement of IFN-γ: The MDA-MB-231 cells were plated into a 24-well plate and allowed to grow to 70% confluency. Cells were transfected with 2'-5' $A_4$ using Lipofectamine RNAiMAX (Life Technologies). Alternatively, MDA-MB-231 cells were mock transfected and treated with vehicle (DMSO) or 5 (5, 50, 500, 5000 nM). Cell culture supernatant was removed at 24 h. The Human IFN-γ ELISA Kit (Bon Opus Biosciences: BE010020) was used to measure interferon gamma levels from the supernatants, per the manufacturer's instructions.

Boyden Chamber Invasion Assay. The MDA-MB-231, MDA-LM2, A375, A549, or MCF-10a cells ($5\times10^4$) were seeded into Hanging Cell Culture Inserts for 24 well plates with uncoated membranes with 8.0 μm pores (Millicell) in serum free growth media. A 3 mg/mL layer (100 μL) of Matrigel (Fisher Scientific: CB40234) diluted with serum free growth media was prepared inside of each membrane. Cells were cultured as described above, with or without compound treatment, and allowed to invade towards complete growth media in the bottom well for 16-24 h before ending the experiment by removing the media in the bottom wells and inserts. The hanging cell culture inserts and bottom wells were washed twice with 1×PBS, gently shaking to mix. Excess liquid and cells inside the insert were removed with cotton swabs, after which 400 μL of 4% paraformaldehyde was placed into the bottom well and incubated for 20 min at room temperature to fix the cells. The wells and inserts were washed twice with 1×PBS and then treated with 400 μL of 0.1% crystal violet solution for 20 min at room temperature to stain the cells. The wells and inserts were washed twice with water, followed by one wash with 1×PBS. Inserts were dried with cotton swabs to remove extra stain and cells inside the insert, then were air-dried, followed by Brightfield microscopic analysis using a Leica DMI3000 B upright fluorescent microscope. Four different fields of view from each captured image were counted for crystal violet stained or unstained cells. Normalized cells invaded was calculated with equation 5 (Eq 5):

$$\text{Normalized Cell Invasion} = \frac{\text{Stained Cells (compound)}}{\text{Stained Cells (vehicle)}} \quad \text{(Eq 5)}$$

where stained cells represent cells counted with crystal violet stain observed in the compound treated or vehicle treated samples, respectively.

Measurement of Catalytic Activity. The MDA-MB-231 cells were plated into a 24-well plates (Corning). At ~80% confluency, the media was aspirated and the cell monolayer was washed with 1×DPBS. Cells were then incubated with 5 (500 nM) or vehicle (DMSO) diluted in cell culture medium for 24 h. Cells were then lysed using 250 μL of RNA Lysis Buffer from a Quick-RNA MiniPrep Kit (Zymo Research). A 100 μL aliquot was transferred to black, non-binding surface, half area 96-well plates (Corning). Fractions of untreated cell lysate were combined and used to generate a standard curve of 5 in cell lysate, by spiking in known concentrations of 5. Fluorescence intensity (Ex: 345 nm, Em: 460 nm) was then measured on a Molecular Devices SpectraMax M5 plate reader to determine compound concentration in cell lysate. Using the generated standard curve, the concentration of 5 in the 50 μL cell lysate aliquot was then used to extrapolate the amount of 5 in pmol in the full 250 μL volume.

RNA was extracted from the cell lysates, followed by RT-qPCR as described above. A standard curve was generated for the pre-miR-21 WT transcript using in vitro transcribed pre-miR-21 (10 ng, 1 ng, 0.1 ng, 0.01 ng, 0.001 ng, 0.0001 ng, 0 ng) completed with each run to accurately calibrate $C_t$ values. The amount of cleaved pre-miR-21 was then calculated by taking the difference between the pmol of pre-miR-21 in untreated samples and the pmol of pre-miR-21 in 5-treated samples. Catalytic activity, or turnover, was calculated by taking the ratio of the pmol of cleaved pre-miR-21 and the pmol of 5 in the sample.

Global proteomics profiling using LC-MS/MS. The MDA-MB-231 cells treated with vehicle (DMSO) or 5 (50 nM) were washed with PBS, harvested by scraping, centrifuged at 1500×g for five minutes at 4° C. and then resuspended in PBS. Cells were lysed by sonication and lysate protein concentrations were determined using a Bradford assay (Bio-Rad). Protein samples (40 μg) were denatured with 6 M urea in 50 mM $NH_4HCO_3$, reduced with 10 mM tris(2-carboxyethyl)phosphine hydrochloride (TCEP) for 30 minutes, and then alkylated with 25 mM iodoacetamide for 30 minutes in the dark. Samples were diluted to 2 M urea with 50 mM $NH_4HCO_3$, and digested with trypsin (2 μL of 0.5 μg/μL) in the presence of 1 mM $CaCl_2$) for 12 hours at 37° C. Samples were then acidified to a final concentration of 5% acetic acid, desalted over a self-packed C18 spin column and dried. Samples were analyzed by LC-MS/MS (see below) and the MS data was processed with MaxQuant and Proteome Discoverer (see below).

LC-MS/MS analysis: Peptides were resuspended in water with 0.1% formic acid (FA) and analyzed using an EASY-nLC 1200 nano-UHPLC coupled to Q Exactive HF-X Quadrupole-Orbitrap mass spectrometer (Thermo Scientific). The chromatography column consisted of a 50 cm long, 75 μm i.d. microcapillary capped by a 5 μm tip and packed with ReproSil-Pur 120 C18-AQ 2.4 μm beads (Dr. Maisch GmbH). The LC solvents were 0.1% FA in $H_2O$ (Buffer A) and 0.1% FA in 90% MeCN: 10% $H_2O$ (Buffer B). The peptides were eluted into the mass spectrometer at a flow rate of 300 nL/minutes over a 240 minutes linear gradient (5-35% Buffer B) at 65° C. Data was acquired in data-dependent mode (top-20, NCE 28, R=7500) after a full MS scan (R=60000, m/z 400-1300). Dynamic exclusion was set to 10 seconds, peptide match was set to prefer and isotope exclusion was enabled. For targeted acquisition of PDCD4 and PTEN a peptide inclusion list was created and data was acquired as above with the exception of a dynamic exclusion set to 2 seconds.

MaxQuant analysis: The MS data was analyzed with MaxQuant (V1.6.1.0)[27] and searched against the human proteome (Uniprot) and a common list of contaminants (included in MaxQuant). The first peptide search tolerance was set at 20 ppm, 10 ppm was used for the main peptide search and fragment mass tolerance was set to 0.02 Da. The false discovery rate for peptides, proteins and sites identification was set to 1%. The minimum peptide length was set to 6 amino acids and peptide re-quantification and label-free quantification (MaxLFQ) were enabled. The minimal number of peptides per protein was set to two. Methionine oxidation was searched as a variable modification and carbamidomethylation of cysteines was searched as a fixed modification.

Proteome Discoverer analysis: The MS data was processed with Proteome Discoverer (V2.1.1.21) using the Sequest HT algorithm[26] and searched against the human proteome (Uniprot). Precursor mass tolerance was set to 10 ppm and 0.02 Da was used for the fragment mass tolerance. The minimum peptide length was set to 6 amino acids, minimum peptides per protein to two, q-value to ≤1% and protein FDR to high. Methionine oxidation was searched as a dynamic modification and carbamidomethylation of cysteines as a static modification.

Protein Pathway Analysis: Significantly differentially expressed proteins (FDR of 1% and $S_0(0.1)$) were uploaded onto the STRING database (Search Tool for the Retrieval of Interacting Genes/Proteins)[29] (string-db.org) for protein-protein interaction analyses using the medium confidence setting (0.400). The functional analyses (Canonical Pathways, Upstream Regulators) were generated through the use of Ingenuity Pathway Analysis (IPA, v01-12; QIAGEN Inc., qiagenbioinformatics.com/products/ingenuity-pathway-analysis)[30].

DMPK Measurements: Male C57BL/6 mice (n=3, 5-7 weeks) were used for pharmacokinetics (PK) assessment. Mice were dosed i.p. (10 mg/kg) with 5 in a formulation of DMSO/Tween-80/$H_2O$ (10/10/80) and blood (25 μL) was drawn at 0.25, 0.5, 1, 2, 4, 6, 8, and 24 h time points. Detection of compound levels in blood plasma was determined using LC/MS-MS on a QTRAP 5500 LC-MS/MS System (AB Sciex).

Statistical Analysis: All plots show means with error bars representing S.E.M., unless dictated otherwise. Experiments were completed independently in triplicate. Data were plotted and statistics were calculated using commercially available software (GraphPad Prism, Perseus). Comparisons between two groups were made using an unpaired, two-tailed Student's t-test. For Volcano plots from qPCR profiling and proteomics data, Perseus was used to calculate the FDR of 1% and a group variance of $S_0(0.1)$. Gini coefficients were calculated as previously described[18]. p values between distributions were calculated using a two-tailed Kolmogorov-Smirnov test. Significance was accepted at $p<0.05$, unless specified otherwise.

Data Availability: All relevant data are included herein. Crystallographic data are available free of charge from the Cambridge Crystallographic Data Centre under reference number: CCDC 1912054.

Code Availability: Custom code was used for cluster analyses to model the RNA binders with the RNA, using a previously described method[45]. Further discussion of the computational modeling is available herein.

Synthetic Experimental Procedures

General. Reagents and solvents were purchased from standard suppliers and used without further purification. The synthetic 2'-5' $A_4$ (lithium salt) was purchased from ChemGenes with HPLC purification. Library compounds (FIGS. 38A-38F) used for the in vitro cleavage screening assay were purchased from Zelinsky Institute Inc. (all C1 series and C2-6, 7, 10-19) and LabNetwork (C2-1-5, 8, and 9). Reactions were monitored with TLC Silica (Agela Technologies). Spots were visualized with UV light, phosphomolybdic acid or Ninhydrin stains. Products were purified by Isolera One (Biotage) using pre-packed silica gel columns (Agela Technologies) or HPLC (Waters 2489 and 1525) using a SunFire® Prep C18 OBD™ 5 μm column (19×150 mm) with a flow rate of 5 mL/min. Purities of products were analyzed by HPLC (Waters 2487 and 1525) using a SunFire® C18 3.5 μm column (4.6×150 mm) with a flow rate of 1 mL/min. NMR spectra were measured using a 400 UltraShield™ (Bruker) (400 MHz for $^1H$ and 100 MHz for $^{13}C$) or an Ascend™ 600 (Bruker) (600 MHz for $^1H$ and 150 MHz for $^{13}C$). The chemical shifts are expressed in ppm relative to TMS for $^1H$ and residual solvent for $^{13}C$ as internal standards. Coupling constants (J values) are represented in hertz. High resolution mass spectra were recorded on 4800 Plus MALDI TOF/TOF Analyzer (Applied Biosystems) using the α-cyano-4-hydroxycinnamic acid matrix and TOF/TOF Calibration Mixture (AB Sciex Pte. Ltd.) or an Agilent 1260 Infinity LC system coupled to an Agilent 6230 TOF (HR-ESI) equipped with a Poroshell 120 EC-C18 column (Agilent, 50 mm×4.6 mm, 2.7 μm). The in vitro cleavage screening assay was performed using a FLx800 plate reader (BioTek). Diffractions for X-ray crystallography were collected on Bruker AXS with Smart APEX detector.

Peptoid synthesis. Peptoids were synthesized using previously reported procedures[21]. Chemicals were procured from the following commercial sources: 2-chlorotritylchloride resin (loading=1.46 mmol/g), Rink Resin SS (loading=0.50 mmol/g). N,N'-diisopropylcarbodiimide (DIC), and Ethyl cyano(hydroxyimino)acetate (Oxyma) from Chem-Impex Int'l Inc.; 1-hydroxy-7-azabenzotriazole (HOAt) from Advanced Chem Tech; 1-[Bis(dimethylamino)methylene]-1H-1,2,3-triazolo[4,5-b]pyridinium 3-oxid hexafluorophosphate (HATU) and trifluoroacetic acid (TFA) from Oakwood Chemical; 1-propylamine from Alfa Aesar; propargylamine, N, N-diisopropylethyl amine (DIPEA) and 2-bromoacetic acid from Sigma Aldrich; and N,N-dimethylformamide (DMF, anhydrous) and dimethyl sulfoxide (DMSO, anhydrous) from EMD and used without further purification.

Determination of concentration of compound stock solutions. The concentration of synthesized compounds in solution was determined by absorbance of the solution recorded on a DU© 800 spectrophotometer (Beckman Coulter). The following extinction coefficients ($M^{-1}$ $cm^{-1}$) of each molecule in PBS (1% DMSO) were used: compound 1 (13,000 at 340 nm), compound 3 (14,902 at 340 nm, 16,472 at 345 nm), compound 4 (10,967 at 340 nm), and compound 24 (45,000 at 345 nm).

Scheme S1. Synthesis of 2 and 13

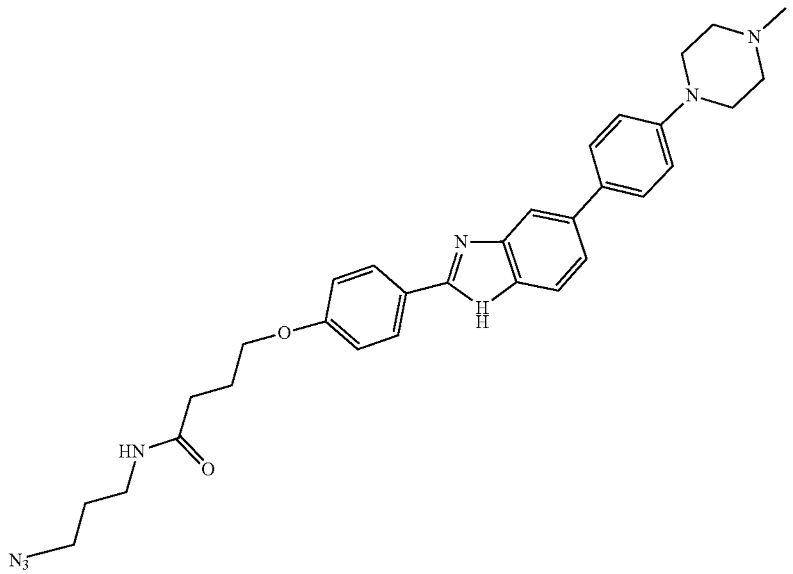

1

+

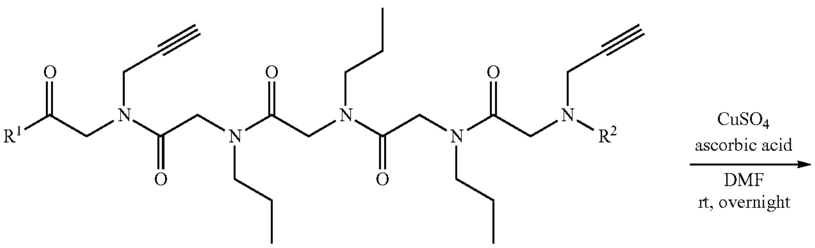

11: $R^1$ = $NH_2$, $R^2$ = H
12: $R^1$ = OH, $R^2$ = Ac

-continued
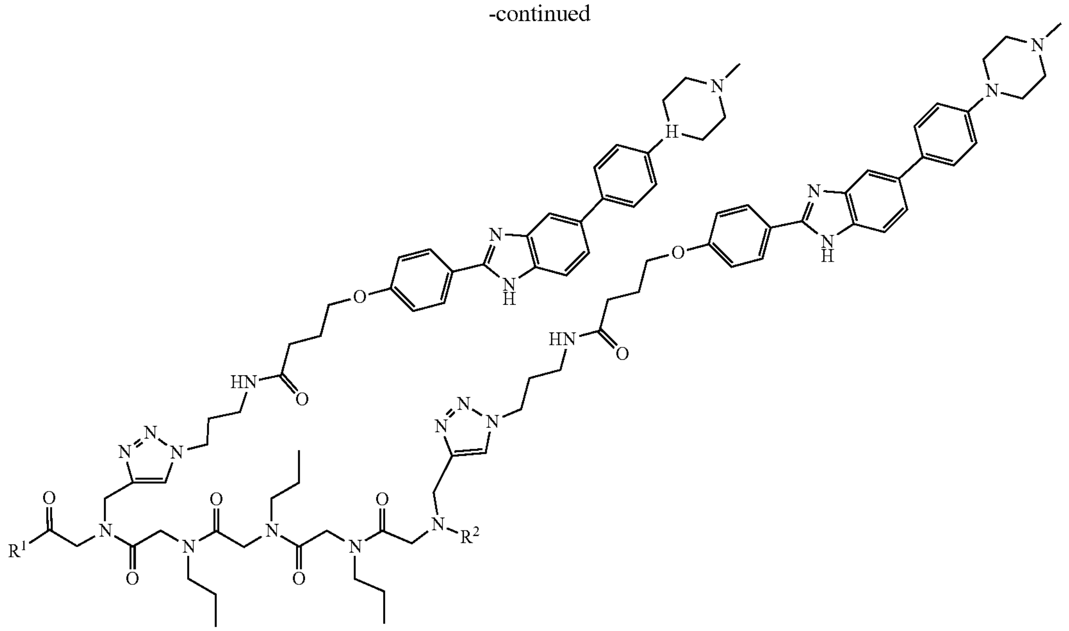
2: $R^1 = NH_2$, $R^2 = H$
13: $R^1 = OH$, $R^2 = Ac$
Scheme S2. Synthesis of 8
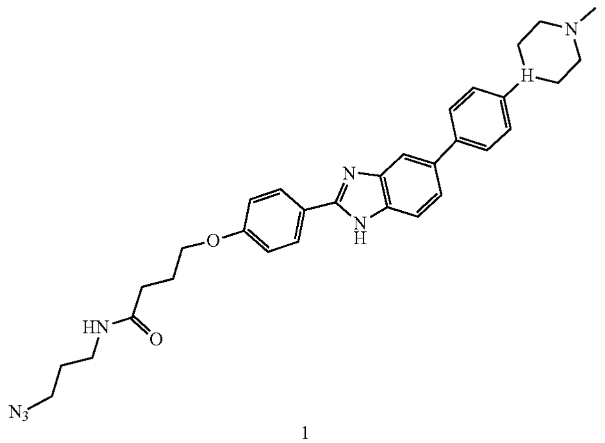
1
+
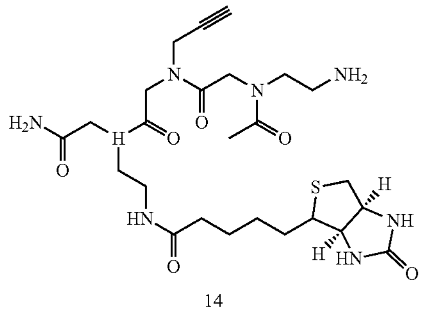
14
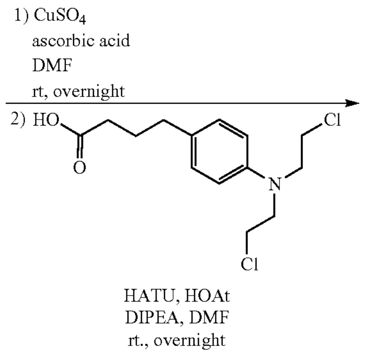

-continued
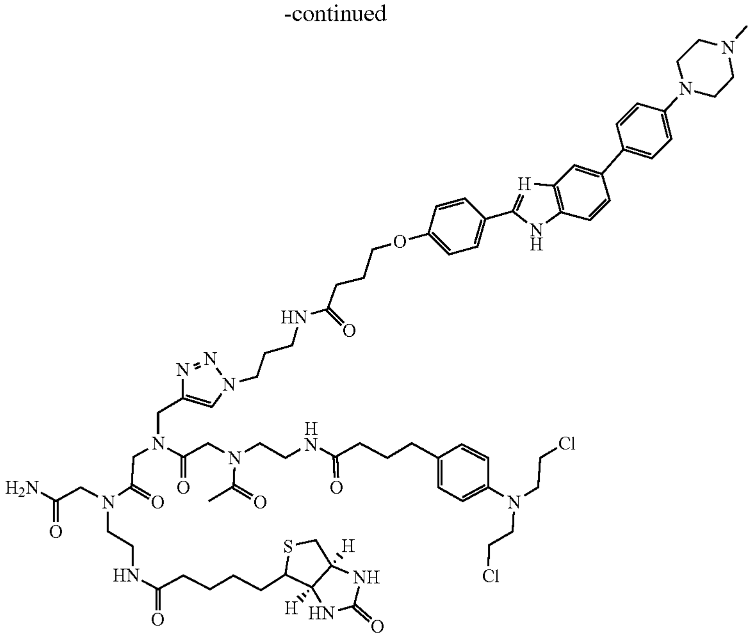
8

Scheme S3. Synthesis of 10
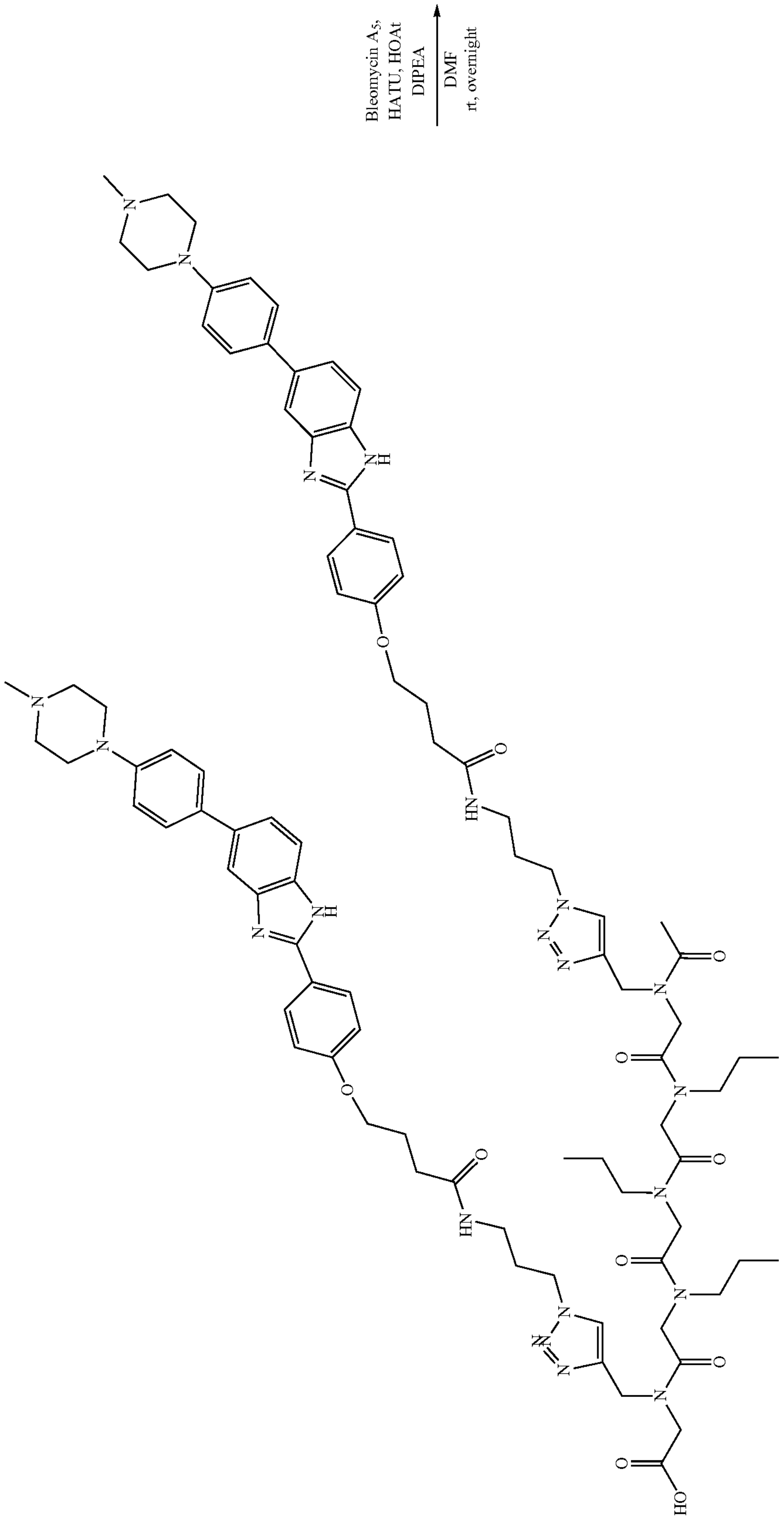
13

-continued
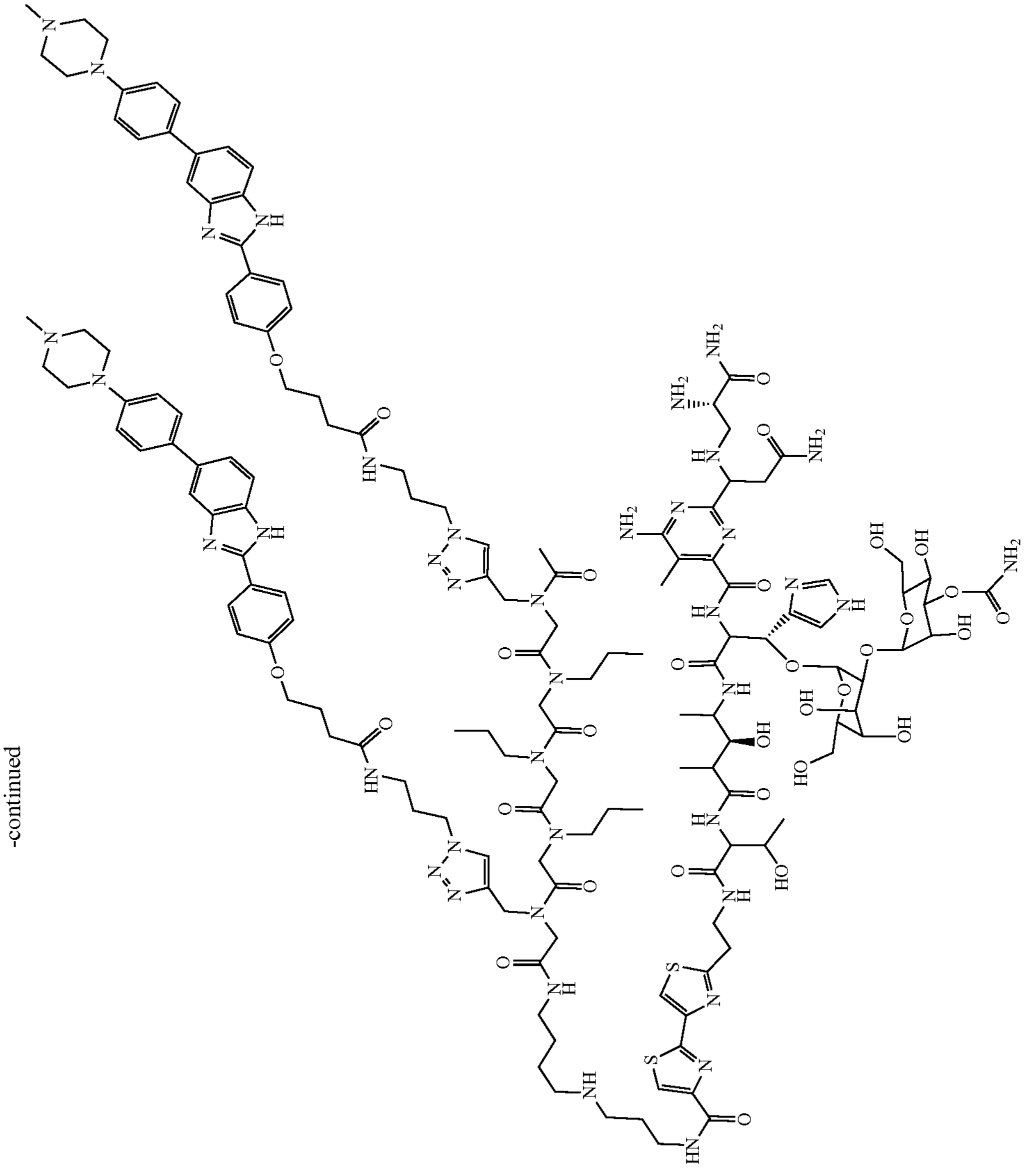

Scheme S4. Synthesis of 5
(1)
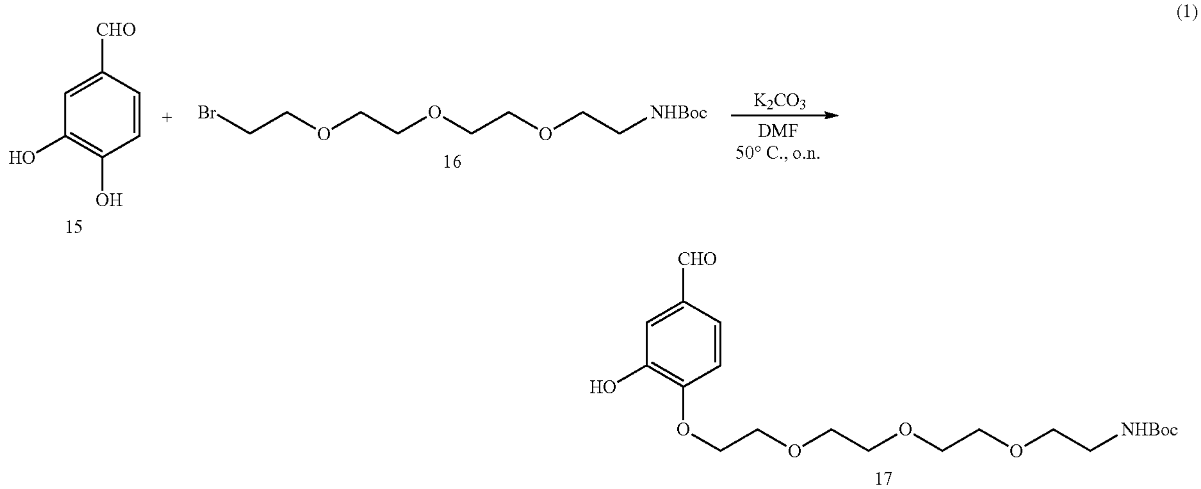
15 16 17
(2)
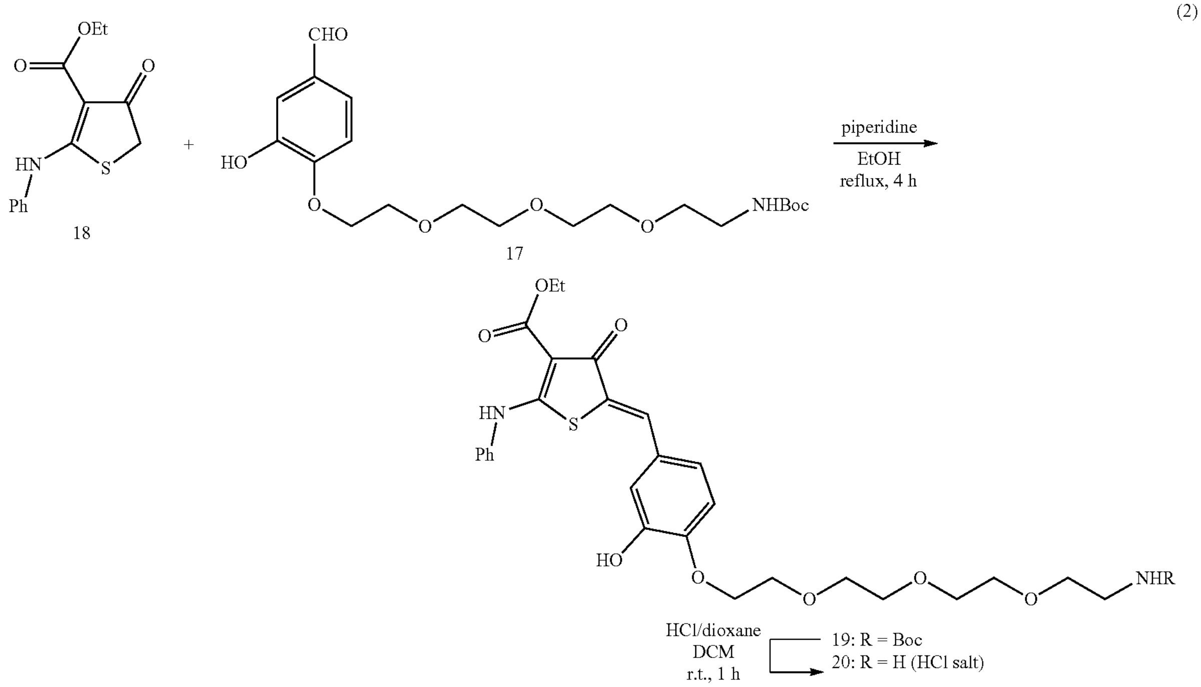
18 17
19: R = Boc
20: R = H (HCl salt)
(3)
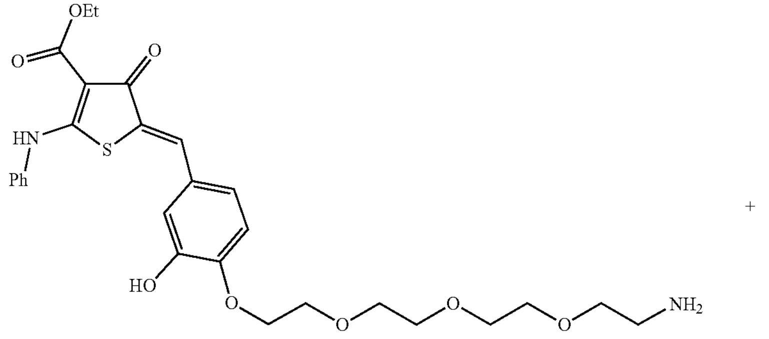
20
+

-continued
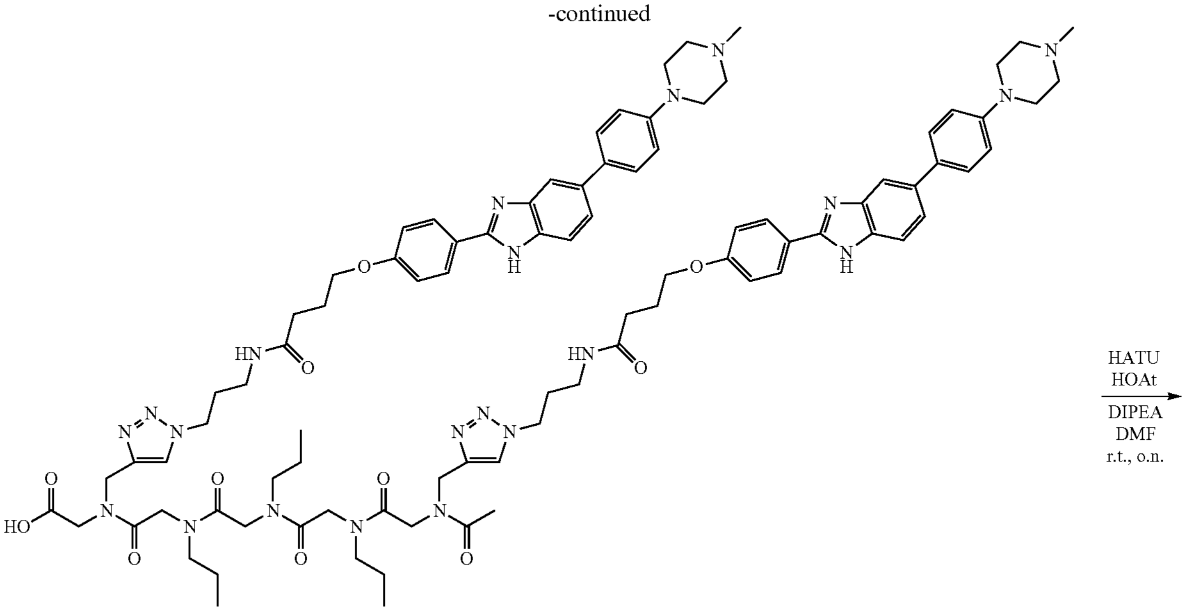
13
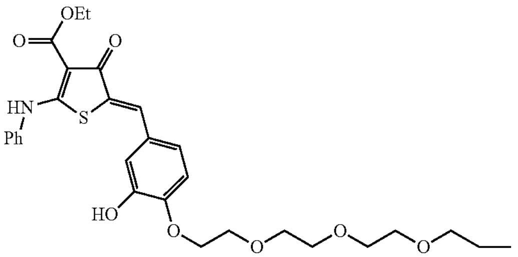
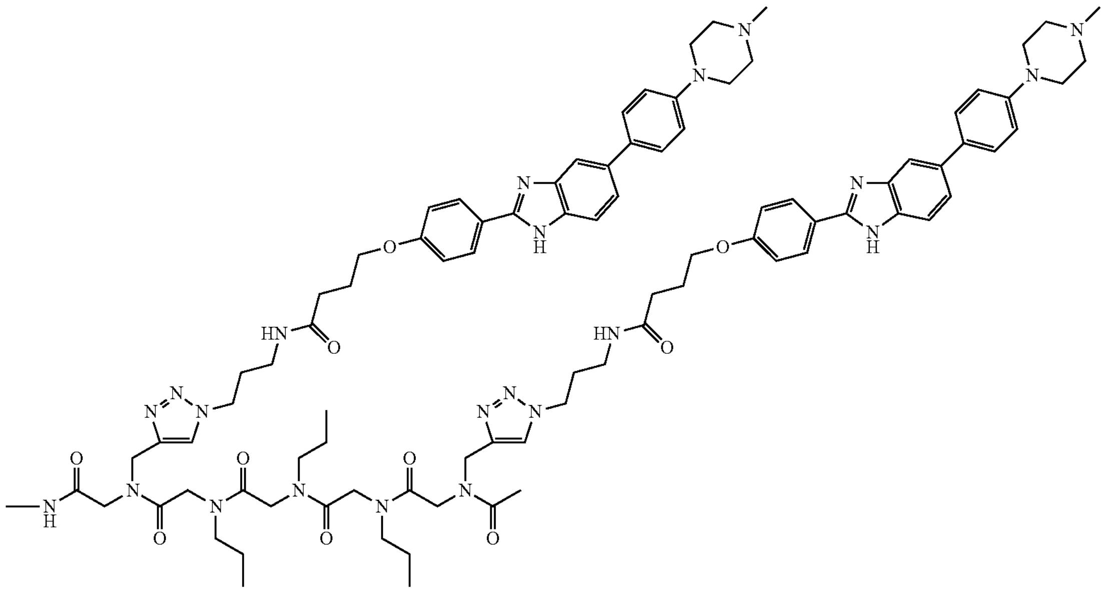
5

Scheme S5. Synthesis of 6
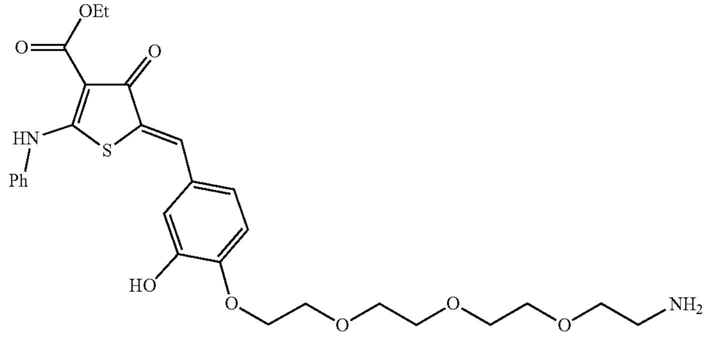
20
+
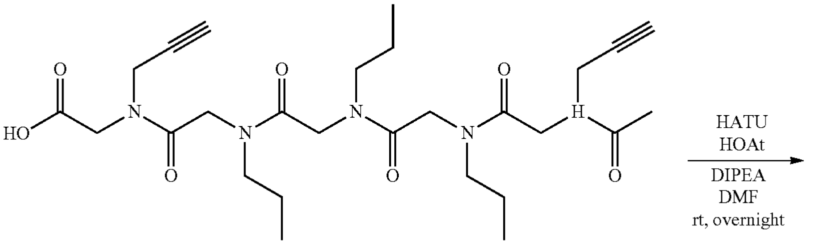
12
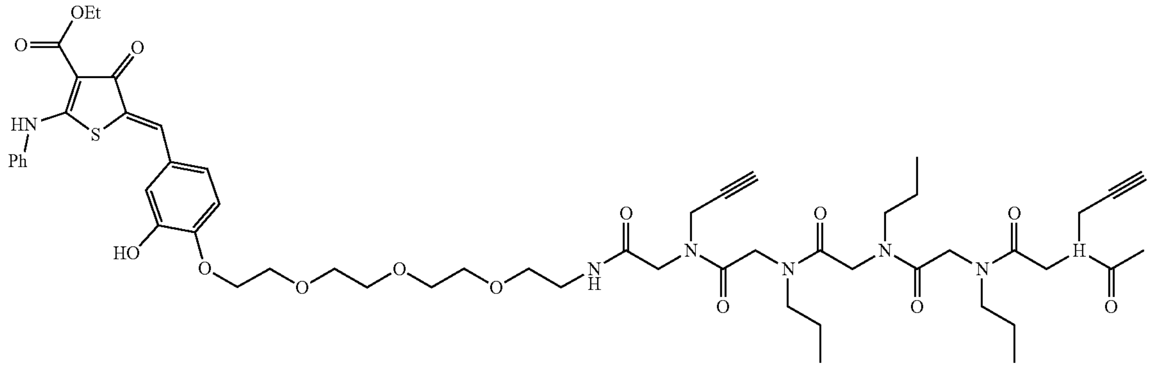
6
Scheme S6. Synthesis of 7
(1)
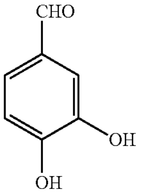
15
+
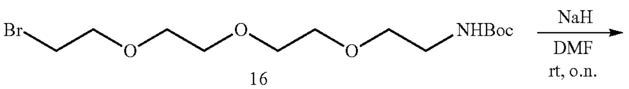
16
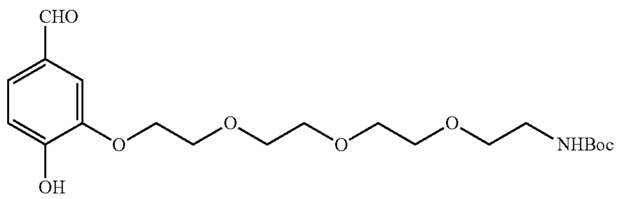
21

-continued
(2)
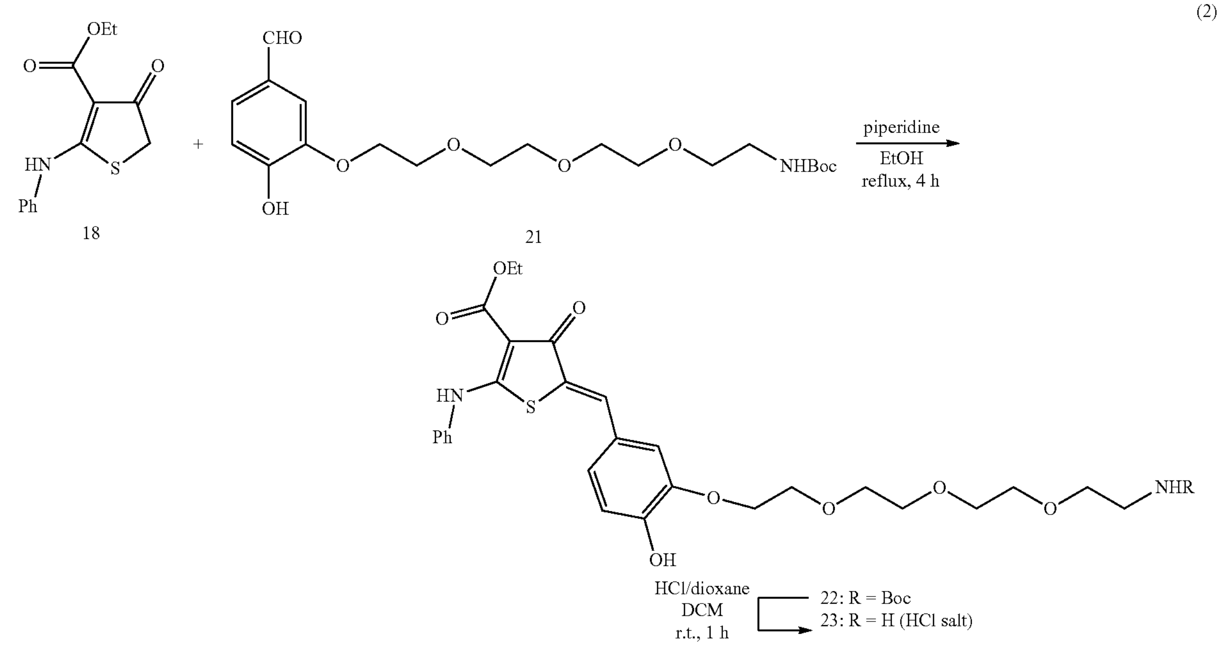
18
21
(3)
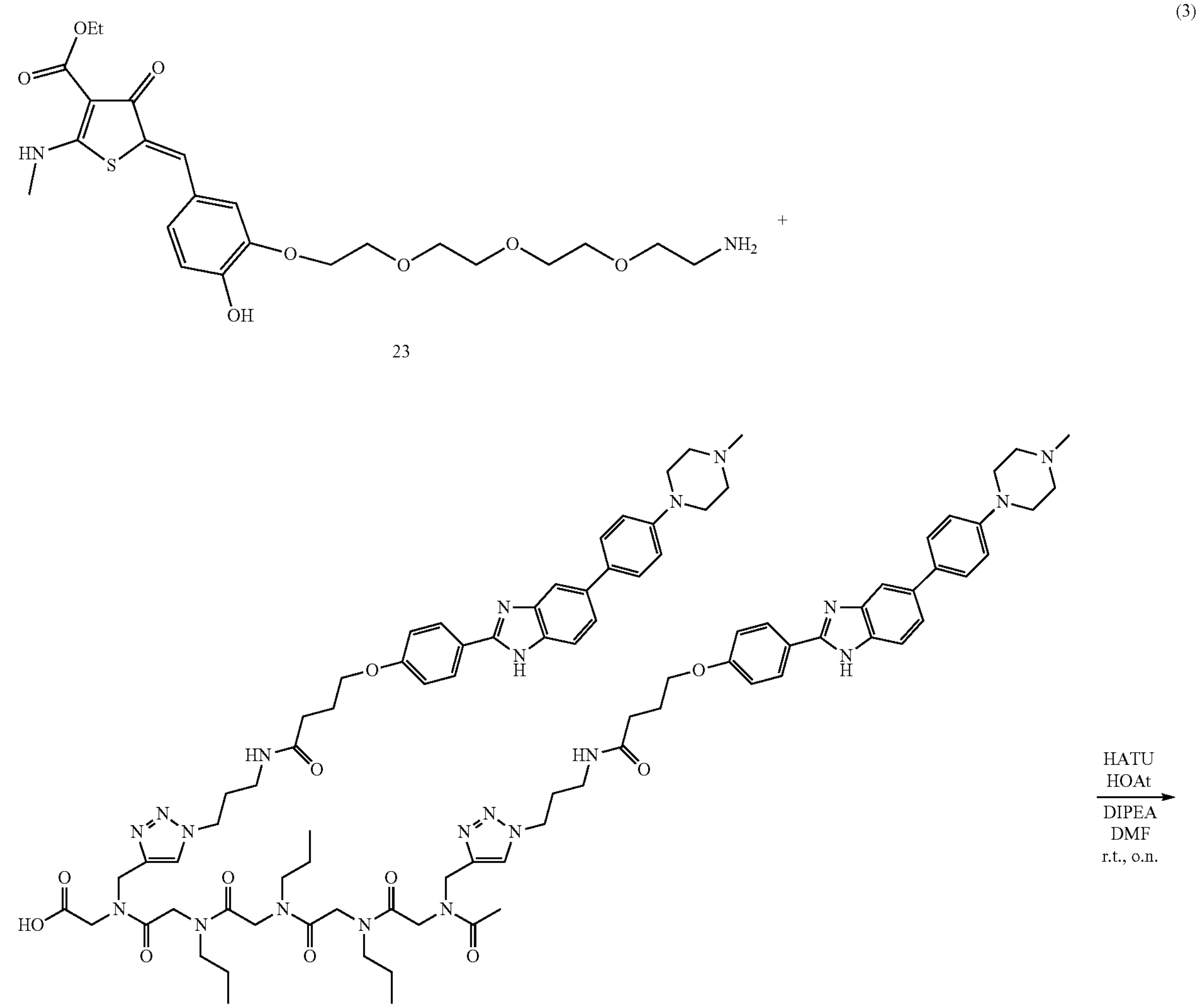
23
13

-continued
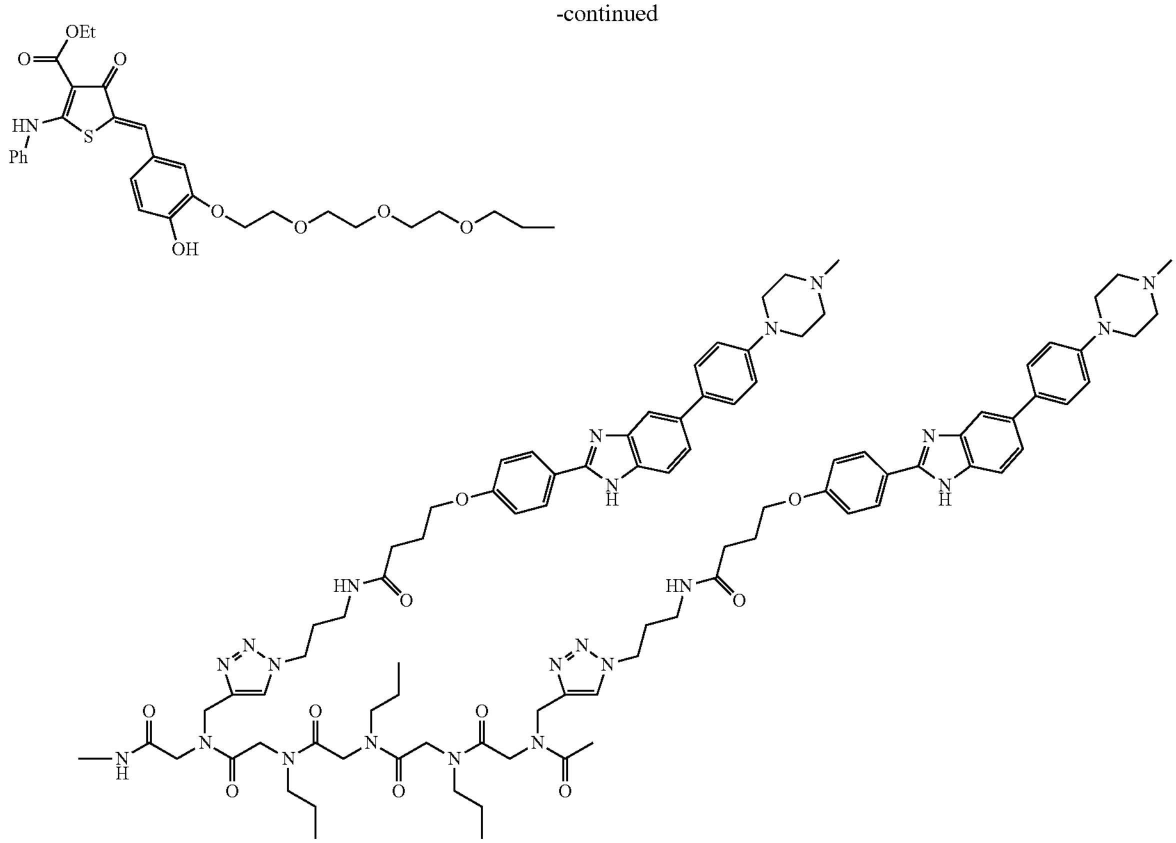
7
Scheme S7. Synthesis of 25
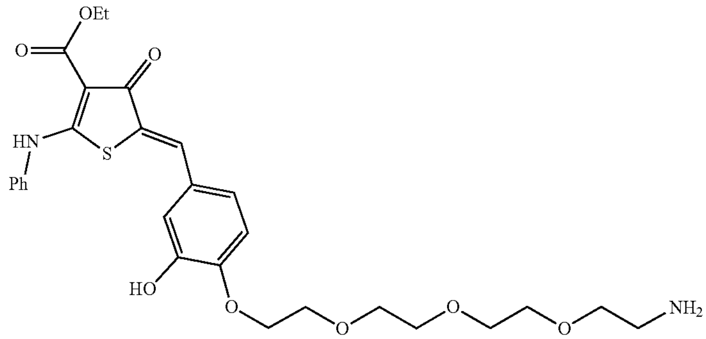
20
+
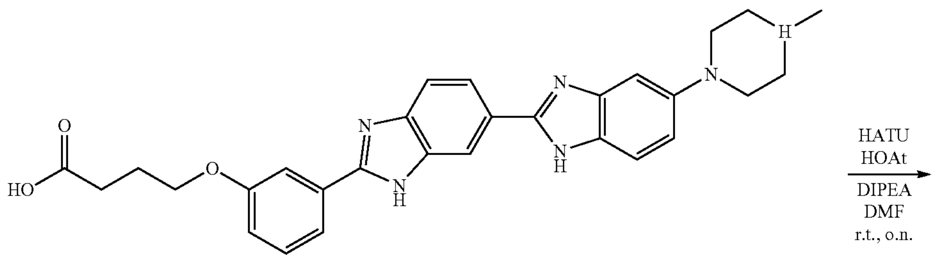
24

-continued

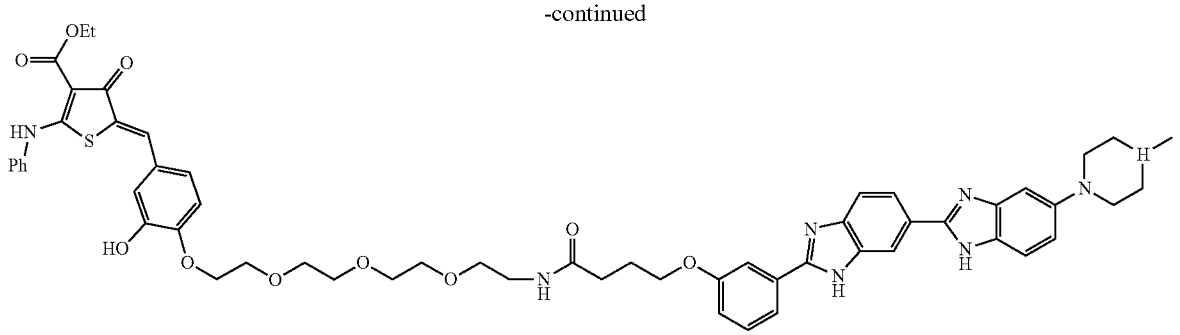

Compound 2:

To a solution of peptoid 11 (62 mg, 100 μmol) and compound 1 (115 mg, 200 μmol) in DMF (2.5 mL) was added $CuSO_4 \cdot 5H_2O$ (54.9 mg, 220 μmol) and L-ascorbic acid (38.7 mg, 220 μmol). The mixture was stirred at room temperature for 24 h. The solvent was evaporated and the product was purified by HPLC (40-65% MeOH/$H_2O$, 0.1% TFA) to give 2 as a yellow solid (73 mg, 37.4 μmol, 37%). $^1$H NMR (400 MHz, DMSO-$d_6$): δ=10.15 (br, 2H), 9.35 (br, 2H), 8.24-8.16 (5H), 8.09-8.01 (2H), 7.92 (s, 2H), 7.83-7.81 (2H), 7.76-7.74 (2H), 7.68-7.66 (4H), 7.28 (d, J=8.7 Hz, 4H), 7.16 (d, J=8.8 Hz, 4H), 4.68-3.79 (26H), 3.57-3.55 (4H), 3.31-2.97 (19H), 2.89 (s, 6H), 2.31-2.28 (4H), 2.02-1.94 (8H), 1.64-1.33 (6H), 0.92-0.75 (9H); $^{13}$C NMR (100 MHz, DMSO-$d_6$): δ=171.7, 162.2, 158.4 (q, J=34.1 Hz), 149.7, 149.0, 137.4, 131.1, 129.7, 127.8, 125.7, 123.9, 116.3, 115.6, 114.3, 110.6, 67.7, 55.1, 52.2, 48.6, 47.4, 45.4, 42.1, 35.7, 31.5, 30.0, 24.7, 20.2, 11.2, 11.1, 11.0; HR-MS (MALDI): Calcd. for $C_{87}H_{113}N_{22}O_9^+$ [M+H]$^+$, 1609.9055; found, 1609.8997.

Compound 2 Family

Compound 2 family (2A-2E) with different peptoid linker lengths (FIG. 30B) was synthesized with the same method as 2.

Compound 2A (n=1, FIG. 30B):

Yield: 1.4 μmol, 28%. HR-MS (MALDI): Calcd. for $C_{77}H_{95}N_{20}O_7^+$ [M+H]$^+$, 1411.7687; found, 1411.7665.

Compound 2B (n=2, FIG. 30B):

Yield: 0.6 μmol, 12%. HR-MS (MALDI): Calcd. for $C_{82}H_{104}N_{21}O_8^+$ [M+H]$^+$, 1510.8371; found, 1510.8385.

Compound 2C (n=4, FIG. 30B):

Yield: 1.9 μmol, 37%. HR-MS (MALDI): Calcd. for $C_{92}H_{122}N_{23}O_{10}^+$ [M+H]$^+$, 1708.9740; found, 1708.9730.

Compound 2D (n=5, FIG. 30B):

Yield: 3.0 μmol, 60%. HR-MS (MALDI): Calcd. for $C_{97}H_{131}N_{24}O_{11}^+$ [M+H]$^+$, 1808.0424; found, 1808.0428.

Compound 2E (n=6, FIG. 30B):

Yield: 3.7 μmol, 73%. HR-MS (MALDI): Calcd. for $C_{102}H_{140}N_{25}O_{12}^+$ [M+H]$^+$, 1907.1108; found, 1907.1100.

Compound 13:

To a solution of peptoid 12 (109.3 mg, 200 μmol) and compound 1 (221 mg, 400 μmol) in DMF (10 mL) was added $CuSO_4 \cdot 5H_2O$ (110 mg, 440 μmol) and L-ascorbic acid (77.5 mg, 440 μmol). The mixture was stirred at room temperature for 24 h. The solvent was evaporated and the crude mixture was washed with water. After drying, the crude reaction mixture was used for the next reaction without further purification. The crude of 13 was obtained as a light brown solid (275 mg, 166 μmol, 83%). The following spectra were collected after purification by HPLC (20-40% MeCN/$H_2O$, 0.1% TFA). $^1$H NMR (400 MHz, DMSO-$d_6$): δ=10.09 (br, 2H), 8.22-8.14 (5H), 8.07-7.91 (5H), 7.87-7.77 (4H), 7.71-7.64 (4H), 7.35-7.25 (4H), 7.21-7.10 (4H), 4.74-3.83 (26H), 3.65-3.46 (4H), 3.31-2.96 (18H), 2.96-2.80 (6H), 2.36-2.23 (4H), 2.17 (br, 1H), 2.06-1.78 (10H), 1.64-1.28 (6H), 0.92-0.69 (9H); $^{13}$C NMR (100 MHz, DMSO-$d_6$): δ=171.6, 162.6, 158.4 (q, J=36.2 Hz), 149.4, 149.2, 137.9, 132.9, 131.0, 130.8, 129.9, 127.9, 124.4, 123.6, 116.3, 115.7, 115.3, 114.1, 110.4, 67.7, 52.2, 47.3, 47.2, 45.4, 42.1, 35.8, 31.5, 29.9, 24.6, 21.4, 21.3, 21.2, 20.4, 20.3, 20.2, 11.2, 11.0; HR-MS (MALDI): Calcd. for $C_{89}H_{114}N_{21}O_{11}^+$ [M+H]$^+$, 1652.9001; found, 1652.8943.

Compound 8:

To a solution of biotin peptoid 14 (2.9 mg, 5 μmol) and compound 1 (5.8 mg, 10 μmol) in DMF (2.5 mL) was added $CuSO_4 \cdot 5H_2O$ (2.7 mg, 11 μmol) and L-ascorbic acid (1.9 mg, 11 μmol). The mixture was stirred at room temperature for 24 h. The solvent was concentrated and the crude product was precipitated with an excess amount of ether. To the crude (1.1 mg, 1.0 μmol) a mixture of Chlorambucil (3.6 mg, 1.2 μmol), HATU (0.8 mg, 2.0 μmol), HOAt (0.3 mg, 2.0 μmol), and DIPEA (0.9 μL, 5.0 μmol) in DMF (1 mL) was added after stirring for 10 min. The mixture was stirred at room temperature overnight and the product was precipitated with an excess amount of ether. The solid was dissolved in 50% MeCN in water with 0.1% TFA and subjected to HPLC purification. The product was purified by HPLC (0-100% MeCN/$H_2O$, 0.1% TFA) to give compound 8 (0.2 mg, 15%). HPLC chromatogram: 0-100%/60 min MeCN/$H_2O$ (0.1% TFA). HR-MS (MALDI): Calcd. for $C_{70}H_{94}Cl_2N_{17}O_9S^+$ [M+H]$^+$, 1418.6513; found, 1418.6487.

Compound 10:

A solution of acid 13 (1.63 mg, 1.0 μmol), HATU (0.8 mg, 2.0 μmol), HOAt (0.3 mg, 2.0 μmol), and DIPEA (0.9 μL, 5.0 μmol) in DMF (1 mL) was stirred for 10 min, and then was added to a DMSO solution of Bleomycin A5 (2.26 mg, 1.5 μmol). The mixture was stirred at room temperature overnight and the product was precipitated with an excess amount of ether. The solid was dissolved in 50% MeOH in water with 0.1% TFA and subjected to HPLC purification. After injection of the solution, the column was washed with 50 mM EDTA (pH 6.7) for 30 min to remove the copper ion and then washed with water for another 30 min. Then the target product was purified by HPLC (0-100% MeOH/$H_2O$, 0.1% TFA) (0.9 mg, 29%). HR-MS (MALDI): Calcd. for $C_{146}H_{201}N_{40}O_{31}S_2^+$ [M+H]$^+$, 3074.4817; found, 3074.4932.

Compound 17:

A solution of phenol 15 (41.4 mg, 0.3 mmol), bromoPEG 16 (107 mg, 0.3 mmol), and $K_2CO_3$ (41.5 mg, 0.3 mmol) in DMF (1 mL) was heated at 50° C. overnight. The solvent was evaporated and the product was purified by silica gel column chromatography (Hexane:AcOEt=1:1-0:1) to give 17 as a light yellow oil (53 mg, 43%). $^{1}H$ NMR (400 MHz, $CDCl_3$): δ=9.84 (s, 1H), 7.48 (br, 1H), 7.44 (d, J=2.0 Hz, 1H), 7.39 (dd, J=8.2, 2.0 Hz, 1H), 6.97 (d, J=8.2 Hz, 1H), 5.20 (br, 1H), 4.28-4.26 (2H), 3.92-3.90 (2H), 3.76-3.74 (2H), 3.71-3.68 (2H), 3.67-3.62 (4H), 3.56-3.54 (2H), 3.35-3.29 (2H), 1.43 (s, 9H); $^{13}C$ NMR (100 MHz, $CDCl_3$): δ=191.1, 156.1, 151.4, 147.3, 131.2, 123.6, 115.6, 112.6, 79.2, 70.6, 70.4, 70.4, 70.2, 69.1, 68.7, 40.3, 28.4; HR-MS (ESI): Calcd. for $C_{20}H_{31}NO_8Na^+$ $[M+Na]^+$, 436.1942; found, 436.1948.

Compound 19:

A solution of thiophene 18 (350 mg, 1.32 mmol), aldehyde 17 (500 mg, 1.21 mmol), and piperidine (120 μL, 0.17 mmol) in EtOH (7 mL) was heated at 80° C. by microwave for 4 h. The solvent was evaporated, and the product was purified by silica gel column chromatography (AcOEt only) to give 19 as a yellow solid (688 mg, 86%). $^{1}H$ NMR (400 MHz, $CDCl_3$): δ=11.49 (br, 1H), 7.73 (s, 1H), 7.49 (m, 2H), 7.42-7.35 (3H), 7.20 (br, 1H), 7.12 (d, J=2.2 Hz, 1H), 7.02 (dd, J=8.6, 2.2 Hz, 1H), 6.90 (d, J=8.4 Hz, 1H), 5.14 (br, 1H), 4.41 (q, J=7.1 Hz, 2H), 4.22-4.19 (2H), 3.87-3.84 (2H), 3.74-3.72 (2H), 3.70-3.67 (2H), 3.66-3.61 (4H), 3.55-3.52 (2H), 3.34-3.26 (2H), 1.44 (t, J=7.1 Hz, 3H), 1.42 (s, 9H); $^{13}C$ NMR (100 MHz, $CDCl_3$): δ=182.2, 176.2, 167.0, 156.0, 147.5, 147.3, 137.1, 131.5, 129.9, 128.5, 127.7, 125.7, 124.1, 123.5, 116.5, 114.0, 97.9, 79.1, 70.6, 70.4, 70.3, 70.2, 69.2, 69.1, 60.6, 40.3, 28.4, 14.4; HR-MS (ESI): Calcd. for $C_{33}H_{43}N_2O_{10}S^+$ $[M+H]^+$, 659.2633; found, 659.2654.

Compound 20:

To a solution of 19 (45 mg, 68.3 μmol) in 2 mL of dichloromethane was added 4 M HCl in 1,4-dioxane (0.5 mL, 2 mmol). The mixture was stirred at room temperature for 30 min, followed by evaporation of the solvent to give 20 as a yellow solid (38.9 mg, 65.4 μmol, 96%). $^{1}H$ NMR (400 MHz, DMSO-$d_6$): δ=11.26 (s, 1H), 9.55 (s, 1H), 7.98 (brs, 3H), 7.58-7.42 (6H), 7.05-6.96 (3H), 4.28 (q, J=7.1 Hz, 2H), 4.13-4.10 (m, 2H), 3.77-3.72 (m, 2H), 3.63-3.51 (10H), 2.94 (m, 2H), 1.29 (t, J=7.1 Hz, 3H); $^{13}C$ NMR (100 MHz, DMSO-$d_6$): δ=180.9, 175.3, 164.9, 148.7, 147.0, 137.5, 130.0, 129.6, 128.2, 126.3, 125.6, 124.7, 123.0, 115.9, 113.7, 96.9, 69.9, 69.8, 69.6, 68.8, 67.9, 66.6, 66.4, 59.5, 38.5, 14.4; HR-MS (ESI): Calcd. for $C_{28}H_{35}N_2O_8S^+$ $[M+H]^+$, 559.2109; found, 559.2131.

Compound 5:

A solution of acid 13 (265 mg, 160 μmol), HATU (73 mg, 192 μmol), HOAt (26 mg, 192 μmol), and DIPEA (83.6 μL, 480 μmol) in DMF (5 mL) was stirred for 10 min, and a solution of amine 20 (114.2 mg, 192 μmol) and DIPEA (83.6 μL, 480 μmol) was added in 2 mL of DMF. The mixture was stirred at room temperature for 24 h. The solvent was evaporated and the product was purified by HPLC (45-75% MeOH/$H_2O$, 0.1% TFA) to give 5 as a yellow solid (70.1 mg, 28.9 μmol, 18%). $^{1}H$ NMR (400 MHz, DMSO-$d_6$): δ=11.23 (s, 1H), 10.11-9.28 (2H), 8.22-8.10 (5H), 8.08-7.89 (4H), 7.87 (s, 2H), 7.78 (d, J=8.4 Hz, 2H), 7.71 (d, J=8.5 Hz, 2H), 7.66 (d, J=8.4 Hz, 4H), 7.56-7.41 (6H), 7.30-7.21 (4H), 7.15 (d, J=8.8 Hz, 4H), 7.02-6.93 (3H), 4.67-2.96 (129H including water peak), 2.93-2.83 (8H), 2.73 (s, 1H), 2.28 (m, 4H), 2.16 (1H), 2.05-1.78 (10H), 1.61-1.32 (6H), 1.28 (t, J=7.1 Hz, 3H), 0.90-0.68 (9H); $^{13}C$ NMR (100 MHz, DMSO-$d_6$): δ=180.9, 175.3, 171.6, 171.6, 164.9, 162.2, 162.1, 158.5, 158.1, 149.8, 149.0, 148.7, 147.0, 143.4, 137.5, 137.3, 137.3, 131.1, 130.0, 129.6, 129.6, 128.2, 127.8, 126.3, 125.6, 124.6, 123.9, 123.1, 116.3, 115.9, 115.6, 114.3, 113.7, 110.6, 96.9, 69.9, 69.8, 69.7, 69.6, 69.5, 68.8, 67.9, 67.6, 59.5, 55.1, 52.2, 48.6, 47.3, 47.2, 47.2, 45.4, 42.1, 35.8, 31.5, 29.9, 24.7, 20.3, 20.3, 20.2, 14.4, 11.2, 11.2, 11.2, 11.0; HR-MS (ESI): Calcd. for $C_{117}H_{148}N_{23}O_{14}S^{3+}$ $[M+3H]^{3+}$, 731.7026; found, 731.7040.

Compound 6:

A solution of acid 12 (12 mg, 22 μmol), HATU (10.9 mg, 28.6 μmol), HOAt (3.9 mg, 28.6 μmol), and DIPEA (3.8 μL, 22 μmol) in DMF (120 μL) was stirred for 10 min, and then a solution of amine 20 (17 mg, 28.6 μmol) and DIPEA (7.6 μL, 44 μmol) in 100 μL of DMF was added. The mixture was stirred at room temperature for 24 h. The solvent was evaporated and the product was purified by HPLC (50-90% MeOH/$H_2O$, 0.1% TFA) to give 6 as a yellow solid (13 mg, 11.9 μmol, 54%). $^{1}H$ NMR (400 MHz, DMSO-$d_6$): δ=11.25 (s, 1H), 7.58-7.42 (6H), 7.06-6.95 (3H), 4.48-3.82 (18H), 3.80-3.70 (2H), 3.64-3.33 (11H), 3.33-3.05 (10H), 2.09 (m, 1H), 1.94-1.76 (2H), 1.64-1.26 (9H), 0.93-0.72 (9H); $^{13}C$ NMR (150 MHz, DMSO-$d_6$): δ=180.9, 175.3, 164.9, 148.7, 147.0, 137.5, 130.0, 129.6, 128.2, 126.3, 125.6, 124.6, 123.1, 115.8, 113.8, 96.9, 69.9, 69.8, 69.7, 69.6, 69.6, 68.8, 67.9, 59.5, 21.1, 21.1, 21.0, 21.0, 20.9, 20.3, 20.2, 20.2, 14.4, 11.3, 11.2, 11.2, 11.2, 11.1, 11.0, 11.0, 11.0; HR-MS (ESI): Calcd. for $C_{55}H_{74}N_7O_{14}S^+$ $[M+H]^+$, 1088.5009; found, 1088.5018.

Compound 21:

To a solution of NaH (84 mg 60% oil dispersed, 2.1 mmol) in DMF (2 mL) was added a solution of 3,4-dihydroxybenzaldehyde 15 (228.3 mg, 1 mmol) in DMF (2 mL) at 0° C. After stirring for 30 min, bromoPEG 16 (356 mg, 1 mmol) in DMF (2 mL) was added. The mixture was gradually warmed to room temperature and stirred overnight. The reaction was quenched by the addition of 1 eq. of acetic acid, after which solvents were evaporated. The crude mixture was purified by silica gel column chromatography (Hexane:AcOEt=1:1-0:1) to give 21 as a colorless oil (110 mg, 54% based on recovery of the starting material). $^{1}H$ NMR (400 MHz, $CDCl_3$): δ=9.80 (s, 1H), 8.27 (br, 1H), 7.46-7.43 (2H), 7.04 (m, 1H), 5.19 (br, 1H), 4.25-4.23 (2H), 3.89-3.87 (2H), 3.76-3.74 (2H), 3.71-3.69 (2H), 3.68-3.62 (4H), 3.57-3.54 (2H), 3.34-3.31 (2H), 1.43 (s, 9H); $^{13}C$ NMR (100 MHz, $CDCl_3$): δ=190.7, 156.1, 153.5, 146.7, 129.4, 128.1, 115.7, 112.7, 79.2, 70.5, 70.4, 70.4, 70.3, 70.2, 69.2, 40.3, 28.4; HR-MS (ESI): Calcd. for $C_{20}H_{32}NO_8^+$ $[M+H]^+$, 414.2122; found, 414.2134.

Compound 22:

A solution of thiophene 18 (58.4 mg, 220 μmol), aldehyde 21 (83.3 mg, 220 μmol), and piperidine (19.8 μL, 220 μmol) in EtOH (1 mL) was heated at 80° C. by microwave for 4 h. The solvent was evaporated and the product was purified by silica gel column chromatography (AcOEt only) to give 22 as a yellow oil (89.1 mg, 68%). $^{1}H$ NMR (400 MHz, $CDCl_3$): δ=11.49 (s, 1H), 7.72 (s, 1H), 7.61 (br, 1H), 7.51-7.47 (2H), 7.41-7.36 (3H), 7.16-7.13 (m, 1H), 7.06 (d, J=2.0 Hz, 1H), 6.95 (d, J=8.3 Hz, 1H), 5.15 (br, 1H), 4.41 (q, J=7.1 Hz, 2H), 4.18-4.16 (2H), 3.84-3.82 (2H), 3.75-3.61 (8H), 3.55-3.53 (2H), 3.34-3.28 (2H), 1.46-1.42 (12H); $^{13}C$ NMR (100 MHz, $CDCl_3$): δ=182.2, 176.0, 167.0, 156.0, 149.5, 146.2, 137.2, 131.5, 129.8, 127.7, 126.2, 125.4, 124.8, 124.1, 118.1, 116.4, 98.0, 79.1, 70.6, 70.5, 70.4, 70.3, 70.2, 70.2, 69.3, 60.6, 40.3, 28.4, 14.4; HR-MS (ESI): Calcd. for $C_{33}H_{43}N_2O_{10}S^+$ $[M+H]^+$, 659.2633; found, 659.2657.

Compound 23:

To a solution of 22 (89.1 mg, 135 μmol) in 4 mL of dichloromethane, a solution of 4 M HCl in 1,4-dioxane (1 mL, 4 mmol) added. The mixture was stirred at room temperature for 30 min. Evaporation of the solvent resulted in 23 as a yellow solid (73.3 mg, 123 μmol, 91%). $^1H$ NMR (400 MHz, DMSO-$d_6$): δ=11.25 (s, 1H), 9.89 (br, 1H), 7.79 (br, 3H), 7.55-7.51 (5H), 7.48-7.42 (1H), 7.18 (d, J=2.0 Hz, 1H), 7.00 (m, 1H), 6.90 (d, J=8.3 Hz, 1H), 4.28 (q, J=7.1 Hz, 2H), 4.11-4.08 (2H), 3.74-3.71 (2H), 3.60-3.52 (10H), 3.00-2.93 (2H), 1.30 (t, J=7.1 Hz, 3H); $^{13}C$ NMR (100 MHz, DMSO-$d_6$): δ=181.0, 175.2, 164.9, 149.2, 147.0, 137.5, 130.3, 129.6, 128.1, 125.5, 124.9, 124.1, 123.2, 116.9, 116.4, 96.9, 69.9, 69.8, 69.6, 69.6, 68.9, 68.1, 66.6, 59.5, 38.6, 14.4; HR-MS (ESI): Calcd. for $C_{28}H_{35}N_2O_8S^+$ $[M+H]^+$, 559.2109; found, 559.2110.

Compound 7:

A solution of acid 13 (66.1 mg, 40 μmol), HATU (18.3 mg, 48 μmol), HOAt (6.5 mg, 48 μmol), and DIPEA (20.9 μL, 120 μmol) in DMF (1 mL) was stirred for 10 min, and was added to a solution of amine 23 (28.5 mg, 48 μmol) and DIPEA (13.9 μL, 80 μmol) in 0.5 mL of DMF. The mixture was stirred at room temperature for 24 h. The solvent was evaporated and the product was purified by HPLC (45-75% MeOH/$H_2O$, 0.1% TFA) to give 7 as a yellow solid (9.4 mg, 3.9 μmol, 10%). $^1H$ NMR (400 MHz, DMSO-$d_6$): δ=11.23 (s, 1H), 9.93 (br, 2H), 8.18-8.16 (4H), 8.09-7.89 (4H), 7.89 (s, 2H), 7.80-7.75 (2H), 7.74-7.63 (6H), 7.55-7.47 (5H), 7.46-7.39 (1H), 7.29-7.21 (4H), 7.17-7.11 (5H), 7.02-6.95 (1H), 6.92-6.85 (1H), 4.73-2.94 (96H including water peak), 2.89 (s, 6H), 2.30-2.26 (4H), 2.04-1.75 (11H), 1.61-1.14 (11H), 0.90-0.68 (9H); $^{13}C$ NMR (150 MHz, DMSO-$d_6$): δ=180.9, 175.1, 172.0, 171.6, 171.6, 169.9, 169.1, 167.9, 164.9, 161.9, 158.1 (q, J=33.3 Hz), 150.0, 149.2, 148.9, 147.0, 137.5, 137.0, 131.3, 130.3, 129.6, 129.4, 128.0, 127.7, 125.4, 124.8, 124.0, 123.6, 123.3, 116.7, 116.3, 115.5, 114.3, 110.6, 96.9, 69.9, 69.8, 69.7, 69.6, 69.5, 68.9, 68.1, 67.6, 59.5, 52.2, 49.3, 49.0, 48.7, 47.3, 47.1, 45.7, 45.4, 42.1, 40.4, 35.7, 31.5, 29.9, 29.8, 24.7, 21.1, 20.2, 14.4, 11.2, 11.2, 11.0; HR-MS (ESI): Calcd. for $C_{117}H_{149}N_{23}O_{18}S^{4+}$ $[M+4H]^{4+}$, 549.0287; found, 549.0322.

Compound 25:

A solution of acid 24 (1 TFA salt) (1.4 mg, 2.2 μmol), EDC (1.3 mg, 6.7 μmol), HOBt (1.0 mg, 6.7 μmol), and DIPEA (1.2 μL, 6.7 μmol) in DMF (50 μL) was stirred for 10 min, and was added to a solution of amine 20 (4 mg, 6.7 μmol) and DIPEA (1.2 μL, 6.7 μmol) in 30 μL of DMF. The mixture was stirred at room temperature for 24 h. The solvent was evaporated and the product was purified by HPLC (50-70% MeOH/$H_2O$, 0.1% TFA) to give 25 as a yellow oil (0.9 mg, 0.8 μmol, 34%). HR-MS (ESI): Calcd. for $C_{57}H_{65}N_8O_{10}S^{3+}$ $[M+3H]^{3+}$, 351.1509; found, 351.1533.

Determination of Geometry at Olefin of Recruiter

Figure 26:
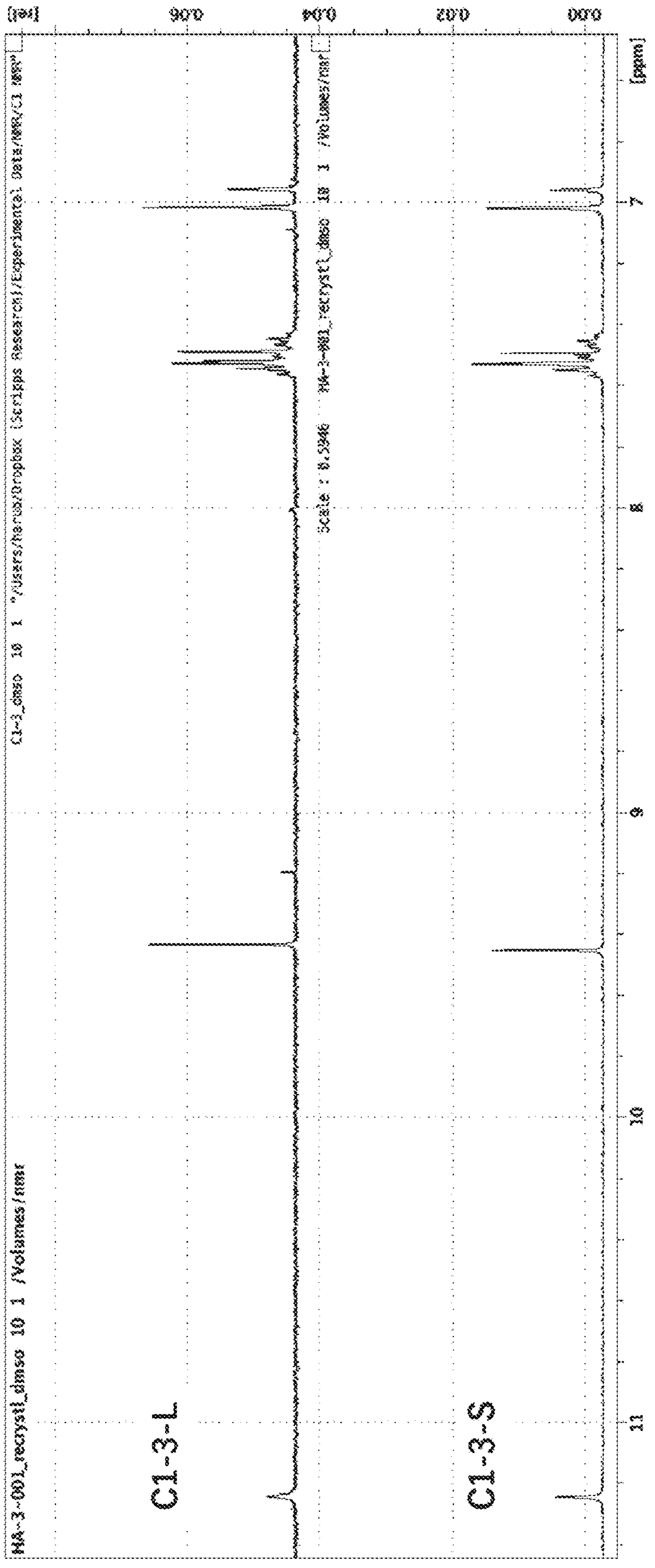
FIG. 26. Comparison of the $^{1}H$-NMR spectra (400 MHz, DMSO-$d_6$) of C1-3-L and C1-3-S.

The small molecule RNase L recruiter C1-3 (3, FIGS. 2A-2C & FIGS. 38A-38F) was synthesized using the same procedure as the synthesis of 20, and the newly synthesized C1-3 (C1-3-S) and C1-3 in the library (C1-3-L) were identical by $^1H$-NMR (DMSO-$d_6$) (FIG. 26). The Z-isomer geometry of the olefin of C1-3-S was confirmed by X-ray crystallography. Finally, by comparison of $^1H$-NMRs of C1-3-S and 20 in $CDCl_3$, we concluded that geometries of olefin of C1-3-L, C1-3-S and 20 were all Z.

Determination of Geometry at Olefin of Negative Control Recruiter C1-4

Figure 27:
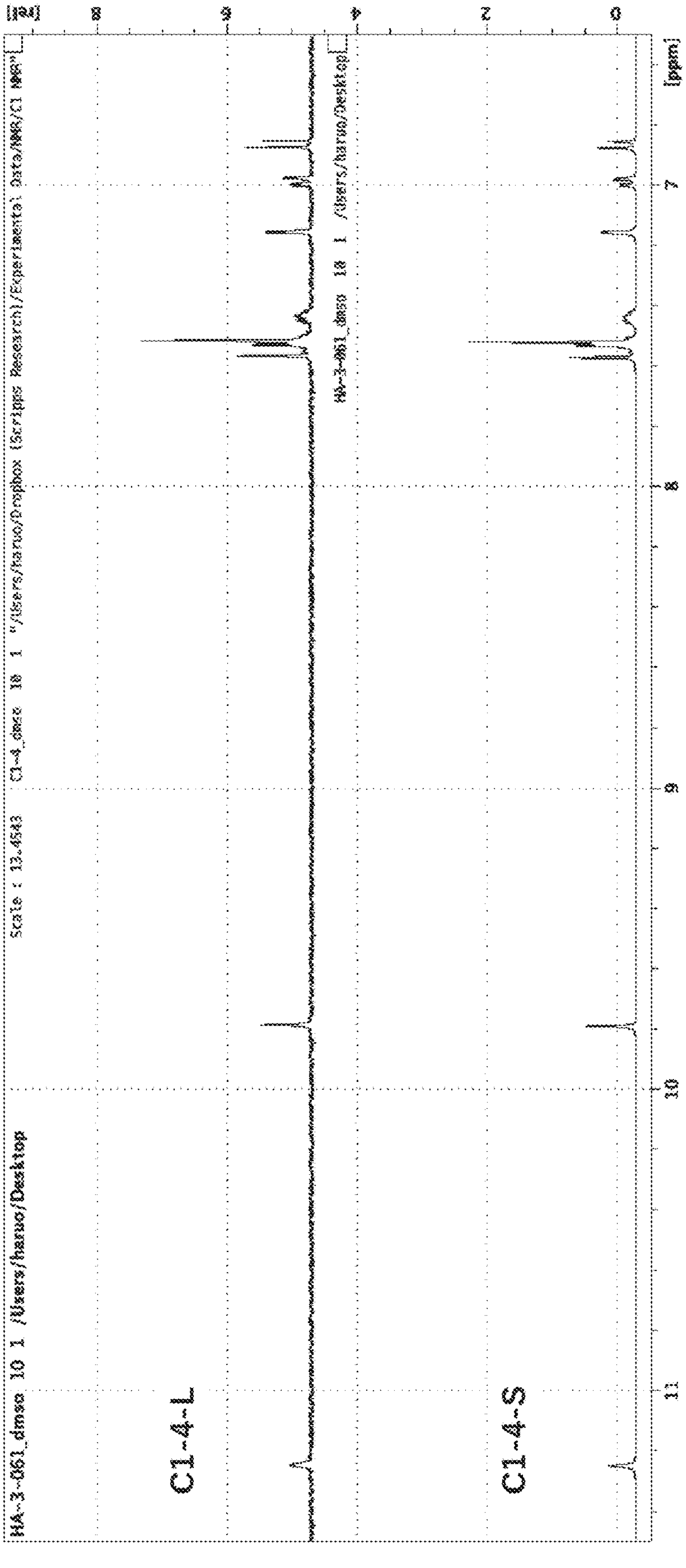
FIG. 27. Comparison of $^{1}H$-NMR spectra (400 MHz, DMSO-$d_6$) of C1-4-L and C1-4-S.

The inactive small molecule RNase L recruiter C1-4 (4, FIG. 2A-2C & FIGS. 38A-38F) was synthesized using the same procedure as the synthesis of 23, and the newly synthesized C1-4 (C1-4-S) and C1-4 in the library (C1-4-L) were identical by $^1H$-NMR (DMSO-$d_6$) (FIG. 27). By comparison of the $^1H$-NMR spectra of C1-4-S and 23 in $CDCl_3$ at the olefinic proton, C1-4-S and 23 have the same geometry. As the synthetic procedure for 23 is same as that for 20, we concluded that the geometries of the olefin of C1-4-L, C1-4-S and 23 are all Z.

Parameterization of RNA binder. The RNA binder molecule contains two distinctive moieties: i) binding module. Force field parameters for these moieties were created using the Generalized Amber Force Field (GAFF)[34]. RESP charges for the binding module were derived using the resp protocol: the molecule was first minimized and then electrostatic potentials at a set of grid points were calculated at the HF/6-31G* basis set[35,36]. The calculations were performed using Gaussian09[37]. The atomic charges for the linker were produced by AM1-BCC method[38] built-in Antechamber program[39]. All the force field parameters and charge information for the binding module and the linker are available in Tables S6 & S7.

Binding studies. Two RNA molecules, r(5'-CGCGACGCG-3'/5'CGCGCGCG-3') (SEQ ID NOs: 16 and 17, respectively) and r(5'-GCGUUGCGC/GCGCACGC-3') (SEQ ID NO: 18), representing model A- and U-bulges were generated by the nucgen module in AMBER16[40] to conduct the binding studies. The Amber99 force fields[41] with revised χ[42] and α/γ[43] torsional parameters were used to describe the RNAs. Watson-Crick (WC) base pairing, torsional, and chirality restraints were imposed on the system to maintain the A-form geometry. All the simulations for the binding study were conducted under the conditions of the modified implicit solvent model ($GB^{OBC}$)[44] with 0.3 M salt concentrations. The previously used dynamic docking methodology[45-47] was applied to investigate the bound states of the binding module to the A- and U-bulge RNAs. First, initial structures were created for each system by placing the binding module at 40 Å away from the bulge RNA site. The distance between the center of mass of the heavy atoms of the adjacent bases to the bulge region and the heavy atoms of the binding module was used as the reaction coordinate during the initial binding process. The binding module was slowly moved toward the bulge-region in 1 Å increments until the reaction coordinate approached to 0 Å. During the so-called 'move-close' process, WC base pairing, torsional, and chirality restraints representing A-form geometry were imposed on the RNA except the bulge region. This allowed the bulge site to re-orient itself while interacting with the binding module. Once at 0 Å, the binding module was moved away from the bulge-site in increments of 1 Å until the distance reached to 40 Å. During this so-called 'move-away' process, WC base pairing, torsional, and chirality restraints representing A-form geometry were imposed on all the RNA residues. This process was repeated 50 times sequentially to provide 50 different initial bound states to be used in MD simulations for the binding studies. Using these initial bound states, 50 independent implicit-solvent MD simulations were conducted. In these MD simulations, again, the WC base pairing, torsional, and chirality restraints were imposed on the RNA except in the bulged region so that the binding module was free to move around the bulge site. Each MD simulation was run for 120 ns yielding a total of 6 μs combined MD trajectory, which was used in cluster analysis for the binding module/A-bulge RNA complex.

Cluster Analysis. An in-house code was utilized in cluster analyses. The combined MD trajectories contained 60K snapshots. Root-mean-square deviation (RMSD) was investigated through the whole snapshots, and the snapshots with RMSD<=1 Å were clustered into the same group. The symmetry of ring atoms of the binding module was considered while calculating the RMSD.

Relative binding free energy calculations using MM-PBSA. MM-PBSA analyses were performed on each cluster to determine the lowest binding free energy states for the binding module/bulge RNA complexes. The MMPBSA.py module of AMBER16[40] was used and applied on clusters, which had more than 100 structures (Tables S8 & S9). The lowest binding energy states of the binding module to model A- and U-bulge RNAs are displayed.

Preparation of pre-miR-21 with RNA binder. The RNA sequence, r(5'-UGUCGGGUAGCUUAUCAGACUGAU-GUUGACUGUUGAAUCUCAUGGCAACACC AGU-CGAUGGCUGUCUGACA-3') (SEQ ID NO: 19), was used to model pre-miR-21. The target RNA structure was modeled in RNAComposer (rnacomposer.cs.put.poznan.pl/) using the secondary structure predicted with ViennaRNA (rna.tbi.univie.ac.at/). The lowest binding free energy states of the binding module to model A- and U-bulge RNAs were utilized in the design of pre-miR-21 RNA interacting with the RNA binder, where the A- and U-bulge regions of pre-miR-21 were replaced with the predicted A- and U-bulges interacting with the binding modules. For this purpose, we utilized VMD (Visual Molecular Dynamics)[48] to homology model the structure. A linker was attached at the ends of the two binding modules to complete the structure of pre-miR-21 RNA interacting with the RNA binder. Finally, the structure was minimized.

Experimental Results

TABLE S1

Measurement of 5 catalytic activity after 24 h of treatment. Data are expressed as mean ± s.d. (n = 6).

| Treated [5] (nM) | 5 Detected (pmol) | Average pre-miR-21 (pmol) | Cleaved pre-miR-21 (pmol) [a] | Turnovers [b] |
|---|---|---|---|---|
| 0 | — | 85 ± 8.1 | 0 | — |
| 500 | 2.6 ± 0.51 | 16 ± 3.8 | 68 ± 6.7 | 26 ± 2.5 |

[a] "Cleaved pre-miR-21" is the difference between the Average pre-miR-21 in the untreated and the Average pre-miR-21 in the 500 nM treated samples.
[b] "Turnovers" is the ratio between "Cleaved pre-miR-21 (pmol)" and "5 Detected (pmol)" in cells and represents catalysis.

8. S. F. Tavazoie, C. Alarcón, T. Oskarsson, D. Padua, Q. Wang, P. D. Bos, W. L. Gerald, J. Massagué, Endogenous human microRNAs that suppress breast cancer metastasis. *Nature* 451, 147 (2008).
9. M. J. C. Hendrix, W. R. Wood, E. A. Seftor, D. Lotan, M. Nakajima, R. L. Misiorowski, R. E. Seftor, W. G. Stetler-Stevenson, S. J. Bevacqua, L. A. Liotta, M. E. Sobel, A. Raz, R. Lotan, Retinoic acid inhibition of human melanoma cell invasion through a reconstituted basement membrane and its relation to decreases in the expression of proteolytic enzymes and motility factor receptor. *Cancer Res.* 50, 4121 (1990).
10. M. Seike, A. Goto, T. Okano, E. D. Bowman, A. J. Schetter, I. Horikawa, E. A. Mathe, J. Jen, P. Yang, H. Sugimura, A. Gemma, S. Kudoh, C. M. Croce, C. C. Harris, MiR-21 is an EGFR-regulated anti-apoptotic factor in lung cancer in never-smokers. *Proc. Natl Acad. Sci. U.S.A.* 106, 12085 (2009).
11. F. Sicard, M. Gayral, H. Lulka, L. Buscail, P. Cordelier, Targeting miR-21 for the therapy of pancreatic cancer. *Mol. Ther.* 21, 986-994 (2013).
12. M. G. Costales, Y. Matsumoto, S. P. Velagapudi, M. D. Disney, Small molecule targeted recruitment of a nuclease to RNA. *J. Am. Chem. Soc.* 140, 6741-6744 (2018).
13. Y. Han, J. Donovan, S. Rath, G. Whitney, A. Chitrakar, A. Korennykh, Structure of human RNase L reveals the basis for regulated RNA decay in the IFN response. *Science* 343, 1244-1248 (2014).

REFERENCES

1. Wu, X. & Bartel, D. P. Widespread influence of 3'-end structures on mammalian mRNA processing and stability. *Cell* 169, 905-917 (2017).
2. Sun, L. et al. RNA structure maps across mammalian cellular compartments. *Nat. Struct. Mol. Biol.* 26, 322-330 (2019).
3. D. P. Bartel, MicroRNAs: genomics, biogenesis, mechanism, and function. *Cell* 116, 281-297 (2004).
4. A. M. Krichevsky, G. Gabriely, miR-21: a small multi-faceted RNA. *J. Cell. Mol. Med.* 13, 39-53 (2009).
5. D. Iliopoulos, S. A. Jaeger, H. A. Hirsch, M. L. Bulyk, K. Struhl, STAT3 activation of miR-21 and miR-181b-1 via PTEN and CYLD are part of the epigenetic switch linking inflammation to cancer. *Mol. Cell* 39, 493-506 (2010).
6. L. B. Frankel, N. R. Christoffersen, A. Jacobsen, M. Lindow, A. Krogh, A. H. Lund, Programmed cell death 4 (PDCD4) is an important functional target of the microRNA miR-21 in breast cancer cells. *J. Biol. Chem.* 283, 1026-1033 (2008).
7. N. M. McLoughlin, C. Mueller, T. N. Grossmann, The therapeutic potential of PTEN modulation: targeting strategies from gene to protein. *Cell Chem. Biol.* 25, 19-29 (2018).
14. C. S. Thakur, B. K. Jha, B. Dong, J. Das Gupta, K. M. Silverman, H. Mao, H. Sawai, A. O. Nakamura, A. K. Banerjee, A. Gudkov, R. H. Silverman, Small-molecule activators of RNase L with broad-spectrum antiviral activity. *Proc. Natl. Acad. Sci. U.S.A.* 104, 9585-9590 (2007).
15. A. Chakrabarti, B. K. Jha, R. H. Silverman, New insights into the role of RNase L in innate immunity. *J. Interferon Cytokine Res.* 31, 49-57 (2011).
16. P. P. Graczyk, Gini coefficient: a new way to express selectivity of kinase inhibitors against a family of kinases. *J. Med. Chem.* 50, 5773-5779 (2007).
17. W. Y. Yang, R. Gao, M. Southern, P. S. Sarkar, M. D. Disney, Design of a bioactive small molecule that targets r(AUUCU) repeats in spinocerebella ataxia 10. *Nat. Commun.* 7, 11647 (2016).
18. V. Agarwal, G. W. Bell, J.-W. Nam, D. P. Bartel, Predicting effective microRNA target sites in mammalian mRNAs. *eLife* 4, e05005 (2015).
19. S. Yang, J. J. Zhang, X.-Y. Huang, Mouse models for tumor metastasis. *Methods Mol. Biol.* 928, 221-228 (2012).
20. S. P. Velagapudi, M. D. Cameron, C. L. Haga, L. H. Rosenberg, M. Lafitte, D. R. Duckett, D. G. Phinney, M.

D. Disney, Design of a small molecule against an oncogenic noncoding RNA. *Proc. Natl. Acad. Sci. U.S.A.* 113, 5898-5903 (2016).
21. B. Dong, R. H. Silverman, A bipartite model of 2-5A-dependent RNase L. *J. Biol. Chem.* 272, 22236-22242 (1997).
22. S. P. Velagapudi, M. G. Costales, B. R. Vummidi, Y. Nakai, A. J. Angelbello, T. Tran, H. S. Haniff, Y. Matsumoto, Z. F. Wang, A. K. Chatterjee, J. L. Childs-Disney, M. D. Disney, Approved anti-cancer drugs target oncogenic non-coding RNAs. *Cell Chem. Biol.* 25, 1086-1094.e1087 (2018).
23. B. Dong, M. Niwa, P. Walter, R. H. Silverman, Basis for regulated RNA cleavage by functional analysis of RNase L and Ire1p. *RNA* 7, 361-373 (2001).
24. K. A. O'Donnell, E. A. Wentzel, K. I. Zeller, C. V. Dang, J. T. Mendell, c-Myc-regulated microRNAs modulate E2F1 expression. *Nature* 435, 839-843 (2005).
25. M. Hampf, M. Gossen, A protocol for combined Photinus and Renilla luciferase quantification compatible with protein assays. *Anal. Biochem.* 356, 94-99 (2006).
26. J. Cox, M. Mann, MaxQuant enables high peptide identification rates, individualized p.p.b.-range mass accuracies and proteome-wide protein quantification. *Nature Biotechnol.* 26, 1367-1372 (2008).
27. J. K. Eng, A. L. McCormack, J. R. Yates III, An approach to correlate tandem mass spectral data of peptides with amino acid sequences in a protein database. *J. Am. Soc. Mass Spectrom.* 5, 976-989 (1994).
28. D. Szklarczyk, A. Franceschini, S. Wyder, K. Forslund, D. Heller, J. Huerta-Cepas, M. Simonovic, A. Roth, A. Santos, K. P. Tsafou, M. Kuhn, P. Bork, L. J. Jensen, C. von Mering, STRING v10: protein-protein interaction networks, integrated over the tree of life. *Nucleic Acids Res.* 43, D447-452 (2015).
29. A. Krämer, J. Green, J. Pollard, Jr., S. Tugendreich, Causal analysis approaches in Ingenuity Pathway Analysis. *Bioinform.* 30, 523-530 (2014).
30. J. L. Childs-Disney, P. B. Tsitovich, M. D. Disney, Using modularly assembled ligands to bind RNA internal loops separated by different distances. *Chembiochem.* 12, 2143-2146 (2011).
31. B. Liu, J. L. Childs-Disney, B. M. Znosko, D. Wang, M. Fallahi, S. M. Gallo, M. D. Disney, Analysis of secondary structural elements in human microRNA hairpin precursors. *BMC Bioinform.* 17, 112 (2016).
32. M. G. Costales, C. L. Haga, S. P. Velagapudi, J. L. Childs-Disney, D. G. Phinney, M. D. Disney, Small molecule inhibition of microRNA-210 reprograms an oncogenic hypoxic circuit. *J. Am. Chem. Soc.* 139, 3446-3455 (2017).
33. J. Wang, R. M. Wolf, J. W. Caldwell, P. A. Kollman, D. A. Case, Development and testing of a general amber force field. *J. Comput. Chem.* 25, 1157-1174 (2004).
34. W. D. Cornell, P. Cieplak, C. 1. Bayly, P. A. Kollman, Application of RESP charges to calculate conformational energies, hydrogen bond energies, and free energies of solvation. *J. Am. Chem. Soc.* 115, 9620-9631 (1993).
35. C. 1. Bayly, P. Cieplak, W. D. Cornell, P. A. Kollman, A well-behaved electrostatic potential based method using charge restraints for deriving atomic charges: the RESP model. *J. Phys. Chem.* 97, 10269-10280 (1993).
36. Gaussian 09. M. J. Frisch, G. W. Trucks, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery, Jr., J. E. Peralta, F. Ogliaro, M. Bearpark, J. J. Heyd, E. Brothers, K. N. Kudin, V. N. Staroverov, R. Kobayashi, J. Normand, K. Raghavachari, A. Rendell, J. C. Burant, S. S. lyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, Ö. Farkas, J. B. Foresman, J. V. Ortiz, J. Cioslowski, and D. J. Fox, Gaussian, Inc., Wallingford CT, 2009.
37. A. Jakalian, D. B. Jack and C. I. Bayly, Fast, efficient generation of high-quality atomic charges. AM1-BCC model: II. Parameterization and validation. *J. Comput, Chem.* 23, 1623-1641 (2002).
38. J. Wang, W. Wang, P. A. Kollman, D. A. Case, Automatic atom type and bond type perception in molecular mechanical calculations. *J. Mol. Graph. Model.* 25, 247-260 (2006).
39. D. A. Case, R. M. Betz, D. S. Cerutti, T. E. Cheatham, Ill, T. A. Darden, R. E. Duke, T. J. Giese, H. Gohlke, A. W. Goetz, N. Homeyer, S. Izadi, P. Janowski, J. Kaus, A. Kovalenko, T. S. Lee, S. LeGrand, P. Li, C. Lin, T. Luchko, R. Luo, B. Madej, D. Mermelstein, K. M. Merz, G. Monard, H. Nguyen, H. T. Nguyen, I. Omelyan, A. Onufriev, D. R. Roe, A. Roitberg, C. Sagui, C. L. Simmerling, W. M. Botello-Smith, J. Swails, R. C. Walker, J. Wang, R. M. Wolf, X. Wu, L. Xiao and P. A. Kollman (2016), AMBER 2016, University of California, San Francisco.
40. W. D. Cornell, P. Cieplak, C. I. Bayly, I. R. Gould, K. M. Merz, D. M. Ferguson, D. C. Spellmeyer, T. Fox, J. W. Caldwell, P. A. Kollman, A second generation force field for the simulation of proteins, nucleic acids, and organic molecules. *J. Am. Chem. Soc.* 117, 5179-5197 (1995).
41. I. Yildirim, H. A. Stern, S. D. Kennedy, J. D. Tubbs and D. H. Turner, Reparameterization of RNA $\chi$ torsioin parameters for the AMBER force field and comparison to NMR spectra for cytidine and uridine. *J. Chem. Theory Comput.* 6, 1520-1531 (2010).
42. D. J. Wales and I. Yildirim, Improving computational predictions of single-stranded RNA tetramers with revised $\alpha/\gamma$ torsional parameters for the AMBER force field. *J. Phys. Chem. B* 121, 2989-2999 (2017).
43. A. Onufriev, D. Bashford, D. A. Case, Exploring protein native states and large-scale conformational changes with a modified generalized born model. *Proteins: Struct. Funct. Bioinf.* 55, 383-394 (2004).
44. Z. -F. Wang, A. Ursu, J. L. Childs-Disney, R. Guertler, W. -Y. Yang, V. Bernat, S. G. Rzuczek, R. Fuerst, Y. -J. Zhang, T. F. Gendron, I. Yildirim, B. G. Dwyer, J. E. Rice, L. Petrucelli, M. D. Disney, The hairpin form of $r(G_4C_2)^{exp}$ in c9ALS/FTD is repeat-associated non-ATG translated and a target for bioactive small molecules. *Cell Chem. Biol.* 26, 179-190 (2019).
45. J. L. Childs-Disney, E. Stepniak-Konieczna, T. Tran, I. Yildirim, H. Park, C. Z. Chen, J. Hoskins, N. Southall, J. J. Marugan, S. Patnaik, W. Zheng, C. P. Austin, G. C. Schatz, K. Sobczak, C. A. Thornton, M. D. Disney, Induction and reversal of myotonic dystrophy type 1 pre-mRNA splicing defects by small molecules. *Nat. Comm.* 4, 2044 (2013).
46. J. L. Childs-Disney, I. Yildirim, H. Park, J. R. Lohman, L. Guan, T. Tran, P. Sarkar, G. C. Schatz, M. D. Disney, Structure of the myotonic dystrophy type 2 RNA and designed small molecules that reduce toxicity. *ACS Chem. Biol.* 9, 538-550 (2014).

47. W. Humphrey, A. Dalke, K. Schulten, VMD: visual molecular dynamics. *J. Mol. Graph.* 14, 33-38 (1996).

Summary Statements

The inventions, examples, biological assays and results described and claimed herein have may attributes and embodiments include, but not limited to, those set forth or described or referenced in this application.

All patents, publications, scientific articles, web sites and other documents and material references or mentioned herein are indicative of the levels of skill of those skilled in the art to which the invention pertains, and each such referenced document and material is hereby incorporated by reference to the same extent as if it had been incorporated verbatim and set forth in its entirety herein. The right is reserved to physically incorporate into this specification any and all materials and information from any such paten, publication, scientific article, web site, electronically available information, textbook or other referenced material or document.

The written description of this patent application includes all claims. All claims including all original claims are hereby incorporated by reference in their entirety into the written description portion of the specification and the right is reserved to physically incorporated into the written description or any other portion of the application any and all such claims. Thus, for example, under no circumstances may the patent be interpreted as allegedly not providing a written description for a claim on the assertion that the precise wording of the claim is not set forth in haec verba in written description portion of the patent.

While the invention has been described in conjunction with the detailed description thereof, the foregoing description is intended to illustrate and not limit the scope of the invention, which is defined by the scope of the appended claims. Thus, from the foregoing, it will be appreciated that, although specific nonlimiting embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred nonlimiting embodiments and are exemplary and not intended as limitations on the scope of the invention. Other objects, aspects, and embodiments will occur to those skilled in the art upon consideration of this specification and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in nonlimiting embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various nonlimiting embodiments and/or preferred nonlimiting embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

What is claimed is:

1. A compound of Formula 5 and the pharmaceutically acceptable salts thereof

Formula 5

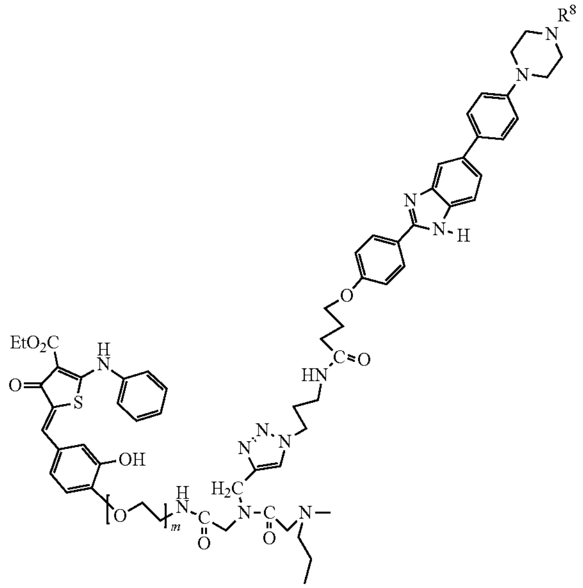

-continued

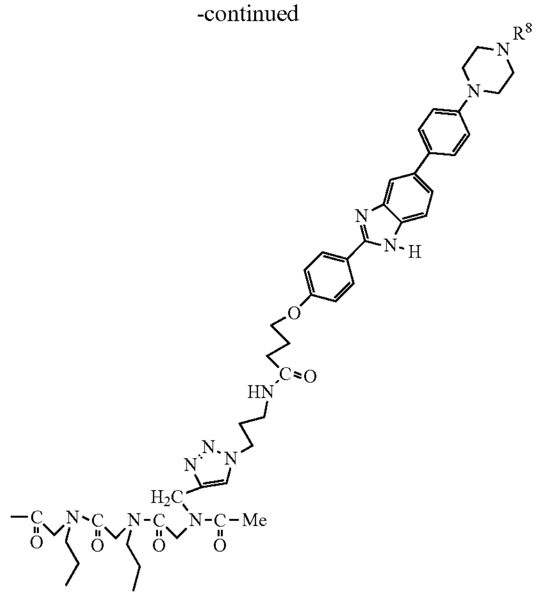

wherein designator m is 4, and each $R^8$ is independently hydrogen or methyl.

2. A pharmaceutical composition comprising a pharmaceutically acceptable carrier and an amount of a compound of claim 1, or a pharmaceutically acceptable salt thereof, which is effective for inhibition of RNA pre-miR-21 activity.

3. A method for decreasing RNA pre-miR-21 activity in a patient, for treatment of cancer in a patient wherein the cancer cells of the patient display miR-21 RNA activity and/or pre-miR-21 expression, or for treatment of a patient's disease mediated by aberrant miR-21 RNA activity, comprising administering to the patient an effective amount of a pharmaceutical composition of claim 2.

4. The method of claim 3, wherein the cancer is breast, lung, pancreatic or melanoma cancer.

5. A method of cellular destruction by targeting an oncogenic non-coding RNA precursor, comprising contacting a cell expressing the oncogenic non-coding RNA precursor with a pharmaceutical composition of claim 2.

6. The method of claim 5 wherein the oncogenic non-coding RNA precursor comprises oncogenic pre-microRNA-21 (pre-miR-21).

* * * * *